US011124737B2

(12) United States Patent
Wood et al.

(10) Patent No.: US 11,124,737 B2
(45) Date of Patent: Sep. 21, 2021

(54) HIGH OLEIC ACID OILS

(71) Applicants: Craig Christopher Wood, Dickson (AU); Qing Liu, Giralang (AU); Xue-Rong Zhou, Evatt (AU); Allan Green, Red Hill (AU); Surinder Pal Singh, Downer (AU); Shijiang Cao, Changchun (CN)

(72) Inventors: Craig Christopher Wood, Dickson (AU); Qing Liu, Giralang (AU); Xue-Rong Zhou, Evatt (AU); Allan Green, Red Hill (AU); Surinder Pal Singh, Downer (AU); Shijiang Cao, Changchun (CN)

(73) Assignee: COMMONWEALTH SCIENTIFIC ANDN INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 16/411,697

(22) Filed: May 14, 2019

(65) Prior Publication Data

US 2019/0330558 A1 Oct. 31, 2019

Related U.S. Application Data

(62) Division of application No. 13/869,763, filed on Apr. 24, 2013, now Pat. No. 10,323,209.

(60) Provisional application No. 61/638,447, filed on Apr. 25, 2012.

(30) Foreign Application Priority Data

Sep. 11, 2012 (AU) ................................ 2012903992

(51) Int. Cl.

| | |
|---|---|
| ***C12N 15/82*** | (2006.01) |
| ***A23D 9/00*** | (2006.01) |
| ***C11B 1/10*** | (2006.01) |
| ***C12N 9/02*** | (2006.01) |

(52) U.S. Cl.

CPC .................. *C11B 1/10* (2013.01); *A23D 9/00* (2013.01); *C12N 9/0071* (2013.01); *C12N 15/8218* (2013.01); *C12N 15/8247* (2013.01); *C12Y 114/19* (2013.01); *C12Y 114/19006* (2013.01)

(58) Field of Classification Search

None

See application file for complete search history.

(56) References Cited

U.S. PATENT DOCUMENTS

| | | | |
|---|---|---|---|
| 4,918,811 A | 8/1990 | Spinner et al. | |
| 5,500,361 A | 3/1996 | Kinney et al. | |
| 5,912,416 A * | 6/1999 | Weisker .................. | A01H 5/10 554/9 |
| 6,100,077 A | 8/2000 | Sturley et al. | |
| 6,344,548 B1 | 2/2002 | Farese et al. | |
| 6,432,684 B1 | 8/2002 | Mukerji et al. | |
| 7,001,771 B1 | 2/2006 | Morell et al. | |
| 7,045,326 B2 | 6/2006 | Cases et al. | |
| 7,109,392 B1 | 9/2006 | Broglie et al. | |
| 7,135,617 B2 | 11/2006 | Lardizabal et al. | |
| 7,244,599 B2 | 7/2007 | Tanner et al. | |
| 7,417,176 B2 | 8/2008 | Lardizabal et al. | |
| 7,521,593 B2 | 4/2009 | Regina et al. | |
| 7,589,253 B2 | 9/2009 | Green et al. | |
| 7,619,105 B2 | 11/2009 | Green et al. | |
| 7,667,114 B2 | 2/2010 | Morell et al. | |
| 7,700,139 B2 | 4/2010 | Bird et al. | |
| 7,700,826 B2 | 4/2010 | Morell et al. | |
| 7,741,532 B2 | 6/2010 | Lardizabal et al. | |
| 7,790,955 B2 | 9/2010 | Li et al. | |
| 7,807,849 B2 | 10/2010 | Singh et al. | |
| 7,812,221 B2 | 10/2010 | Morell et al. | |
| 7,834,248 B2 | 11/2010 | Green et al. | |
| 7,834,250 B2 | 11/2010 | Singh et al. | |
| 7,888,499 B2 | 2/2011 | Morell et al. | |
| 7,892,803 B2 | 2/2011 | Tanner et al. | |
| 7,919,132 B2 | 4/2011 | Regina et al. | |
| 7,932,438 B2 | 4/2011 | Singh et al. | |
| 7,932,440 B2 | 4/2011 | Reid et al. | |
| 7,993,686 B2 | 8/2011 | Bird et al. | |
| 8,049,069 B2 | 11/2011 | Wu et al. | |
| 8,071,341 B2 | 12/2011 | Singh et al. | |
| 8,106,226 B2 | 1/2012 | Singh et al. | |
| 8,115,087 B2 | 2/2012 | Regina et al. | |
| 8,158,392 B1 | 4/2012 | Singh et al. | |

(Continued)

FOREIGN PATENT DOCUMENTS

| | | |
|---|---|---|
| CA | 2180386 | 1/1998 |
| EP | 0496504 A1 | 7/1992 |

(Continued)

OTHER PUBLICATIONS

McCallum et al 2000 (Plant Physiology 123: p. 439-442) (Year: 2000).*
Rabiei et al 2007 (Helia 30:47, p. 175-182) (Year: 2007).*
Schlueter et al (2007) (The Plant Genome 1: p. S14-S26) (Year: 2007).*
Heppard (1996) (Plant Physiology 110: p. 311-319) (Year: 1996).*
U.S. Appl. No. 13/093,252, filed Apr. 25, 2011, Singh et al.
U.S. Appl. No. 13/011,779, filed Jan. 21, 2011, Liu et al.
U.S. Appl. No. 12/989,405, filed May 16, 2011, Zhou et al.
U.S. Appl. No. 13/129,940, filed May 18, 2011, Petrie et al.
U.S. Appl. No. 13/171,032, filed Jun. 28, 2011, Petrie et al.

(Continued)

*Primary Examiner* — Matthew R Keogh
(74) *Attorney, Agent, or Firm* — Gary J. Gershik

(57) ABSTRACT

The present invention relates to extracted lipid with high levels, for example 90% to 95% by weight, oleic acid. The present invention also provides genetically modified plants, particularly oilseeds such as safflower, which can used to produce the lipid. Furthermore, provided are methods for genotyping and selecting plants which can be used to produce the lipid.

Figure 1:
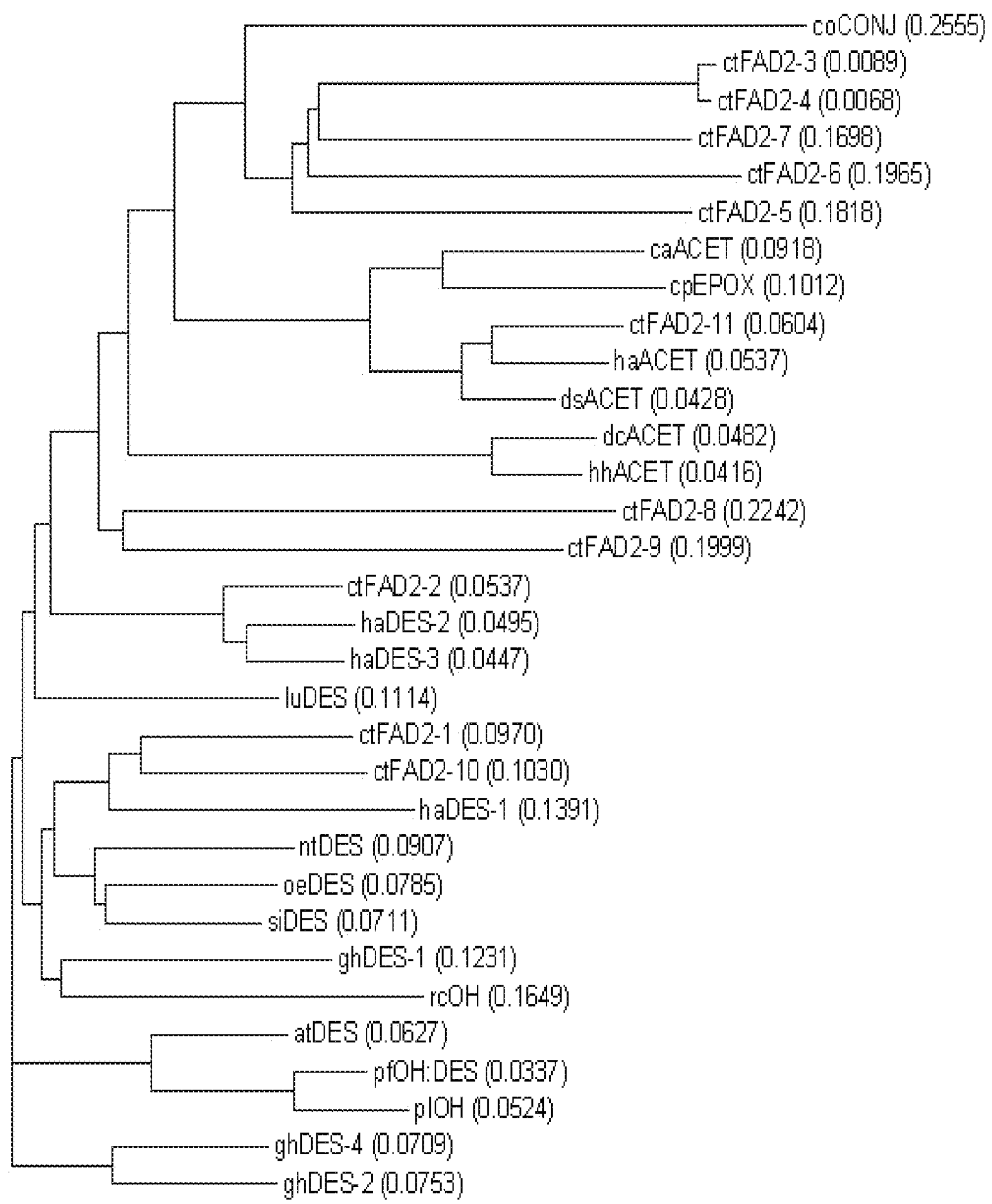

15 Claims, 16 Drawing Sheets
(8 of 16 Drawing Sheet(s) Filed in Color)

Specification includes a Sequence Listing.

(56) References Cited

U.S. PATENT DOCUMENTS 8,178,759 B2 5/2012 Morell et al.
8,188,336 B2 5/2012 Li et al.
8,269,082 B2 9/2012 Millar et al.
8,288,572 B2 10/2012 Singh et al.
8,501,262 B2 8/2013 Bird et al.
8,525,917 B2 9/2013 Singh et al.
8,530,724 B2 9/2013 Whitelaw et al.
8,735,111 B2 5/2014 Vanhercke et al.
8,778,644 B2 7/2014 Singh et al.
8,809,026 B2 8/2014 Vanhercke
8,809,559 B2 8/2014 Petrie et al.
8,816,106 B2 8/2014 Damceyski et al.
8,853,432 B2 10/2014 Singh et al.
9,061,992 B2 6/2015 Vanhercke et al.
9,499,829 B2 11/2016 Vanhercke et al.
9,512,438 B2 12/2016 Vanhercke et al.
2002/0104124 A1 8/2002 Green et al.
2004/0221335 A1 11/2004 Shewmaker et al.
2005/0106697 A1 5/2005 Cases et al.
2005/0262588 A1 11/2005 Dehesh et al.
2006/0094088 A1 5/2006 Pictaggio et al.
2006/0206963 A1* 9/2006 Voelker .................... A23D 9/00 800/281
2008/0268539 A1 10/2008 Singh et al.
2008/0311580 A1 12/2008 Abrahams et al.
2009/0308041 A1 12/2009 Whitelaw et al.
2010/0184130 A1 7/2010 Koprowski et al.
2010/0221400 A1 9/2010 Chapman et al.
2011/0015415 A1 1/2011 Singh et al.
2011/0045127 A1 2/2011 Ral et al.
2011/0054198 A1 3/2011 Singh et al.
2011/0126325 A1 5/2011 Zhou et al.
2011/0190521 A1 8/2011 Damcevski et al.
2011/0218348 A1 9/2011 Zhou et al.
2011/0223311 A1 9/2011 Liu et al.
2011/0229623 A1 9/2011 Liu et al.
2011/0281818 A1 11/2011 Jenkins et al.
2011/0314725 A1 12/2011 Petrie et al.
2012/0016144 A1 1/2012 Petrie et al.
2012/0114770 A1 5/2012 Regina et al.
2012/0129805 A1 5/2012 Li et al.
2012/0208198 A1 8/2012 Bogs et al.
2013/0115362 A1 5/2013 Regina et al.
2013/0164798 A1 6/2013 Vanhercke et al.
2013/0247451 A1 9/2013 Vanhercke et al.
2013/0288318 A1 10/2013 Wood et al.
2014/0120225 A1 5/2014 Whitelaw et al.
2014/0256006 A1 9/2014 Vanhercke et al.
2014/0371477 A1 12/2014 Wood et al.

FOREIGN PATENT DOCUMENTS

EP 1806398 7/2007
EP 1837397 9/2007
EP 1944375 7/2008
WO WO 1998/055631 12/1998
WO WO 1999/049050 9/1999
WO WO 1999/067268 12/1999
WO WO 1999/067403 12/1999
WO WO 2000/001713 1/2000
WO WO 2000/011176 3/2000
WO WO 2000/032756 6/2000
WO WO 2000/032793 6/2000
WO WO 2000/036114 6/2000
WO WO 2000/060095 10/2000
WO WO 2000/66750 10/2000
WO WO 2000/066749 11/2000
WO WO 2002/068595 9/2002
WO WO 2003/078639 9/2003
WO WO 2004/011671 2/2004
WO WO 2004/042014 5/2004
WO WO 2005/003322 1/2005
WO WO 2005/063988 7/2005
WO WO 2005/103253 11/2005
WO WO 2006/127789 11/2006
WO WO 2007/095243 8/2007
WO WO 2007/107738 9/2007
WO WO 2008/025068 6/2008
WO WO 2008/130248 10/2008
WO WO 2008/147935 12/2008
WO WO 2008/157226 12/2008
WO WO 2008/157827 12/2008
WO WO 2009/027335 3/2009
WO WO 2009/085169 7/2009
WO WO 2009/086196 7/2009
WO WO 2009/129582 10/2009
WO WO 2009/143397 11/2009
WO WO 2010/009499 1/2010
WO WO 2010/009500 1/2010
WO WO 2010/057246 5/2010
WO WO 2011/062748 5/2011
WO WO 2012/000026 1/2012

OTHER PUBLICATIONS

U.S. Appl. No. 13/841,641, filed Mar. 15, 2013, Vanhercke et al.
U.S. Appl. No. 14/021,173, filed Sep. 9, 2013, Whitelaw et al.
Abdullah, R., Cocking, E. C., & Thompson, J. A. (Dec. 1986). Efficient plant regeneration from rice protoplasts through somatic embryogenesis. Biotechnology, 4, 1087-1090.
Agarwal et el. (2003) "Cottonseed Oil Quality, Utilization and Processing" CICR Technical Bulletin No. 25, pp. 1-16.
Aghoram, K., Wilson, R.F., Burton, J.W., Dewey, R.E. 2006. A mutation in a 3-keto-acyl-acp synthase ii gene is associated with elevated palmitic acid levels in soybean seeds. Crop Sci. 46:2453-2459.
Akagi et al. (1995) Nucleotide Sequence of a Stearoyl-Acel carrier Protein Desaturase cDNA from Developing Seeds of Rice. Plant Physiol. 108, 845-846.
Alemanno et al. (2008) "Characterization of *leafy cotyledonl-like* during embryogenesis in *Theobroma cacao* L." Planta 227:853-866.
Almeida and Allshire, (2005) "RNA silencing and genome regulation." Trends in Cell Biology, 15:251-258.
Alonso et al. (2010) "Catalytic conversion of biomass to biofuels" Green Chem. 12:1493-1513.
Anai et al. (2003) Improvement of rice (*Oryza sativa* L.) seed oil quality through introduction of a soybean microsomal omega-3 fatty acid desaturase gene. Plant Cell Rep. 21,988-992.
Andrianov et al. (2010) "Tobacco as a production platform for biofuel: overexpression of *Arabidopsis* DGAT and LECZ genes increases accumulation and shifts the composition of lipids in green biomass" Plant Biotech. J. 8:277-287.
Apr. 28, 2017 Office Action, issued in connection with Eurasian Patent Application No. 201491956, including English Language Translation.
Ascherio and Willett (1997) "Health effects of trans fatty acids" Am. J. Clin. Nutr. 66: 1006S-1010S.
Aug. 24, 2018 Office Action issued in connection with Eurasian patent application 201491956, including English language translation.
Aug. 27, 2015 First Office Action, issued in connection with Chinese Patent Application No. 201280070729.5, including English language translation.
Aug. 30, 2017 Second Office Action, issued in connection with Chinese Patent Application No. 201380033472.0, including English Language Translation.
Awai et al., (2006) "A phosphatidic acid-binding protein of the chloroplast inner envelope membrane involved in lipid trafficking" PNAS 103(28):10817-22.
Bao and Ohlrogge, (1999) "Supply of Fatty Acid is One Limiting Factor in the Accumulation of Triacylglycerol in Developing Embryos." Plant Physiology, 120:1057-1062.
Barthole et al. (2011) "Controlling lipid accumulation in cereal grains" Plant Sci. 185-186:33-39.
Bäumlein, H., et al., (1991) "A Novel Seed Protein Gene From Vicia faba is Developmentally Regulated in Transgenic Tobacco and *Arabidopsis* Plants," Molecular and General Genetics, 225(3): 459-467.

(56) References Cited

OTHER PUBLICATIONS

Belide S et al., "Agrobacterium-mediated transformation of safflower and the efficient recovery of transgenic plants via grafting" Plant Methods, 7:12 (2011).
Benning, (2008) "A role for lipid trafficking in chloroplast biogenesis" Progress in Lipid Research 47, 381-389.
Benning, (2009) "Mechanisms of Lipid Transport Involved in Organelle Biogenesis in Plant Cells" Annu. Rev. Cell Dev. Biol. 25:71-91.
Bergman J W et al., "Registration of 'Montola 2004' Safflower" Crop Science, 46:4 p. 1818 (2006).
Bligh and Dyer (1959) "A Rapid Method of Total Lipid Extraction and Purification" Canadian Journal of Biochemistry and Physiology 37:911-917.
Bligh and Dyer, (1959) "Orange-red Flesh in Cod and Haddock" J. Fish. Res. Bd. Canada, 16(4):449-452.
Boggs et al. (1964) "Relation of Hexanal in Vapor Above Stored Potato Granules to Subjective Flavor Extimatos." J. Food Sci. 29:487-489.
Bonanome and Grundy (1988) "Effect of Dietary Stearic Acid on Plasma Cholesterol and Lipoprotein Levels" N. Engl. Med. 318: 1244-1248.
Bouvier-Nave et al. (2000) "Expression in yeast and tobacco of plant cDNAs encoding acyl CoA:diacylglycerol acyltransferase" European Journal of Biochemistry/FEBS 267:85-96.
Brandt et al., (1985) "Primary Structure of a B1 Hordein Gene from Barley" Carlsberg Res. Commun., 50:333-345.
Broun et al. (1998) "A bifunctional oleate 12-hydroxylase: desaturasc from Lesquerella fenleri." The Pant Journal, 13(2):201-210.
Buhr et al. (2002) "Ribozyme termination of RNA transcripts down-regulate seed fatty acid genes in transgenic soybean" Plant J. 30:155-163.
Burgal et al., (2008) "Metabolic engineering of hydroxy fatty acid production in plants: ReDGAT2 drives dramatic increases in ricinoleate levels in seed oil" Plant Biotechnology Journal 6(8):819-831.
Cahoon E et al., "Fungal responsive fatty acid acetylenases occur widely in evolutionarily distant plant families" The Plant Journal, 34 pp. 671-683 (2003).
Cao et al., (2003) "Properties of the Mouse Intestinal Acyl-CoA:Monoacylglycerol Acyltransferase, MGAT2." The Journal of Biological Chemistry, 278(28)25657-25669.
Cases et al., (1998) "Identification of a gene encoding an acyl CoA:diacylglycerol acyltransferase, a key enzyme in triacylglycerol synthesis" PNAS 95:13018-13023.
Cases et al., J. Biol. Chem. (2001) "Cloning of DGAT2, a Second Mammalian Diacylglycerol Acyltransferase, and Related Family Members" 276(42):38870-38876.
Cernac (2004) "Wrinkled1 encodes an AP2/EREB domain protein involved in the control of storage compound biosynthesis in *Arabidopsis*" The Plant Journal 40, 575-585.
Cernac and Bennlng (2004) "*Wrinkled1* encodes an AP2/EREB oomaln protein involved in the control of storage compound biosynthesis in *Arabidopsis*" Plant J. 40:575-585.
Champagne et al. (1995) "Stabilization of Brown Rice Products Using Ethanol Vapors as an Antioxidant Delivery System" Cereal Chem 72:255-258.
Chang et al., (1978) "Chemical Reactions Involved in the Deep-Fat Frying of Foods." Journal of American Oil Chemists' Society, 55:718-727.
Chapman et al. (2001) "Transgenic Cotton Plants with Increased Seed Oleic Acid Content" Journal of American Chemists' Chemistry; vol. 78 No. 9, 941-947.
Cheng et al., (2003) "Identification of Acyl Coenzyme A: Monoacylglycerol Acyltransferase 3, an Intestinal Specific Enzyme Implicated in Dietary Fat Absorption." The Journal of Biological Chemistry, 278(126):13611-13614.
Cherry, (1983) "Cottonseed Oil" J. Am. Oil Chem. Soc. 60: 360-367.
Choudhury et al. (1980) "Lipids in Developing and Mature Rice Grain" Phytochemistry 19: 1063-1069.
Cicero et al. (2001) "Rice bran oil and [gamma]-oryzanol in the treatment of hyperlipoproteinaemias and other conditions" Phytotherapy Research; vol. 15 No. 4, 277-289.
Clapp et al., (1993) "The 16-Kilodalton N-Terminal Fragment of Human Prolactin is a Potent Inhibitor of Angiogenesis" Endocrinology, 133(3):1292-1299.
Colot et al., (1987) "Localization of sequences in wheat endosperm protein genes which confer tissue-specific expression in tobacco" The EMBO Journal, 6(12):3559-3564.
Comai et al., (2004) "Efficient discovery of DNA polymorphisms in natural populations by Ecotilling" The Plant Journal, 37:778-786.
Connolly et al. (1998) GenBank Accession No. AC004236, NCBI, pp. 1-11.
Covello and Reed, "Functional Expression of the Extreplastidial *Arabadopsis thaliana* Oleate Desaturase Gene (FAD2) in *Saccharomyces cerevisiae*" Plant Physiol., 111 pp. 223-226 (1996).
Domergue et al., (2005) "In vivo characterization of the first acyl-CoA Δ6-desaturase from a member of the plant kingdom, the microalga *Ostreococcus tauri*." Biochem J. 389, 483-490.
Dougherty et al. (1995). Effects of diets containing high or low amounts of stearic acid on plasma lipoprotein fractions and fecal fatty acid excretion of men. Am. J. Clin. Nutr. 61:1120-1128.
Dowd et al., (2004) "Gene Expression Profile Changes in Cotton Root and Hypocotyl Tissues in Response to Infection with *Fusarium oxysporum* f. sp. *vasinfectum*" Molecular Plant-Microbe Interactions. 17: 654-667.
Dubois et al. (2007) "Fatty acid profiles of 80 vegetable oils with regard to their nutritional potential" European Journal of Lipid Science Technology 109(7):710-732.
Dulermo and Nicaud (2011) "Involvement of the G3P shuttle and β-oxidation pathway in the control of TAG synthesis and lipid accumulation in *Yarrowia lipolytica*" Metab. Eng. 13:482-491.
Durrett et al. (2008) "Plant triacylglycerols as feedstocks for the production of biofuels" Plant J. 54:593-607.
Dyer J et al., "Molecular Analysis of a Bifunctional Fatty Acid Conjugase/Desaturase from Tung. Implications for the Evolution of Plant Fatty Acid Diversity" Plant Physiol. 130 pp. 2027-2038.
Eastmond, (2006) "Sugar-Dependent1 Encodes a Patatin Domain Triacylglycerol Lipase That Initiates Storage Oil Breakdown in Germinating *Arabidopsis* Seeds". The Plant Cell, vol. 18, 665-675.
Endalew et al. (2011) "Inorganic heterogeneous catalysts for biodiesel production from vegetable oils" Biomass and Bioenergy 35:3787-3809.
European Patent Office Communication Pursuant to Rules ,70(2) and 70a(2) EPC dated Dec. 11, 2015 in connection with European Patent Application No. EP13782495.9, filed Apr. 24, 2013.
European Patent Office Extended European Search Report dated Nov. 25, 2015 in connection with European Patent Application No. EP13782495.9, filed Apr. 24, 2013.
Falcone D et al., "Identification of a Gene that Complements an *Arabidopsis* Mutant Deficient in Chloroplast ω6 Desaturase Activity" Plant Physiol., 106 pp. 1453-1459 (1994).
Feb. 19, 2019 Response to May 2, 2018 Examination Report filed in connection with corresponding European Patent Application No. 13782495.9.
Feb. 2, 2018 Response to Jul. 24, 2017 Office Action issued in connection with European patent application 13782495.9.
Feb. 28, 2019 First Examination Report issued in connection with corresponding Canadian Patent Application No. 2,871,503.
Fernandez-Martinez J et al., "Survey of safflower (*Carthamus tinctorius* L.) germplasm for variants in fatty acid composition and other seed characters" Euphytica, 69 pp. 115-122 (1993).
File History for U.S. Patent Publication No. 2009-0308041, Whitelaw et al., Dec. 17, 2009 (U.S. Appl. No. 12/309,276, filed Jul. 6, 2009).
File History of U.S. Patent Application Publication No. 2011/0015415, Singh et al., published Jan. 20, 2011 (U.S. Appl. No. 12/661,978, filed Mar. 26, 2010).
File History of U.S. Patent Application Publication No. 2011/0190521, Damcevski et al., published Aug. 4, 2011 (U.S. Appl. No. 12/310,645, filed Feb. 16, 2011).
History of U.S. Patent Application Publication No. 2013/0164790; Vanhercke et al., published Jun. 27, 2013 (U.S. Appl. No. 13/725,404, filed Dec. 21, 2013).

(56) References Cited

OTHER PUBLICATIONS

File History of U.S. Pat. No. 7,589,253, Green et al., issued Sep. 15, 2009 (U.S. Appl. No. 09/981,124, filed Oct. 17, 2011).
File History of U.S. Pat. No. 7,807,849, Singh et al., issued Oct. 5, 2010 (U.S. Appl. No. 11/112,882, filed Apr. 22, 2005).
History of U.S. Pat. No. 7,834,248, Green et al., issued Nov. 16, 2010 (U.S. Appl. No. 11/699,817, filed Jan. 30, 2007).
File History of U.S. Pat. No. 7,834,250, Singh et al., issued Nov. 16, 2010 (U.S. Appl. No. 11/587,092, filed Oct. 20, 2006).
History of U.S. Pat. No. 7,932,438, Singh et al., issued (U.S. Appl. No. 12/945,708, filed Nov. 12, 2010).
History of U.S. Patent Publication No. 2011-0223311, Liu et al., published Sep. 15, 2011 (U.S. Appl. No. 13/011,773, filed Jan. 21, 2011).
History of U.S. Patent Publication No. 2011-0229623, Liu et al., Sep. 22, 2011 (U.S. Appl. No. 13/011,779, filed Jan. 21, 2011).
File History of U.S. Patent Publication No. 2011-0229623, Liu et al., Sep. 22, 2011 (U.S. Appl. No. 13/011,779, filed Jan. 21, 2011).
File History of U.S. Patent Publication No. 2011-0314725, Petrie et al., published Dec. 29, 2011 (U.S. Appl. No. 13/171,032, filed. Jun. 28, 2011).
File History of U.S. U.S. Appl. No. 12/989,405, Zhou et al., filed May 16, 2011.
Fofana B. et al., "Cloning of fatty acid biosynthetic genes β-ketoacyi CoA synthase, fatty acid elongase, stearoyl-ACP desaturase, and fatty acid desaturase and analysis of expression in the early developmental stages of flax (*Linum usitatissimum* L.) seeds" Plant Science, 166 pp. 1487-1496 (2004).
Folch et al., (1957) "A Simple Method for the Isolation and Purification of total Lipides From Animal Tissues" J. Biol. Chem. 226: 497.
Fuller et al., (1966) "A Gas Chromatographic Method for Continuous Accelerated Study of O2 Uptake in Fats" JAOCS. 43: 477-478.
GenBank accession No. AAK26632.1, submitted Mar. 26, 2001.
GenBank accession No. AAL68983.1, submitted Jan. 30, 2002.
GenBank accession No. AY166773.1, submitted Jun. 2, 2003.
Ghosal et al. (2007) "*Saccharomyces cerevisiae* phospholipid-:diacylglycerol acyl transferase (PDAT) devoid of its membrane anchor region is a soluble and active enzyme retaining its substrate specificities" Biochimica et Biophysica Acta 1771:1457-1463.
Goffman et al., (2003) "Genetic Diversity for Lipid Content and Fatty Acid Profile in Rice Bran," Journal of the American Oil Chemists' Society 80:485-490.
Gong and Jiang (2011) "Biodiesel production with microalgae as feedstock: from strains to biodiesel" Biotechnol. Lett. 33:1269-1284.
Greenwell et al. (2010) "Placing microalgae on the biofuels priority list: a review of the technological challenges" J. R. Soc. Interface 7:703-726.
Guan L et al., "Molecular Cloning and Expression Analysis of Genes Encoding Two Microsomal Oleate Desaturases (FAD2) from Safflower" Plant Mol. Biol. Rep., 30:139-148 (2012).
Ha (2005) "Bioactive components in rice bran oil Improve lipid profiles in rats fed on high-cholesterol diet" Nutrition research 25, 597-606.
Hamdan Y et al., "Inheritance of high oleic acid content in safflower" Euphytica, 168 pp. 61-69 (2009).
Haseloff, J. and Gerlach, W.L., (1988) "Simple RNA Enzymes With New and Highly Specific Endoribonuclease Activities," Nature, 334: 585-591.
Henlkoff et al., (2004) "Tilling. Traditional Mutagenesis Meets Functional Genpmics." Plant Physiology, 2004, 135:630-636.
Hepperd E et al., "Developmental and Growth Temperature Regulation of Two Different Microsomal ω-6 Desaturase Genes in Soybeans" Plant Physiol., 110 pp. 311-319 (1996).
Hernandez M et al., "Molecular cloning and characterization of genes encoding two microsomal oleate desaturases (FAD2) from olive" Phytochemistry, 66 pp. 1417-1426 (2005).
Hill and Knowles, "Fatty Acid Composition of the Oil of Developing Seeds of Different Varieties of Safflower" Crop Science, 8:3 pp. 275-277 (1968).
Hu et al. (1997) "Dietary Fat Intake and the Rist of Coronary Heart Disease in Women." N. Engl. J. Med. 337: 1491-1499.
Hutchins et al., (1968) "A New Process for the Selective Hydrogenation Cyclopropenoids in Cottonseed Oil" Journal of American Oil Chemists Society 45: 397-399.
International Search Report dated Aug. 13, 2013 in connection with international Patent Application No. PCT/AU2013/000426, filed Apr. 24, 2013.
Jain et al., (2000) "Enhancement of seed oil content by expression of glycerol-3-phosphate acyltransferase genes" Biochemical Society Transactions 28(6):958-961.
Jako et al., (2001) "Seed-Specific Over-Expression of an *Arabidopsis* cDNA Encoding a Diacylglycerol Acyltransferase Enhances Seed Oil Content and Seed Weight" Plant Physiology 126:861-874.
Jan. 10, 2018 Office Action issued in connection with Eurasian patent application 201491956, including English language translation.
Jan. 22, 2015 Office Action, issued in connection with Eurasian Patent Application No. 201491956, including English Language Translation.
Jennings and Akoh (2000) "Lipase-Catalyzed Modification of Rice Bran Oil to Incorporate Capric Acid." Journal of Agricultural and Food Chemistry, 48:4439-4443.
Jones et al. (1995) "Palmitoyi-Acyl Carrier Protein (ACP) Thioesterase and the Evolutionary Origin of Plant Acyl-ACP Thioesterases." Plant Cell 7: 359-371.
Jul. 24, 2017 First Examination Report, issued in connection with European Patent Application No. 13782495.9.
Kargiotidou et al., (2008) "Low temperature and light regulate delta 12 fatty acid desaturases (FAD2) at a transcriptional level in cotton (*Gossypium hirsutum*)" Journal of Experimental Botany 2008 in 59(8): 2043-2056.
Karmakar et al. (2010) "Properties of various plants and animals feedstocks for biodiesel production" Bioresource Technology 101:7201-7210.
Kelly et al. (2012) "Suppression of the *Sugar-Dependent1* triacylglycerol lipase family during seed development enhances oil yield in oilseed rape (*Brassica napus* L.)" *Plant Biotechnology Journal*, pp. 1-7.
Kelly et al., (2011) "Seed Storage Oil Mobilization is Important but not Essential for Germination or Seedling Establishment in *Arabidopsis*" Plant Physiology, vol. 157, pp. 866-875.
Khadake R et al., "Cloning of a Novel Omega-6 Desaturase from Flax (*Linum usitatissimum* L.) and Its Functional Analysis in *Saccharomyces cerevisiae*" Mol. Biotechnol., 42 pp. 168-174 (2009).
Kim et al., (1999) GenBank Accesion No. AF213480, NCBI, p. 1.
Kinney (1996) "Development of Genetically Engineered Soybean Oils for Food Applications." J. Food Lipids 3: 273-292.
Klahre et al. (2002) "High molecular weight RNAs and Small interfering RNAs induce systemic posttranscriptional gene silencing in plants." PNAS 99(28): 11981-11986.
Knowles and Hill, "Inheritance of Fatty Acid Content in the Seed Oil of a Safflower Introduction from Iran" Crop Science, 4:4 pp. 406-409 (1964).
Knowles P F, "Associations of High Levels of Oleic Acid in the Seed Oil of Safflower (*Carthamus tinctorius*) with Other Plant and Seed Characteristics" Economic Botany, 22:2 pp. 195-200 (1968).
Knowles P F, "The Plant Geneticist's Contribution Toward Changing Lipid and Amino Acid Composition of Safflower" Journal of the American Oil Chemists' Society, 49 pp. 27-29 (1972).
Kodama et al. (1997) "Structure, chromosomal location and expression of a rice gene encoding the microsome ω-3 fatty acid desaturase." Plant Molecular Biology 33:493-502.
Kohno-Murase et al. (2006) "Production of trans-10, cis-12 conjugated linoleic acid in rice." Transgenic Research 15:95-100.
Kozeil et al. (1996) "Optimizing expression of transgenes with an emphasis on post-transcriptional events." Plant Molecular Biology, 32:393-405.
Langridge et al., Trends in genetic and genome analysis in wheat: a review. Aust. J. Agric. Res., 2001, 52:1043-1077.

(56) References Cited

OTHER PUBLICATIONS

Lardizabal et al. (2001) "DGAT2 is a New Diacylglycerol Acyltransferase Gene Family" J. Biol. Chem. 276:38862-3886.
Lardizabal et al. (2008) "Expression of Umbelopsis ramanniana DGAT2A in Seed Increases Oil in Soybean" Plant Physiol. 148: 89-96.
Lee, M., et al., (1998) "Identification of Non-Heme Diiron Proteins That Catalyze Triple Bond and Epoxy Group Formation," Science, 280(5365): 915-918.
Lemieux B., (2000) "High Throughput Single Nucleotide Polymorphism Genotyping Technology." Current Genomics, 2000, 1:301-311.
Leonard et al. (1997) "Cuphea wrightii thioesterases have unexpected broad specificlties on saturated fatty acids." Plant Molecular Biology, vol. 34, Issue 4: 669-679.
Li et al., (1997) "Comparison of promoters and selectable marker genes for use in Indica rice transformation." Molecular Breeding, 3:1-14.
Liu et al. (1997) EMBL Nucleotide Sequence Database as X97016.
Liu et al. (1999) "Molecular cloning and expression of a cDNA encoding a microsomal ω-6 fatty acid desaturase from cotton (*Gossypium hirsutum*)" Aust. J. Plant Physiol. 26:101-106.
Liu et al. (2002) "High-Oleic and High-Stearic Cottonseed Oils: Nutritionally Improved Cooking Oils Developed Using Gene Silencing." J. Am. Coll. Nutr. 21: 205S-211S.
Liu et al. (2010) "Producing biodiesel from high free fatty acids waste cooking oil assisted by radio frequency heating" Fuel 89:2735-2740.
Liu et al., (1999) "Cloning and Sequence Analysis of a Novel Member (Accession No. Y10112) of the Microsomal ω-6 Fatty Acid Desaturasc Family from Cotton" Plant Physiol. (PGR 99-063) 120: 339.
Liu et al., (2000) "Genetic modification of cotton seed oil using inverted-repeat gene-silencing techniques." Biochemical Society Transations, 28(6):927-929.
Liu et al., (2002) "High-Stearic and High-Oleic Cottonseed Oils Produced by Hairpin RNA-Mediated Post-Transcriptional Gene Silencing." Plant Physiology, 129(4):1732-1743.
Liu et al., (2005) GenBank Accession No. AY574036.
Liu et al., (2005) GenBank Accession No. AY574037.
Liu et al., (2005) GenBank Accession No. AY574038.
Liu Q et al., "High-Oleic and High-Stearic Cottonseed Oils: Nutritionally Improved Cooking Oils Developed Using Gene Silencing" Journal of the American College of Nutrition, 21:3 pp. 2058-2118 (2002).
Liu Q et al., "High-Stearic and High-Oleic Cottonseed Oils Produced by Hairpin RNA-Mediated Post-Transcriptional Gene Silencing" Plant Physiol., 129 pp. 1732-1743 (2002).
Lu et al. (1993) "High efficiency retroviral mediated gene transduction into single isolated immature and replatable CD343+ hematoppietic stem/progenitor cells from human umbilical cord blood." J. Exp. Med., 178, 2089-2096.
Lu et al., (2011) "New frontiers in oilseed biotechnology: meeting the global demand for vegetable oils for food, feed, biofuel, and industrial applications" Current Opinion in Biotechnology, 22:252-259.
Maher and Bressler (2007) "Pyrolysis of triglyceride materials for the production of renewable fuels and chemicals" Bioresource Technology 98:2351-2368.
Mar. 11, 2019 Response to Office Action filed in connection with corresponding Philippine patent application 1-2014-502381.
Mar. 25, 2015 First Examination Report, issued in connection with New Zealand Patent Application No. 627107.
Mar. 6, 2017 Office Action, issued in connection with Japanese Patent Application No. 2015-507304, including Engligh language translation.
Martinez-Rivas J et al., "Spatial and temporal regulation of three different microsomal oleate desaturase genes (FAD2) from normal-type and high-oleic varieties of sunflower (*Helianthus annuus* L.)" Molecular Breeding, 8 pp. 159-168 (2001).
Mensink and Katan (1990) "Effect of Dietary Trans Fatty Acids on High-Density and Low-Density Lipoprotein Cholesterol Levels in Healthy Subjects." N. Engl. J. Med. 323: 439-445.
Mikkilineni and Rocheford (2003) "Sequence variation and genomic organization of fatty acid desaturase-2 (fad2) and fatty acid desaturase-6 (fad6) cDNAs in maize." Theor. Applied Genetics, 106, 1326-1332.
Millar and Waterhouse (2005) "Plant and animal microRNAs: similarities and differences." Funct Integr Genomics, 2005, 5:129-135.
Miquel et al. (1992) "*Arabidopsis* mutants deficient in polyunsaturated fatty acid synthesis: Biochemical and genetic characterization of a plant oleoyl-phosphatidylcholine desaturase" Journal of Biological Chemistry; vol. 267 No. 3, 1502-1509.
Moghadasian and Frohlich (1999) "Effects of Dietary Phytosterols on Cholesterol Metabolism and Atherosclerosis: Clinical and Experimental Evidence." Am. J. Med. 107: 588-94.
Mojovic et al., (1993) "Rhizopus arrhizus lipase-catalyzed interesterification of the midfraction of palm oil to a cocoa butter equivalent fat" Enzyme Microb Technol. 15: 438-443.
Morrison (1988) "Lipids in Cereal Starches: A Review." J Cereal Sci. 8:1-15.
Most et al. (2005) "Rice bran oil, not fiber, lowers cholesterol in humans." Am J Clin Nutr 81:64-8.
Mounts et al., (1998) "Effect of Altered Fatty Acid Composition on Soybean Oil Stability" J Am. Oil Chem. Soc. 65: 624-628.
Needleman & Wunsch (1970) "A general method applicable to the search for similarities in the amino acid sequence of two proteins." J. Mol. Biol., 48, 443-453.
Nielsen et al. (2004) Formation of Volatile Compounds in Model Experiments with Crude Leek (*Allium ampeloprasum* var. *Lancelot*) Enzyme Extract and Linoleic Acid or Linolenic Acid. Journal of Agricultural and Food Chemistry 52:2315-2321.
Noakes and Clifton (1998) "Oil blends containing partially hydrogenated or interesterified fats: differential effects on plasma lipids." Am. J. Clin. Nutr. 98: 242-247.
O'Brien (2005) "Cottonseed Oil" Bailey's Industrial Oil and Fat Products, 6th Edition, edited by Fereidoon Shahidi.
O'Brien, (2002) Cottonseed Oil. In: F.D. Gunstone (Ed.) Vegetable Oils in Food Technology: Composition, Properties and Uses. Blackwell Publishing, Oxford, pp. 203-230.
Oct. 14, 2015 Application to Amend a Complete Specification, filed in connection with South African Patent Application No. 2014/05075.
Office Action dated Jan. 9, 2019 which issued in connection with corresponding Philippine patent application 1-2014-502381.
Office Action dated Mar. 5, 2018 in connection with counterpart Philippine Patent Application No. 1-2014-502381.
Ohlrogge and Jaworski (1997) "Regulation of Fatty Acid Synthesis. Annu Rev Plant Physiol Plant Mol Biol." 48:109-136.
Okuley et al. (1994) "*Arabidopsis* FAD2 Gene Encodes the Enzyme that is Essential for Polyunsaturated Lipid Synthesis." Plant Cell, 6:147-158.
Parthibane et al. (2012) "Oleosin is a Bifunctional Enzyme That has Both Monoacylglycerol Acyltransferase and Phospholipase Activities" J. Biol. Chem. 287:1946-1954.
PCT International Patent Application International Search Report, dated Dec. 6, 2011 for the related application PCT/AU2001/000794.
Perez-Vich et al. (1998) "Determination of Seed Oil Content and Fatty Acid Composition in Sunflower Through the Analysis of Intact Seeds, Husked Seeds, Meal and Oil by Near-Infrared Reflectance Spectroscopy" JAOCS 75:547-555.
Perriman, R., et al., (1992) "Extended Target-Site Specificity for a Hammerhead Ribozyme," Gene, 113(2): 157-163.
Petrie et al. (2012) "Recruiting a New Substrate for Triacylglycerol Synthesis in Plants: The Monoacylglycerol Acyltransferase Pathway" PLoS One 7:e35214.
Petrie et al., (2012) "Recruiting a New Substrate for Triacylglycarol Synthesis in Plants: The Monoacylglycerol Acyltransferase Pathway" PLoS One 7(4): e35214, pp. 1-8.
Petrie J et al., "Rapid expression of transgenes driven by seed-specific constructs in leaf tissue: DHA production" Plant Methods, 6:8 (2010).

(56) References Cited

OTHER PUBLICATIONS

Phillips K et al., "Free and Esterified Sterol Composition of Edible Oils and Fats" Journal of Food Composition and Analysis, 15 pp. 123-142 (2002).
Pirtle et al. (1999) "Characterization of a Palmitoyl-Acyl Carrier Protein Thioesterase (FatB1) in Cotton" Plant Cell Physiology 40:2 p. 155-163.
Pirtle et al., (2001) "Molecular cloning and functional expression of the gene for a cotton v-12 fatty acid desaturase (FAD2)" Biochim. Biophys. Acta 1522: 122-129.
Pokharkar et al., (2008) "Synthesis and Characterization of Fatty Acid Methyl Ester by In-Situ Transesterification in Capparis Deciduas Seed" Leonardo Electronic Journal of Practices and Technologies 13:12-18.
Radcliffe et al. (1997) "Serum Lipids in Rats Fed Diets Containing Rice Bran Oil or High-Linolenic Acid Safflower Oil." Biochemical Archives 13:87-95.
Response to First Examination Report filed on Apr. 10, 2018 in connection with Australian patent application 2013252489.
Response to Rules 70(2) and 70a(2) EPC, filed Oct. 12, 2016 in connection with European Patent Application No. EP13782495.9.
Resurreccion et al. (1979) "Nutrient Content and Distribution in Milling Fractions of Rice Grain." Journal of the Science of Food and Agriculture, 30: 475-481.
Roche and Gibney (2000) "Effect of long-chain n-3 polyunsaturated fatty acids on fasting and postprandial triacylglycerol metabolism." Am. J. Clin. Nutr. 71: 232S-237S.
Roston et al., (2012) "TGD1, -2, and -3 Proteins Involved in Lipid Trafficking Form ATP-binding Cassette (ABC) Transporter with Multiple Substrate-binding Proteins" The Journal of Biological Chemistry vol. 287, No. 25, pp. 21406-21415.
Rukmini and Raghuram (1991) "Nutritional and Biochemical Aspects of the Hypolipidemic Action of Rice Bran Oil: A Review." Journal of the American College of Nutrition 10(6):593-601.
Sanjaya et al. (2011) "Increasing the energy density of vegetative tissues by diverting carbon from starch to oil biosynthesis in transgenic *Arabidopsis*" Plant Biotech. J. 9:874-883.
Sanjaya et al., (2011) "Increasing the energy density of vegetative tissues by diverting carbon from starch to oil biosynthesis in transgenic *Arabidopsis*" Plant Biotechnology Journal 9, pp. 874-883.
Sasaki et al., (1999) GenBank Accession No. AP000399, NCBI, pp. 1-33.
Sasaki et al., (2001) GenBank Accession No. AP004047, NCBI, pp. 1-36.
Sasaki et al., (2001) Genbank Accession No. AP004236, NCBI, pp. 1-37.
Sasaki et al., (2002) GenBank Accession No. AP005168, NCBI, pp. 1-31; and.
Sasaki et al., (2002) GenBank Accession No. AP005291, NCBI, pp. 1-38.
Scheffler J et al., "Desaturase multigene families of Brassica napus arose through genome duplication" Theor. Appl. Genet., 94 pp. 583-591 (1997).
Second Examination Report dated May 2, 2018 in connection with European patent application 13782495.9.
Second Office Action dated Feb. 26, 2018 in connection with counterpart Japanese Patent Application No. 2015-507304, including English language translation thereof.
Semwal et al. (2011) "Biodiesel production using heterogeneous catalysts" Bioresource Technology 102:2151-2161.
Senior I.J., (1998) "Uses of Plant Gene Silencing." Biotechnology & Genetic Engineering Reviews, Ed. Tombs, M.P., 15:79-119.
Sep. 11, 2017 Office Action, issued in connection with Ukrainian Patent Application No. 201412633, including English Language Translation.
Sep. 23, 2015 Partial Supplementary European Search Report, issued in connection with European Patent Application No. 12863568.7.
Sharma et al., (2003) GenBank Accesion No. AC108870, NCBI, pp. 1-27.
Shenstone and Vickery, (1961) "Occurrence of Cyclo-Propene Acids in Some Plants of the Order Malvales" Nature 190: 68-169.
Shiina et al. (1997) "Identification of Promoter Elements Involved in Cytosolic Ca2+-Mediated Photoregulation of Maize cab-m1 Expression" Plant Physiol. 115:477-483.
Shin et al. (1986) "Correlation Between Oxidative Deterioration of Unsaturated Lipid and n-Hexanal during Storage of Brown Rice." J. Food Sci. 51:460-463.
Shippy, R., et al., (1999) "The Hairpin Ribozyme—Discovery, Mechanism, and Development for Gene Therapy," Molecular Biotechnology, 12(1): 117-129.
Singh et al. (2012) "Accumulating Triacylglycerol in leaves via the Monoacylglycerol Acyltransferase Pathway" 20th International Symposium on Plant Lipids.
Sivaraman et al. (2004) "Development of high oleic and low linoleic acid transgenics in a zero erucic acid *Brassica juncea* L. (Indian mustard) line by antisense suppression of the fad2 gene" Molecular Breeding, Kluwer Academic Publishers, DO; vol. 13 No. 1, 365-375.
Slade and Knauf, (2005) "Tilling moves beyond functional genomics into crop improvement." Transgenic Research, 14:109-115.
Smith et al. (2000) "Total silencing by intron-spliced hairpon RNAs" Nature 407:319-320.
Srinivasan et al. (2007) "Heterologous expression of the Baby Boom AP2/ERF transcription factor enhances the regeneration capacity of tobacco (*Nicotiana tabacum* L.)" Planta 225:341-51.
St Angelo et al. (1980) "Identification of Lipoxygenase-Linoleate Decomposition Products by Direct Gas Chromatography-Mass Spectrometry." J Lipids 1:45-49.
Stalberg et al., (1993) "Deletion Analysis of a 2S Seed Storage Protein Promoter of *Brassica napus* in Transgenic Tobacco," Plant Molecular Biology, 23(4): 671-683.
Stoutjesdijk et al. (2002) "hpRNA-mediated targeting of the *Arabidopsis* FAD2 gene gives highly efficient and stable silencing" Plant Physiology, American Society of Plant Physiologists, Rockville, MD, US; vol. 129, 1723-31.
Stoutjesdijk et al., (2000) "High-oleic acid Australian *Brassica napus* and *B. juncea* varieties produced by co-suppression of endogenous Δ12-desaturases." Biochem. Soc. Trans. 28: 938-940.
Suzuki et al. (1999) "Volatile Components in Stored Rice [*Oryza sativa* (L.)] of Varieties with and without Lipoxygenase-3 in Seeds." J. Agric. Food Chem. 47: 1119-1124.
Taira and Chang (1986) "Lipid content and fatty acid composition of Indira and Japonica types of nonglutinous brown rice." Agric. Food Chem. 34:542-545.
Taira et al. (1986) "Lipid Content and Fatty-Acid Composition of Indica and Japonica Types of Nonglutinous Brown Rice" Journal of Aqriculture and Food Chemistry; vol. 34 No. 3, 542-545.
Taira et al. (1988) "Fatty Acid Composition of Indica Sinica Javanica and Japonica Groups of Nonglutinous Brown Rice" Journal of Agricultural and Food Chemistry; vol. 36 No. 1, 45-47.
Taira et al. (1989) "Fatty Acid Composition of Indica-Types and Japonica-Types of Rice Bran and Milled Rice" Journal of the American Oil Chemists' Society; vol. 66 No. 9, 1326-1329.
Thelen and Ohlrogge (2002) "Metabolic Engineering of Fatty Acid Biosynthesis in Plants." Metabolic Engineering 4: 12-21.
Theriault et al. (1999). "Tocotrienol: A Review of its Therapeutic Potential." Clin. Biochem. 32: 309-19.
Third Office Action dated Apr. 17, 2018 in connection with Chinese patent application 201380033472.0, including English language translation.
Tholstrup et al. (1994) "Fat high in stearic acid favorably affects blood lipids and factor VII coagulant activity in comparison with fats high in palmitic acid or high in myristic and lauric acids." Am. J. Clin. Nutr. 59: 371-377.
To et al., (2012) "Wrinkled Transcription Factors Orchestrate Tissue-Specific Regulation of Fatty Acid Biosynthesis in *Arabidopsis*" The Plant Cell, vol. 24: 5007-5023.
Toriyama et al., "Haploid and diploid plant regeneration from protoplasts of anther callus in rice." Theor Appl Genet, 1986, 73:16-19.

(56) References Cited

OTHER PUBLICATIONS

Trautwein, E.A., (2001) "n-3 Fatty Acids—Physiological and Technical Aspects for Their Use in Food," European Journal of Lipid Science and Technology, 103(1): 45-55.
Tsugita et al (1983) "Cooking Flavor and Texture of Rice Stored under Different Conditions." Agricultural and Biological Chemistry 47: 543-549.
Tsuzuki et al (2004) "Oxidation Rate of Conjugated Linoleic Acid and Conjugated Linolenic Acid is Slowed by Triacylglycerol Esterification and α-Tocopherol." Lipids 39:475-480.
Valvekens, D., et al., (1988) "Agrobacterium tumefaciens-Mediated Transformation of *Arabidopsis thaliana* Root. Explants by Using Kanamycin Selection," Proceedings of the National Academy of Sciences of the United States of America, 85(15) 5536-5540.
van de Loo, F. J., Broun, P., Turner, S., & Somerville, C. (1995) "An oleate 12-hydroxylase from *Ricinus communis* L. is a fatty acyl desaturase homolog." Proc. Natl. Acad. Sci. USA, 92, 6743-6747.
Vanhercke et al. (2012) "Maximizing lipid accumulation in vegetative plant tissues" 8th International Symposium on Biocatalysis and Agricultural Biotechnology.
Vanhercke et al. (2013) "Synergistic effect of WRI1 and DGAT1 coexpression on triacylglycerol biosynthesis in plants" FEBS Letters 587:364-369.
Voelker et al. (1996) "Genetic engineering of a quantitative trait: metabolic and genetic parameters influencing the accumulation of laurate in rapeseed." Plant J. 9: 229-241.
Wagner et al. (1992) "Coupling of adenovirus to transferrin-polylysine/DNA complexes greatly enhances receptor-mediated gene delivery and expression of transfected genes." Proc. Natl. Acad. Sci. USA, 89, 6099-6103.
Wang et al., (1998) "Improved Vectors for Agrobacterium tumefaciens-Mediated Transformation of Monocot Plants." Acta Hort, 1998, 461:401-407.
Waterhouse, P.M., et al., (1998) "Virus Resistance and Gene Silencing in Plants can be Induced by Simultaneous Expression of Sense and Antisense RNA," Proceedings of the National Academy of Sciences of the United States of America, 95(23): 13959-13964.
Weselake et al. (2009) "Increasing the flow of carbon into seed oil" Biotechnology Advances 27:866-878.
Whitelaw et al. (1986) "A Rice FATB Insertional Mutant Exhibits Improved Growth and Reduced Photoinhibition at High Temperatures" Proceedings of the 55th Australian Cereal Chemistry Conference, 55th Australian Cereal Chemistry Conference, Jul. 3-7, 2008, Sydney Australia, Jul. 3, 2005, pp. 101-104.
Whitelaw et al., (2004) "Investigation of lipid synthesis in the rice grain: modification of fatty acids in rice bran oil." In C.K. Black, J.F. Panozzo, and G.J. Rebetzke (Eds.), Cereals 2004: Proceedings of the 54th Australian Cereal Chemistry Conference and 11th Wheat Breeders Assembly, 21st-245th Sep. 2004, Canberra ACT, North Melbourne VIC: Cereal Chemistry Division, Royal Australian Chemical Institute, AU (pp. 418-420).
Williams et al. (1999) "Impaired Endothelial Function Following a Meal Rich in Used Cooking Fat." J. Am. Coll. Cardiol. 33:1050-1055.
Wood et al. (2009) "A leaf-based assay using interchangeable design principles to rapidly assemble multistep recombinant pathways" Plant Biotech. J. 7: 914-924.
Wood, Presentation at the 20th International Symposium on Plant Lipids, published Jul. 2012.
Written Opinion of the International Searching Authority dated Aug. 13, 2013 in connection with International Patent Application No. PCT/AU2013/000426, filed Apr. 24, 2013.
Xu et al., (2005) "Mutation of the TGD1 Chloroplast Envelope Protein Affects Phosphatidate Metabolism in *Arabidopsis*" The Plant Cell, vol. 17, 3094-3110.
Xu et al., (2008) "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content" Plant Biotechnology Journal 6, pp. 799-818.
Xu et al., (2008) "Lipid Trafficking between the Endoplasmic Reticulum and the Plastid in *Arabidopsis* Requires the Extraplastidic TGD4 Protein" The Plant Cell, vol. 20: 2190-2204.
Xu et al., (2010) "Lipid Transport Mediated by *Arabidopsis* TGD Proteins is Unidirectional from the Endoplasmic Reticulum to the Plastid" Plant Cell Physiol, 51(6): 1019-1028.
Yang et al. (2010) "A distinct type of glycerol-3-phosphate acyltransferase with sn-2 preference and phosphatase activity producing 2-monoacylglycerol" PNAS 107:12040-12045.
Yasumatsu et al. (1966) "Studies on Cereals Part V Stale Flavor of Stored Rice." Agric. Biol. Chem. 30:483-486.
Yen et al., (2002) "Identification of a gene encoding MGAT1, a monoacylglycerol acyltransferase" PNAS USA 99(13):8512-8517.
Zhou et al. (2002) "Ageing of Stored Rice: Changes in Chemical and Physical Attributes." Journal of Cereal Science 35:65-78.
Zock et al. (1994) "Impact of myristic acid versus palmitic acid on serum lipid and piloproteih levels in healthy women and men." Arterioscler Thromb. 14: 567-575.
May 29, 2019 Office Action, issued in connection with Eurasian Patent Application No. 201491956, including English language translation thereof.
Jul. 17, 2019 Office Action issued in connection with Philippine Patent Application No. 1-2014-502381.
Jul. 12, 2019 Notice of Preliminary Rejection issued in connection with South Korean Patent Application No. 10-2014-7033143 including English language translation thereof.
Mar. 30, 2020 Notice of Preliminary Rejection issued in connection with reexamination of South Korean patent application 10-2014-7033143, including English translation.
Sep. 26, 2019 First Examination Report issued in connection with Indian patent application 2355/MUMNP/2014.
Jul. 17, 2019 Response to Office Action filed in connection with Philippine patent application 1-2014-502381.
Jan. 30, 2020 Notice of Final Rejection issued in connection with South Korean patent application 10-2014-7033143, including English translation.
Feb. 25, 2020 Second Examination Report issued in connection with Canadian patent application 2,871,503.
Aug. 26, 2019 Response to Examiner's Requisition filed in connection with Canadian patent application 2,871,503.
Jun. 23, 2020 Response to Examiner's Requisition filed in connection with Canadian patent application 2,871,503.
Jun. 25, 2020 Response to First Examination Report filed in connection with Indian patent application 2355/MUMNP/2014.
Feb. 2, 2021 Notice of Hearing issued in connection with corresponding Indian Patent Application No. 2355/MUMNP/2014.
Mar. 1, 2021 Office Action issued in connection with Canadian Patent Application No. 2,871,503.

* cited by examiner

Figure 3:
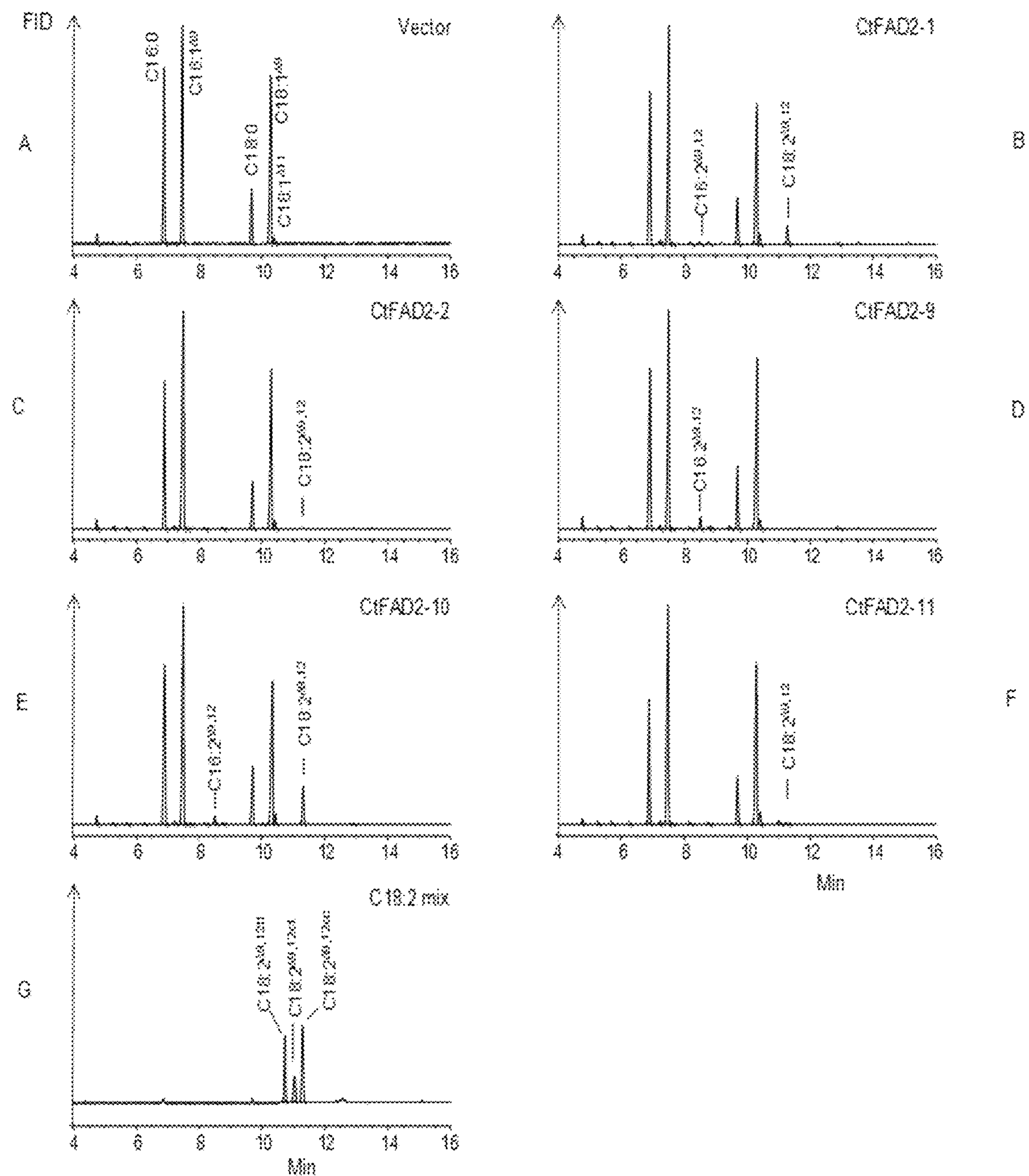

H
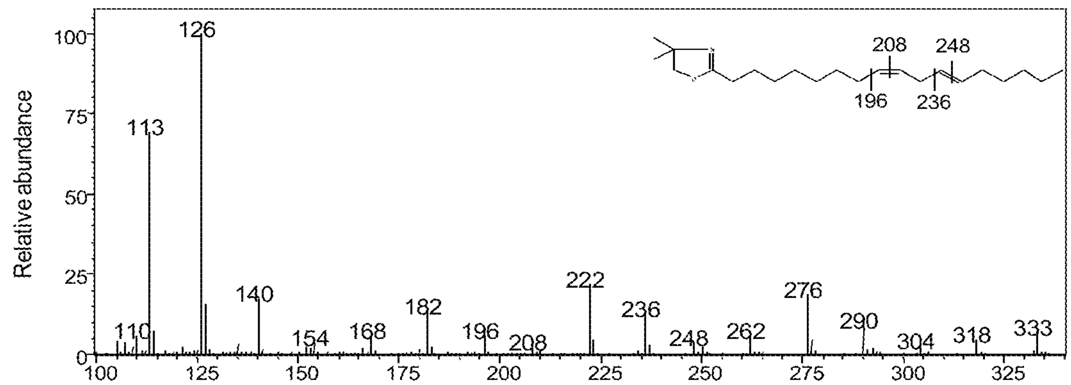
I
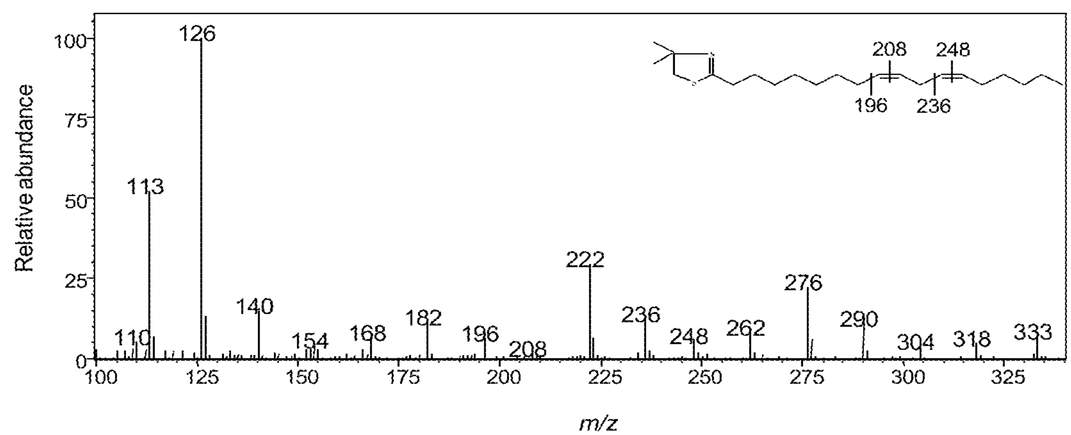
Figure 3 (continued)

```
                 601                                              650
SU(wt)     (601) TGTCTTTCAACGTCTCCGGAAGACCCTATGACCGTTTCGCCTGCCACTAC
S-317      (601) TGTCTTTCAACGTCTCTGGAAGACC-TACAACCGTTTCGCCTGCCACTAT
CW99-OL    (601) TGTCTTTCAACGTCTCTGGAAGACC-TACAACCGTTTCGCCTGCCACTAT
LeSaf496   (595) TGTCTTTCAACGTCTCTGGAAGACC-TACAACCGTTTCGCCTGCCACTAT
```

Figure 6

```
                    1                                                50
CtFAD2-1-SU   (1)   GTGCATTCTCTCATTCTCAAAACCTTTCTGCTATTCATCTGATCAATGT-
CtFAD2-1-ol   (1)   GTGCATTCTCTCA--------ACCTTCCTGCTTTTCGTCTGATCAATGTT

                    51      ------> HL-sense primer                 100
CtFAD2-1-SU  (50)   -----ATTCAGTTATGGTT-CGATCAT--------------CGACCATTA
CtFAD2-1-ol  (43)   AATGTATTCAGTTATCGTTTCGATGATTTCCTATTAAATGTCGACCATTA

                    101                                              150
CtFAD2-1-SU  (80)   TTGTTTGTTATTTTAATTTTAATTTTTAGGTTGATTTAGCTGCATTGTTG
CtFAD2-1-ol  (93)   TCGTTTGTTATT----TTTTA--TTTTAGGTAGATTTAGCTGCATTGTTG

                    151                                              200
CtFAD2-1-SU (130)   GTCGATGAATAGATCTGTCGATTACGGTCTTCTGCAGTTTCAGTTT--GA
CtFAD2-1-ol (137)   GTTGATGAATAGATCTGTAGATTACGGTCCTCTGCGCTTTCAGTTTTTGA

                    201                                              250
CtFAD2-1-SU (178)   TTTATTTCAGTCCGTTTTTCTCCTGTAAATTTGTGTATCTATCTGTGTTG
CtFAD2-1-ol (187)   TTCATTTCACTCCGTTTT-CTTCTGTAAATTTGTGTATCTATCTGTGCTG

                    251                                              300
CtFAD2-1-SU (228)   CATGTAATTTTGTTTCCTTTAGATTATAGAAATGAAAATCCATAATTTTA
CtFAD2-1-ol (236)   CATGTAATTTTGTTTCCTTTAGATTATAGAAATGAAAATCCATAATTTTA

                    301                                              350
CtFAD2-1-SU (278)   GGGCTGCTTGTCTTGTTTGGATTTGTGTTATTAGGTTTTGATCACAGTAA
CtFAD2-1-ol (286)   GGGCTGCTTCTCTTGTTTGGATTTGTGTTATTAGGTTTTAATTACAGTAA

                    351                                              400
CtFAD2-1-SU (328)   CTTCCGTACGTTTAATATGTTAAATGCTAAACAAAATGATTTATTTTTTA
CtFAD2-1-ol (336)   CTTCCGTACGTTTAATATGTCAAATGCTAAACAAAATGATTTGTTTTTTA

                    401                                              450
CtFAD2-1-SU (378)   TATTTATGGCTTCTCGGTGGTCGGATTTGTGTTTTTAATTCCTGAAGTTT
CtFAD2-1-ol (386)   TATTTATGGCTTCTCGGTGGTCGGATTTGTGTTTTTAATTCCTGAAGTTT

                    451                                              500
CtFAD2-1-SU (428)   CTGTATACAATGATTTCGAATTTTGGCGATTAGGCATCTCTTTACTTTGG
CtFAD2-1-ol (436)   CTGTATACAATGATTTCGAATTTTGGCGATTAGGCATCTCTTTACTTTGG

                    501                                              550
CtFAD2-1-SU (478)   AAGGAATTTCAGATTTTCTT-------------AATCTCATAGAGAAGTG
CtFAD2-1-ol (486)   AAGGATTTCTAGATTTTCTTTGCCGGATTCCTTAATCTTATATAGAAATG

                    551                                              600
CtFAD2-1-SU (515)   CTGAT-----TG------GGAATTTGCTTAAAGATATAAGCACTTTTCAG
CtFAD2-1-ol (536)   ATGATATCATTGACAAATGGCAATTGCTTAAAGATACAAGCATTTTTCAG

                    601                                              650
CtFAD2-1-SU (554)   TTCATTGATTGTTTGATGGACATCAGA-TGGTTTTTTTGCTGATGCCATG
CtFAD2-1-ol (586)   TTCATTGAATGTTTGATGGACATCAAAATGGATTTTTTGCTGATC-----

                    651                          <------HL-antisense  700
CtFAD2-1-SU (603)   ATGTCTATTGTGTTGAATGTATCTTCAATAAGTGCCTTCAATATGTATAG
```

Figure 7

```
CtFAD2-1-ol    (631) ---TCTACTGTGTTGAATGTACCTTCAATAAGG-----------------

                        701                                          750
CtFAD2-1-SU    (653) CAAAACTGAGCTAAGGCTGTGTTTGGCAAACTACCTGATAAGCTATATGT
CtFAD2-1-ol    (661) -----CTGTGTTCACG---GGTTTGGCATGCTAGCTGATAG---------
                       ---> H0 sense primer

                        751                                          800
CtFAD2-1-SU    (703) TGACTGATAAGCTAGTTTGTGAATAAATTATGTTTGGCAAAAACTAGCAT
CtFAD2-1-ol    (694) ---CTGATAAGCTAGCTTATGAATAAATTATGTTTGGTAAAAACTAGCTT

                        801                                          850
CtFAD2-1-SU    (753) ATGAGTATGTAAAATGACTAAAAAGGGTATCTTGGGGTATAATAGTTAAT
CtFAD2-1-ol    (741) ATGAGTATGTAAAATGACAAAAAAGG-TACCTCGGAGTGTAATAATTAAT

                        851                                          900
CtFAD2-1-SU    (803) ATTGATAAGGATAGAATTGGAGAAGGCTACAAAAAGCCCTTGAAATGCTA
CtFAD2-1-ol    (790) ATTAATAAGGGTATAATTGGAAGAGCCTACTAAAAGCTCCTAGAACGCTA

                        901                                          950
CtFAD2-1-SU    (853) CTCCAACTAGTGTTTCAATAAGCTGG-CTTATGGTCTATCCAAACATGTA
CtFAD2-1-ol    (840) CTCCAACTAACGTTTCAATAAGCTTAACTTATGGTCCATCCAAACATGTA

                        951                                          1000
CtFAD2-1-SU    (902) CTAGATTATCATCTAGCTTATTTTTGCCAAACACAGCCTAAATG-TTTGA
CtFAD2-1-ol    (890) CTAGCTTATAAGCGAGCTTATTTTTGCCAAACACAGCCAAAGTACTTTCA

                        1001                                         1050
CtFAD2-1-SU    (951) TGGTCGATGGC-----------------------TGGCAC-----TTGAC
CtFAD2-1-ol    (940) TGGTTGATATCCTTGTATCCCCAACTGAGCTAAATGGTCCGATGGTCGAC
                            <--- H0 antisense primer

                        1051                                         1100
CtFAD2-1-SU    (973) AATTTGACATCATTATAACT----------GAAACAATAA----------
CtFAD2-1-ol    (990) GAGTTGACATCATTATAATTATATATTTTTGAATCCTTAAGGCTAACGTT

                        1101                                         1150
CtFAD2-1-SU   (1003) -----------TATTCACCTT-------------TACATAACATTCACCT
CtFAD2-1-ol   (1040) TCCTTAGTTTTTATTTATGTTGTGATGGTGGCATTACATAATATTCACCT

                        1151                                         1200
CtFAD2-1-SU   (1029) TTAGCCAAAAACTAGATGTTCACCTACGAACTGATCCATATGGAACATTT
CtFAD2-1-ol   (1090) TTAGCTAAAAACTAGATGTTCACCTACGAACTGATCCATATGGAACATTT

                        1201
CtFAD2-1-SU   (1079) TGCAG
CtFAD2-1-ol   (1140) TGCAG
```

Figure 7 (contintued)

A)
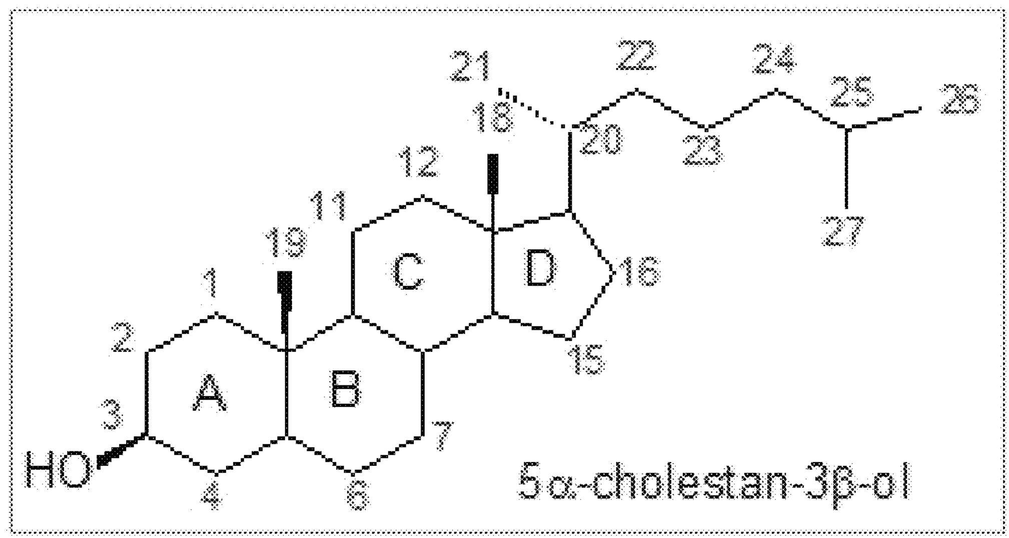
B)
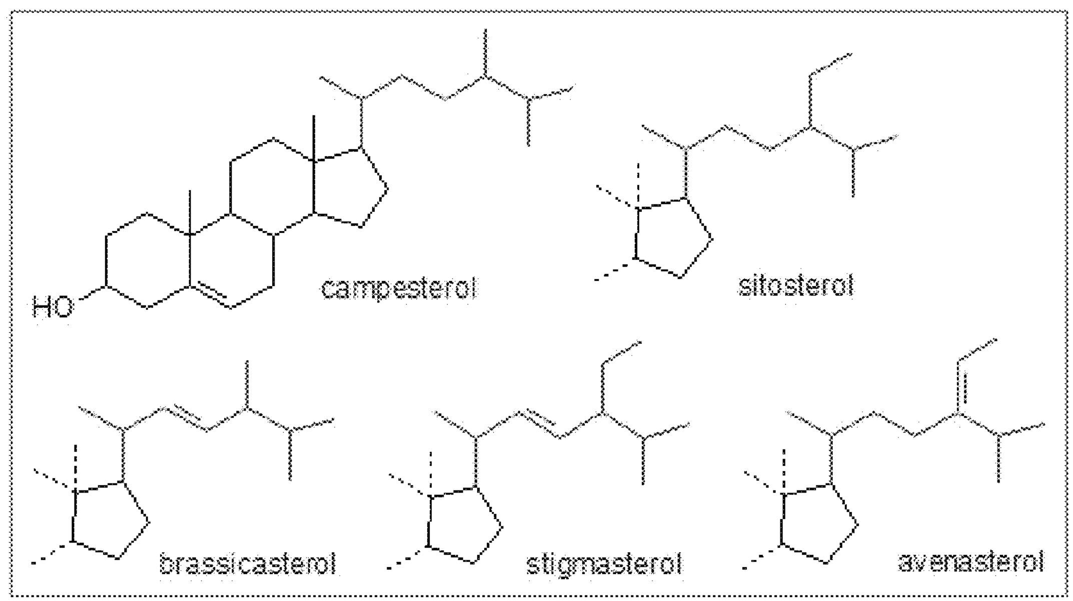
Figure 14

HIGH OLEIC ACID OILS

CROSS-REFERENCE TO RELATED APPLICATIONS

This application is a divisional of U.S. application Ser. No. 13/869,763, filed Apr. 24, 2013, now allowed, claiming priority of Australian Patent Application No. 2012903992, filed Sep. 11, 2012 and the benefit of U.S. Provisional Application No. 61/638,447, filed Apr. 25, 2012, the contents of each of which are hereby incorporated by reference in their entirety.

REFERENCE TO SEQUENCE LISTING

This application incorporates-by-reference nucleotide and/or amino acid sequences which are present in the file named "190514_84095-AZ_Sequence_Listing_CAS.txt," which is 134 kilobytes in size, and which was created May 14, 2019 in the IBM-PC machine format, having an operating system compatibility with MS-Windows, which is contained in the text file filed May 14, 2019 as part of this application.

FIELD OF THE INVENTION

The present invention relates to extracted lipid with high levels, for example 90% to 95% by weight, oleic acid. The present invention also provides genetically modified plants, particularly oilseeds such as safflower, which can used to produce the lipid. Furthermore, provided are methods for genotyping and selecting plants which can be used to produce the lipid.

BACKGROUND OF THE INVENTION

Plant oils are an important source of dietary fat for humans, representing about 25% of caloric intake in developed countries (Broun et al., 1999). World production of plant oils is at least about 110 million tons per year, of which 86% is used for human consumption. Almost all of these oils are obtained from oilseed crops such as soybean, canola, safflower, sunflower, cottonseed and groundnut, or plantation trees such as palm, olive and coconut (Gunstone, 2001; Oil World Annual, 2004). The growing scientific understanding and community recognition of the impact of the individual fatty acid components of food oils on various aspects of human health is motivating the development of modified vegetable oils that have improved nutritional value while retaining the required functionality for various food applications. These modifications require knowledge about the metabolic pathways for plant fatty acid synthesis and genes encoding the enzymes for these pathways (Liu et al., 2002a; Thelen and Ohlrogge, 2002).

Considerable attention is being given to the nutritional impact of various fats and oils, in particular the influence of the constituents of fats and oils on cardiovascular disease, cancer and various inflammatory conditions. High levels of cholesterol and saturated fatty acids in the diet are thought to increase the risk of heart disease and this has led to nutritional advice to reduce the consumption of cholesterol-rich saturated animal fats in favour of cholesterol-free unsaturated plant oils (Liu et al., 2002a).

While dietary intake of cholesterol present in animal fats can significantly increase the levels of total cholesterol in the blood, it has also been found that the fatty acids that comprise the fats and oils can themselves have significant effects on blood serum cholesterol levels. Of particular interest is the effect of dietary fatty acids on the undesirable low density lipoprotein (LDL) and desirable high density lipoprotein (HDL) forms of cholesterol in the blood. In general, saturated fatty acids, particularly myristic acid (14:0) and palmitic acid (16:0), the principal saturates present in plant oils, have the undesirable property of raising serum LDL-cholesterol levels and consequently increasing the risk of cardiovascular disease (Zock et al., 1994; Hu et al., 1997). However, it has become well established that stearic acid (18:0), the other main saturate present in plant oils, does not raise LDL-cholesterol, and may actually lower total cholesterol (Bonanome and Grundy, 1988; Dougherty et al., 1995). Stearic acid is therefore generally considered to be at least neutral with respect to risk of cardiovascular disease (Tholstrup, et al., 1994). On the other hand, unsaturated fatty acids, such as the monounsaturate oleic acid (18:1), have the beneficial property of lowering LDL-cholesterol (Mensink and Katan, 1989; Roche and Gibney, 2000), thus reducing the risk of cardiovascular disease.

Oil high in oleic acid also has many industrial uses such as, but not limited to, lubricants often in the form of fatty acid esters, biofuels, raw materials for fatty alcohols, plasticizers, waxes, metal stearates, emulsifiers, personal care products, soaps and detergents, surfactants, pharmaceuticals, metal working additives, raw material for fabric softeners, inks, transparent soaps, PVC stabilizer, alkyd resins, and intermediates for many other types of downstream oleochemical derivatives.

Oil processors and food manufacturers have traditionally relied on hydrogenation to reduce the level of unsaturated fatty acids in oils, thereby increasing their oxidative stability in frying applications and also providing solid fats for use in margarine and shortenings. Hydrogenation is a chemical process that reduces the degree of unsaturation of oils by converting carbon-carbon double bonds into carbon-carbon single bonds. Complete hydrogenation produces a fully saturated fat. However, the process of partial hydrogenation results in increased levels of both saturated fatty acids and monounsaturated fatty acids. Some of the monounsaturates formed during partial hydrogenation are in the trans isomer form (such as elaidic acid, a trans isomer of oleic acid) rather than the naturally occurring cis isomer (Sebedio et al., 1994; Fernandez San Juan, 1995). In contrast to cis-unsaturated fatty acids, trans-fatty acids are now known to be as potent as palmitic acid in raising serum LDL cholesterol levels (Mensink and Katan, 1990; Noakes and Clifton, 1998) and lowering serum HDL cholesterol (Zock and Katan, 1992), and thus contribute to increased risk of cardiovascular disease (Ascherio and Willett, 1997). As a result of increased awareness of the anti-nutritional effects of trans-fatty acids, there is now a growing trend away from the use of hydrogenated oils in the food industry, in favour of fats and oils that are both nutritionally beneficial and can provide the required functionality without hydrogenation, in particular those that are rich in either oleic acid where liquid oils are required or stearic acid where a solid or semi-solid fat is preferred.

There is a need for further lipids and oils with high oleic acid content and sources thereof.

SUMMARY OF THE INVENTION

The present inventors have produced new lipid compositions and methods of producing these lipids.

In a first aspect, the present invention provides lipid extracted from an oilseed, the lipid comprising triacylglycerols (TAG) which consist of fatty acids esterified to glycerol, wherein i) the fatty acids comprise palmitic acid and oleic acid, ii) at least 95% by weight of the lipid is TAG, iii) about 90% to about 95% by weight of the total fatty acid content of the lipid is oleic acid, iv) less than about 3.1% by weight of the total fatty acid content of the lipid is palmitic acid, and v) the lipid has an oleic desaturation proportion (ODP) of less than about 0.037 and/or a palmitic-linoleic-oleic value (PLO) of less than about 0.063.

In an embodiment, the lipid has one or more or all of the following features, a) about 90% to about 94%, or about 91% to about 94%, or about 91% to about 92%, or about 92%, or about 93%, by weight of the total fatty acid content of the lipid is oleic acid, b) less than about 3%, or less than about 2.75%, or less than about 2.5%, or about 3%, or about 2.75%, or about 2.5%, or about 2.3% by weight of the total fatty acid content of the lipid is palmitic acid, c) about 0.1% to about 3%, or about 2% to about 3%, or about 3%, or about 2%, by weight of the total fatty acid content of the lipid is polyunsaturated fatty acids (PUFA), d) less than about 3%, or less than about 2.5%, or less than about 2.25%, or about 3%, or about 2.5%, or about 2.25%, by weight of the total fatty acid content of the lipid is linoleic acid, e) less than about 1%, or less than about 0.5%, by weight of the total fatty acid content of the lipid is α-linolenic acid (ALA), about 0.5% to about 1% by weight of the total fatty acid content of the lipid is 18:1Δ1, g) the ODP of the fatty acid content of the lipid is about 0.033 to about 0.01, or about 0.033 to about 0.016, or about 0.033 to about 0.023, or is about 0.03, or about 0.02, or about 0.01, h) the PLO value of the fatty acid content of the lipid is about 0.020 to about 0.063, or about 0.020 to about 0.055, or about 0.020 to about 0.050, or about 0.050 to about 0.055, or about 0.063, or about 0.055, or about 0.050, or about 0.040, or about 0.030, or about 0.020, i) about 90% to about 96%, or about 92% to about 96%, or about 93%, or about 94%, by weight of the total fatty acid content of the lipid is monounsaturated fatty acids, j) the lipid has an oleic monounsaturation proportion (OMP) of less than about 0.02, or less than about 0.015, or about 0.005 to about 0.02, k) the lipid is in the form of a purified oil, and l) the lipid is non-hydrogenated.

In an embodiment, 1) about 91% to about 94% by weight of the total fatty acid content of the lipid is oleic acid, 2) less than about 2.75% by weight of the total fatty acid content of the lipid is palmitic acid, 3) less than about 3% by weight of the total fatty acid content of the lipid is linoleic acid, 4) α-linolenic acid is undetectable in the fatty acid content of the lipid, 5) the ODP of the fatty acid content of the lipid is about 0.033 to about 0.023, or about 0.033 to about 0.018, 6) the PLO value of the fatty acid content of the lipid is about 0.020 to about 0.063, 7) about 96%, or about 93%, or about 94%, by weight of the total fatty acid content of the lipid is monounsaturated fatty acids, and 8) the lipid has an oleic monounsaturation proportion (OMP) of less than about 0.02, or less than about 0.015, or about 0.005 to about 0.02.

In a further embodiment, 1) about 91% to about 94% by weight of the total fatty acid content of the lipid is oleic acid, 2) less than about 2.75% by weight of the total fatty acid content of the lipid is palmitic acid, 3) less than about 3% by weight of the total fatty acid content of the lipid is linoleic acid, 4) α-linolenic acid is undetectable in the fatty acid content of the lipid, 5) about 96%, or about 93%, or about 94%, by weight of the total fatty acid content of the lipid is monounsaturated fatty acids, and 6) the lipid has an oleic monounsaturation proportion (OMP) of less than about 0.02, or less than about 0.015, or about 0.005 to about 0.02.

In an embodiment, the PUFA is linoleic acid.

In an embodiment, α-linolenic acid is undetectable in the fatty acid content of the lipid.

In a further embodiment, about 55% to about 80%, or about 60% to about 80%, or about 70% to about 80%, or at least about 60%, or at least about 70%, or about 60%, or about 70%, or about 80%, of the TAG content of the lipid is triolein.

In another embodiment, less than about 5%, or less than about 2%, or about 0.1% to about 5%, of the oleic acid content of the lipid is in the form of diacylglycerols (DAG).

In a further embodiment, the lipid is in the form of an oil, wherein at least 90%, or least 95%, at least about 98%, or about 95% to about 98%, by weight of the oil is the lipid.

In a preferred embodiment, the oilseed is a non-photosynthetic oilseed. Examples of non-photosynthetic oilseed include, but are not necessarily limited to, seed from safflower, sunflower, cotton or castor. In a preferred embodiment, the non-photosynthetic oilseed is safflower seed.

In an embodiment, the lipid further comprises one or more sterols.

In a further embodiment, the lipid is in the form of an oil, and which comprises less than about 5 mg of sterols/g of oil, or about 1.5 mg of sterols/g of oil to about 5 mg of sterols/g of oil.

In an embodiment, the lipid comprises one or more or all of a) about 1.5% to about 4.5%, or about 2.3% to about 4.5%, of the total sterol content is ergost-7-en-3β-ol, b) about 0.5% to about 3%, or about 1.5% to about 3%, of the total sterol content is triterpenoid alcohol, c) about 8.9% to about 20%, of the total sterol content is Δ7-stigmasterol/stigmast-7-en-3β-ol, and d) about 1.7% to about 6.1% of the total sterol content is Δ7-avenasterol.

In a further embodiment, the lipid has a volume of at least 1 litre and/or a weight of at least 1 kg, and/or which was extracted from oilseed obtained from field-grown plants.

In an embodiment, the lipid has been extracted from an oilseed by crushing and comprises less than about 7% water by weight. In another embodiment, the lipid is purified lipid (solvent extracted and refined) and comprises less than about 0.1%, or less than about 0.05% water, by weight.

In another aspect, the present invention provides a composition comprising a first component which is lipid of the invention, and a second component, preferably where the composition was produced by mixing the lipid with the second component.

As the skilled person will appreciate, the second component can be selected from a wide range of different compounds/compositions. In one example, the second component is a non-lipid substance such as an enzyme, a non-protein (non-enzymatic) catalyst or chemical (for example, sodium hydroxide, methanol or a metal), or one or more ingredients of a feed.

The present invention also provides a process for producing oil, the process comprising i) obtaining an oilseed comprising, and/or which is capable of producing a plant which produces oilseed comprising, oil, wherein the oil content of the oilseed is a lipid as defined in herein, and ii) extracting oil from the oilseed so as to thereby produce the oil.

In a preferred embodiment, the oilseed comprises a first exogenous polynucleotide which encodes a first silencing RNA which is capable of reducing the expression of a Δ12 desaturase (FAD2) gene in a developing oilseed relative to a corresponding oilseed lacking the exogenous polynucleotide, and wherein the polynucleotide is operably linked to a promoter which directs expression of the polynucleotide in the developing oilseed.

In another aspect, the present invention provides a process for producing oil, the process comprising i) obtaining safflower seed whose oil content comprises, and/or which is capable of producing a plant which produces seed whose oil content comprises, triacylglycerols (TAG) which consist of fatty acids esterified to glycerol, and wherein a) the fatty acids comprise palmitic acid and oleic acid, b) at least 95% by weight of the oil content of the seed is TAG, c) about 75% to about 95% by weight of the total fatty acids of the oil content of the seed is oleic acid, d) less than about 5.1% by weight of the total fatty acids of the oil content of the seed is palmitic acid, and e) the oil content of the seed has an oleic desaturation proportion (ODP) of less than about 0.17 and/or a palmitic-linoleic-oleic (PLO) value of less than about 0.26, and ii) extracting oil from the safflower seed so as to thereby produce the oil, wherein the safflower seed comprises a first exogenous polynucleotide which encodes a first silencing RNA which is capable of reducing the expression of a Δ12 desaturase (FAD2) gene in a developing safflower seed relative to a corresponding safflower seed lacking the exogenous polynucleotide, and wherein the polynucleotide is operably linked to a promoter which directs expression of the polynucleotide in the developing safflower seed.

In an embodiment, the oilseed or safflower seed comprises a second exogenous polynucleotide which encodes a second silencing RNA which is capable of reducing the expression of a palmitoyl-ACP thioesterase (FATB) gene in a developing oilseed or safflower seed relative to a corresponding oilseed or safflower seed lacking the second exogenous polynucleotide, and wherein the second exogenous polynucleotide is operably linked to a promoter which directs expression of the polynucleotide in the developing oilseed or safflower seed.

In another embodiment, the oilseed or safflower seed comprises a third exogenous polynucleotide which encodes a third silencing RNA which is capable of reducing the expression of a plastidial ω6 fatty acid desaturase (FAD6) gene in a developing oilseed or safflower seed relative to a corresponding oilseed or safflower seed lacking the third exogenous polynucleotide, and wherein the third exogenous polynucleotide is operably linked to a promoter which directs expression of the polynucleotide in the developing oilseed or safflower seed.

In an embodiment, 1) the FAD2 gene is one or more or each of a CtFAD2-1 gene, a CtFAD2-2 gene, and a CtFAD2-10 gene, preferably a CtFAD2-1 gene and/or a CtFAD2-2 gene, and/or 2) the FATB gene is a CtFATB-3 gene, and/or 3) the FADE gene is a CtFAD6 gene.

In an embodiment, the oil content of the safflower seed has one or more or all of the following features, a) about 80% to about 94%, or about 85% to about 94%, or about 90% to about 94%, or about 91% to about 94%, or about 91% to about 92%, or about 92%, or about 93% by weight of the total fatty acids of the oil content of the seed is oleic acid, b) less than about 5%, or less than about 4%, or less than about 3%, or less than about 2.75%, or less than about 2.5%, or about 3%, or about 2.75%, or about 2.5% by weight of the total fatty acids of the oil content of the seed is palmitic acid, c) about 0.1% to about 15%, or about 0.1% to about 10%, or about 0.1% to about 7.5%, or about 0.1% to about 5%, or about 0.1% to about 3%, or about 2% to about 3%, or about 3%, or about 2%, by weight of the total fatty acids of the oil content of the seed is polyunsaturated fatty acids (PUFA), d) less than about 15%, or less than about 10%, or less than about 5%, or less than about 3%, or less than about 2.5%, or less than about 2.25%, or about 3%, or about 2.5%, or about 2.25%, by weight of the total fatty acids of the oil content of the seed is linoleic acid (LA), e) about 80% to about 96%, or about 90% to about 96%, or about 92% to about 96%, or about 93%, or about 94%, by weight of the total fatty acid content of the lipid is monounsaturated fatty acids, f) the lipid has an oleic monounsaturation proportion (OMP) of less than about 0.05, or less than about 0.02, or less than about 0.015, or about 0.005 to about 0.05, or about 0.005 to about 0.02, g) the ODP of the oil content of the seed is about 0.17 to about 0.01, or about 0.15 to about 0.01, or about 0.1 to about 0.01, or about 0.075 to about 0.01, or about 0.050 to about 0.01, or about 0.033 to about 0.01, or about 0.033 to about 0.016, or about 0.033 to about 0.023, or is about 0.03, or about 0.02, or about 0.01, and h) the PLO value of the oil content of the seed is about 0.20 to about 0.026, or about 0.020 to about 0.2, or about 0.020 to about 0.15, or about 0.020 to about 0.1, or about 0.020 and about 0.075, or about 0.050 and about 0.055, or is about 0.05, or about 0.040, or about 0.030, or about 0.020.

In an embodiment, the step of extracting the oil comprises crushing the oilseed or the safflower seed.

In yet another embodiment, the process further comprising a step of purifying the oil extracted from the oilseed or the safflower seed, wherein the purification step comprises one or more or all of the group consisting of: degumming, deodorising, decolourising, drying and/or fractionating the extracted oil, and/or removing at least some, preferably substantially all, waxes and/or wax esters from the extracted oil.

In another aspect, the present invention provides an oilseed whose oil content comprises, and/or which is capable of producing a plant which produces oilseed whose oil content comprises, triacylglycerols (TAG) which consist of fatty acids esterified to glycerol, and wherein i) the fatty acids comprise palmitic acid and oleic acid, ii) at least 95% by weight of the oil content of the oilseed is TAG, iii) about 90% to about 95% by weight of the total fatty acids of the oil content of the oilseed is oleic acid, iv) less than about 3.1% by weight of the total fatty acids of the oil content of the oilseed is palmitic acid, and v) the oil content of the oilseed has an oleic desaturation proportion (ODP) of less than about 0.037 and/or a palmitic-linoleic-oleic (PLO) value of less than about 0.063.

In an embodiment, the oilseed is a non-photosynthetic oilseed, preferably seed from safflower, sunflower, cotton or castor.

In another embodiment, the oilseed comprises a first exogenous polynucleotide which encodes a first silencing RNA which is capable or reducing the expression of a Δ12 desaturase (FAD2) gene in a developing oilseed relative to a corresponding oilseed lacking the exogenous polynucleotide, and wherein the first exogenous polynucleotide is operably linked to a promoter which directs expression of the polynucleotide in the developing oilseed.

In yet a further aspect, the present invention provides a safflower seed whose oil content comprises, and/or which is capable of producing a plant which produces seed whose oil content comprises, triacylglycerols (TAG) which consist of fatty acids esterified to glycerol, and wherein i) the fatty acids comprise palmitic acid and oleic acid, ii) at least 95% by weight of the oil content of the seed is TAG, iii) about 75% to about 95% by weight of the total fatty acids of the oil content of the seed is oleic acid, iv) less than about 5.1% by weight of the total fatty acids of the oil content of the seed is palmitic acid, and v) the oil content of the seed has an oleic desaturation proportion (ODP) of less than about 0.17 and/or a palmitic-linoleic-oleic (PLO) value of less than about 0.26, and wherein the safflower seed comprises a first exogenous polynucleotide which encodes a first silencing RNA which is capable of reducing the expression of a Δ12 desaturase (FAD2) gene in a developing safflower seed relative to a corresponding safflower seed lacking the exogenous polynucleotide, and wherein the first exogenous polynucleotide is operably linked to a promoter which directs expression of the polynucleotide in the developing safflower seed.

In an embodiment, the oil content of the safflower seed has one or more of the following features, a) about 80% to about 94%, or about 85% to about 94%, or about 90% to about 94%, or about 91% to about 94%, or about 91% to about 92%, or about 92%, or about 93% by weight of the total fatty acids of the oil content of the seed is oleic acid, b) less than about 5%, or less than about 4%, or less than about 3%, or less than about 2.75%, or less than about 2.5%, or about 3%, or about 2.75%, or about 2.5% by weight of the total fatty acids of the oil content of the seed is palmitic acid, c) about 0.1% to about 15%, or about 0.1% to about 10%, or about 0.1% to about 7.5%, or about 0.1% to about 5%, or about 0.1% to about 3%, or about 2% to about 3%, or about 3%, or about 2% by weight of the total fatty acids of the oil content of the seed is polyunsaturated fatty acids (PUFA), d) less than about 15%, or less than about 10%, or less than about 5%, or less than about 3%, or less than about 2.5%, or less than about 2.25%, or about 3%, or about 2.5%, or about 2.25%, by weight of the total fatty acids of the oil content of the seed is linoleic acid (LA), e) about 80% to about 96%, or about 90% to about 96%, or about 92% to about 96%, or about 93%, or about 94%, by weight of the total fatty acid content of the lipid is monounsaturated fatty acids, f) the lipid has an oleic monounsaturation proportion (OMP) of less than about 0.05, or less than about 0.02, or less than about 0.015, or about 0.005 to about 0.05, or about 0.005 to about 0.02, g) the ODP of the oil content of the seed is about 0.17 to about 0.01, or about 0.15 to about 0.01, or about 0.1 to about 0.01, or about 0.075 to about 0.01, or about 0.050 to about 0.01, or about 0.033 to about 0.01, or about 0.033 to about 0.016, or about 0.033 to about 0.023, or is about 0.03, or about 0.02, or about 0.01, and h) the PLO value of the oil content of the seed is about 0.020 to about 0.26, or about 0.020 to about 0.2, or about 0.020 to about 0.15, or about 0.020 to about 0.1, or about 0.020 and about 0.075, or about 0.050 and about 0.055, or is about 0.050, or about 0.040, or about 0.030, or about 0.020.

In a further embodiment, the oil content of the oilseed or safflower seed is lipid which is further characterized by one or more of the above-mentioned features.

In another embodiment, the oilseed or safflower seed comprises a second exogenous polynucleotide which encodes a second silencing RNA which is capable of reducing the expression of a palmitoyl-ACP thioesterase (FATB) gene in a developing oilseed or safflower seed relative to a corresponding oilseed or safflower seed lacking the second exogenous polynucleotide, and wherein the second exogenous polynucleotide is operably linked to a promoter which directs expression of the polynucleotide in the developing oilseed or safflower seed.

In a further embodiment, the oilseed or safflower seed comprises a third exogenous polynucleotide which is capable of reducing the expression of a plastidial ω6 fatty acid desaturase (FADE) gene in a developing oilseed or safflower seed relative to a corresponding oilseed or safflower seed lacking the third exogenous polynucleotide, and wherein the third exogenous polynucleotide is operably linked to a promoter which directs expression of the polynucleotide in the developing oilseed or safflower seed.

In another embodiment, the first silencing RNA reduces the expression of more than one endogenous gene encoding FAD2 in developing oilseed or safflower seed and/or wherein the second silencing RNA reduces the expression of more than one endogenous gene encoding FATB in developing oilseed or safflower seed.

In yet a further embodiment, the first exogenous polynucleotide and either or both of the second exogenous polynucleotide and the third exogenous polynucleotide are covalently joined on a single DNA molecule, optionally with linking DNA sequences between the first, second and/or the third exogenous polynucleotides.

In another embodiment, the first exogenous polynucleotide and either or both of the second exogenous polynucleotide and the third exogenous polynucleotide are under the control of a single promoter such that, when the first exogenous polynucleotide and the second exogenous polynucleotide and/or the third exogenous polynucleotide are transcribed in the developing oilseed or safflower seed, the first silencing RNA and the second silencing RNA and/or the third silencing RNA are covalently linked as parts of a single RNA transcript.

In another embodiment, the oilseed or safflower seed comprises a single transfer DNA integrated into the genome of the oilseed or safflower seed, and wherein the single transfer DNA comprises the first exogenous polynucleotide and either or both of the second exogenous polynucleotide and the third exogenous polynucleotide.

Preferably, the oilseed or safflower seed is homozygous for the transfer DNA.

In an embodiment, the first silencing RNA, the second silencing RNA and the third silencing RNA are each independently selected from the group consisting of: an antisense polynucleotide, a sense polynucleotide, a catalytic polynucleotide, a microRNA and a double stranded RNA.

In a further embodiment, any one or more, preferably all, of the promoters are seed specific, and preferably preferentially expressed in the embryo of developing oilseed or safflower seed.

In another embodiment, the oilseed or safflower seed comprises one or more mutations in one or more FAD2 genes, wherein the mutation(s) reduce the activity of the one or more FAD2 genes in developing oilseed or safflower seed relative to a corresponding oilseed or safflower seed lacking the mutation(s).

In another embodiment, the oilseed or safflower seed comprises a mutation of a FAD2 gene relative to a wild-type FAD2 gene in a corresponding oilseed or safflower seed, which mutation is a deletion, an insertion, an inversion, a frameshift, a premature translation stop codon, or one or more non-conservative amino acid substitutions.

In a further embodiment, the mutation is a null mutation in the FAD2 gene.

In another embodiment, at least one of the mutations is in a FAD2 gene which encodes more FAD2 activity in the developing oilseed or safflower seed lacking the mutation(s) than any other FAD2 gene in the developing oilseed or safflower seed.

In another embodiment, the seed is a safflower seed and the FAD2 gene is the CtFAD2-1 gene. In this embodiment, it is also preferred that the first silencing RNA is at least capable or reducing the expression of a CtFAD2-2 gene.

In another embodiment, the seed is a safflower seed comprising an ol allele of the CtFAD2-1 gene or an ol1 allele of the CtFAD2-1 gene, or both alleles. In an embodiment, the ol allele or the ol1 allele of the CtFAD2-1 gene is present in the homozygous state.

In another embodiment, FAD2 protein is undetectable in the oilseed or safflower seed.

In another embodiment, the seed is a safflower seed and the first silencing RNA reduces the expression of both CtFAD2-1 and CtFAD2-2 genes.

In another embodiment, the seed is a safflower seed where 1) the FAD2 gene is one or more of a CtFAD2-1 gene, a CtFAD2-2 gene, and a CtFAD2-10 gene, preferably a CtFAD2-1 gene and/or a CtFAD2-2 gene, and/or 2) the FATB gene is a CtFATB-3 gene, and/or 3) the FADE gene is a CtFAD6 gene.

Also provided is an oilseed plant or safflower plant capable of producing the seed of the invention.

In an embodiment, the plant is transgenic and homozygous for each exogenous polynucleotide, and/or comprises the first exogenous polynucleotide and either or both of the second exogenous polynucleotide or the third exogenous polynucleotide.

In another aspect, the present invention provides a substantially purified and/or recombinant polypeptide which comprises amino acids having a sequence as provided in any one of SEQ ID NOs: 27 to 37, 44, 45 or 48, a biologically active fragment thereof, or an amino acid sequence which is at least 40% identical to any one or more of SEQ ID NOs: 27 to 37, 44, 45 or 48.

In an embodiment, the polypeptide which is a fatty acid modifying enzyme, preferably an oleate Δ12 desaturase, Δ12-acetylenase, a palmitoleate Δ12 desaturase or a palmitoyl-ACP thioesterase (FATB).

In a further aspect, the present invention provides an isolated and/or exogenous polynucleotide comprising one or more of i) nucleotides having a sequence as provided in any one of SEQ ID NOs: 1 to 25, 40 to 43, 46 or 47, ii) nucleotides having a sequence encoding a polypeptide of the invention, iii) nucleotides which hybridize to a sequence as provided in any one of SEQ ID NOs: 1 to 25, 40 to 43, 46 or 47, and iv) nucleotides having a sequence such that when expressed in a seed of an oilseed plant reduces the expression of a gene encoding at least one polypeptide of the invention.

In a particularly preferred embodiment, polynucleotide comprises nucleotides having a sequence such that when expressed in a seed of an oilseed plant reduces the expression of a gene encoding at least one polypeptide of the invention.

In an embodiment, the polynucleotide of part iv) comprises a sequence of nucleotides provided in any one of SEQ ID NOs: 49 to 51 (where thymine (T) is uracil (U)).

In an embodiment, the polynucleotide of part iv) is selected from: an antisense polynucleotide, a sense polynucleotide, a catalytic polynucleotide, a microRNA, a double stranded RNA (dsRNA) molecule or a processed RNA product thereof.

In a further embodiment, the polynucleotide is a dsRNA molecule, or a processed RNA product thereof, comprising at least 19 consecutive nucleotides which is at least 95% identical to the complement of any one or more of SEQ ID NOs: 1 to 25, 40 to 43, 46, 47 or 49 to 51 (where thymine (T) is uracil (U)).

In another embodiment, the dsRNA molecule is a microRNA (miRNA) precursor and/or wherein the processed RNA product thereof is a miRNA.

In yet a further embodiment, the polynucleotide is transcribed in a developing oilseed or safflower seed under the control of a single promoter, wherein the dsRNA molecule comprises complementary sense and antisense sequences which are capable of hybridising to each other, linked by a single stranded RNA region.

In yet a further embodiment, the polynucleotide, when present in a developing safflower seed, i) reduces the expression of an endogenous gene encoding oleate Δ12 desaturase (FAD2) in the developing seed, the FAD2 having an amino acid sequence as provided in any one or more of SEQ ID NOs: 27, 28 or 36, preferably at least one or both of SEQ ID NOs: 27 and 28;

ii) reduces the expression of an endogenous gene encoding palmitoyl-ACP thioesterase (FATB) in the developing seed, the FATB having an amino acid sequence as provided in SEQ ID NO: 45; and/or iii) reduces the expression of a gene encoding an ω6 fatty acid desaturase (FAD6) in the developing seed, the FAD6 having an amino acid sequence as provided in SEQ ID NO: 48.

Also provided is a chimeric vector comprising the polynucleotide of the invention, operably linked to a promoter.

In an embodiment, the promoter is functional in an oilseed, or is a seed specific promoter, preferably is preferentially expressed in the embryo of a developing oilseed.

In another aspect, the present invention provides a recombinant cell comprising an exogenous polynucleotide of the invention, and/or a vector of the invention.

The cell can be any cell type such as, but not limited to, bacterial cell, yeast cell or plant cell.

Preferably, the cell is a plant cell, preferably a plant seed cell. More preferably, the plant cell is an oilseed plant cell. Even more preferably, the plant cell is a non-photosynthetic seed cell, preferably a safflower, sunflower, cotton or castor seed cell.

In another aspect, the present invention provides a transgenic non-human organism comprising one or more of the polynucleotides of the invention, a vector of the invention, and a cell of the invention.

Preferably, the transgenic non-human organism of is a plant. More preferably, an oilseed plant.

In yet another aspect, the present invention provides a method of producing the cell of the invention, the method comprising the step of introducing the polynucleotide of the invention, and/or a vector of the invention, into a cell.

Also provided is the use of the polynucleotide of the invention and/or a vector of the invention to produce a recombinant cell.

In another aspect, the present invention provides a method of producing a transgenic oilseed plant which produces a seed of the invention, or seed thereof, the method comprising i) introducing at least one polynucleotide of the invention and/or at least one vector of the invention, into a cell of an oilseed plant, ii) regenerating a transgenic plant from the cell, and iii) optionally producing one or more progeny plants or seed thereof from the transgenic plant, thereby producing the transgenic oilseed plant or seed thereof.

In an embodiment, the seed is safflower seed of the invention.

In further embodiment, the one or more progeny plants or seed thereof comprises i) the first exogenous polynucleotide, and/or ii) the second exogenous polynucleotide, and/or iii) the third exogenous polynucleotide, preferably all three exogenous polynucleotides.

In a further embodiment, the one or more progeny plants or seed thereof comprises one or more mutations as defined above.

In yet a further aspect, the present invention provides a method of obtaining an oilseed plant, the method comprising i) crossing a first parental oilseed plant which comprises a first polynucleotide of the invention, or a first vector of the invention, with a second parental oilseed plant which comprises a second polynucleotide of the invention, or a first vector of the invention, ii) screening progeny plants from the cross for the presence of both polynucleotides or both vectors; and iii) selecting a progeny plant comprising both (a) the first polynucleotide or the first vector and (b) the second polynucleotide or the second vector, and further having an increased proportion of oleic acid and a decreased proportion of palmitic acid in the oil content of the seed of the plant.

In a further aspect, the present invention provides a method of genotyping a safflower plant, the method comprising detecting a nucleic acid molecule of the plant, wherein the nucleic acid molecule is linked to, and/or comprises at least part of, one or more of the CtFAD2-1, CtFAD2-2 or CtFAD2-10 genes, preferably at least one or both of the CtFAD2-1 and CtFAD2-2 genes, or at least the CtFAD2-1 gene, of a safflower plant.

In an embodiment, the method comprises determining the level of expression, and/or sequence, of one or more of the CtFAD2-1, CtFAD2-2 or CtFAD2-10 genes of the plant.

In an embodiment, the method comprises:

i) hybridising a second nucleic acid molecule to said nucleic acid molecule of the plant, ii) optionally hybridising at least one other nucleic acid molecule to said nucleic acid molecule of the plant; and iii) detecting a product of said hybridising step(s) or the absence of a product from said hybridising step(s).

In yet a further embodiment, the second nucleic acid molecule is used as a primer to reverse transcribe or replicate at least a portion of the nucleic acid molecule of the plant.

The nucleic acid can detected using variety of well known techniques such as, but not limited to, restriction fragment length polymorphism analysis, amplification fragment length polymorphism analysis, microsatellite amplification, nucleic acid sequencing, and/or nucleic acid amplification.

In an embodiment, the method detects the absence of presence of an allele of the CtFAD2-1 gene, preferably the ol allele.

In a further aspect, the present invention provides a method of selecting a safflower plant from a population of safflower plants, the method comprising;

i) genotyping said population of plants using a method of the invention, wherein said population of plants was obtained from a cross between two plants of which at least one plant comprises an allele of a CtFAD2-1, CtFAD2-2 or CtFAD2-10 gene, preferably at least one or both of the CtFAD2-1 and CtFAD2-2 genes, or at least the CtFAD2-1 gene, which confers upon developing seed of said plant a reduced level of Δ12 desaturase activity, relative to a corresponding seed of a safflower plant lacking said allele, and ii) selecting the safflower plant on the basis of the presence or absence of said allele.

In a further aspect, the present invention provides a method of introducing an allele of a CtFAD2-1, CtFAD2-2 or CtFAD2-10 gene into a safflower plant lacking the allele, the method comprising;

i) crossing a first parent safflower plant with a second parent safflower plant, wherein the second plant comprises said allele of a CtFAD2-1, CtFAD2-2 or CtFAD2-gene, and ii) backcrossing the progeny of the cross of step i) with plants of the same genotype as the first parent plant for a sufficient number of times to produce a plant with a majority of the genotype of the first parent but comprising said allele, wherein the allele confers upon developing seed of said plant a reduced level of Δ12 desaturase activity, relative to a corresponding seed of a safflower plant lacking said allele, and wherein progeny plants are genotyped for the presence or absence of said allele using a method of the invention.

Also provided is a transgenic plant, or progeny plants thereof, or seed thereof, produced using the method of the invention.

In a further aspect, the present invention provides a method of producing seed, the method comprising, a) growing a plant of the invention, preferably in a field as part of a population of at least 1000 such plants, and b) harvesting the seed.

In yet a further aspect, the present invention provides oil obtained or obtainable by one or more of the process of the invention, from the oilseed or safflower seed of the invention, from the plant or part thereof of the invention, from the cell of the invention, and/or from the non-human transgenic organism or part thereof of the invention.

In another aspect, the present invention provides a composition comprising one or more of the lipid of the invention, the oilseed or safflower seed of the invention, the polypeptide of the invention, the polynucleotide of the invention, the vector of the invention, the host cell of the invention, or oil of the invention, and one or more acceptable carriers.

Also provided is the use of one or more of the lipid of the invention, the composition of the invention, the process of the invention, the oilseed or safflower seed of the invention, the plant or part thereof of the invention, the host cell of the invention, the non-human transgenic organism or part thereof of the invention, or oil of the invention, for the manufacture of an industrial product.

In another aspect, the present invention provides a process for producing an industrial product, the process comprising the steps of:

i) obtaining one or more of the lipid of the invention, the composition of the invention, the oilseed or safflower seed of the invention, the plant or part thereof of the invention, the host cell of the invention, the non-human transgenic organism or part thereof of the invention, or oil of the invention, ii) optionally physically processing the one or more of the lipid of the invention, the composition of the invention, the oilseed or safflower seed of the invention, the plant or part thereof of the invention, the host cell of the invention, the non-human transgenic organism or part thereof of the invention, or oil of the invention, of step i), ii) converting at least some of the lipid of the invention, or lipid in one or more of the composition of the invention, the oilseed or safflower seed of the invention, the plant or part thereof of the invention, the host cell of the invention, the non-human transgenic organism or part thereof of the invention, or oil of the invention, or the physically processed product of step ii), to the industrial product by applying heat, chemical, or enzymatic means, or any combination thereof, to the lipid, and iii) recovering the industrial product, thereby producing the industrial product.

In yet a further aspect, the present invention provides a method of producing fuel, the method comprising i) reacting one or more of the lipid of the invention, or lipid in one or more of the invention, the oilseed or safflower seed of the invention, the plant or part thereof of the invention, the host cell of the invention, the non-human transgenic organism or part thereof of the invention, or oil of the invention, with an alcohol, optionally in the presence of a catalyst, to produce alkyl esters, and ii) optionally, blending the alkyl esters with petroleum based fuel.

In an embodiment, the alkyl esters are methyl esters.

In a further aspect, the present invention provides a method of producing a feedstuff, the method comprising admixing one or more of the lipid of the invention, the composition of the invention, oilseed or safflower seed of the invention, the plant or part thereof of the invention, the host cell according of the invention, the non-human transgenic organism or part thereof of the invention, or oil of the invention, with at least one other food ingredient.

Also provided is feedstuffs, cosmetics or chemicals comprising one or more of the lipid of the invention, the composition of the invention, oilseed or safflower seed of the invention, the plant or part thereof of the invention, the host cell according of the invention, the non-human transgenic organism or part thereof of the invention, or oil of the invention, In yet a further aspect, provided is a product produced from or using one or more of the lipid of the invention, or lipid in one or more of the composition of the invention, the process of the invention, the oilseed or safflower seed of the invention, the plant or part thereof of the invention, the host cell of the invention, the non-human transgenic organism or part thereof of the invention, or oil of the invention.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

The patent or application file contains at least one drawing executed in color. Copies of this patent or patent application publication with color drawing(s) will be provided by the Office upon request and payment of the necessary fee.

FIG. 1. Phylogenetic comparison of amino acid sequences encoded by safflower FAD2-like gene family and divergent FAD2-like enzymes from other plants. The phylogenetic tree shown was generated by use of Vector NTI (invitrogen). Included in AAK26632.1; caACET, ABC00769.1; cpEPDX, CAA76156.1; haACET, ABC59684.1; dsACET, AA038036.1; dcACET, AA038033.1; hhACET, AA038031.1; haDES-2, AAL68982.1; haDES-3, AAL68983.1; luDES, ACF49507; haDES-1, AAL68982.1; ntDES, AAT72296.2; oeDES, AAW63040; siDES, AAF80560.1; ghDES-1, CAA65744.1; rcOH, AAC49010.1; atDES, AAM61113.1; pfOH:DES, AAC32755.1; plOH, ABQ01458.1; ghDES-4, AAQ16653.1; ghDES-2, CAA71199.1. (co, *Calendula officinalis*; ca, *Crepis alpine*; cp, *Crepis palaestina*; ha, *Helianthus annuus*; ds, *Dimorphotheca* sinuate; dc, *Daucus carota*; hh, *Hedera helix*; lu, *Linum usitatissimum*; nt, *Nicotiana tabacum*; oe, *Olea europaea*; si, *Sesamum indicum*; rc, *Ricinus communis*; at, *Arabidopsis thaliana*; pf, *Physaria fendleri*; pl, *Physaria lindheimeri.*

Figure 2:
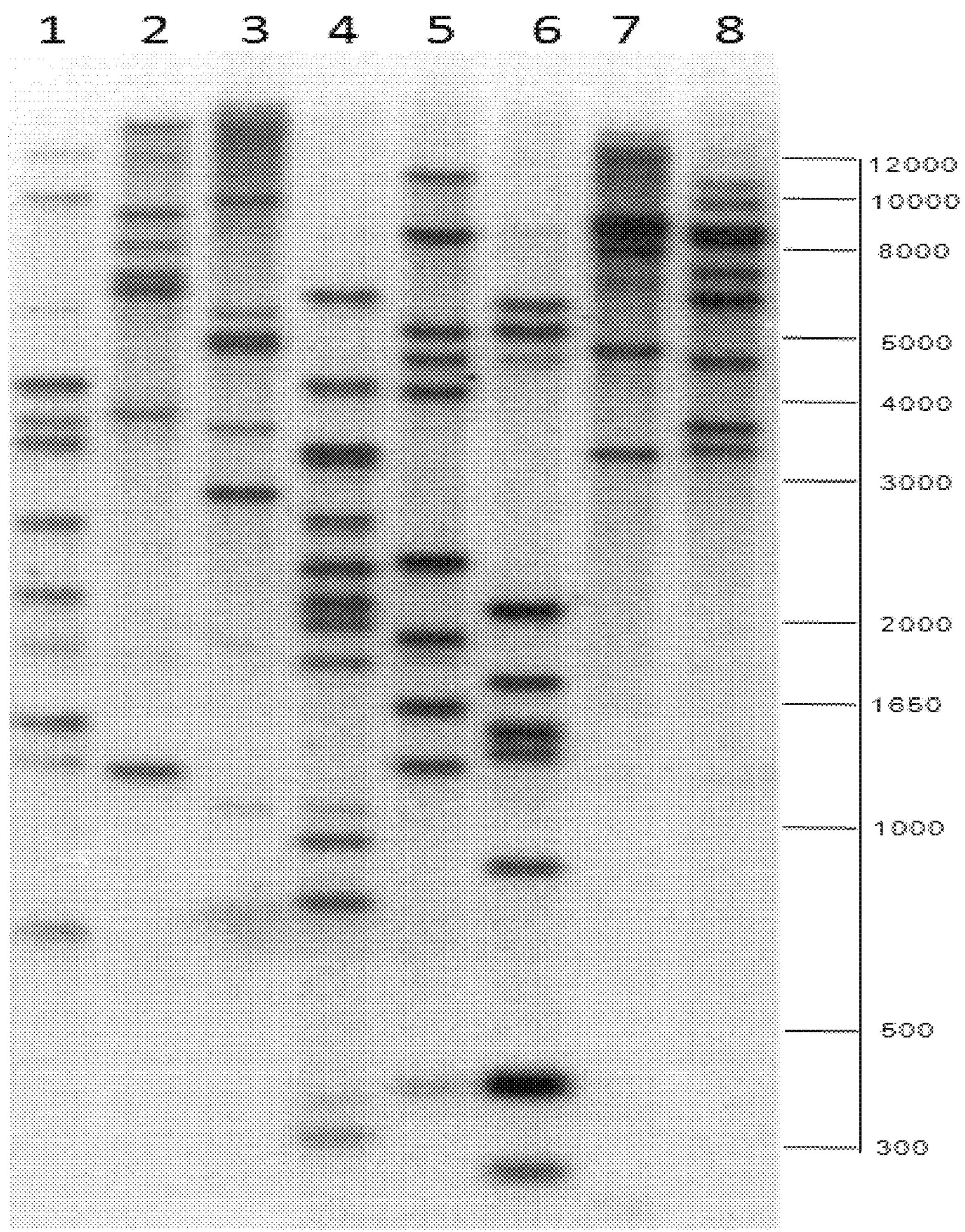

FIG. 2. Southern blot hybridisation analysis of CtFAD2-like genomic structure in safflower genotype SU. Genomic DNA was digested with eight different restriction enzymes prior to separation on an agarose gel. These enzymes were AccI (lane 1), BglII (2), BamHI (3), EcoRI (4), EcoRV (5), HindIII (6), XbaI (7) and XhoI (8). The blot was probed with radio-labelled entire coding region of CtFAD2-6 and washed at low stringency conditions.

FIG. 3. GC-MS fatty acid analysis of fatty acid composition from yeast expressing CtFAD2-1 (B), CtFAD2-2 (C), CtFAD2-9 (D), CtFAD2-10 (E) and CtFAD2-11 (F). Empty vector (A) and GC trace of the mixture of C18:2 isomers (G).

Figure 4:
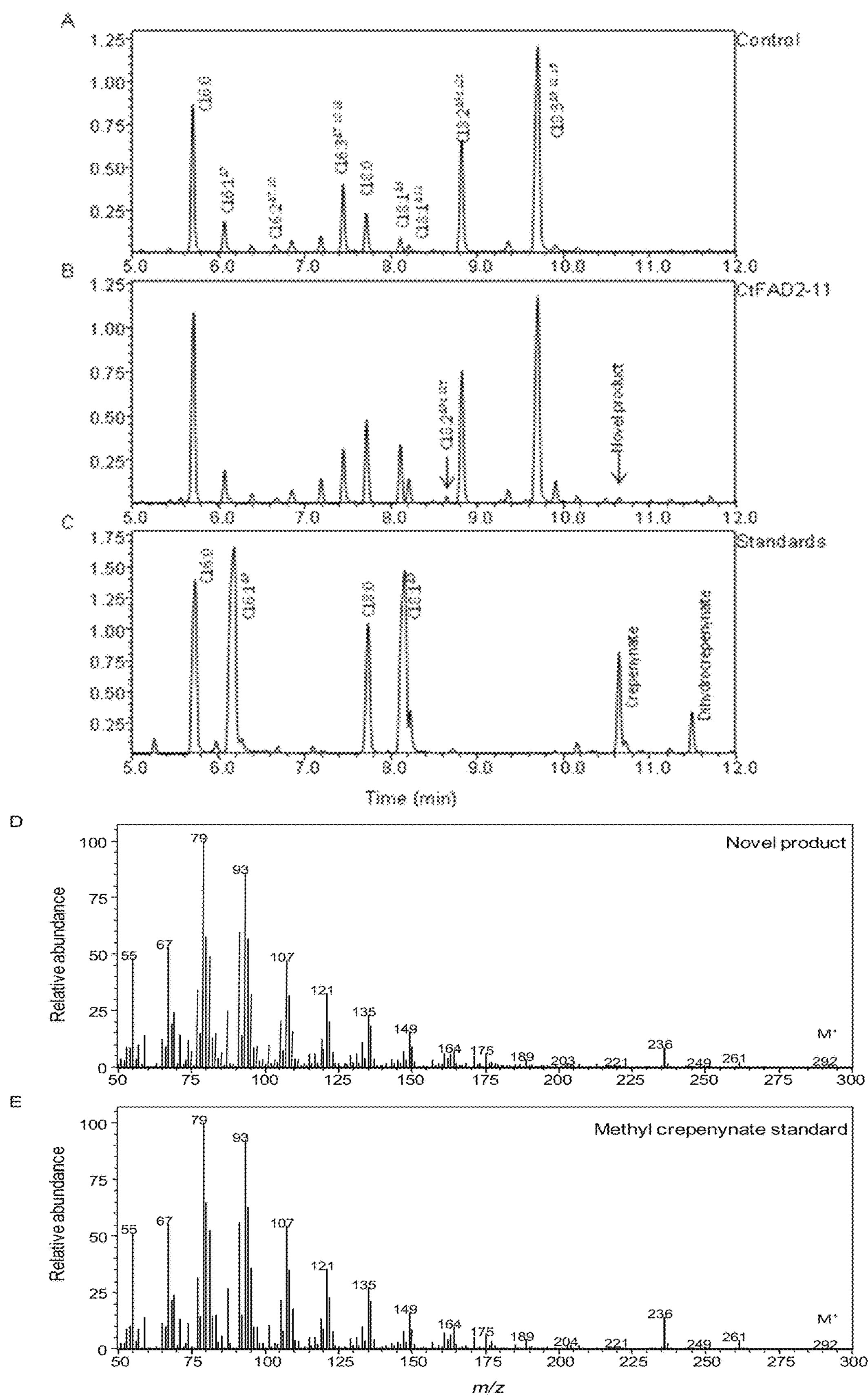

FIG. 4. GC-MS fatty acid analysis of fatty acid composition after CtFAD2-11 was transiently expressed in *N. benthamiana* leaves.

Figure 5:
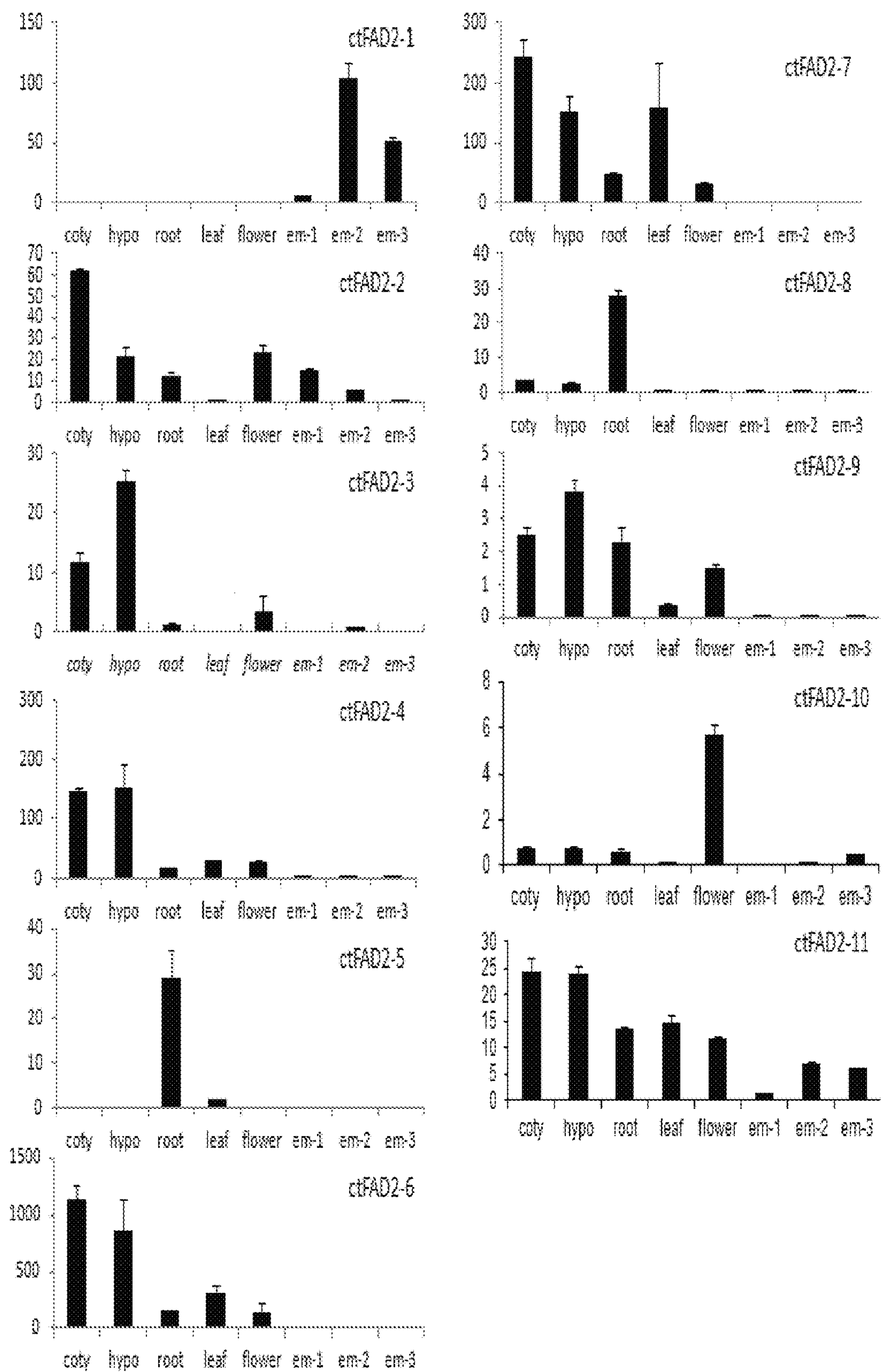

FIG. 5. RT-qPCR expression analysis of safflower CtFAD2 genes.

FIG. 6. Nucleotide comparison of a region of the CtFAD2-1 alleles from wild-type SU (SEQ ID NO:56) and three high oleic genotypes, namely S-317, CW99-OL and Lesaf496, showing a nucleotide deletion in the middle of the CtFAD2-1 coding region in the mutants (SEQ ID NO:57).

FIG. 7. DNA sequence comparison of the CtFAD2-1 5'UTR introns in the wild-type variety SU (SEQ ID NO:170) and the high oleic genotype S-317 (SEQ ID NO:171). Boxed DNA sequences were used to design the perfect PCR markers for high oleic specific and wild type specific PCR products.

Figure 8:
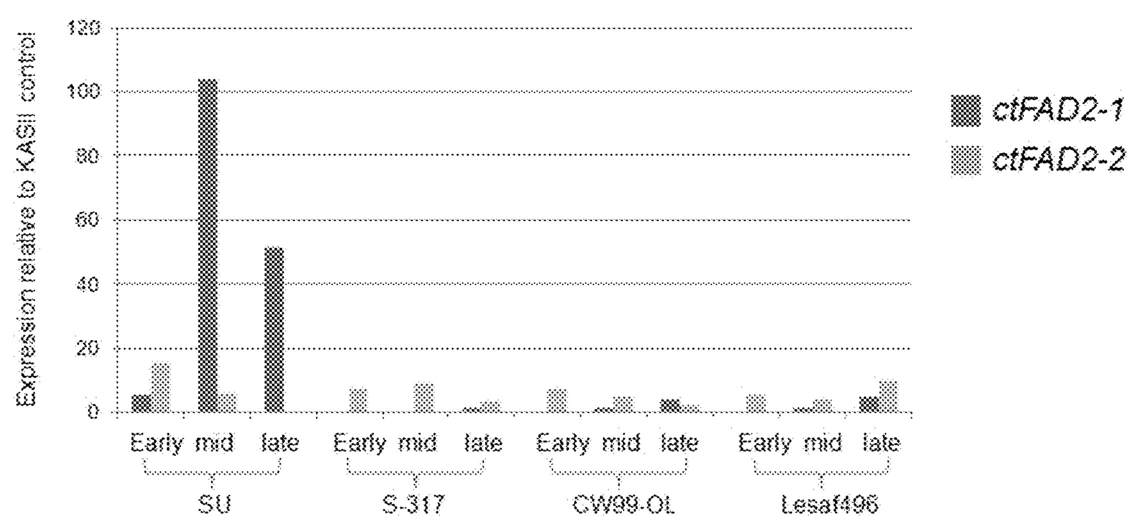

FIG. 8. Real time q-PCR analysis of CtFAD2-1 and CtFAD2-2 mRNA levels in developing embryos of three development stages, early (7 DPA), mid (15 DPA) and late (20 DPA). The safflower varieties include wild-type SU, and three high oleic varieties: S-317, CW99-OL and Lesaf496.

Figure 9:
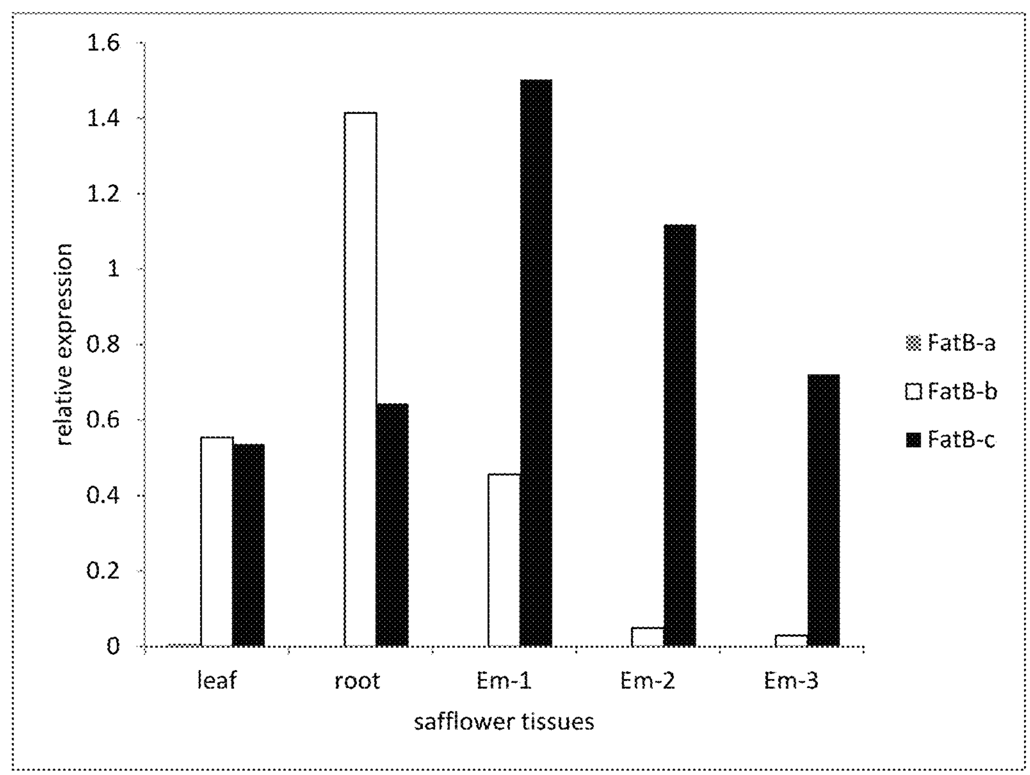

FIG. 9. Real time qPCR analysis of CtFatB genes in leaf, root, and developing embryos of safflower variety SU. Em-1 (early stage), Em-2 (middle stage), and Em-3 (late stage).

Figure 10:
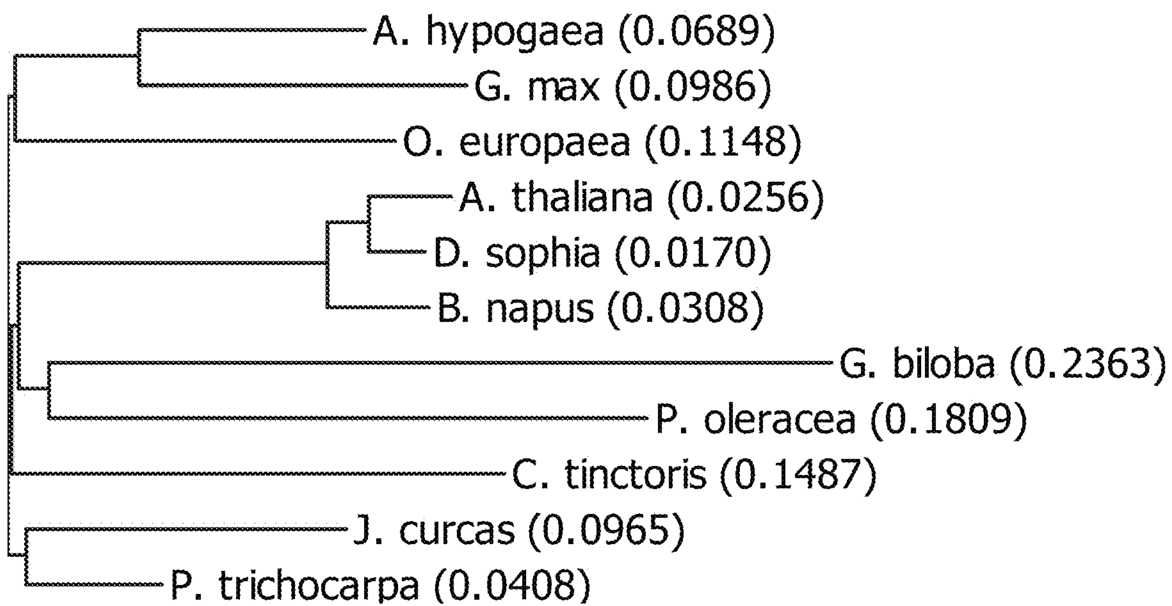

FIG. 10. A dendrogram showing the phylogenetic relationship between the safflower FAD6 sequences and representative FAD6 plastidial Δ12 desaturase identified in higher plants. *Jatropha curcas* (EU106889); *Olea europaea* (AY733075); *Populus trichocarpa* (EF147523); *Arabidopsis thaliana* (AY079039); *Descuriana sophia* (EF524189); *Glycine max* (AK243928); *Brassica napus* (L29214); *Portulaca oleracea* (EU376530); *Arachis hypogaea* (FJ768730); *Ginkgo biloba* (HQ694563).

Figure 11:
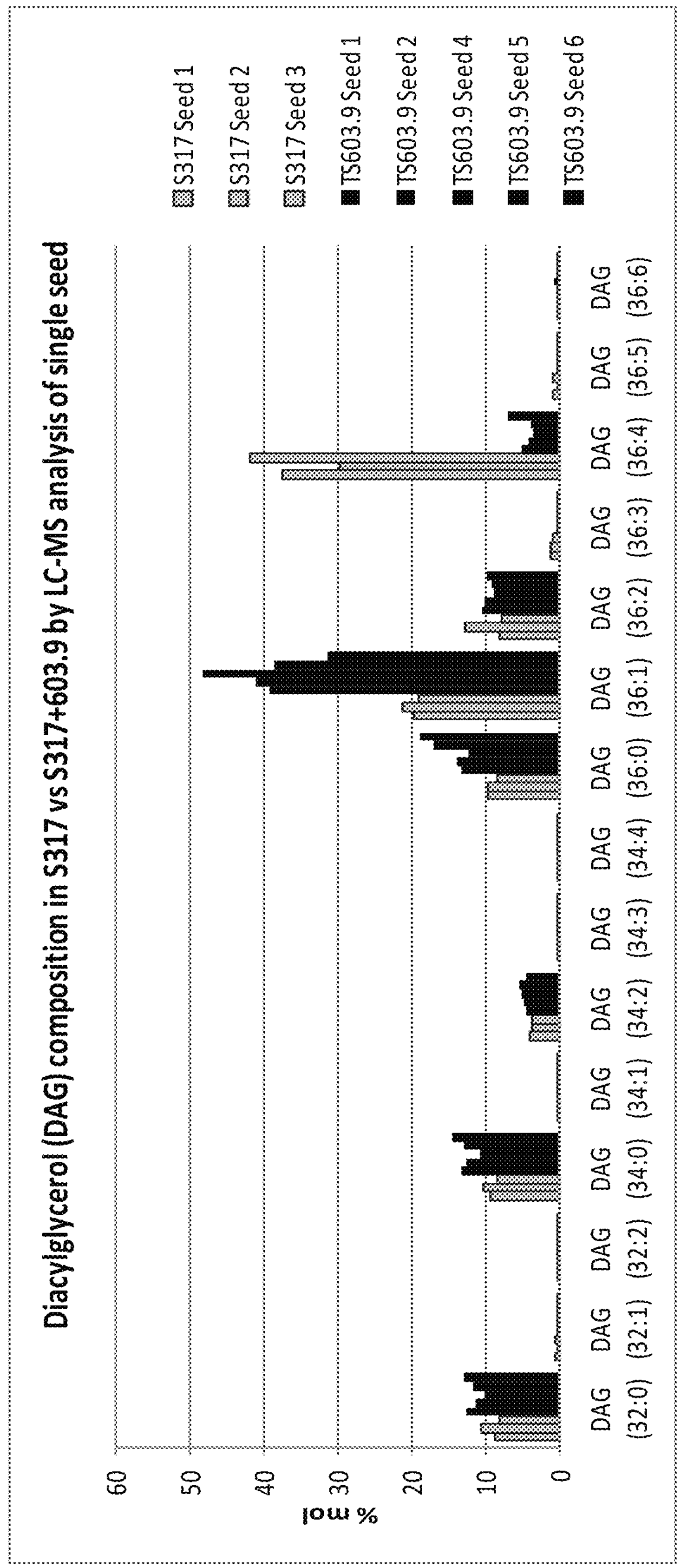

FIG. 11. Diacylglycerol (DAG) composition (mol %) in S317 versus S317+603.9 by LC-MS analysis of single seed.

Figure 12:
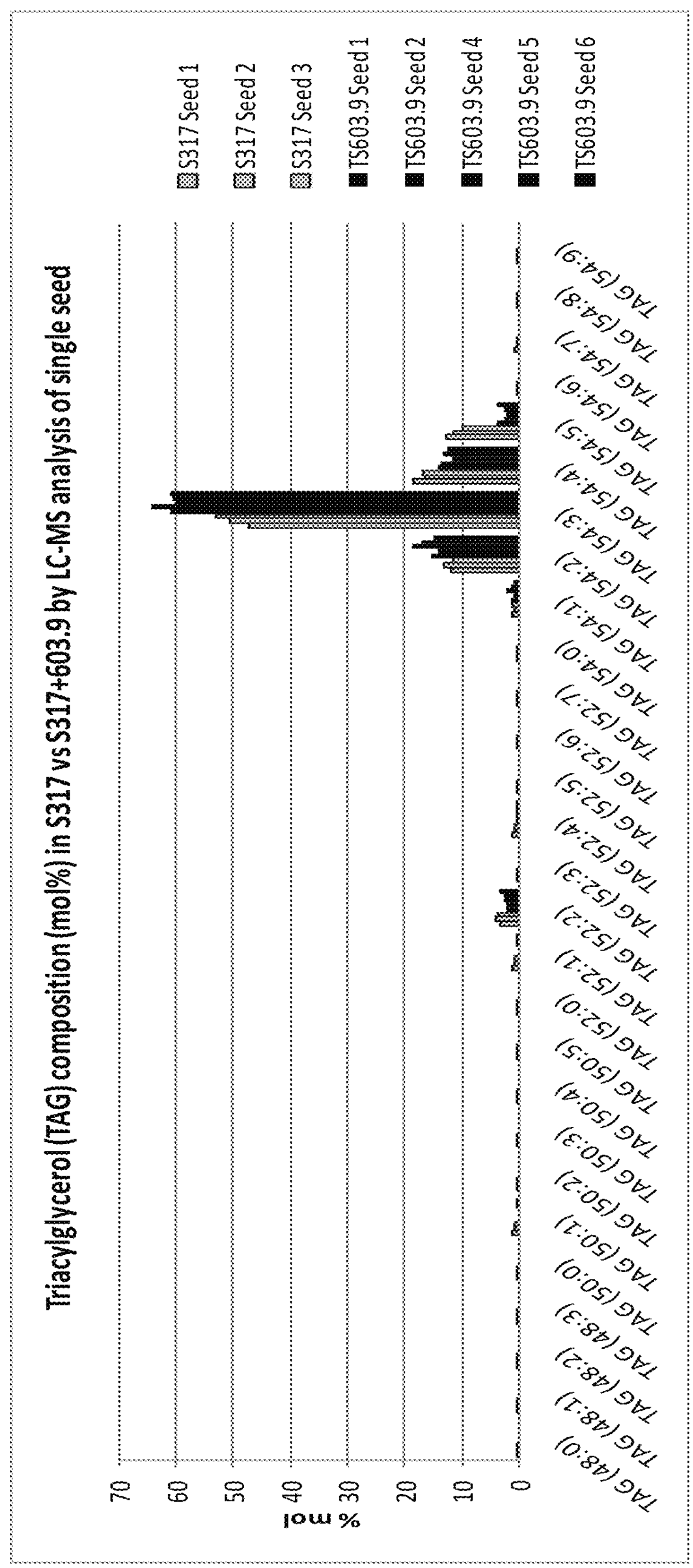

FIG. 12. Triacylglycerol (TAG) composition (mol %) in S317 versus S317+603.9 by LC-MS analysis of single seed.

Figure 13:
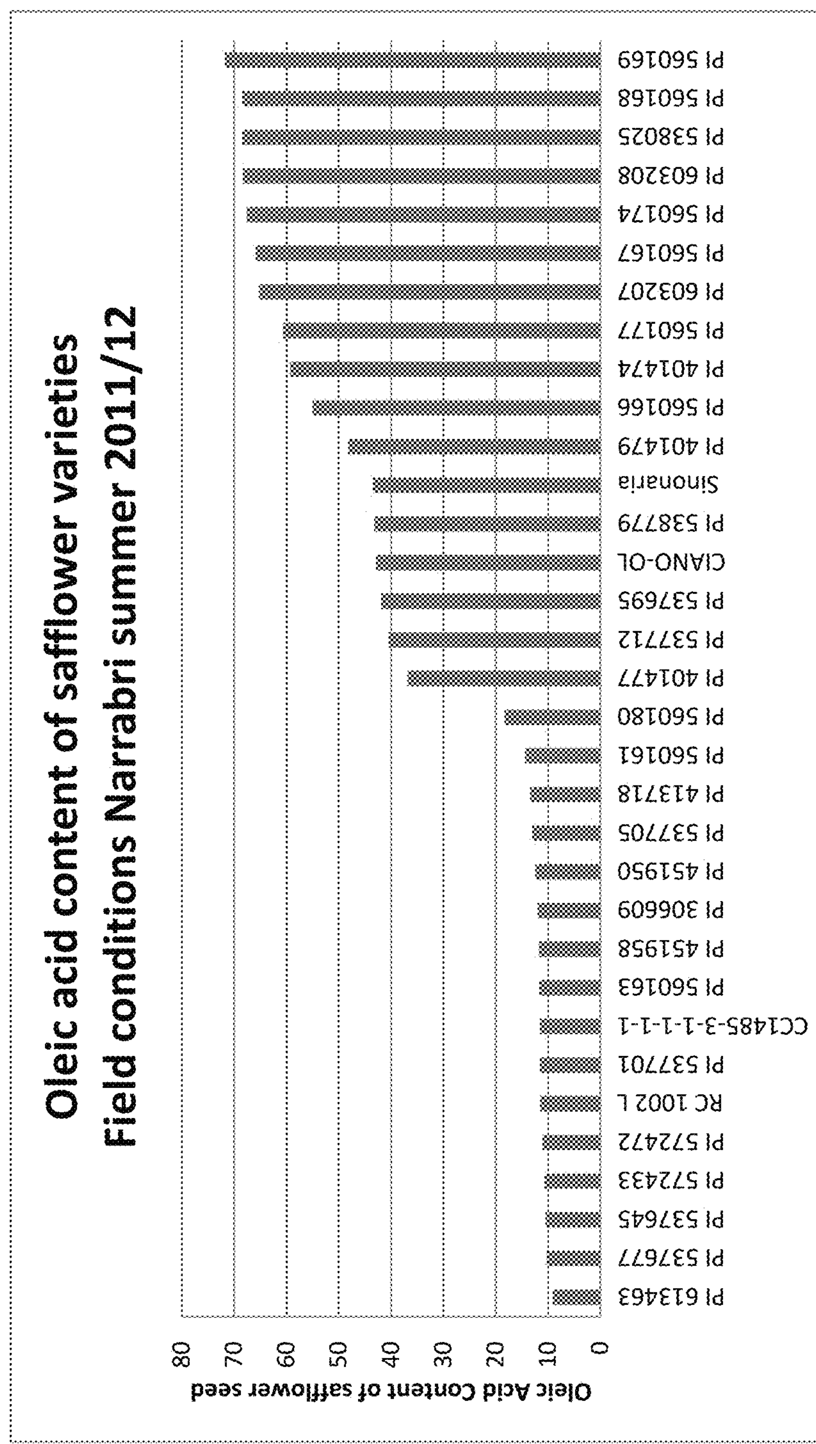

FIG. 13. Oleic acid content of safflower varieties under field conditions at Narrabri in the Australian summer of 2011/2012.

FIG. 14. (A) Basic phytosterol structure with ring and side chain numbering. (B) Chemical structures of some of the phytosterols.

KEY TO THE SEQUENCE LISTING

SEQ ID NO: 1—cDNA encoding safflower FAD2-1.
SEQ ID NO: 2—cDNA encoding safflower FAD2-2.
SEQ ID NO: 3—cDNA encoding safflower FAD2-3.
SEQ ID NO: 4—cDNA encoding safflower FAD2-4.
SEQ ID NO: 5—cDNA encoding safflower FAD2-5.
SEQ ID NO: 6—cDNA encoding safflower FAD2-6.
SEQ ID NO: 7—cDNA encoding safflower FAD2-7.
SEQ ID NO: 8—cDNA encoding safflower FAD2-8.
SEQ ID NO: 9—cDNA encoding safflower FAD2-9.
SEQ ID NO: 10—cDNA encoding safflower FAD2-10.
SEQ ID NO: 11—cDNA encoding safflower FAD2-11.
SEQ ID NO: 12—Open reading frame encoding safflower FAD2-1.
SEQ ID NO: 13—Open reading frame encoding safflower FAD2-2.
SEQ ID NO: 14—Open reading frame encoding safflower FAD2-3.
SEQ ID NO: 15—Open reading frame encoding safflower FAD2-4.
SEQ ID NO: 16—Open reading frame encoding safflower FAD2-5.
SEQ ID NO: 17—Open reading frame encoding safflower FAD2-6.
SEQ ID NO: 18—Open reading frame encoding safflower FAD2-7.
SEQ ID NO: 19—Open reading frame encoding safflower FAD2-8.
SEQ ID NO: 20—Open reading frame encoding safflower FAD2-9.
SEQ ID NO: 21—Open reading frame encoding safflower FAD2-10.
SEQ ID NO: 22—Open reading frame encoding safflower FAD2-11.
SEQ ID NO: 23—Intron sequence of safflower FAD2-1 gene.
SEQ ID NO: 24—Intron sequence of safflower FAD2-2 gene.
SEQ ID NO: 25—Intron sequence of safflower FAD2-10 gene.
SEQ ID NO: 26—cDNA encoding truncated safflower FAD2-1 (HO mutant).
SEQ ID NO: 27—Safflower FAD2-1.
SEQ ID NO: 28—Safflower FAD2-2.
SEQ ID NO: 29—Safflower FAD2-3.
SEQ ID NO: 30—Safflower FAD2-4.
SEQ ID NO: 31—Safflower FAD2-5.
SEQ ID NO: 32—Safflower FAD2-6.
SEQ ID NO: 33—Safflower FAD2-7.
SEQ ID NO: 34—Safflower FAD2-8.
SEQ ID NO: 35—Safflower FAD2-9.
SEQ ID NO: 36—Safflower FAD2-10.
SEQ ID NO: 37—Safflower FAD2-11.
SEQ ID NO:38—Truncated safflower FAD2-1 (HO mutant).
SEQ ID NO: 39—cDNA of safflower FATB-1.
SEQ ID NO: 40—cDNA encoding safflower FATB-2.
SEQ ID NO: 41—cDNA encoding safflower FATB-3.
SEQ ID NO: 42—Open reading frame encoding safflower FATB-2.
SEQ ID NO: 43—Open reading frame encoding safflower FATB-3.
SEQ ID NO: 44—Safflower FATB-2.
SEQ ID NO: 45—Safflower FATB-3.
SEQ ID NO: 46—cDNA encoding safflower FAD6.
SEQ ID NO: 47—Open reading frame encoding safflower FAD6.
SEQ ID NO: 48—Safflower FAD6.
SEQ ID NO: 49—CtFAD2-2 sequence used in RNA silencing construct.
SEQ ID NO: 50—CtFATB-3 sequence used in RNA silencing construct.
SEQ ID NO: 51—CtFAD6 sequence used in RNA silencing construct.
SEQ ID NO: 52—*Arabidopsis thaliana* oleosin promoter.
SEQ ID NO: 53—Flax linin promoter.
SEQ ID NO: 54—Nos polyadenylation signal.
SEQ ID NO: 55—Ocs polyadenylation signal.
SEQ ID NO: 56—Wild type CtFAD2-1 sequence corresponding to region of ol allele.
SEQ ID NO: 57—Ol allele CtFAD2-1 sequence with frameshift (same for S-317, CW99-OL and LeSaf496).
SEQ ID NO's 58 to 158 —Oligonucleotide primers.
SEQ ID NO's 159 to 169—Motifs of CtFAD2 enzymes.
SEQ ID NO: 170—Wild type safflower variety SU CtFAD2-1 5'UTR intron.
SEQ ID NO: 171—High oleic acid safflower variety S-317 CtFAD2-1 5'UTR intron.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, more preferably +/−4%, more preferably +/−3%, more preferably +/−2%, more preferably +/−1.5%, more preferably +/−1%, even more preferably +/−0.5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "extracted lipid" refers to a lipid composition which comprises at least 60% (w/w) lipid and which has been extracted, for example by crushing, from a transgenic organism or part thereof. Furthermore, as used herein, the term "extracted oil" refers to an oil composition which comprises at least 60% (w/w) oil and which has been extracted from a transgenic organism or part thereof.

As used herein, the term "purified" when used in connection with lipid or oil of the invention typically means that that the extracted lipid or oil has been subjected to one or more processing steps of increase the purity of the lipid/oil component. For example, a purification step may comprise one or more or all of the group consisting of: degumming, deodorising, decolourising, drying and/or fractionating the extracted oil. However, as used herein, the term "purified" does not include a transesterification process or other process which alters the fatty acid composition of the lipid or oil of the invention so as to increase the oleic acid content as a percentage of the total fatty acid content. Expressed in other words, the fatty acid composition of the purified lipid or oil is essentially the same as that of the unpurified lipid or oil. The fatty acid composition of the extracted lipid or oil, such as for example the oleic, linoleic and palmitic acid contents, is essentially the same as the fatty acid composition of the lipid or oil in the plant seed from which it is obtained. In this context, "essentially the same" means+/−1%, or, preferably, +/−0.5%.

As used herein, the term "oleic desaturation proportion" or "ODP" refers to a calculation which involves dividing the relative amount of linoleic acid and α-linolenic acid expressed as a percentage of the lipid fatty acid composition by the sum of the relative amounts of oleic acid, linoleic and α-linolenic acids, each expressed as percentages. The formula is:

$$ODP=(\%\ \text{linoleic}+\%\alpha\text{-linolenic})/(\%\ \text{oleic}+\%\ \text{linoleic}+\%\alpha\text{-linolenic})$$

For example, TG603.12(5) of Example 15 has a total linoleic acid and α-linolenic acid content of 2.15% and an linoleic acid, α-linolenic acid oleic acid content of 93.88% making the ODP 0.0229.

As used herein, the term "palmitic-linoleic-oleic value" or "PLO" refers to a calculation which involves dividing the relative amount of linoleic acid and palmitic acid expressed as a percentage of the lipid fatty acid composition by the relative amount of oleic acid expressed as a percentage. The formula is:

$$PLO=(\%\ \text{palmitic}+\%\ \text{linoleic})/\%\ \text{oleic}$$

For example, TG603.12(5) of Example 15 has a total linoleic acid and palmitic content of 4.71% and an oleic acid content of 91.73% making the PLO 0.0513.

As used herein, the term "oleic monounsaturation proportion" or "OMP" refers to a calculation which involves dividing the relative amount of non-oleic monounsaturated fatty acids expressed as a percentage of the lipid fatty acid composition by the relative amount of oleic acid expressed as a percentage. The formula is:

$$OMP=(\%\ \text{monounsaturated fatty acids}-\%\ \text{oleic})/\%\ \text{oleic}$$

For example, TG603.12(5) of Example 15 has a total monounsaturated fatty acid content excluding oleic acid (0.84% C18:1Δ11+0.29% C20:1) of 1.13% and an oleic acid content of 91.73% making the OMP 0.0123.

The term "corresponding" refers to a cell, or plant or part thereof (such as a seed) that has the same or similar genetic background as a cell, or plant or part thereof (seed) of the invention but that has not been modified as described herein (for example, the cell, or plant or part thereof lacks an exogenous polynucleotide of the invention). A corresponding cell or, plant or part thereof (seed) can be used as a control to compare, for example, one or more of the amount of oleic acid produced, FAD2 activity, FATB activity or FAD6 activity with a cell, or plant or part thereof (seed) modified as described herein. A person skilled in the art is able to readily determine an appropriate "corresponding" cell, plant or part thereof (seed) for such a comparison.

As used herein, the term "seedoil" refers to a composition obtained from the seed of a plant which comprises at least 60% (w/w) lipid, or obtainable from the seed if the seedoil is still present in the seed. That is, seedoil of, or obtained using, the invention includes seedoil which is present in the seed or portion thereof such as cotyledons or embryo, unless it is referred to as "extracted seedoil" or similar terms in which case it is oil which has been extracted from the seed. The seedoil is preferably extracted seedoil. Seedoil is typically a liquid at room temperature. Preferably, the total fatty acid (TFA) content in the seedoil is >70% C18 fatty acids, preferably >90% oleic acid (C18:1Δ9). The fatty acids are typically in an esterified form such as for example, TAG, DAG, acyl-CoA or phospholipid. Unless otherwise stated, the fatty acids may be free fatty acids and/or in an esterified form. In an embodiment, at least 50%, more preferably at least 70%, more preferably at least 80%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% of the fatty acids in seedoil of the invention can be found as TAG. In an embodiment, seedoil of the invention is "substantially purified" or "purified" oil that has been separated from one or more other lipids, nucleic acids, polypeptides, or other contaminating molecules with which it is associated in the seed or in a crude extract. It is preferred that the substantially purified seedoil is at least 60% free, more preferably at least 75% free, and more preferably, at least 90% free from other components with which it is associated in the seed or extract. Seedoil of the invention may further comprise non-fatty acid molecules such as, but not limited to, sterols (see Example 17). In an embodiment, the seedoil is safflower oil (*Carthamus tinctorius*), sunflower oil (*Helianthus annus*), cottonseed oil (*Gossypium hirsutum*), castor oil (*Ricinus communis*), canola oil (*Brassica napus, Brassica rapa* ssp.), mustard oil (*Brassica juncea*), other Brassica oil (e.g., *Brassica napobrassica, Brassica camelina*), linseed oil (*Linum usitatissimum*), soybean oil (*Glycine max*), corn oil (*Zea mays*), tobacco oil (*Nicotiana tabacum*), peanut oil (*Arachis hypogaea*), palm oil (*Elaeis guineensis*), coconut oil (*Cocos nucifera*), avocado oil (*Persea americana*), olive oil (*Olea europaea*), cashew oil (*Anacardium occidentale*), macadamia oil (*Macadamia intergrifolia*), almond oil (*Prunus amygdalus*), oat seed oil (*Avena sativa*), rice oil (*Oryza sativa* or *Oryza glaberrima*), camelina oil (*Camelina sativa*), *crambe* oil (*Crambe abyssinica*) or *Arabidopsis* seed oil (*Arabidopsis thaliana*). Seedoil may be extracted from seed by any method known in the art. This typically involves extraction with nonpolar solvents such as hexane, diethyl ether, petroleum ether, chloroform/methanol or butanol mixtures, generally associated with first crushing or rolling of the seeds. Lipids associated with the starch in the grain may be extracted with water-saturated butanol. The seedoil may be "de-gummed" by methods known in the art to remove polysaccharides and/or phospholipids or treated in other ways to remove contaminants or improve purity, stability, or colour. The TAGs and other esters in the seedoil may be hydrolysed to release free fatty acids such as by acid or alkali treatment or by the action of lipases, or the seedoil hydrogenated, treated chemically, or enzymatically as known in the art. However, once the seedoil is processed so that it no longer comprises the TAG, it is no longer considered seedoil as referred to herein.

The free and esterified sterol (for example, sitosterol, campesterol, stigmasterol, brassicasterol, Δ5-avenasterol, sitostanol, campestanol, and cholesterol) concentrations in the purified and/or extracted lipid or oil may be as described in Phillips et al. (2002) and/or as provided in Example 17. Sterols in plant oils are present as free alcohols, esters with fatty acids (esterified sterols), glycosides and acylated glycosides of sterols. Sterol concentrations in naturally occurring vegetable oils (seedoils) ranges up to a maximum of about 1100 mg/100 g. Hydrogenated palm oil has one of the lowest concentrations of naturally occurring vegetable oils at about 60 mg/100 g. The recovered or extracted seedoils of the invention preferably have between about 100 and about 1000 mg total sterol/100 g of oil. For use as food or feed, it is preferred that sterols are present primarily as free or esterified forms rather than glycosylated forms. In the seedoils of the present invention, preferably at least 50% of the sterols in the oils are present as esterified sterols, except for soybean seedoil which has about 25% of the sterols esterified. The safflower seedoil of the invention preferably has between about 150 and about 400 mg total sterol/100 g, typically about 300 mg total sterol/100 g of seedoil, with sitosterol the main sterol. The canola seedoil and rapeseed oil of the invention preferably have between about 500 and about 800 mg total sterol/100 g, with sitosterol the main sterol and campesterol the next most abundant. The corn seedoil of the invention preferably has between about 600 and about 800 mg total sterol/100 g, with sitosterol the main sterol. The soybean seedoil of the invention preferably has between about 150 and about 350 mg total sterol/100 g, with sitosterol the main sterol and stigmasterol the next most abundant, and with more free sterol than esterified sterol. The cottonseed oil of the invention preferably has between about 200 and about 350 mg total sterol/100 g, with sitosterol the main sterol. The coconut oil and palm oil of the invention preferably have between about 50 and about 100 mg total sterol/100 g, with sitosterol the main sterol. The peanut seedoil of the invention preferably has between about 100 and about 200 mg total sterol/100 g, with sitosterol the main sterol. The sesame seedoil of the invention preferably has between about 400 and about 600 mg total sterol/100 g, with sitosterol the main sterol. The sunflower seedoil of the invention preferably has between about 200 and 400 mg total sterol/100 g, with sitosterol the main sterol.

As used herein, the term "fatty acid" refers to a carboxylic acid with a long aliphatic tail of at least 8 carbon atoms in length, either saturated or unsaturated. Typically, fatty acids have a carbon-carbon bonded chain of at least 12 carbons in length. Most naturally occurring fatty acids have an even number of carbon atoms because their biosynthesis involves acetate which has two carbon atoms. The fatty acids may be in a free state (non-esterified) or in an esterified form such as part of a TAG, DAG, MAG, acyl-CoA (thio-ester) bound, or other covalently bound form. When covalently bound in an esterified form, the fatty acid is referred to herein as an "acyl" group. The fatty acid may be esterified as a phospholipid such as a phosphatidylcholine (PC), phosphatidylethanolamine, phosphatidylserine, phosphatidylglycerol, phosphatidylinositol, or diphosphatidylglycerol. Saturated fatty acids do not contain any double bonds or other functional groups along the chain. The term "saturated" refers to hydrogen, in that all carbons (apart from the carboxylic acid [—COOH] group) contain as many hydrogens as possible. In other words, the omega (ω) end contains 3 hydrogens (CH3-) and each carbon within the chain contains 2 hydrogens (—CH2-). Unsaturated fatty acids are of similar form to saturated fatty acids, except that one or more alkene functional groups exist along the chain, with each alkene substituting a singly-bonded "—CH2-CH2-" part of the chain with a doubly-bonded "—CH═CH—" portion (that is, a carbon double bonded to another carbon). The two next carbon atoms in the chain that are bound to either side of the double bond can occur in a cis or trans configuration.

As used herein, the terms "polyunsaturated fatty acid" or "PUFA" refer to a fatty acid which comprises at least 12 carbon atoms in its carbon chain and at least two alkene groups (carbon-carbon double bonds).

As used herein, the term "monounsaturated fatty acids" refers to fatty acids that have a single double bond in their acyl chain, such as oleic acid (C18:1Δ9), C18:1D11 and C20:1.

"Triacylglyceride" or "TAG" is glyceride in which the glycerol is esterified with three fatty acids. In the Kennedy pathway of TAG synthesis, DAG is formed as described above, and then a third acyl group is esterified to the glycerol backbone by the activity of DGAT. Alternative pathways for formation of TAG include one catalysed by the enzyme PDAT and the MGAT pathway (PCT/AU2011/000794).

"Diacylglyceride" or "DAG" is glyceride in which the glycerol is esterified with two fatty acids. As used herein, DAG comprises a hydroxyl group at a sn-1,3 or sn-1,2/2,3 position, and therefore DAG does not include phosphorylated molecules such as PA or PC. DAG is thus a component of neutral lipids in a cell. In the Kennedy pathway of DAG synthesis, the precursor sn-glycerol-3-phosphate (G-3-P) is esterified to two acyl groups, each coming from a fatty acid coenzyme A ester, in a first reaction catalysed by a glycerol-3-phosphate acyltransferase (GPAT) at position sn-1 to form LysoPA, followed by a second acylation at position sn-2 catalysed by a lysophosphatidic acid acyltransferase (LPAAT) to form phosphatidic acid (PA). This intermediate is then de-phosphorylated to form DAG. In an alternative anabolic pathway, DAG may be formed by the acylation of either sn-1 MAG or preferably sn-2 MAG, catalysed by MGAT. DAG may also be formed from TAG by removal of an acyl group by a lipase, or from PC essentially by removal of a choline headgroup by any of the enzymes CPT, PDCT or PLC.

As used herein, the term "desaturase" refers to an enzyme which is capable of introducing a carbon-carbon double bond into the acyl group of a fatty acid substrate which is typically in an esterified form such as, for example, fatty acid CoA esters. The acyl group may be esterified to a phospholipid such as phosphatidylcholine (PC), or to acyl carrier protein (ACP), to CoA, or in a preferred embodiment to PC. Desaturases generally may be categorized into three groups accordingly. In one embodiment, the desaturase is a front-end desaturase.

As used herein, the terms "Δ12 desaturase" and "FAD2" refer to a membrane bound Δ12 fatty acid desturase which performs a desaturase reaction converting oleic acid ($18{:}1^{\Delta9}$) to linoleic acid ($C18{:}2^{\Delta9,12}$). Thus, the term "Δ12 desaturase activity" refers to the conversion of oleic acid to linoleic acid. These fatty acids may be in an esterified form, such as, for example, as part of a phospholipid, preferably in the form of PC. In an embodiment, a FAD2 enzyme as defined herein comprises three histidine-rich motifs (His boxes) (see Table 5 for examples of His boxes of enzymes of the invention). Such His-rich motifs are highly conserved in FAD2 enzymes and have been implicated in the formation of the diiron-oxygen complex used in biochemical catalysis (Shanklin et al., 1998).

As used herein, the terms "FAD2-1" and "CtFAD2-1" and variations thereof refer to a safflower FAD2 polypeptide whose amino acid sequence is provided as SEQ ID NO:27, such as a polypeptide encoded by nucleotides having a sequence provided as SEQ ID NO:12. As used herein, a FAD2-1 gene is a gene encoding such a polypeptide or a mutant allele thereof. These terms also include naturally occurring or artificially induced or produced variants of the sequences provided. In an embodiment, FAD2-1 of the invention comprises an amino acid sequence which is at least 95% identical, more preferably at least 99% identical, to the sequence provided as SEQ ID NO:27. CtFAD2-1 genes include alleles which are mutant, that is, that encode polypeptides with altered desaturase activity such as reduced activity, or do not encode functional polypeptides (null alleles). Such alleles may be naturally occurring or induced by artificial mutagenesis. An example of such an allele is the FAD2-1 ol allele described herein.

As used herein, the terms "FAD2-2" and "CtFAD2-2" and variations thereof refer to a safflower FAD2 polypeptide whose amino acid sequence is provided as SEQ ID NO:28, such as a polypeptide encoded by nucleotides having a sequence provided as SEQ ID NO:13. As used herein, a FAD2-2 gene is a gene encoding such a polypeptide or a mutant allele thereof. These terms also include naturally occurring or artificially induced or produced variants of the sequences provided. In an embodiment, FAD2-2 of the invention comprises an amino acid sequence which is at least 95% identical, more preferably at least 99% identical, to the sequence provided as SEQ ID NO:28. CtFAD2-2 genes include alleles which are mutant, that is, that encode polypeptides with altered desaturase activity such as reduced activity, or do not encode functional polypeptides (null alleles). Such alleles may be naturally occurring or induced by artificial mutagenesis.

As used herein, the terms "FAD2-10" and "CtFAD2-10" and variations thereof refer to a safflower FAD2 polypeptide whose amino acid sequence is provided as SEQ ID NO:36, such as a polypeptide encoded by nucleotides having a sequence provided as SEQ ID NO:21. As used herein, a FAD2-10 gene is a gene encoding such a polypeptide or a mutant allele thereof. These terms also include naturally occurring or artificially induced or produced variants of the sequences provided. In an embodiment, FAD2-10 of the invention comprises an amino acid sequence which is at least 95% identical, more preferably at least 99% identical, to the sequence provided as SEQ ID NO:36. CtFAD2-10 genes include alleles which are mutant, that is, that encode polypeptides with altered desaturase activity such as reduced activity, or do not encode functional polypeptides (null alleles). Such alleles may be naturally occurring or induced by artificial mutagenesis.

As used herein, the term "palmitoyl-ACP thioesterase" and "FATB" refer to a protein which hydrolyses palmitoyl-ACP to produce free palmitic acid. Thus, the term "palmitoyl-ACP thioesterase activity" refers to the hydrolysis of palmitoyl-ACP to produce free palmitic acid.

As used herein, the terms "FATB-3" and "CtFATB-3" and variations thereof refer to a safflower FATB polypeptide whose amino acid sequence is provided as SEQ ID NO:45, such as a polypeptide encoded by nucleotides having a sequence provided as SEQ ID NO:43. As used herein, a FATB-3 gene is a gene encoding such a polypeptide or a mutant allele thereof. These terms also include naturally occurring or artificially induced or produced variants of the sequences provided. In an embodiment, FATB-3 of the invention comprises an amino acid sequence which is at least 95% identical, more preferably at least 99% identical, to the sequence provided as SEQ ID NO:45. CtFATB-3 genes include alleles which are mutant, that is, that encode polypeptides with altered palmitoyl-ACP thioesterase activity such as reduced activity, or do not encode functional polypeptides (null alleles). Such alleles may be naturally occurring or induced by artificial mutagenesis.

As used herein, "plastidial ω6 fatty acid desaturase", variations thereof, and "FAD6" refer to a chloroplast enzyme that desaturates 16:1 and 18:1 fatty acids to 16:2 and 18:2, respectively, on all 16:1- or 18:1-containing chloroplast membrane lipids including phosphatidyl glycerol, monogalactosyldiacylglycerol, digalactosyl-diacylglycerol, and sulfoguinovosyldiacylglycerol.

As used herein, the terms "FAD6" and "CtFAD6" and variations thereof refer to a safflower FAD6 polypeptide whose amino acid sequence is provided as SEQ ID NO:48, such as a polypeptide encoded by nucleotides having a sequence provided as SEQ ID NO:47. As used herein, a FAD6 gene is a gene encoding such a polypeptide or a mutant allele thereof. These terms also include naturally occurring or artificially induced or produced variants of the sequences provided. In an embodiment, FAD6 of the invention comprises an amino acid sequence which is at least 95% identical, more preferably at least 99% identical, to the sequence provided as SEQ ID NO:48. CtFAD6 genes include alleles which are mutant, that is, that encode polypeptides with altered desaturase activity such as reduced activity, or do not encode functional polypeptides (null alleles). Such alleles may be naturally occurring or induced by artificial mutagenesis.

As used herein, the term "acetylenase" or "fatty acid acetylenase" refers to an enzyme that introduces a triple bond into a fatty acid resulting in the production of an acetylenic fatty acid.

The term "Ct" is used herein before terms such as FAD2, FATB and FAD6 to indicate the enzyme/gene is from safflower.

As used herein, the term "silencing RNA which is capable of reducing the expression of" and variants thereof, refers to a polynucleotide that encodes an RNA molecule that reduces (down-regulates) the production and/or activity (for example, encoding an siRNA, hpRNAi), or itself down regulates the production and/or activity (for example, is an siRNA which can be delivered directly to, for example, a cell) of an endogenous enzyme for example, a Δ12 desaturase, a palmitoyl-ACP thioesterase, a plastidial ω6 fatty acid desaturase, or a combination of two or more or all three thereof. In an embodiment, the silencing RNA is an exogenous RNA which is produced from a transgene in the cell and which transcriptionally and/or post-transcriptionally reduces the amount of the endogenous enzyme that is produced in the cell, such as by reducing the amount of mRNA encoding the endogenous enzyme or reducing its translation. The silencing RNA is typically an RNA of 21-24 nucleotides in length which is complementary to the endogenous mRNA and which may be associated with a silencing complex known as a RISC in the cell.

As used herein, the term "mutation(s) reduce the activity of" refers to naturally occurring or man-made mutants (such as produced by chemical mutagenesis or site-specific mutagenesis) which have lower levels of the defined enzymatic activity (for example, FAD2 enzymatic activity in the seed) when compared to phenotypically normal seeds (for example, seeds which produce FAD2 enzymes which comprise the amino acid sequences provided as SEQ ID NOs 27, 28 and 36). Examples of phenotypically normal safflower varieties include, but are not limited to, Centennial, Finch, Nutrasaff and Cardinal. The first identified high oleic trait in safflower, found in a safflower introduction from India, was controlled by a partially recessive allele designated ol at a single locus OL (Knowles and Hill, 1964). As described herein, the OL locus corresponds to the CtFAD2-1 gene. The oleic acid content of seedoil in olol genotypes was usually 71-75% for greenhouse-grown plants (Knowles, 1989). Knowles (1968) incorporated the ol allele into a safflower breeding program and released the first high oleic (HO) safflower variety "UC-1" in 1966 in the US, which was followed by the release of improved varieties "Oleic Leed" and the Saffola series including Saffola 317 (S-317), S-517 and S-518. The high oleic (olol) genotypes were relatively stable in the oleic acid level when grown at different temperatures in the field (Bartholomew, 1971). In addition, Knowles (1972) also described a different allele $ol_1$ at the same locus, which produced in homozygous condition between 35 and 50% oleic acid. In contrast to olol genotype, the $ol_1ol_1$ genotype showed a strong response to temperature (Knowles, 1972). As determined herein, the allele of the ol mutation which confers reduced FAD2-1 activity (and overall FAD2 activity) in safflower seed is a mutant FAD2-1 gene comprising the frameshift mutation (due to deletion of a single nucleotide) depicted in FIG. 6 (see also Example 7 and SEQ ID NOs 26 and 38).

As used herein, the phrase "which is capable of producing a plant which produces seed whose oil content comprises" or "which is capable of producing a plant which produces oilseed whose oil content" or variations thereof means that the plant produced from the seed, preferably an oilseed plant and more preferably a safflower plant, has the capacity to produce the oil with the defined components when grown under optimal conditions, for instance in greenhouse conditions such as those referred to in the Examples. When in possession of seed from a plant, it is routine to grow a progeny plant from at least one of the seeds under suitable greenhouse conditions and test the oil content and fatty acid composition in seedoil from the progeny plant using standard procedures such as those described herein. Accordingly, as the skilled person would understand whilst seed grown in a field may not meet all of the requirements defined herein due to unfavourable conditions in a particular year such heat, cold, drought, flooding, frost, pest stresses etc, such seed are nonetheless encompassed by the present invention because the seed is capable of producing a progeny plant which produces the defined oil content or fatty acid composition when grown under more favourable conditions.

As used herein, the term "by weight" refers to the weight of a substance (for example, oleic acid, palmitic acid or PUFA such as linoleic acid or linolenic acid) as a percentage of the weight of the composition comprising the substance or a component in the composition. For example, the weight of a particular fatty acid such as oleic acid may be determined as a percentage of the weight of the total fatty acid content of the lipid or seedoil, or the seed.

As used herein, the term "biofuel" refers to any type of fuel, typically as used to power machinery such as automobiles, trucks or petroleum powered motors, whose energy is derived from biological carbon fixation rather than from fossil fuel. Biofuels include fuels derived from biomass conversion, as well as solid biomass, liquid fuels and biogases. Examples of biofuels include bioalcohols, biodiesel, synthetic diesel, vegetable oil, bioethers, biogas, syngas, solid biofuels, algae-derived fuel, biohydrogen, biomethanol, 2,5-Dimethylfuran (DMF), biodimethyl ether (bioDME), Fischer-Tropsch diesel, biohydrogen diesel, mixed alcohols and wood diesel.

As used herein, the term "industrial product" refers to a hydrocarbon product which is predominantly made of carbon and hydrogen such as fatty acid methyl- and/or ethyl-esters or alkanes such as methane, mixtures of longer chain alkanes which are typically liquids at ambient temperatures, a biofuel, carbon monoxide and/or hydrogen, or a bioalcohol such as ethanol, propanol, or butanol, or biochar. The term "industrial product" is intended to include intermediary products that can be converted to other industrial products, for example, syngas is itself considered to be an industrial product which can be used to synthesize a hydrocarbon product which is also considered to be an industrial product. The term industrial product as used herein includes both pure forms of the above compounds, or more commonly a mixture of various compounds and components, for example the hydrocarbon product may contain a range of carbon chain lengths, as well understood in the art.

Polynucleotides

The terms "polynucleotide", and "nucleic acid" are used interchangeably. They refer to a polymeric form of nucleotides of any length, either deoxyribonucleotides or ribonucleotides. A polynucleotide of the invention may be of genomic, cDNA, semisynthetic, or synthetic origin, double-stranded or single-stranded and by virtue of its origin or manipulation: (1) is not associated with all or a portion of a polynucleotide with which it is associated in nature, (2) is linked to a polynucleotide other than that to which it is linked in nature, or (3) does not occur in nature. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), ribozymes, cDNA, recombinant polynucleotides, plasmids, vectors, isolated DNA of any sequence, isolated RNA of any sequence, chimeric DNA of any sequence, nucleic acid probes, and primers. Preferred polynucleotides of the invention include double-stranded DNA molecules which are capable of being transcribed in plant cells and silencing RNA molecules.

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals, in which case, the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns", "intervening regions", or "intervening sequences." Introns are segments of a gene which are transcribed into nuclear RNA (nRNA). Introns may contain regulatory elements such as enhancers. Introns are removed or "spliced out" from the nuclear or primary transcript; introns therefore are absent in the mRNA transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

An "allele" refers to one specific form of a genetic sequence (such as a gene) within a cell, an individual plant or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations".

As used herein, "chimeric DNA" refers to any DNA molecule that is not naturally found in nature; also referred to herein as a "DNA construct". Typically, chimeric DNA comprises regulatory and transcribed or protein coding sequences that are not naturally found together in nature. Accordingly, chimeric DNA may comprise regulatory sequences and coding sequences that are derived from different sources, or regulatory sequences and coding sequences derived from the same source, but arranged in a manner different than that found in nature. The open reading frame may or may not be linked to its natural upstream and downstream regulatory elements. The open reading frame may be incorporated into, for example, the plant genome, in a non-natural location, or in a replicon or vector where it is not naturally found such as a bacterial plasmid or a viral vector. The term "chimeric DNA" is not limited to DNA molecules which are replicable in a host, but includes DNA capable of being ligated into a replicon by, for example, specific adaptor sequences.

A "transgene" is a gene that has been introduced into the genome by a transformation procedure. The transgene may be in an initial transformed plant produced by regeneration from a transformed plant cell or in progeny plants produced by self-fertilisation or crossing from the initial transformant or in plant parts such as seeds. The term "genetically modified" and variations thereof include introducing a gene into a cell by transformation or transduction, mutating a gene in a cell and genetically altering or modulating the regulation of a gene in a cell, or the progeny of any cell modified as described above.

A "genomic region" as used herein refers to a position within the genome where a transgene, or group of transgenes (also referred to herein as a cluster), have been inserted into a cell, or predecessor thereof, such that they are co-inherited in progeny cells after meiosis.

A "recombinant polynucleotide" or "exogenous polynucleotide" of the invention refers to a nucleic acid molecule which has been constructed or modified by artificial recombinant methods. The recombinant polynucleotide may be present in a cell in an altered amount or expressed at an altered rate (e.g., in the case of mRNA) compared to its native state. An exogenous polynucleotide is a polynucleotide that has been introduced into a cell that does not naturally comprise the polynucleotide. Typically an exogenous DNA is used as a template for transcription of mRNA which is then translated into a continuous sequence of amino acid residues coding for a polypeptide of the invention within the transformed cell. In another embodiment, part of the exogenous polynucleotide is endogenous to the cell and its expression is altered by recombinant means, for example, an exogenous control sequence is introduced upstream of an endogenous polynucleotide to enable the transformed cell to express the polypeptide encoded by the polynucleotide. For example, an exogenous polynucleotide may express an antisense RNA to an endogenous polynucleotide.

A recombinant polynucleotide of the invention includes polynucleotides which have not been separated from other components of the cell-based or cell-free expression system in which it is present, and polynucleotides produced in said cell-based or cell-free systems which are subsequently purified away from at least some other components. The polynucleotide can be a contiguous stretch of nucleotides existing in nature, or comprise two or more contiguous stretches of nucleotides from different sources (naturally occurring and/or synthetic) joined to form a single polynucleotide. Typically, such chimeric polynucleotides comprise at least an open reading frame encoding a polypeptide of the invention operably linked to a promoter suitable of driving transcription of the open reading frame in a cell of interest.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 50%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of, or useful for, the present invention may selectively hybridise, under stringent conditions, to a polynucleotide defined herein. As used herein, stringent conditions are those that: (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS, and/or (3) employ low ionic strength and high temperature for washing, for example, 0.015 M NaCl/0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above).

Polynucleotide for Reducing Expression Levels of Endogenous Proteins

In one embodiment, the cell/seed/plant/organism of the invention comprises an introduced mutation or an exogenous polynucleotide which down-regulates the production and/or activity of an endogenous enzyme, typically which results in an increased production of oleic acid, and preferably a decreased production of palmitic acid and PUFA such as linoleic acid, when compared to a corresponding cell lacking the introduced mutation or exogenous polynucleotide. Examples of such polynucleotides include an antisense polynucleotide, a sense polynucleotide, a catalytic polynucleotide, a microRNA, a polynucleotide which encodes a polypeptide which binds the endogenous enzyme and a double stranded RNA.

RNA Interference

RNA interference (RNAi) is particularly useful for specifically inhibiting the production of a particular protein. This technology relies on the presence of dsRNA molecules that contain a sequence that is essentially identical to the mRNA of the gene of interest or part thereof and a sequence that is complementary thereto. Conveniently, the dsRNA can be produced from a single promoter in a recombinant vector or host cell, where the sense and anti-sense sequences are covalently joined by a sequence, preferably an unrelated sequence, which enables the sense and anti-sense sequences in the corresponding transcript to hybridize to form the dsRNA molecule with the joining sequence forming a loop structure, although a sequence with identity to the target RNA or its complement can form the loop structure. Typically, the dsRNA is encoded by a double-stranded DNA construct which has sense and antisense sequences in an inverted repeat structure, arranged as an interrupted palindrome, where the repeated sequences are transcribed to produce the hybridising sequences in the dsRNA molecule, and the interrupt sequence is transcribed to form the loop in the dsRNA molecule. The design and production of suitable dsRNA molecules is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology, preferably at least 19 consecutive nucleotides complementary to a region of, a target RNA, to be inactivated. The DNA therefore comprises both sense and antisense sequences that, when transcribed into RNA, can hybridize to form the double stranded RNA region. In one embodiment of the invention, the sense and antisense sequences are separated by a spacer region that comprises an intron which, when transcribed into RNA, is spliced out. This arrangement has been shown to result in a higher efficiency of gene silencing. The double stranded RNA region may comprise one or two RNA molecules, transcribed from either one DNA region or two. The presence of the double stranded molecule is thought to trigger a response from an endogenous system that destroys both the double stranded RNA and also the homologous RNA transcript from the target gene, efficiently reducing or eliminating the activity of the target gene.

The length of the sense and antisense sequences that hybridize should each be at least 19 contiguous nucleotides, corresponding to part of the target mRNA. The full-length sequence corresponding to the entire gene transcript may be used. The degree of identity of the sense and antisense sequences to the targeted transcript should be at least 85%, at least 90%, or at least 95% to 100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the organism in which it is to be introduced, for example, as determined by standard BLAST search.

As an example, a dsRNA of the invention comprises a nucleotide sequence provided as any one of SEQ ID NOs 49 to 51 (where each T is a U).

microRNA

MicroRNAs (abbreviated miRNAs) are generally 19-25 nucleotides (commonly about 20-24 nucleotides in plants)

non-coding RNA molecules that are derived from larger precursors that form imperfect stem-loop structures.

miRNAs bind to complementary sequences on target messenger RNA transcripts (mRNAs), usually resulting in translational repression or target degradation and gene silencing.

In plant cells, miRNA precursor molecules are believed to be initially processed in the nucleus. The pri-miRNA (containing one or more local double-stranded or "hairpin" regions as well as the usual 5' "cap" and polyadenylated tail of an mRNA) is processed to a shorter miRNA precursor molecule that also includes a stem-loop or fold-back structure and is termed the "pre-miRNA". In plants, the pre-miRNAs are cleaved by distinct DICER-like (DCL) enzymes, in particular DCL-1, yielding miRNA:miRNA* duplexes. Prior to transport out of the nucleus, these duplexes are methylated. In contrast, hairpin RNA molecules having longer dsRNA regions are processed in particular by DCL-3 and DCL-4.

In the cytoplasm, the miRNA strand from the miRNA: miRNA duplex is selectively incorporated into an active RNA-induced silencing complex (RISC) for target recognition. The RISC-complexes contain a particular subset of Argonaute proteins that exert sequence-specific gene repression post-transcriptionally (see, for example, Millar and Waterhouse, 2005; Pasquinelli et al., 2005; Almeida and Allshire, 2005).

Cosuppression

Genes can suppress the expression of related endogenous genes and/or transgenes already present in the genome, a phenomenon termed homology-dependent gene silencing. Most of the instances of homology dependent gene silencing fall into two classes—those that function at the level of transcription of the transgene, and those that operate post-transcriptionally.

Post-transcriptional homology-dependent gene silencing (i.e., cosuppression) describes the loss of expression of a transgene and related endogenous or viral genes in transgenic plants. Cosuppression often, but not always, occurs when transgene transcripts are abundant, and it is generally thought to be triggered at the level of mRNA processing, localization, and/or degradation. Several models exist to explain how cosuppression works (see in Taylor, 1997).

Cosuppression involves introducing an extra copy of a gene or a fragment thereof into a plant in the sense orientation with respect to a promoter for its expression. A skilled person would appreciate that the size of the sense fragment, its correspondence to target gene regions, and its degree of sequence identity to the target gene can vary. In some instances, the additional copy of the gene sequence interferes with the expression of the target plant gene. Reference is made to WO 97/20936 and EP 0465572 for methods of implementing co-suppression approaches.

Expression Vector

As used herein, an "expression vector" is a DNA or RNA vector that is capable of transforming a host cell and of effecting expression of one or more specified polynucleotides. Preferably, the expression vector is also capable of replicating within the host cell or being integrated into the host cell genome. Expression vectors are typically viruses or plasmids. Expression vectors of the present invention include any vectors that function (i.e., direct gene expression) in host cells of the present invention, including in fungal, algal, and plant cells.

"Operably linked" as used herein, refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence of a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements such as enhancers, need not be physically contiguous or located in close proximity to the coding sequences whose transcription they enhance.

Expression vectors of the present invention contain regulatory sequences such as transcription control sequences, translation control sequences, origins of replication, and other regulatory sequences that are compatible with the host cell and that control the expression of polynucleotides of the present invention. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the recombinant cells of the present invention. The choice of the regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences are known to those skilled in the art. Particularly preferred transcription control sequences are promoters active in directing transcription in plants, either constitutively or stage and/or tissue specific, depending on the use of the plant or part(s) thereof A number of vectors suitable for stable transfection of plant cells or for the establishment of transgenic plants have been described in for example, Pouwels et al., Cloning Vectors: A Laboratory Manual, 1985, supp. 1987, Weissbach and Weissbach, Methods for Plant Molecular Biology, Academic Press, 1989, and Gelvin et al., Plant Molecular Biology Manual, Kluwer Academic Publishers, 1990. Typically, plant expression vectors include for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants, see for example, WO 84/02913. All of these promoters have been used to create various types of plant-expressible recombinant DNA vectors.

For the purpose of expression in source tissues of the plant such as the leaf, seed, root or stem, it is preferred that the promoters utilized in the present invention have relatively high expression in these specific tissues. For this purpose, one may choose from a number of promoters for genes with tissue- or cell-specific, or -enhanced expression. Examples of such promoters reported in the literature include, the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from *Arabidopsis thaliana.*

A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter), (3) hormones such as abscisic acid, (4) wounding (e.g., WunI), or (5) chemicals such as methyl jasmonate, salicylic acid, steroid hormones, alcohol, Safeners (WO 97/06269), or it may also be advantageous to employ (6) organ-specific promoters.

As used herein, the term "plant storage organ specific promoter" refers to a promoter that preferentially, when compared to other plant tissues, directs gene transcription in a storage organ of a plant. The plant storage organ is preferably a seed. Preferably, the promoter only directs expression of a gene of interest in the storage organ, and/or expression of the gene of interest in other parts of the plant such as leaves is not detectable by Northern blot analysis and/or RT-PCR. Typically, the promoter drives expression of genes during growth and development of the storage organ, in particular during the phase of synthesis and accumulation of storage compounds in the storage organ. Such promoters may drive gene expression in the entire plant storage organ or only part thereof such as the seedcoat, embryo or cotyledon(s) in seeds of dicotyledonous plants or the endosperm or aleurone layer of seeds of monocotyledonous plants.

Other promoters can also be used to express a protein in specific tissues such as seeds or fruits. The promoter for β-conglycinin or other seed-specific promoters such as the napin, zein, linin and phaseolin promoters, can be used. In one embodiment, the promoter directs expression in tissues and organs in which lipid biosynthesis take place. Such promoters act in seed development at a suitable time for modifying lipid composition in seeds. In one embodiment, the plant storage organ specific promoter is a seed specific promoter. In a more preferred embodiment, the promoter preferentially directs expression in the embryo and/or cotyledons of a dicotyledonous plant or in the endosperm of a monocotyledonous plant, relative to expression in other organs in the plant such as leaves. Preferred promoters for seed-specific expression include: 1) promoters from genes encoding enzymes involved in lipid biosynthesis and accumulation in seeds such as desaturases and elongases, 2) promoters from genes encoding seed storage proteins, and 3) promoters from genes encoding enzymes involved in carbohydrate biosynthesis and accumulation in seeds. Seed specific promoters which are suitable are, a flax linin promoter (e.g. Cnl1 or Cnl2 promoters) the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230), or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998), Potenza et al. (2004), US 20070192902 and US 20030159173. In an embodiment, the seed specific promoter is preferentially expressed in defined parts of the seed such as the embryo, cotyledon(s) or the endosperm. Examples of cotyledon specific promoters include, but are not limited to, the FP1 promoter (Ellerstrom et al., 1996), the pea legumin promoter (Perrin et al., 2000), and the bean phytohemagglutnin promoter (Perrin et al., 2000). In a further embodiment, the seed specific promoter is not expressed, or is only expressed at a low level, in the embryo and/or after the seed germinates.

When there are multiple promoters present, each promoter may independently be the same or different.

The 5' non-translated leader sequence can be derived from the promoter selected to express the heterologous gene sequence of the polynucleotide, or may be heterologous with respect to the coding region of the enzyme to be produced, and can be specifically modified if desired so as to increase translation of mRNA.

The termination of transcription is accomplished by a 3' non-translated DNA sequence operably linked in the expression vector to the polynucleotide of interest.

The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in, for example, plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Recombinant DNA technologies can be used to improve expression of a transformed polynucleotide by manipulating for example, the number of copies of the polynucleotide within a host cell, the efficiency with which those polynucleotide are transcribed, the efficiency with which the resultant transcripts are translated, and the efficiency of post-translational modifications.

To facilitate identification of transformants, the recombinant vector desirably comprises a selectable or screenable marker gene as, or in addition to, the nucleic acid sequence of a polynucleotide defined herein. By "marker gene" is meant a gene that imparts a distinct phenotype to cells expressing the marker gene and thus, allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, that is, by "screening" (e.g., β-glucuronidase, luciferase, GFP or other enzyme activity not present in untransformed cells). The marker gene and the nucleotide sequence of interest do not have to be linked, since co-transformation of unlinked genes as for example, described in U.S. Pat. No. 4,399,216, is also an efficient process in for example, plant transformation. The actual choice of a marker is not crucial as long as it is functional (i.e., selective) in combination with the cells of choice such as a plant cell.

Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as for example, described in EP 256223; a glutamine synthetase gene conferring, upon overexpression, resistance to glutamine synthetase inhibitors such as phosphinothricin as for example, described in WO 87/05327; an acetyltransferase gene from *Streptomyces viridochromogenes* conferring resistance to the selective agent phosphinothricin as for example, described in EP 275957; a gene encoding a 5-enolshikimate-3-phosphate synthase (EPSPS) conferring tolerance to N-phosphonomethylglycine as for example, described by Hinchee et al. (1988); a bar gene conferring resistance against bialaphos as for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS) which confers resistance to imidazolinone, sulfonylurea, or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985) which may be employed in calcium-sensitive bioluminescence detection; a green fluorescent protein gene (Niedz et al., 1995) or derivatives thereof; or a luciferase (luc) gene (Ow et al., 1986) which allows for bioluminescence detection. By "reporter molecule" it is meant a molecule that, by its chemical nature, provides an analytically identifiable signal that facilitates determination of promoter activity by reference to protein product.

Preferably, the recombinant vector is stably incorporated into the genome of the cell such as the plant cell. Accordingly, the recombinant vector may comprise appropriate elements which allow the vector to be incorporated into the genome, or into a chromosome of the cell.

Transfer Nucleic Acids

Transfer nucleic acids can be used to deliver an exogenous polynucleotide to a cell and comprise one, preferably two, border sequences and a polynucleotide of interest. The transfer nucleic acid may or may not encode a selectable marker. Preferably, the transfer nucleic acid forms part of a binary vector in a bacterium, where the binary vector further comprises elements which allow replication of the vector in the bacterium, selection, or maintenance of bacterial cells containing the binary vector. Upon transfer to a eukaryotic cell, the transfer nucleic acid component of the binary vector is capable of integration into the genome of the eukaryotic cell.

As used herein, the term "extrachromosomal transfer nucleic acid" refers to a nucleic acid molecule that is capable of being transferred from a bacterium such as *Agrobacterium* sp., to a eukaryotic cell such as a plant cell. An extrachromosomal transfer nucleic acid is a genetic element that is well-known as an element capable of being transferred, with the subsequent integration of a nucleotide sequence contained within its borders into the genome of the recipient cell. In this respect, a transfer nucleic acid is flanked, typically, by two "border" sequences, although in some instances a single border at one end can be used and the second end of the transferred nucleic acid is generated randomly in the transfer process. A polynucleotide of interest is typically positioned between the left border-like sequence and the right border-like sequence of a transfer nucleic acid. The polynucleotide contained within the transfer nucleic acid may be operably linked to a variety of different promoter and terminator regulatory elements that facilitate its expression, that is, transcription and/or translation of the polynucleotide. Transfer DNAs (T-DNAs) from *Agrobacterium* sp. such as *Agrobacterium tumefaciens* or *Agrobacterium rhizogenes*, and man made variants/mutants thereof are probably the best characterized examples of transfer nucleic acids. Another example is P-DNA ("plant-DNA") which comprises T-DNA border-like sequences from plants.

As used herein, "T-DNA" refers to for example, T-DNA of an *Agrobacterium tumefaciens* Ti plasmid or from an *Agrobacterium rhizogenes* Ri plasmid, or man made variants thereof which function as T-DNA. The T-DNA may comprise an entire T-DNA including both right and left border sequences, but need only comprise the minimal sequences required in cis for transfer, that is, the right and T-DNA border sequence. The T-DNAs of the invention have inserted into them, anywhere between the right and left border sequences (if present), the polynucleotide of interest. The sequences encoding factors required in trans for transfer of the T-DNA into a plant cell such as vir genes, may be inserted into the T-DNA, or may be present on the same replicon as the T-DNA, or preferably are in trans on a compatible replicon in the *Agrobacterium* host. Such "binary vector systems" are well known in the art.

As used herein, "P-DNA" refers to a transfer nucleic acid isolated from a plant genome, or man made variants/mutants thereof, and comprises at each end, or at only one end, a T-DNA border-like sequence. The border-like sequence preferably shares at least 50%, at least 60%, at least 70%, at least 75%, at least 80%, at least 90%, or at least 95%, but less than 100% sequence identity, with a T-DNA border sequence from an *Agrobacterium* sp. such as *Agrobacterium tumefaciens* or *Agrobacterium rhizogenes*. Thus, P-DNAs can be used instead of T-DNAs to transfer a nucleotide sequence contained within the P-DNA from, for example *Agrobacterium*, to another cell. The P-DNA, before insertion of the exogenous polynucleotide which is to be transferred, may be modified to facilitate cloning and should preferably not encode any proteins. The P-DNA is characterized in that it contains, at least a right border sequence and preferably also a left border sequence.

As used herein, a "border" sequence of a transfer nucleic acid can be isolated from a selected organism such as a plant or bacterium, or be a man made variant/mutant thereof. The border sequence promotes and facilitates the transfer of the polynucleotide to which it is linked and may facilitate its integration in the recipient cell genome. In an embodiment, a border-sequence is between 5-100 base pairs (bp) in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length. Border sequences from T-DNA from *Agrobacterium* sp. are well known in the art and include those described in Lacroix et al. (2008), Tzfira and Citovsky (2006) and Glevin (2003).

Whilst traditionally only *Agrobacterium* sp. have been used to transfer genes to plants cells, there are now a large number of systems which have been identified/developed which act in a similar manner to *Agrobacterium* sp. Several non-*Agrobacterium* species have recently been genetically modified to be competent for gene transfer (Chung et al., 2006; Broothaerts et al., 2005). These include *Rhizobium* sp. NGR234, *Sinorhizobium meliloti* and *Mezorhizobium loti*. The bacteria are made competent for gene transfer by providing the bacteria with the machinery needed for the transformation process, that is, a set of virulence genes encoded by an *Agrobacterium* Ti-plasmid and the T-DNA segment residing on a separate, small binary plasmid. Bacteria engineered in this way are capable of transforming different plant tissues (leaf disks, calli and oval tissue), monocots or dicots, and various different plant species (e.g., tobacco, rice).

As used herein, the terms "transfection", "transformation" and variations thereof are generally used interchangeably. "Transfected" or "transformed" cells may have been manipulated to introduce the polynucleotide(s) of interest, or may be progeny cells derived therefrom.

Recombinant Cells

The invention also provides a recombinant cell, for example, a recombinant plant cell, which is a host cell transformed with one or more polynucleotides or vectors defined herein, or combination thereof. The term "recombinant cell" is used interchangeably with the term "transgenic cell" herein. Suitable cells of the invention include any cell that can be transformed with a polynucleotide or recombinant vector of the invention, encoding for example, a polypeptide or enzyme described herein. The cell is preferably a cell which is thereby capable of being used for producing lipid. The recombinant cell may be a cell in culture, a cell in vitro, or in an organism such as for example, a plant, or in an organ such as, for example, a seed or a leaf. Preferably, the cell is in a plant, more preferably in the seed of a plant, more preferably in the seed of an oilseed plant such as safflower. In an embodiment, the plant cell comprises lipid or oil having the fatty acid composition as described herein.

Host cells into which the polynucleotide(s) are introduced can be either untransformed cells or cells that are already transformed with at least one nucleic acid. Such nucleic acids may be related to lipid synthesis, or unrelated. Host cells of the present invention either can be endogenously (i.e., naturally) capable of producing polypeptide(s) defined herein, in which case the recombinant cell derived therefrom has an enhanced capability of producing the polypeptide(s), or can be capable of producing said polypeptide(s) only after being transformed with at least one polynucleotide of the invention. In an embodiment, a recombinant cell of the invention has an enhanced capacity to produce non-polar lipid. The cells may be prokaryotic or eukaryotic. Preferred host cells are yeast, algal and plant cells. In a preferred embodiment, the plant cell is a seed cell, in particular, a cell in a cotyledon or endosperm of a seed. Examples of algal cells useful as host cells of the present invention include, for example, *Chlamydomonas* sp. (for example, *Chiamydomonas reinhardtii*), *Dunaliella* sp., *Haematococcus* sp., *Chlorella* sp., *Thraustochytrium* sp., *Schizochytrium* sp., and *Volvox* sp.

The host cells may be of an organism suitable for a fermentation process, such as, for example, *Yarrowia lipolytica* or other yeasts.

Transgenic Plants

The invention also provides a plant comprising an exogenous polynucleotide or polypeptide of the invention, a cell of the invention, a vector of the invention, or a combination thereof. The term "plant" refers to whole plants, whilst the term "part thereof" refers to plant organs (e.g., leaves, stems, roots, flowers, fruit), single cells (e.g., pollen), seed, seed parts such as an embryo, endosperm, scutellum or seed coat, plant tissue such as vascular tissue, plant cells and progeny of the same. As used herein, plant parts comprise plant cells.

As used herein, the term "plant" is used in it broadest sense. It includes, but is not limited to, any species of grass, ornamental or decorative plant, crop or cereal (e.g., oilseed plants, maize, soybean), fodder or forage, fruit or vegetable plant, herb plant, woody plant, flower plant, or tree. It is not meant to limit a plant to any particular structure. It also refers to a unicellular plant (e.g., microalga). The term "part thereof" in reference to a plant refers to a plant cell and progeny of same, a plurality of plant cells that are largely differentiated into a colony (e.g., volvox), a structure that is present at any stage of a plant's development, or a plant tissue. Such structures include, but are not limited to, leaves, stems, flowers, fruits, nuts, roots, seed, seed coat, embryos. The term "plant tissue" includes differentiated and undifferentiated tissues of plants including those present in leaves, stems, flowers, fruits, nuts, roots, seed, for example, embryonic tissue, endosperm, dermal tissue (e.g., epidermis, periderm), vascular tissue (e.g., xylem, phloem), or ground tissue (comprising parenchyma, collenchyma, and/or sclerenchyma cells), as well as cells in culture (e.g., single cells, protoplasts, callus, embryos, etc.). Plant tissue may be in planta, in organ culture, tissue culture, or cell culture.

A "transgenic plant", "genetically modified plant" or variations thereof refers to a plant that contains a transgene not found in a wild-type plant of the same species, variety or cultivar. Transgenic plants as defined in the context of the present invention include plants and their progeny which have been genetically modified using recombinant techniques to cause production of at least one polypeptide defined herein in the desired plant or part thereof "Transgenic plant parts" has a corresponding meaning.

The terms "seed" and "grain" are related terms as used herein, and have overlapping meanings. "Grain" refers to mature grain such as harvested grain or grain which is still on a plant but ready for harvesting, but can also refer to grain after imbibition or germination, according to the context. Mature grain commonly has a moisture content of less than about 18-20%. "Seed" includes "developing seed" as well as "grain" which is mature grain, but not grain after imbibition or germination. "Developing seed" as used herein refers to a seed prior to maturity, typically found in the reproductive structures of the plant after fertilisation or anthesis, but can also refer to such seeds prior to maturity which are isolated from a plant. Seed development in planta is typically divided into early-, mid-, and late phases of development.

As used herein, the term "plant storage organ" refers to a part of a plant specialized to store energy in the form of for example, proteins, carbohydrates, lipid. Examples of plant storage organs are seed, fruit, tuberous roots, and tubers. A preferred plant storage organ of the invention is seed.

As used herein, the term "vegetative tissue" or "vegetative plant part" or variants thereof is any plant tissue, organ or part that does not include the organs for sexual reproduction of plants or the seed bearing organs or the closely associated tissues or organs such as flowers, fruits and seeds. Vegetative tissues and parts include at least plant leaves, stems (including bolts and tillers but excluding the heads), tubers and roots, but excludes flowers, pollen, seed including the seed coat, embryo and endosperm, fruit including mesocarp tissue, seed-bearing pods and seed-bearing heads. In one embodiment, the vegetative part of the plant is an aerial plant part. In another or further embodiment, the vegetative plant part is a green part such as a leaf or stem. Vegetative parts include those parts principally involved in providing or supporting the photosynthetic capacity of the plant or related function, or anchoring the plant.

As used herein, the term "phenotypically normal" refers to a genetically modified plant or part thereof, particularly a storage organ such as a seed of the invention not having a significantly reduced ability to grow and reproduce when compared to an unmodified plant or plant thereof. In an embodiment, the genetically modified plant or part thereof which is phenotypically normal comprises at least one exogenous polynucleotide as defined herein and has an ability to grow or reproduce which is essentially the same as a corresponding plant or part thereof not comprising said polynucleotide(s). Preferably, the biomass, growth rate, germination rate, storage organ size, seed size and/or the number of viable seeds produced is not less than 90% of that of a plant lacking said exogenous polynucleotide when grown under identical conditions. This term does not encompass features of the plant which may be different to the wild-type plant but which do not effect the usefulness of the plant for commercial purposes.

Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. The plants may be vegetable or ornamental plants. The plants of the invention may be: safflower (*Carthamus tinctorius*), corn (*Zea mays*), canola (*Brassica napus, Brassica rapa* ssp.), other Brassicas such as, for example, rutabaga (*Brassica napobrassica*), mustard (*Brassica juncea*), Ethiopian mustard (*Brassica carinata*), crambe (*Crambe abyssinica*), camelina (*Camelina sativa*), sugarbeet (*Beta vulgaris*), clover (*Trifolium* sp.), flax (*Linum usitatissimum*), alfalfa (*Medicago sativa*), rice (*Oryza sativa*), rye (*Secale cerale*), sorghum (*Sorghum bicolor, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardiurn occidentale*), macadamia (*Macadamia intergrifolia*), almond (*Prunus amygdalus*), jatropha (*Jatropha curcas*), lupins, Eucalypts, palm, nut sage, pongamia, oats, or barley.

Other preferred plants include C4 grasses such as *Andropogon gerardi, Bouteloua curtipendula, B. gracilis, Buchloe dactyloides, Panicum virgatum, Schizachyrium scoparium, Miscanthus* species for example, *Miscanthus* x *giganteus* and *Miscanthus sinensis, Sorghastrum nutans, Sporobolus cryptandrus*, Switchgrass (*Panicum virgatum*), sugarcane (*Saccharum officinarum*), Brachyaria; C3 grasses such as *Elymus canadensis*, the legumes *Lespedeza capitata* and *Petalostemum villosum*, the forb *Aster azureus*; and woody plants such as *Quercus ellipsoidalis* and *Q. macrocarpa.*

In a preferred embodiment, the plant is an angiosperm.

In a preferred embodiment, the plant is an oilseed plant, preferably an oilseed crop plant. As used herein, an "oilseed plant" is a plant species used for the commercial production of lipid from the seeds of the plant. "Commercial production" herein means the production of lipid, preferably oil, for sale in return for revenue. The oilseed plant may be oil-seed rape (such as canola), maize, sunflower, safflower, soybean, sorghum, flax (linseed) or sugar beet. Furthermore, the oilseed plant may be other Brassicas, cotton, peanut, poppy, rutabaga, mustard, castor bean, sesame, safflower, or nut producing plants. The plant may produce high levels of lipid in its fruit such as olive, oil palm or coconut. Horticultural plants to which the present invention may be applied are lettuce, endive, or vegetable Brassicas including cabbage, broccoli, or cauliflower. The present invention may be applied in tobacco, cucurbits, carrot, strawberry, tomato, or pepper. More preferred plants are oilseed plants whose developing seeds are non-photosynthetic, also referred to as "white seeds" plants, such as safflower, sunflower, cotton and castor.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene such as for example, in F1 progeny which have been grown from hybrid seed. Such plants may provide advantages such as hybrid vigour, well known in the art.

Transformation of Plants

Transgenic plants can be produced using techniques known in the art, such as those generally described in Slater et al., Plant Biotechnology—The Genetic Manipulation of Plants, Oxford University Press (2003), and Christou and Klee, Handbook of Plant Biotechnology, John Wiley and Sons (2004).

As used herein, the terms "stably transforming", "stably transformed" and variations thereof refer to the integration of the polynucleotide into the genome of the cell such that they are transferred to progeny cells during cell division without the need for positively selecting for their presence. Stable transformants, or progeny thereof, can be selected and/or identified by any means known in the art such as Southern blots on chromosomal DNA, or in situ hybridization of genomic DNA.

*Agrobacterium*-mediated transfer is a widely applicable system for introducing genes into plant cells because DNA can be introduced into cells in whole plant tissues, plant organs, or explants in tissue culture, for either transient expression, or for stable integration of the DNA in the plant cell genome. The use of *Agrobacterium*-mediated plant integrating vectors to introduce DNA into plant cells is well known in the art (see for example, U.S. Pat. Nos. 5,177,010, 5,104,310, 5,004,863, or U.S. Pat. No. 5,159,135). The region of DNA to be transferred is defined by the border sequences, and the intervening DNA (T-DNA) is usually inserted into the plant genome. Further, the integration of the T-DNA is a relatively precise process resulting in few rearrangements. In those plant varieties where *Agrobacterium*-mediated transformation is efficient, it is the method of choice because of the facile and defined nature of the gene transfer. Preferred *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985)).

Acceleration methods that may be used include for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Such methods are well known in the art. In another embodiment, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986). Other methods of cell transformation can also be used and include but are not limited to the introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polynucleotide is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908), soybean (U.S. Pat. Nos. 5,569,834, 5,416,011), *Brassica* (U.S. Pat. No. 5,463,174), peanut (Cheng et al., 1996), and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, PCT/US97/10621, U.S. Pat. Nos. 5,589,617, 6,541,257. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

A transgenic plant formed using *Agrobacterium* or other transformation methods typically contains a single transgenic locus on one chromosome. Such transgenic plants can be referred to as being hemizygous for the added gene(s). More preferred is a transgenic plant that is homozygous for the added gene(s), that is, a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

For the transformation of safflower, particularly useful methods are described by Belide et al. (2011).

Tilling

In one embodiment, TILLING (Targeting Induced Local Lesions IN Genomes) can be used to produce plants in which endogenous genes are knocked out, for example genes encoding a Δ12 desaturase, a palmitoyl-ACP thioesterase, a ω6 or a Δ6 desaturase activity, or a combination of two or more thereof.

In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cell, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique. TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Mutagenesis Procedures

Techniques for generating mutant plant lines are known in the art. Examples of mutagens that can be used for generating mutant plants include irradiation and chemical mutagenesis. Mutants may also be produced by techniques such as T-DNA insertion and transposon-induced mutagenesis. Mutations in any desired gene in a plant, can be introduced in a site-specific manner by artificial zinc finger nuclease (ZFN), TAL effector (TALEN) or CRISPR technologies (using a Cas9 type nuclease) as known in the art. The mutagenesis procedure may be performed on any parental cell of a plant, for example a seed or a parental cell in tissue culture.

Chemical mutagens are classifiable by chemical properties, e.g., alkylating agents, cross-linking agents, etc. Useful chemical mutagens include, but are not limited to, N-ethyl-N-nitrosourea (ENU); N-methyl-N-nitrosourea (MNU); procarbazine hydrochloride; chlorambucil; cyclophosphamide; methyl methanesulfonate (MMS); ethyl methanesulfonate (EMS); diethyl sulfate; acrylamide monomer; triethylene melamine (TEM); melphalan; nitrogen mustard; vincristine; dimethylnitrosamine; N-methyl-N'-nitro-Nitrosoguani-dine (MNNG); 7,12 dimethylbenzanthracene (DMBA); ethylene oxide; hexamethylphosphoramide; and bisulfan.

An example of suitable irradiation to induce mutations is by gamma radiation, such as that supplied by a Cesium 137 source. The gamma radiation preferably is supplied to the plant cells in a dosage of approximately 60 to 200 Krad., and most preferably in a dosage of approximately 60 to 90 Krad.

Plants are typically exposed to a mutagen for a sufficient duration to accomplish the desired genetic modification but insufficient to completely destroy the viability of the cells and their ability to be regenerated into a plant.

The mutagenesis procedures described above typically result in the generation of mutants in a gene of interest at a frequency of at least 1 in 1000 plants, which means that screening of mutagenised populations of the plants is a practicable means to identify mutants in any gene of interest. The identification of mutants can also be achieved by massively parallel nucleotide sequencing technologies.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed “embryo rescue”, used in combination with DNA extraction at the three leaf stage and analysis for the desired genotype allows rapid selection of plants carrying the desired trait, which may be nurtured to maturity in the greenhouse or field for subsequent further backcrossing to the recurrent parent.

Any molecular biological technique known in the art which is capable of detecting a FAD2, FATB or FAD6 gene can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of (for example) a FAD2, FATB or FAD6 gene which confer the desired phenotype. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al. (2001).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from plant cells. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et al. (supra). Sequencing can be carried out by any suitable method, for example, dideoxy sequencing, chemical sequencing or variations thereof. Direct sequencing has the advantage of determining variation in any base pair of a particular sequence.

Hybridization based detection systems include, but are not limited to, the TaqMan assay and molecular beacon assay (U.S. Pat. No. 5,925,517). The TaqMan assay (U.S. Pat. No. 5,962,233) uses allele specific (ASO) probes with a donor dye on one end and an acceptor dye on the other end such that the dye pair interact via fluorescence resonance energy transfer (FRET).

In one embodiment, the method described in Example 7 is used in selection and breeding programs to identify and select safflower plants with the ol mutation. For instance, the method comprises performing an amplification reaction on genomic DNA obtained from the plant using one or both of the following sets of primers;

```
i) 5'-ATAAGGCTGTGTTCACGGGTTT-3'   (SEQ ID NO: 140)
and

5'-GCTCAGTTGGGGATACAAGGAT-3',     (SEQ ID NO: 141)
and

ii) 5'-AGTTATGGTTCGATGATCGACG-3'  (SEQ ID NO: 142)
and

5'-TTGCTATACATATTGAAGGCACT -3.    (SEQ ID NO: 143)
```

Polypeptides

The terms "polypeptide" and "protein" are generally used interchangeably. A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length. The polypeptide or class of polypeptides may have the same enzymatic activity as, or a different activity than, or lack the activity of, the reference polypeptide. Preferably, the polypeptide has an enzymatic activity of at least 10% of the activity of the reference polypeptide.

As used herein a "biologically active fragment" is a portion of a polypeptide of the invention which maintains a defined activity of a full-length reference polypeptide for example, Δ12 desaturase, palmitoyl-ACP thioesterase or Δ6 desaturase activity. Biologically active fragments as used herein exclude the full-length polypeptide. Biologically active fragments can be any size portion as long as they maintain the defined activity. Preferably, the biologically active fragment maintains at least 10% of the activity of the full length polypeptide.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 50%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides defined herein can be prepared by introducing appropriate nucleotide changes into a nucleic acid defined herein, or by in vitro synthesis of the desired polypeptide. Such mutants include for example, deletions, insertions, or substitutions of residues within the amino acid sequence. A combination of deletions, insertions and substitutions can be made to arrive at the final construct, provided that the final polypeptide product possesses the desired characteristics.

Mutant (altered) polypeptides can be prepared using any technique known in the art, for example, using directed evolution or rationale design strategies (see below). Products derived from mutated/altered DNA can readily be screened using techniques described herein to determine if they possess, or lack, Δ12 desaturase, palmitoyl-ACP thioesterase or ω6 Δ6 desaturase activity.

In designing amino acid sequence mutants, the location of the mutation site and the nature of the mutation will depend on characteristic(s) to be modified. The sites for mutation can be modified individually or in series for example, by (1) substituting first with conservative amino acid choices and then with more radical selections depending upon the results achieved, (2) deleting the target residue, or (3) inserting other residues adjacent to the located site. As the skilled person will appreciate, the use of non-conservative substitutions can be used when producing a mutant with reduced enzymatic activity.

Amino acid sequence deletions generally range from about 1 to 15 residues, more preferably about 1 to 10 residues and typically about 1 to 5 contiguous residues, but may be much longer particularly when the mutant is designed to reduce enzymatic activity.

Substitution mutants have at least one amino acid residue in the polypeptide removed and a different residue inserted in its place. The sites of greatest interest for substitutional mutagenesis to inactivate an enzyme include sites identified as the active site(s). Other sites of interest are those in which particular residues obtained from various strains or species are identical. These positions may be important for biological activity. Conservative substitutions are shown in Table 1, while non-conservative substitutions are substitutions which are not conservative substitutions. In one embodiment, a polypeptide of the invention is a Δ12 desaturase and which comprises amino acids having a sequence as provided in any one of SEQ ID NOs: 27 to 34, 36 or 37, a biologically active fragment thereof, or an amino acid sequence which is at least 40% identical to any one or more of SEQ ID NOs: NOs: 27 to 34, 36 or 37.

In another embodiment, a polypeptide of the invention is oleate Δ12 desaturase present in the seed (oilseed) of an oilseed plant which comprises amino acids having a sequence as provided in any one of SEQ ID NOs: 27, 28 or 36, a biologically active fragment thereof, or an amino acid sequence which is at least 40% identical to any one or more of SEQ ID NOs: 27, 28 or 36.

In another embodiment, a polypeptide of the invention is a Δ12-acetylenase which comprises amino acids having a sequence as provided in SEQ ID NO:37, a biologically active fragment thereof, or an amino acid sequence which is at least 40% identical to SEQ ID NO:37.

In another embodiment, a polypeptide of the invention is a palmitoleate Δ12 desaturase which comprises amino acids having a sequence as provided in SEQ ID NO:35, a biologically active fragment thereof, or an amino acid sequence which is at least 40% identical to SEQ ID NO:35.

In another embodiment, a polypeptide of the invention is a palmitoyl-ACP thioesterase (FATB) which comprises amino acids having a sequence as provided in any one of SEQ ID NOs: 44 or 45, a biologically active fragment thereof, or an amino acid sequence which is at least 40% identical to any one or more of SEQ ID NOs: 44 or 45.

TABLE 1

Conservative substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In another embodiment, a polypeptide of the invention is a palmitoyl-ACP thioesterase (FATB) present in the seed of an oilseed plant which comprises amino acids having a sequence as provided in SEQ ID NO:45, a biologically active fragment thereof, or an amino acid sequence which is at least 40% identical to SEQ ID NO:45.

In another embodiment, a polypeptide of the invention is a 46 desaturase which comprises amino acids having a sequence as provided in SEQ ID NO:48, a biologically active fragment thereof, or an amino acid sequence which is at least 40% identical to SEQ ID NO:48.

Preferred features of the enzymes of the invention are provided in the Examples section, in particular Example 2 in relation to safflower FAD2's.

Polypeptides as described herein may be expressed as a fusion to at least one other polypeptide. In a preferred embodiment, the at least one other polypeptide is selected from the group consisting of: a polypeptide that enhances the stability of the fusion protein, and a polypeptide that assists in the purification of the fusion protein.

Production of Lipids and/or Oils High in Oleic Acid

Techniques that are routinely practiced in the art can be used to extract, process, purify and analyze the lipids produced by the plants, in particular the seeds, of the instant invention. Such techniques are described and explained throughout the literature in sources such as, Fereidoon Shahidi, Current Protocols in Food Analytical Chemistry, John Wiley & Sons, Inc. (2001) D1.1.1-D1.1.11, and Perez-Vich et al. (1998).

Production of Seedoil

Typically, plant seeds are cooked, pressed, and/or extracted to produce crude seedoil, which is then degummed, refined, bleached, and deodorized. Generally, techniques for crushing seed are known in the art. For example, oilseeds can be tempered by spraying them with water to raise the moisture content to, for example, 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the lipid droplets, and agglomerates protein particles, all of which facilitate the extraction process.

In an embodiment, the majority of the seedoil is released by passage through a screw press. Cakes expelled from the screw press are then solvent extracted for example, with hexane, using a heat traced column. Alternatively, crude seedoil produced by the pressing operation can be passed through a settling tank with a slotted wire drainage top to remove the solids that are expressed with the seedoil during the pressing operation. The solid residue from the pressing and extraction, after removal of the hexane, is the seedmeal, which is typically used as animal feed. The clarified seedoil can be passed through a plate and frame filter to remove any remaining fine solid particles. If desired, the seedoil recovered from the extraction process can be combined with the clarified seedoil to produce a blended crude seedoil.

Once the solvent is stripped from the crude seedoil, the pressed and extracted portions are combined and subjected to normal lipid processing procedures such as, for example, degumming, caustic refining, bleaching, and deodorization. Some or all steps may be omitted, depending on the nature of the product path, e.g. for feed grade oil, limited treatment may be needed whereas for oleochemical applications, more purification steps are required.

Degumming

Degumming is an early step in the refining of oils and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and triacylglycerols and is also known as lecithin. Degumming can be performed by addition of concentrated phosphoric acid to the crude seedoil to convert non-hydratable phosphatides to a hydratable form, and to chelate minor metals that are present. Gum is separated from the seedoil by centrifugation.

Alkali Refining

Alkali refining is one of the refining processes for treating crude oil, sometimes also referred to as neutralization. It usually follows degumming and precedes bleaching. Following degumming, the seedoil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments (carotenoids, chlorophyll, gossypol etc), and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the seedoil at a rate of about 0.1 ml/minute/100 ml of seedoil. After about 30 minutes of sparging, the seedoil is allowed to cool under vacuum. The seedoil is typically transferred to a glass container and flushed with argon before being stored under refrigeration. This treatment improves the colour of the seedoil and removes a majority of the volatile substances or odorous compounds including any remaining free fatty acids, monoacylglycerols and oxidation products.

Winterisation

Winterization is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Transesterification

Transesterification is a process that exchanges the fatty acids within and between TAGs, initially by releasing fatty acids from the TAGs either as free fatty acids or as fatty acid esters, usually fatty acid ethyl esters. When combined with a fractionation process, transesterification can be used to modify the fatty acid composition of lipids (Marangoni et al., 1995). Transesterification can use either chemical or enzymatic means, the latter using lipases which may be position-specific (sn-1/3 or sn-2 specific) for the fatty acid on the TAG, or having a preference for some fatty acids over others (Speranza et al, 2012). The fatty acid fractionation to increase the concentration of LC-PUFA in an oil can be achieved by any of the methods known in the art, such as, for example, freezing crystallization, complex formation using urea, molecular distillation, supercritical fluid extraction and silver ion complexing. Complex formation with urea is a preferred method for its simplicity and efficiency in reducing the level of saturated and monounsaturated fatty acids in the oil (Gamez et al., 2003). Initially, the TAGs of the oil are split into their constituent fatty acids, often in the form of fatty acid esters, by hydrolysis or by lipases and these free fatty acids or fatty acid esters are then mixed with an ethanolic solution of urea for complex formation. The saturated and monounsaturated fatty acids easily complex with urea and crystallize out on cooling and may subsequently be removed by filtration. The non-urea complexed fraction is thereby enriched with LC-PUFA.

Hydrogenation

Hydrogenation of fatty acids involves treatment with hydrogen, typically in the presence of a catalyst. Non-catalytic hydrogenation takes place only at very high temperatures.

Hydrogenation is commonly used in the processing of plant oils. Hydrogenation converts unsaturated fatty acids to saturated fatty acids, and in some cases, trans fats. Hydrogenation results in the conversion of liquid plant oils to solid or semi-solid fats, such as those present in margarine. Changing the degree of saturation of the fat changes some important physical properties such as the melting range, which is why liquid oils become semi-solid. Solid or semi-solid fats are preferred for baking because the way the fat mixes with flour produces a more desirable texture in the baked product. Because partially hydrogenated vegetable oils are cheaper than animal source fats, are available in a wide range of consistencies, and have other desirable characteristics (e.g., increased oxidative stability/longer shelf life), they are the predominant fats used as shortening in most commercial baked goods.

In an embodiment, the lipid/oil of the invention has not been hydrogenated. An indication that a lipid or oil has not been hydrogenated is the absence of any trans fatty acids in its TAG.

Uses of Lipids

The lipids such as the seedoil, preferably the safflower seedoil, produced by the methods described herein have a variety of uses. In some embodiments, the lipids are used as food oils. In other embodiments, the lipids are refined and used as lubricants or for other industrial uses such as the synthesis of plastics. It may be used in the manufacture of cosmetics, soaps, fabric softeners, electrical insulation or detergents. It may be used to produce agricultural chemicals such as surfactants or emulsifiers. In some embodiments, the lipids are refined to produce biodiesel. The oil of the invention may advantageously be used in paints or varnishes since the absence of linolenic acid means it does not discolour easily.

An industrial product produced using a method of the invention may be a hydrocarbon product such as fatty acid esters, preferably fatty acid methyl esters and/or a fatty acid ethyl esters, an alkane such as methane, ethane or a longer-chain alkane, a mixture of longer chain alkanes, an alkene, a biofuel, carbon monoxide and/or hydrogen gas, a bioalcohol such as ethanol, propanol, or butanol, biochar, or a combination of carbon monoxide, hydrogen and biochar. The industrial product may be a mixture of any of these components, such as a mixture of alkanes, or alkanes and alkenes, preferably a mixture which is predominantly (>50%) C4-C8 alkanes, or predominantly C6 to C10 alkanes, or predominantly C6 to C8 alkanes. The industrial product is not carbon dioxide and not water, although these molecules may be produced in combination with the industrial product. The industrial product may be a gas at atmospheric pressure/room temperature, or preferably, a liquid, or a solid such as biochar, or the process may produce a combination of a gas component, a liquid component and a solid component such as carbon monoxide, hydrogen gas, alkanes and biochar, which may subsequently be separated. In an embodiment, the hydrocarbon product is predominantly fatty acid methyl esters. In an alternative embodiment, the hydrocarbon product is a product other than fatty acid methyl esters.

Heat may be applied in the process, such as by pyrolysis, combustion, gasification, or together with enzymatic digestion (including anaerobic digestion, composting, fermentation). Lower temperature gasification takes place at, for example, between about 700° C. to about 1000° C. Higher temperature gasification takes place at, for example, between about 1200° C. to about 1600° C. Lower temperature pyrolysis (slower pyrolysis), takes place at about 400° C., whereas higher temperature pyrolysis takes place at about 500° C. Mesophilic digestion takes place between about 20° C. and about 40° C. Thermophilic digestion takes place from about 50° C. to about 65° C.

Chemical means include, but are not limited to, catalytic cracking, anaerobic digestion, fermentation, composting and transesterification. In an embodiment, a chemical means uses a catalyst or mixture of catalysts, which may be applied together with heat. The process may use a homogeneous catalyst, a heterogeneous catalyst and/or an enzymatic catalyst. In an embodiment, the catalyst is a transition metal catalyst, a molecular sieve type catalyst, an activated alumina catalyst or sodium carbonate as a catalyst. Catalysts include acid catalysts such as sulphuric acid, or alkali catalysts such as potassium or sodium hydroxide or other hydroxides. The chemical means may comprise transesterification of fatty acids in the lipid, which process may use a homogeneous catalyst, a heterogeneous catalyst and/or an enzymatic catalyst. The conversion may comprise pyrolysis, which applies heat and may apply chemical means, and may use a transition metal catalyst, a molecular sieve type catalyst, an activated alumina catalyst and/or sodium carbonate as a catalyst.

Enzymatic means include, but are not limited to, digestion by microorganisms in, for example, anaerobic digestion, fermentation or composting, or by recombinant enzymatic proteins.

Biofuel

As used herein the term "biofuel" includes biodiesel and bioalcohol. Biodiesel can be made from oils derived from plants, algae and fungi. Bioalcohol is produced from the fermentation of sugar. This sugar can be extracted directly from plants (e.g., sugarcane), derived from plant starch (e.g., maize or wheat) or made from cellulose (e.g., wood, leaves or stems).

Biofuels currently cost more to produce than petroleum fuels. In addition to processing costs, biofuel crops require planting, fertilising, pesticide and herbicide applications, harvesting and transportation. Plants, algae and fungi of the present invention may reduce production costs of biofuel.

General methods for the production of biofuel can be found in, for example, Maher and Bressler (2006), Maher and Bressler (2007), Greenwell et al. (2011), Karmakar et al. (2010), Alonso et al. (2010), Lee and Mohamed (2010), Liu et al. (2010), Gong and Jiang (2011), Endalew et al. (2011) and Semwal et al. (2011).

Biodiesel

The production of biodiesel, or alkyl esters, is well known. There are three basic routes to ester production from lipids: 1) Base catalysed transesterification of the lipid with alcohol; 2) Direct acid catalysed esterification of the lipid with methanol; and 3) Conversion of the lipid to fatty acids, and then to alkyl esters with acid catalysis.

Any method for preparing fatty acid alkyl esters and glyceryl ethers (in which one, two or three of the hydroxy groups on glycerol are etherified) can be used. For example, fatty acids can be prepared, for example, by hydrolyzing or saponifying triglycerides with acid or base catalysts, respectively, or using an enzyme such as a lipase or an esterase. Fatty acid alkyl esters can be prepared by reacting a fatty acid with an alcohol in the presence of an acid catalyst. Fatty acid alkyl esters can also be prepared by reacting a triglyceride with an alcohol in the presence of an acid or base catalyst. Glycerol ethers can be prepared, for example, by reacting glycerol with an alkyl halide in the presence of base, or with an olefin or alcohol in the presence of an acid catalyst.

In some preferred embodiments, the lipids are transesterified to produce methyl esters and glycerol. In some preferred embodiments, the lipids are reacted with an alcohol (such as methanol or ethanol) in the presence of a catalyst (for example, potassium or sodium hydroxide) to produce alkyl esters. The alkyl esters can be used for biodiesel or blended with petroleum based fuels.

The alkyl esters can be directly blended with diesel fuel, or washed with water or other aqueous solutions to remove various impurities, including the catalysts, before blending. It is possible to neutralize acid catalysts with base. However, this process produces salt. To avoid engine corrosion, it is preferable to minimize the salt concentration in the fuel additive composition. Salts can be substantially removed from the composition, for example, by washing the composition with water.

In another embodiment, the composition is dried after it is washed, for example, by passing the composition through a drying agent such as calcium sulfate.

In yet another embodiment, a neutral fuel additive is obtained without producing salts or using a washing step, by using a polymeric acid, such as Dowex 50™, which is a resin that contains sulfonic acid groups. The catalyst is easily removed by filtration after the esterification and etherification reactions are complete.

Plant Triacylglycerols as a Biofuel Source

Use of plant triacylglycerols for the production of biofuel is reviewed in Durrett et al. (2008). Briefly, plant oils are primarily composed of various triacylglycerols (TAGs), molecules that consist of three fatty acid chains (usually 18 or 16 carbons long) esterified to glycerol. The fatty acyl chains are chemically similar to the aliphatic hydrocarbons that make up the bulk of the molecules found in petrol and diesel. The hydrocarbons in petrol contain between 5 and 12 carbon atoms per molecule, and this volatile fuel is mixed with air and ignited with a spark in a conventional engine. In contrast, diesel fuel components typically have 10-15 carbon atoms per molecule and are ignited by the very high compression obtained in a diesel engine. However, most plant TAGs have a viscosity range that is much higher than that of conventional diesel: 17.3-32.9 $mm^2 s^{-1}$ compared to 1.9-4.1 $mm^2 s^{-1}$, respectively (ASTM D975; Knothe and Steidley, 2005). This higher viscosity results in poor fuel atomization in modern diesel engines, leading to problems derived from incomplete combustion such as carbon deposition and coking (Ryan et al., 1984). To overcome this problem, TAGs are converted to less viscous fatty acid esters by esterification with a primary alcohol, most commonly methanol. The resulting fuel is commonly referred to as biodiesel and has a dynamic viscosity range from 1.9 to 6.0 $mm^2s^{-1}$ (ASTM D6751). The fatty acid methyl esters (FAMEs) found in biodiesel have a high energy density as reflected by their high heat of combustion, which is similar, if not greater, than that of conventional diesel (Knothe, 2005). Similarly, the cetane number (a measure of diesel ignition quality) of the FAMEs found in biodiesel exceeds that of conventional diesel (Knothe, 2005).

Plant oils are mostly composed of five common fatty acids, namely palmitate (16:0), stearate (18:0), oleate (18:1), linoleate (18:2) and linolenate (18:3), although, depending on the particular species, longer or shorter fatty acids may also be major constituents. These fatty acids differ from each other in terms of acyl chain length and number of double bonds, leading to different physical properties. Consequently, the fuel properties of biodiesel derived from a mixture of fatty acids are dependent on that composition. Altering the fatty acid profile can therefore improve fuel properties of biodiesel such as cold-temperature flow characteristics, oxidative stability and NOx emissions. Altering the fatty acid composition of TAGs may reduce the viscosity of the plant oils, eliminating the need for chemical modification, thus improving the cost-effectiveness of biofuels.

Feedstuffs

The lipid/oil of the invention has advantages in food applications because of its very high oleic acid content and the low levels of linoleic acid (<3.2%) and saturated fatty acids such as palmitic acid, and the essentially zero level of linolenic acid. This provides the oil with a high oxidative stability, producing less rancidity and making it ideal for food applications where heating is required, such as in frying applications, for example for French fries. The oil has a high OSI (oxidative stability index) which is measured as the length of time an oil may be held at 110° C., such as greater than 20 or hours, preferably greater than 30 hours or greater than 50 hours. The low levels of saturated fatty acids relative to other vegetable oils provides for health benefits since saturated fatty acids have been associated with deleterious effects on health. The oils also have essentially zero trans fatty acid content which is desirable in some markets as trans fatty acids have also been associated with negative effects on heart health or raising LDL cholesterol. Moreover, due to its very low level of polyunsaturated fatty acids, the oil does not require hydrogenation to lower the levels of PUFA—such hydrogenation produces trans fatty acids. The oils are also advantageous for reducing the incidence or severity of obesity and diabetes. They are also desirable for food applications in that they contain only naturally occurring fatty acids (Scarth and Tang, 2006).

For purposes of the present invention, "feedstuffs" include any food or preparation for human or animal consumption (including for enteral and/or parenteral consumption) which when taken into the body: (1) serve to nourish or build up tissues or supply energy, and/or (2) maintain, restore or support adequate nutritional status or metabolic function. Feedstuffs of the invention include nutritional compositions for babies and/or young children.

Feedstuffs of the invention comprise for example, a cell of the invention, a plant of the invention, the plant part of the invention, the seed of the invention, an extract of the invention, the product of a method of the invention, or a composition along with a suitable carrier(s). The term "carrier" is used in its broadest sense to encompass any component which may or may not have nutritional value. As the person skilled in the art will appreciate, the carrier must be suitable for use (or used in a sufficiently low concentration) in a feedstuff, such that it does not have deleterious effect on an organism which consumes the feedstuff.

The feedstuff of the present invention comprises a lipid produced directly or indirectly by use of the methods, cells or organisms disclosed herein. The composition may either be in a solid or liquid form. Additionally, the composition may include edible macronutrients, vitamins, and/or minerals in amounts desired for a particular use. The amounts of these or other ingredients will vary depending on whether the composition is intended for use with normal individuals or for use with individuals having specialized needs such as individuals suffering from metabolic disorders and the like.

The foods may be produced by mixing the oil with one or more other ingredients so that the food comprises the oil, or mixed with one or more other ingredients to make a food additive such as salad dressing or mayonnaise. The food or food additive may comprise 1%-10% or more of the oil by weight. The oil may be blended with other vegetable oils to provide for optimal composition or with solid fats or with palm oil to provide semisolid shortening. Foods or food additives produced from the oil include salad dressing, mayonnaise, margarine, bread, cakes, biscuits (cookies), croissants, baked goods, pancakes or pancake mixes, custards, frozen desserts, non-dairy foods.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include, but are not limited to, glucose, edible lactose, and hydrolyzed starch. Additionally, examples of proteins which may be utilized in the nutritional composition of the invention include, but are not limited to, soy proteins, electrodialysed whey, electrodialysed skim milk, milk whey, or the hydrolysates of these proteins.

With respect to vitamins and minerals, the following may be added to the feedstuff compositions of the present invention, calcium, phosphorus, potassium, sodium, chloride, magnesium, manganese, iron, copper, zinc, selenium, iodine, and vitamins A, E, D, C, and the B complex. Other such vitamins and minerals may also be added.

The components utilized in the feedstuff compositions of the present invention can be of semi-purified or purified origin. By semi-purified or purified is meant a material which has been prepared by purification of a natural material.

A feedstuff composition of the present invention may also be added to food even when supplementation of the diet is not required. For example, the composition may be added to food of any type, including, but not limited to, margarine, modified butter, cheeses, milk, yogurt, chocolate, candy, snacks, salad oils, cooking oils, cooking fats, meats, fish and beverages.

Additionally, lipid produced in accordance with the present invention or host cells transformed to contain and express the subject genes may also be used as animal food supplements to alter an animal's tissue or milk fatty acid composition or fatty acod composition of eggs, to one more desirable for human or animal consumption, or for animal health and wellbeing. Examples of such animals include sheep, cattle, horses, poultry, pets such as dogs and cats and the like.

Furthermore, feedstuffs of the invention can be used in aquaculture to increase the levels of fatty acids in fish for human or animal consumption.

Preferred feedstuffs of the invention are the plants, seed and other plant parts such as leaves, fruits and stems which may be used directly as food or feed for humans or other animals. For example, animals may graze directly on such plants grown in the field, or be fed more measured amounts in controlled feeding.

Compositions

The present invention also encompasses compositions, particularly pharmaceutical compositions, comprising one or more lipids or oils produced using the methods of the invention.

A pharmaceutical composition may comprise one or more of the lipids, in combination with a standard, well-known, non-toxic pharmaceutically-acceptable carrier, adjuvant or vehicle such as phosphate-buffered saline, water, ethanol, polyols, vegetable oils, a wetting agent, or an emulsion such as a water/oil emulsion. The composition may be in either a liquid or solid form. For example, the composition may be in the form of a tablet, capsule, ingestible liquid, powder, topical ointment or cream. Proper fluidity can be maintained for example, by the maintenance of the required particle size in the case of dispersions and by the use of surfactants. It may also be desirable to include isotonic agents for example, sugars, sodium chloride, and the like. Besides such inert diluents, the composition can also include adjuvants such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth, or mixtures of these substances.

Solid dosage forms such as tablets and capsules can be prepared using techniques well known in the art. For example, lipid produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant lipid(s).

For intravenous administration, the lipids produced in accordance with the present invention or derivatives thereof may be incorporated into commercial formulations.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid is desirable. However, it will be appreciated that any amount of fatty acid will be beneficial to the subject.

Possible routes of administration of the pharmaceutical compositions of the present invention include for example, enteral and parenteral. For example, a liquid preparation may be administered orally. Additionally, a homogenous mixture can be completely dispersed in water, admixed under sterile conditions with physiologically acceptable diluents, preservatives, buffers or propellants to form a spray or inhalant.

The dosage of the composition to be administered to the subject may be determined by one of ordinary skill in the art and depends upon various factors such as weight, age, overall health, past history, immune status, etc., of the subject.

Additionally, the compositions of the present invention may be utilized for cosmetic purposes. The compositions may be added to pre-existing cosmetic compositions, such that a mixture is formed, or a fatty acid produced according to the invention may be used as the sole "active" ingredient in a cosmetic composition.

EXAMPLES

Example 1. General Materials and Methods

Plant Materials and Growth Conditions

Safflower plants (*Carthamus tinctorius*) genotypes SU, S-317, 5-517, LeSaf496, CW99-OL, and Ciano-OL were grown from seed in the glasshouse in a perlite and sandy loam potting mix under a day/night cycle of 16 hrs (25° C.)/8 hrs (22° C.). The wild type variety SU, which is a high linoleic variety, was obtained from Heffeman Seeds in NSW. Seeds of PI 603208 (LeSaf496, ATC 120562) and CW 99-OL (ATC 120561) were obtained from the Australian Temperate Field Crops Collection.

Plant tissues for DNA and RNA extraction including leaves, roots, cotyledons and hypocotyls were harvested from safflower seedlings 10 days post-germination. Flowering heads were obtained at the first day of flower opening and developing embryos were harvested at three developmental stages at 7 (early), 15 (middle) and 20 (late) days post anthesis (DPA). Samples were immediately chilled in liquid nitrogen and stored at −80° C. until DNA and RNA extraction was carried out.

Safflower florets are tubular and largely self-pollinating with generally less than 10% outcrossing (Knowles 1969). Insects, but not wind, can increase levels of out crossing in the field. The unpollinated stigma may remain receptive for several days. Each capitula (safflower head) contains about 15-30 achenes. Seed mass of the developing seed in the plant increases rapidly during the first 15 days after flowering. Oil content increases 5- to 10-fold during the period of 10-15 DAP and reaches a maximum level at about 28 DPA (Hill and Knowles 1968). Safflower seed and plants are physiologically mature about 5 weeks after flowering and the seed ready to harvest when most of the leaves have turned brown and only a tint of green remains on the bracts of the latest flowering heads. Seeds were readily harvested by rubbing the heads by hand.

Lipid Analysis

Isolation of Lipid Samples from Single Seeds for Rapid Fatty Acid Composition Analysis After being harvested at plant maturity, safflower seeds were dried by storing the seeds for 3 days at 37° C. and subsequently at room temperature if not analysed right away. Single seeds or pooled seeds were crushed between small filter papers and the exuded seedoil samples that soaked into the papers analysed for fatty acid composition by GC methods as described below.

Total Lipid Isolation from Half Cotyledons Post Germination

For screening purposes, for example for progeny seeds from transgenic plants, safflower seeds were germinated on a wet filter paper in a petri dish for 1 day. A cotyledon was carefully removed from each germinated seed for lipid analysis. The remainder of each seedling was transferred to soil and the resultant plants grown to maturity followed by harvesting of seeds to maintain the transgenic line.

Extraction of Oil from Seeds Using Soxhlet Apparatus

For quantitative extraction of seedoil, harvested safflower seeds were dried in an oven at 105° C. overnight and then ground in a Puck Mill for 1 min. The ground seed material (~250 grams) was collected into a pre-weighed thimble and weighed prior to oil extraction. After adding a layer of cotton wool on top of the meal, the oil was extracted in a Soxhlet Extraction apparatus with solvent (Petroleum Spirit 40-60 C), initially at 70-80° C. The mixture was then refluxed overnight with the solvent syphoning to the extraction flask every 15-20 min. The dissolved, extracted oil was recovered by evaporating off the solvent using a rotary evaporator under vacuum. The weight of the extracted oil was measured and the oil content was determined. To determine the fatty acid composition of the extracted oil, small aliquots were diluted in chloroform and analysed by gas chromatography.

Total Lipid Isolation from Leaf Material

Leaf tissue samples were freeze-dried, weighed and total lipids extracted from samples of approximately 10 mg dry weight as described by Bligh and Dyer (1959).

Fractionation of Lipids

When required, TAG fractions were separated from other lipid components using a 2-phase thin-layer chromatography (TLC) system on pre-coated silica gel plates (Silica gel 60, Merck). An extracted lipid sample equivalent to 10 mg dry weight of leaf tissue was chromatographed in a first phase with hexane/diethyl ether (98/2 v/v) to remove non-polar waxes and then in a second phase using hexane/diethyl ether/acetic acid (70/30/1 v/v/v). When required, polar lipids were separated from non-polar lipids in lipid samples extracted from an equivalent of 5 mg dry weight of leaves using two-dimensional TLC (Silica gel 60, Merck), using chloroform/methanol/water (65/25/4 v/v/v) for the first direction and chloroform/methanol/$NH_4OH$/ethylpropylamine (130/70/10/1 v/v/v/v) for the second direction. The lipid spots, and appropriate standards run on the same TLC plates, were visualized by brief exposure to iodine vapour, collected into vials and transmethylated to produce FAME for GC analysis as follows.

Fatty Acid Methyl Esters (FAME) Preparation and Gas Chromatography (GC) Analysis For fatty acid composition analysis by GC, extracted lipid samples prepared as described above were transferred to a glass tube and transmethylated in 2 mL of 1 M HCl in methanol (Supelco) at 80° C. for 3 hours. After cooling to room temperature, 1.3 mL 0.9% NaCl and 800 μL hexane were added to each tube and FAMEs were extracted into the hexane phase. To determine the fatty acid composition, the FAMEs were separated by gas-chromatography (GC) using an Agilent Technologies 7890A gas chromatograph (Palo Alto, Calif., USA) equipped with a 30-m BPX70 column essentially as described by Zhou et al. (2011) except that the temperature ramping program was changed to initial temperature at 150° C., holding for 1 min, ramping 3° C./min to 210° C., then 50° C./min to 240° C. for a final holding of 2 min. Peaks were quantified with Agilent Technologies ChemStation software (Rev B.03.01 (317), Palo Alto, Calif., USA). Peak responses were similar for the fatty acids of authentic Nu-Check GLC standard-411 (Nu-Check Prep Inc, Minn., USA) which contained equal proportions of 31 different fatty acid methyl esters, including 18:1, 18:0, 20:0 and 22:0 was used for calibration. The proportion of each fatty acid in the samples was calculated on the basis of individual and total peaks areas for the fatty acids.

Analysis of FAMES by Gas Chromatography—Mass Spectrometry

Confirming double bond positions in the FAME by 2,4-dimethyloxazoline (DMOX) modification and GC-MS analysis were carried out as previously described (Zhou et al., 2011), except with a Shimadzu GC-MS QP2010 Plus equipped with a 30-m BPX70 column. The column temperature was programmed for an initial temperature at 150° C. for 1 min, ramping at 5° C./min to 200° C. then 10° C./min to 240° C. with holding for 5 min. Mass spectra were acquired and processed with GCMSsolution software (Shimadzu, Version 2.61). The free fatty acids and FAME standards were purchased from Sigma-Aldrich (St. Louis, Mo., USA).

Analysis of Lipid Species by LC-MS

Mature individual single seeds were subjected to lipidomics analysis using LC-MS at the School of Botany, University of Melbourne. Total lipids were extracted as described by Bligh and Dyer (1959) and dissolved in $CHCl_3$. Aliquots of one mg lipid were dried with $N_2$, dissolved in 1 mL of 10 mM butylated hydroxytoluene in butanol:methanol (1:1 v/v), and analysed using an Agilent 1200 series LC and 6410B electrospray ionisation triple quadrupole LC-MS. Lipids were chromatographically separated using an Ascentis Express RP-Amide column (5 cm×2.1 mm, Supelco) and a binary gradient with a flow rate of 0.2 mL/min. The mobile phases were: A, 10 mM ammonium formate in $H_2O$:methanol: tetrahydrofuran (50:20:30, v/v/v); B. 10 mM ammonium formate in $H_2O$:methanol: tetrahydrofuran (5:20:75, v/v/v). Selected neutral lipids (TAG and DAG) and phosphocholine (PC) with fatty acids 16:0, 16:1 18:0, 18:1, 18:2, 18:3 were analysed by multiple reaction monitoring (MRM) using a collision energy of 25 V and fragmentor of 135 V. Individual MRM TAGs and DAGs were identified based on ammoniated precursor ion and product ion from neutral loss of fatty acid. TAGs and DAGs were quantified using the 10 uM tristearin external standard.

Analysis of the Sterol Content of Oil Samples

Samples of approximately 10 mg of oil together with an added aliquot of C24:0 monol as an internal standard were saponified using 4 mL 5% KOH in 80% MeOH and heating for 2 h at 80° C. in a Teflon-lined screw-capped glass tube. After the reaction mixture was cooled, 2 mL of Milli-Q water were added and the sterols were extracted into 2 mL of hexane: dichloromethane (4:1 v/v) by shaking and vortexing. The mixture was centrifuged and the sterol extract was removed and washed with 2 mL of Milli-Q water. The sterol extract was then removed after shaking and centrifugation. The extract was evaporated using a stream of nitrogen gas and the sterols silylated using 200 mL of BSTFA and heating for 2 h at 80° C.

For GC/GC-MS analysis of the sterols, sterol-OTMSi derivatives were dried under a stream of nitrogen gas on a heat block at 40° C. and then re-dissolved in chloroform or hexane immediately prior to GC/GC-MS analysis. The sterol-OTMS derivatives were analysed by gas chromatography (GC) using an Agilent Technologies 6890A GC (Palo Alto, Calif., USA) fitted with an Supelco Equity™-1 fused silica capillary column (15 m×0.1 mm i.d., 0.1 μm film thickness), an FID, a split/splitless injector and an Agilent Technologies 7683B Series auto sampler and injector. Helium was the carrier gas. Samples were injected in splitless mode at an oven temperature of 120° C. After injection, the oven temperature was raised to 270° C. at 10° C. $min^{-1}$ and finally to 300° C. at 5° C. $min^{-1}$. Peaks were quantified with Agilent Technologies ChemStation software (Palo Alto, Calif., USA). GC results are subject to an error of ±5% of individual component areas.

GC-mass spectrometric (GC-MS) analyses were performed on a Finnigan Thermoquest GCQ GC-MS and a Finnigan Thermo Electron Corporation GC-MS; both systems were fitted with an on-column injector and Thermoquest Xcalibur software (Austin, Tex., USA). Each GC was fitted with a capillary column of similar polarity to that described above. Individual components were identified using mass spectral data and by comparing retention time data with those obtained for authentic and laboratory standards. A full procedural blank analysis was performed concurrent to the sample batch.

Quantification of TAG Via Iatroscan

One μl of each plant extract is loaded on one Chromarod-SII for TLC-FID Iatroscan™ (Mitsubishi Chemical Medience Corporation—Japan). The Chromarod rack is then transferred into an equilibrated developing tank containing 70 ml of a Hexane/$CHCl_3$/2-Propanol/Formic acid (85/10.716/0.567/0.0567 v/v/v/v) solvent system. After 30 min of incubation, the Chromarod rack is then dried for 3 min at 100° C. and immediately scanned on an Iatroscan MK-$6_S$ TLC-FID analyser (Mitsubishi Chemical Medience Corporation—Japan). Peak areas of a DAGE internal standard and the TAG are integrated using SIC-48011 integration software (Version:7.0-E SIC System instruments Co., LTD—Japan).

TAG quantification is carried out in two steps. First, the DAGE internal standard is scanned in all samples to correct the extraction yields after which concentrated TAG samples are selected and diluted. Next, the amount of TAG is quantified in diluted samples with a second scan according to the external calibration using glyceryl trilinoleate as external standard (Sigma-Aldrich).

Expression of Candidate FAD2 Genes in *Saccharomyces cerevisiae*

The DNA fragments containing the entire open reading frames of candidate FAD2 cDNAs were excised from pGEMT-easy vector as EcoRI fragments and inserted into the corresponding site of the vector pENTR11 (Invitrogen, Carlsbad, Calif., USA). The inserts were then cloned into the destination expression vector pYES2-DEST52, to place the open reading frames under the control of the GAL1 promoter for inducible gene expression in yeast cells, using the Gateway® Cloning recombination technology (Stratagene, La Jolla, Calif., USA). The gene sequences in the resultant plasmids were verified by DNA sequencing. The resulting plasmids and the pYES2-DEST52 vector lacking any cDNA insert as a control were introduced into cells of yeast *Saccharomyces cerevisiae* strain YPH499 by lithium acetate-mediated transformation. Expression of these candidate FAD2 genes in yeast cells with or without exogenous fatty acid substrate feeding was essentially as previously described by Zhou et al. (2006). Each experiment was carried out in triplicate.

Expression of Genes in Plant Cells in a Transient Expression System

Genes were expressed in *Nicotiana benthamiana* leaf cells using a transient expression system essentially as described by Voinnet et al. (2003) and Wood et al. (2009). A vector for constitutive expression of the viral silencing suppressor protein, P19, under the control of the CaMV 35S promoter was obtained from the laboratory of Peter Waterhouse, CSIRO Plant Industry, Canberra, Australia. The chimeric binary vector 35S:P19 was introduced into *Agrobacterium tumefaciens* strain AGL1. All other binary vectors containing a coding region to be expressed in the plant cells from a promoter, often the 35S promoter, were also introduced into *A. tumefaciens* strain AGL1. The recombinant cells were grown to stationary phase at 28° C. in 5 mL LB broth supplemented with 50 mg/L rifampicin and either 50 mg/L kanamycin or 80 mg/L spectinomycin according to the selectable marker gene on the binary vector. The bacteria from each culture were pelleted by centrifugation at 3000×g for 5 min at room temperature before being resuspended in 1.0 ml of infiltration buffer containing 5 mM MES, pH 5.7, 5 mM $MgSO_4$ and 100 μM acetosyringone. The resuspended cell cultures were then incubated at 28° C. with shaking for another 3 hours. A 10-fold dilution of each culture in infiltration buffer was then mixed with an equal volume of the 35S:P19 culture, diluted in the same manner, and the mixtures infiltrated into the underside of the fully expanded *N. benthamiana* leaves. Mixed cultures comprising genes to be expressed included the 35S:P19 construct in *Agrobacterium* unless otherwise stated. Control infiltrations included only the 35S:P19 construct in *Agrobacterium.*

Leaves were infiltrated with the *Agrobacterium* cell mixtures and the plants were typically grown for a further five days after infiltration before leaf discs were recovered for total lipid isolation and fatty acid analysis. *N. benthamiana* plants were grown in growth cabinets under a constant 24° C. with a 14/10 hr light/dark cycle with a light intensity of approximately 200 lux using Osram 'Soft White' fluorescent lighting placed directly over plants. Typically, 6 week old plants were used for experiments and true leaves that were nearly fully-expanded were infiltrated. All non-infiltrated leaves were removed post infiltration to avoid shading.

Real-Time Quantitative PCR (RT-qPCR)

Gene expression analysis was performed by quantitative RT-PCR using a BIORAD CFX96™ Real-time PCR detection system and iQ™ SYBR® Green Supermix (BioRad, Hercules, Calif., USA). Primers of 19-23 nucleotides in length and having a melting temperature (Tm) of about 65° C. and were designed for gene-specific amplifications that would result in amplification products of about 100-200 bp. PCR reactions were carried out in 96-well plates. All RT-PCR reactions were performed in triplicate. The reaction mixture contained 1× iQ™ SYBR® Green Supermix (Bio-Rad, Hercules, Calif., USA), 5 μM forward and reverse primers and 400 ng of cDNA and was used at a volume of 10 uL per well. The thermal cycling conditions were 95° C. for 3 min, followed by 40 cycles of 95° C. for 10 s, 60° C. for 30 s and 68° C. for 30 s. The specificity of the PCR amplification was monitored by melting curve analysis following the final step of the PCR from 60° C. through 95°

C. at 0.1° C./sec. Additionally, PCR products were also checked for purity by agarose gel electrophoresis and confirmed by sequencing. The constitutively expressed gene KASII was used as an endogenous reference to normalise expression levels. The data were calibrated relative to the corresponding gene expression level following the $2^{-\Delta\Delta Ct}$ method for relative quantification (Schmittgen, 2008). The data were presented as means±SD of three reactions performed on independent 96-well plates.

DNA Isolation and Southern Blot Analysis

Genomic DNA of safflower seedlings, genotype "SU", was isolated from fully expanded leaves using CTAB buffer and following the method described by Paterson et al. (1993). Further purification was carried out using CsCl gradients as previously described (Liu et al., 1999). Aliquots of 10 μg of safflower genomic DNA were digested separately with eight different restriction enzymes, namely AccI, BglII, BamHI, EcoRI, EcoRV, HindIII, XbaI and XhoI. Genomic DNA digested with each restriction enzyme was electrophoresed through 1% agarose gels. The gel was soaked in 0.5 M NaOH, 1.5 M NaCl for 30 min and the DNA blotted onto a Hybond-$N^+$ nylon membrane (Amersham, UK). The filters were probed with an $\alpha$-$P^{32}$ dCTP-labelled DNA fragment corresponding to the entire coding region of the safflower CtFAD2-6 gene as a representative of the CtFAD2 gene family at low stringency hybridization conditions. The hybridizations were performed overnight at 65° C. in a solution containing 6×SSPE, 10% Denhardt's solution, 0.5% SDS and 100 μg/mL denatured salmon sperm DNA. Following the hybridisation and after a brief wash in 2×SSC/0.1% SDS at 50° C., the filters were washed three times, for 20 min each time, in 0.2×SSC/0.1% SDS at 50° C. prior to autoradiography.

Transformation of Safflower and *Arabidopsis thaliana*

Chimeric vectors comprising genes to be used to transform *Arabidopsis* were introduced into *A. tumefaciens* strain AGL1 and cells from cultures of the transformed *Agrobacterium* used to treat *A. thaliana* (ecotype Columbia) plants using the floral dip method for transformation (Clough and Bent, 1998). Transformed safflower plants were produced as described by Belide et al. (2011) using the transformed Agrobacterial cultures.

Example 2. Isolation of Safflower cDNAs which are Candidates for Encoding FAD2

Total RNA Extraction and cDNA Synthesis

In order to produce cDNA from safflower, total RNA was isolated from 100 mg samples of frozen safflower tissues including developing embryos, leaves, roots and hypocotyls. This was done for each tissue separately using an RNeasy® Plant total RNA kit (Qiagen, Hilden, Germany) according to the supplier's protocol. The RNA concentration in the preparations was determined with a NanoDrop™ spectrophotometer ND1000 (Thermo Fisher Scientific, Victoria, Australia) and the RNA concentrations were equalized before analysis. The quality and relative quantities of the RNA in each preparation were visualized by gel electrophoresis of samples through 1% (w/v) agarose gels containing formaldehyde. The RNA preparations were treated with RQ1 RNase-free DNase (Qiagen, Hilden, Germany) to remove contaminating genomic DNA. First-strand cDNA was synthesized from 400 ng of each DNA-free RNA preparation using the SuperScript III First-Strand Synthesis System (Qiagen, Hilden, Germany) with oligo$(dT)_{20}$ primer, following the manufacturer's instructions.

Isolation of Seed-Expressed FAD2 cDNAs from a Developing Seed cDNA Library

Initially, the seed expressed safflower FAD2 cDNAs were obtained by screening a cDNA library derived from developing embryos of safflower genotype "SU" (wild-type, high linoleic acid levels). Library construction began with RNA extraction from a mixture of immature embryos of different developmental stages which were harvested and ground to powder in liquid nitrogen and RNA extraction was carried out using TRIzol following the manufacturer's instruction (Invitrogen, Carlsbad, Calif., USA). Poly(A)-containing RNA was isolated using a Qiagen mRNA purification kit (Qiagen, Hilden, Germany).

First strand oligo(dT)-primed cDNA was synthesised and converted to double stranded DNA using a Stratagene cDNA synthesis kit, according to the manufacturer's instructions (Stratagen, La Jolla, Calif., USA). The blunt-ended cDNA was ligated with EcoRI adaptors, phosphorylated, and size fractionated by gel-filtration in a Chroma spin+TE-400 column (Clontech, Calif., USA). The recombinant cDNAs were propagated in the *E. coli* strain XL-1 Blue MRF' using a Stratagene Predigested Lambda ZAP II/EcoRI/CIAP cloning kit.

To identify the FAD2 clones, the library was screened using a DNA fragment corresponding to the coding region of *Arabidopsis* FAD2 (GenBank accession no. L26296), following the protocol previously described (Liu et al., 1999). Positive plaques were purified through two successive rounds of screening and the purified phagemids containing putative FAD2 cDNAs were excised as outlined in the Stratagene λZAPII cDNA Synthesis Kit instruction manual. Sequence analysis of the FAD2 sequences were done by the NCBI Blast program (www.ncbi.nlm.nih.gov/BLAST/). The open reading frame was predicted by using VectorNTI. Two different full length cDNAs were isolated from developing seed cDNA library and named as CtFAD2-1 and CtFAD2-2, respectively.

Identification of ESTs for Candidate FAD2 Genes

To identify additional candidate FAD2 cDNAs, the Compositae Genome Project (CGP) expressed sequence tag (EST) database of safflower (cgpdb.ucdavis.edu/cgpdb2.) was interrogated using the program BLASTp for ESTs that encoded polypeptides having similarity with the *A. thaliana* FAD2 (GenBank accession No. L26296). At least eleven distinct FAD2 cDNA sequence contigs were identified, among which two contigs showed identical sequences with CtFAD2-1 and CtFAD2-2 isolated from safflower seed cDNA library. In addition, nine different cDNAs were identified and designated as CtFAD2-3 through to CtFAD2-11, respectively.

3'- and 5' RACE

The longest EST clone of each of the 9 contigs (CtFAD2-3 through to CtFAD2-11) was selected as the starting point for isolation of the corresponding full length cDNA sequences. The process used 3'- and 5'-Rapid Amplification of cDNA Ends (RACE) using cDNA produced from RNAs obtained from various safflower tissues including developing embryos, leaves, roots, hypocotyls and flowers. Gene specific primers (GSP) were designed from the longest EST clone of each contig. 3'-RACE was performed using a one-step RT-PCR kit following the manufacturer's instructions (Bioline, London, UK). A gene-specific primer (GSP) was used in a first round of PCR amplification for each of the selected ESTs in combination with a poly(dT) primer with a NotI site at its 3' end. A second round of PCR was performed on the product of the first round using a nested GSP in combination with the poly(dT) primer. GSPs for 3' RACE are listed in Table 2.

Cloning of the 5' end of the CtFAD2-6 cDNA was performed with 5' RACE System Kit (Invitrogen, Carlsbad, Calif., USA). Only the CtFAD2-6 mRNA was reverse transcribed to cDNA using a gene-specific primer GSP1, 5'-ACCTAACGACAGTCATGAACAAG-3' (SEQ ID NO: 76). A nested gene-specific primer GSP2, 5'-GTGAGGAAAGCGGAGTGGACAAC-3' (SEQ ID NO: 77) was used in the first PCR amplification. The reaction conditions used a hot start at 95° C. for 4 min before adding the polymerase, 33 cycles of denaturation at 94° C. for 45 s, annealing at 55° C. for 1 min and extension at 72° C. for 2 min.

The amplified 3' and 5' fragments were subcloned into the vector pGEM-Teasy and sequenced from both directions. Sequence comparisons of the 3' and 5' ends of the cloned fragments with the corresponding ESTs showed overlapping regions that matched with each other, thereby providing the 3' and 5' sequences for each gene and allowing the assembly of a putative full length sequence for each of the 11 cDNAs.

Isolation of Full Length cDNA Sequences for the Candidate CtFAD2 Genes

To isolate full length protein coding regions for the nine CtFAD2 genes, the ORFs were amplified using the One-step RT-PCR kit using total RNAs derived from several safflower tissues including developing embryos, leaves, roots, hypocotyls and flowers (Stratagene, La Jolla, Calif., USA). The primers (Table 3) used to amplify the ORFs were based on the DNA sequences located in the 5' and 3' UTR of each cDNA. The amplified PCR products were cloned to vector pGEM-Teasy®, and their nucleotide sequences obtained by DNA sequencing.

Characteristics of the Candidate FAD2 Sequences from Safflower

Characteristics of the 11 cDNAs are summarised in Table 4 and of the polypeptides in Table 5.

The predicted amino acid sequences of the encoded polypeptides CtFAD2-1 to CtFAD2-11 shared extensive sequence identity, from about 44% to 86% identity with each other. They showed 53% to 62% sequence identity with *Arabidopsis* FAD2. The sizes of the predicted polypeptides were in the range from 372 to 388 amino acids, that is, they were all about 380aa residues in length. The cDNAs had unique 5' and 3' untranslated region (UTR) sequences, therefore the endogenous genes could readily be recognised by their UTR sequences. Amplification of the protein coding regions from safflower genomic DNA resulted in identical DNA sequences with the corresponding cDNA for each of the 11 genes, indicating that there were no introns interrupting their protein-coding regions.

TABLE 2

Oligonucleotide primers used in the 3'RACE of multiple FAD2 genes in safflower.

| Primer gene | Sense sequence | Antisense sequence |
|---|---|---|
| CtFAD2-3 | 5'-CTTCAGCGAGTACCAATGGCTCGAC-3' (SEQ ID NO: 58) | 5'-GGTTTCATCGTCCACTCCTTGA -3' (SEQ ID NO: 59) |
| CtFAD2-4 | 5'-CTTCAGCGAGTACCAATGGCTCGAC-3' (SEQ ID NO: 60) | 5'-GGTTTCATCGTCCACTCCTTGA -3' (SEQ ID NO: 61) |
| CtFAD2-5 | 5'-ATGACACCATTGGCTTCATCTGCCA -3' (SEQ ID NO: 62) | 5'-CTTTCTGCTCACTCCATACTTC -3' (SEQ ID NO: 63) |
| CtFAD2-6 | 5'-AGCGAATATCAGTGGCTTGACGATG -3' (SEQ ID NO: 64) | 5'-ACTCCGCTTTCCTCACTCCGTAC -3' (SEQ ID NO: 65) |
| CtFAD2-7 | 5'-CATGAATGTGGTCATCATGCCTTTAG -3' (SEQ ID NO: 66) | 5'-CTTCTTCATCCATTCGGTTTGC -3' (SEQ ID NO: 67) |
| CtFAD2-8 | 5'-CGTGGTTGAATGACACCATTGGTTAC -3' (SEQ ID NO: 68) | 5'-ACCTTCTACACACCGGTATGCCT -3' (SEQ ID NO: 69) |
| CtFAD2-9 | 5'-CATGGAAGATAAGCCACCGTCGACATC -3' (SEQ ID NO: 70) | 5'-AACACGGGTTCGCTTGAGCACGA -3' (SEQ ID NO: 71) |
| CtFAD2-10 | 5'-TGCATACCCGCAAGCAAAACCG -3' (SEQ ID NO: 72) | 5'-CCATCTCTCGAGAGTTCCTTAC -3' (SEQ ID NO: 73) |
| CtFAD2-11 | 5'-ATGTGGTCACCATGCCTTTAGTGAG -3' (SEQ ID NO: 74) | 5'-TGGAATGGTCCTCCATTCCGCTC -3' (SEQ ID NO: 75) |

TABLE 3

| Oligonucleotide primers used for amplification of the entire coding region of FAD2 genes in safflower. | | |
|---|---|---|
| Primer gene | Sense sequence | Antisense sequence |
| CtFAD2-1 | 5'-TGAAAGCAAGATGGGAGGAGG -3' (SEQ ID NO: 78) | 5'-TCACAACTTTACTTATTCTTGT -3' (SEQ ID NO: 79) |
| CtFAD2-2 | 5'-ATTGAACAATGGGTGCAGGC -3' (SEQ ID NO: 80) | 5'-CATCATCTTCAAATCTTATTC -3' (SEQ ID NO: 81) |
| CtFAD2-3 | 5'-AATCAGCAGCAGCACAAGC -3' (SEQ ID NO: 82) | 5'-CAAACATACCACCAAATGCTACT -3' (SEQ ID NO: 83) |
| CtFAD2-4 | 5'-CTCAGTAACCAGCCTCAAAACTTG -3' (SEQ ID NO: 84) | 5'-GCGGATTGATCAAATACTTGTG -3' (SEQ ID NO: 85) |
| CtFAD2-5 | 5'-ATCACAGGAAGCTCAAAGCATCT -3' (SEQ ID NO: 86) | 5'-GTAGGTTATGTAACAATCGTG -3' (SEQ ID NO: 87) |
| CtFAD2-6 | 5'-TGAAGACGTTAAGATGGGAGCTG -3' (SEQ ID NO: 88) | 5'-GTAGGTTATGTAACAATCGTG -3' (SEQ ID NO: 89) |
| CtFAD2-7 | 5'-CAGATCCAACACTTCACCACCAG -3' (SEQ ID NO: 90) | 5'-AGATCTAAAGAATTTCCATGGTG -3' (SEQ ID NO: 91) |
| CtFAD2-8 | 5'-CTGCTCTCTACGACACTAAATTCAC -3' (SEQ ID NO: 92) | 5'-TCTATCTAATGAGTATCAAGGAAC -3' (SEQ ID NO: 93) |
| CtFAD2-9 | 5'-CTGAATTCACACCCACAGATAGCTAG -3' (SEQ ID NO: 94) | 5'-ACATCCCTTCTTAGCTTTAACTA-3' (SEQ ID NO: 95) |
| CtFAD2-10 | 5'-ACTTCGCCCTCTGTTATCTGG -3' (SEQ ID NO: 96) | 5'-CCATACACATACATCCTACACGAT -3' (SEQ ID NO: 97) |
| CtFAD2-11 | 5'-ACTCACAATAACTTCATCTCTCTC -3' (SEQ ID NO: 98) | 5'-CTACTAGCCATACAATGTCTTCG -3' (SEQ ID NO: 99) |

TABLE 4

| Characteristics of the candidate FAD2 cDNAs from safflower. | | | | | | | |
|---|---|---|---|---|---|---|---|
| Gene designation | cDNA length (nt) | Protein coding region | Size of 5'UTR | Size of 3'UTR | Position of intron | Size of intron | ORF nucleotide SEQ ID NO. |
| CtFAD2-1 | 1422 | 124-1266 | 123 | 156 | −13 | 1144 | 12 |
| CtFAD2-2 | 1486 | 81-1233 | 80 | 253 | −12 | 3090 | 13 |
| CtFAD2-3 | 1333 | 51-1197 | 50 | 136 | −11 | 114 | 14 |
| CtFAD2-4 | 1403 | 52-1227 | 51 | 176 | −11 | 124 | 15 |
| CtFAD2-5 | 1380 | 66-1194 | 65 | 186 | −33 | 122 | 16 |
| CtFAD2-6 | 1263 | 15-1146 | 14 | 117 | * | * | 17 |
| CtFAD2-7 | 1375 | 66-1185 | 65 | 190 | −29 | 253 | 18 |
| CtFAD2-8 | 1345 | 58-1207 | 57 | 138 | * | * | 19 |
| CtFAD2-9 | 1326 | 108-1172 | 107 | 154 | * | * | 20 |
| CtFAD2-10 | 1358 | 56-1199 | 55 | 159 | −38 | 2247 | 21 |
| CtFAD2-11 | 1229 | 58-1092 | 57 | 137 | −22 | 104 | 22 |

TABLE 5

| Characteristics of candidate CtFAD2 polypeptides. | | | | | |
|---|---|---|---|---|---|
| Gene designation | Polypetide length (No. of amino acids) | Position (& sequence) of first His box | Position (& sequence) of second His box | Position (& sequence) of third His box | Amino acid SEQ ID NO. |
| CtFAD2-1 | 380 | 105 HECGH* | 141 HRRHH | 315 HVVHH | 27 |
| CtFAD2-2 | 384 | 106 HECGH | 142 HRRHH | 316 HVTHH | 28 |
| CtFAD2-3 | 381 | 104 HECGH | 140 HRTHH | 314 HAVHH | 29 |
| CtFAD2-4 | 380 | 103 HECGH | 139 HRTHH | 313 HAVHH | 30 |
| CtFAD2-5 | 375 | 102 HDCGH | 138 HRTHH | 311 HVVHH | 31 |
| CtFAD2-6 | 376 | 101 HDLGH | 137 HRSHH | 310 HVVHH | 32 |
| CtFAD2-7 | 372 | 99 HECGH | 135 HRTHH | 308 HAVHH | 33 |
| CtFAD2-8 | 382 | 103 HECGH | 139 HRTHH | 313 HAVHH | 34 |
| CtFAD2-9 | 387 | 107 HECGH | 143 HRTHH | 318 HAVHH | 35 |
| CtFAD2-10 | 380 | 104 HECGH | 140 HRRHH | 314 HVVHH | 36 |
| CtFAD2-11 | 377 | 100 HECGH | 136 HRNHH | 310 HVLHH | 37 |

*HECGH (SEQ ID NO: 159), HDCGH (SEQ ID NO: 160), HDLGH (SEQ ID NO: 161), HRRHH (SEQ ID NO: 162), HRTHH (SEQ ID NO: 163), HRSHH (SEQ ID NO: 164), HRNHH (SEQ ID NO: 165), HVVHH (SEQ ID NO: 166), HVTHH (SEQ ID NO: 167), HAVHH (SEQ ID NO: 168), and HVLHH (SEQ ID NO: 169).

To investigate the relationship of the safflower candidate FAD2 polypeptides to known FAD2 enzymes, the 11 deduced polypeptide sequences were aligned with plant FAD2 sequences and a neighbour-joining tree was constructed using Vector NTI (FIG. 1). As shown in FIG. 1, the amino acid sequences of CtFAD2-1 and CtFAD2-10 were most closely related, first of all to each other and then to seed expressed FAD2s from other species. CtFAD2-2 was more closely related to constitutively expressed genes from other species than to other candidate FAD2s in safflower. CtFAD2-3, -4, -5, -6 and -7 formed a new branch in the neighbour-joining tree, most likely as the evolutionary result of a recently diverged gene becoming multiplied in safflower. Interestingly, in relatedness to other species, these were most closely related to a functionally divergent FAD2 conjugase from *Calendula officinalis*. FAD2-11 was more closely related to acetylenases from several plant species, including the sunflower vFAD2 which was induced by fungal elicitors (Cahoon et al., 2003). It appeared that CtFAD2-8 and -9 were more divergent than the other candidate FAD2s from safflower. However, this analysis also showed that the sequence comparisons, although they gave some hints about possible function, could not by themselves provide reliable conclusions about the function of the different FAD2 candidates. Therefore, functional analysis was required to make conclusions about the function of each gene/polypeptide.

The sequence comparisons showed that the safflower candidate FAD2 polypeptides shared about 50%-60% sequence identity and 52%-65% similarity to known FAD2 enzymes from other species. The extent of DNA sequence divergence among the safflower CtFAD2 genes reflected their phylogenetic relationships, in that CtFAD2-3, -4 and -5 are all more similar to each other than to CtFAD2-1, or CtFAD2-10, and vice versa. These numbers have close parallels in the amino acid identity matrix (Table 6).

TABLE 6

| Sequence identity of the coding region DNA and deduce amino acids in safflower FAD2 genes. | | | | | | | | | | | |
|---|---|---|---|---|---|---|---|---|---|---|---|
| | Deduced amino acid identity (%) | | | | | | | | | | |
| | CtFAD2-1 | CtFAD2-2 | CtFAD2-3 | CtFAD2-4 | CtFAD2-5 | CtFAD2-6 | CtFAD2-7 | CtFAD2-8 | CtFAD2-9 | CtFAD2-10 | CtFAD2-11 |
| CtFAD2-1 | — | 70.3 | 53.2 | 52.5 | 53.5 | 50.9 | 54.1 | 59.7 | 59.5 | 80.1 | 56.4 |
| CtFAD2-2 | 70.0 | — | 54.5 | 55.0 | 54.2 | 51.7 | 57.8 | 60.6 | 62.5 | 69.5 | 58.6 |
| CtFAD2-3 | 62.0 | 62.0 | — | 97.1 | 62.0 | 61.8 | 63.1 | 52.7 | 50.9 | 51.2 | 56.8 |
| CtFAD2-4 | 62.7 | 63.3 | 95.1 | — | 61.4 | 61.4 | 63.3 | 53.1 | 50.9 | 50.9 | 56.9 |
| CtFAD2-5 | 61.9 | 60.3 | 69.7 | 70.6 | — | 63.2 | 62.0 | 51.4 | 51.3 | 51.7 | 53.9 |

TABLE 6-continued

Sequence identity of the coding region DNA and deduce amino acids in safflower FAD2 genes.

| | Deduced amino acid identity (%) | | | | | | | | | | |
|---|---|---|---|---|---|---|---|---|---|---|---|
| | CtFA D2-1 | CtFA D2-2 | CtFA D2-3 | CtFA D2-4 | CtFA D2-5 | CtFA D2-6 | CtFA D2-7 | CtFA D2-8 | CtFA D2-9 | CtFA D2-10 | CtFA D2-11 |
| CtFA D2-6 | 60.6 | 59.9 | 68.8 | 69.6 | 72.0 | — | 63.1 | 49.3 | 50.8 | 50.1 | 56.2 |
| CtFA D2-7 | 62.2 | 65.8 | 69.4 | 69.3 | 66.6 | 68.2 | — | 51.7 | 49.2 | 51.4 | 60.7 |
| CtFA D2-8 | 65.2 | 66.2 | 63.1 | 62.8 | 60.8 | 61.7 | 61.2 | — | 58.8 | 58.1 | 56.40 |
| CtFA D2-9 | 64.9 | 66.2 | 59.5 | 59.5 | 58.3 | 59.2 | 59.5 | 63.5 | — | 59.3 | 55.9 |
| CtFA D2-10 | 78.9 | 72.0 | 60.7 | 62.0 | 59.8 | 61.0 | 60.7 | 64.3 | 64.1 | — | 57.2 |
| CtFA D2-11 | 60.0 | 62.9 | 64.1 | 64.4 | 62.4 | 64.1 | 62.7 | 63.9 | 60.9 | 61.7 | — |

Characteristics of the Candidate CtFAD2 Polypeptides

The predicted polypeptides of the 11 candidate CtFAD2s each contained an aromatic amino acid-rich motif at the very end of the C-terminus. Such motifs have been identified in other plant FAD2 polypeptides, and are thought to be necessary for maintaining localization in the ER (McCartney et al., 2004). Consistent with other plant membrane bound fatty acid desaturase enzymes, the predicted CtFAD2 polypeptides each contained three histidine-rich motifs (His boxes). Such His-rich motifs are highly conserved in FAD2 enzymes and have been implicated in the formation of the diiron-oxygen complex used in biochemical catalysis (Shanklin et al., 1998). In most of the candidate CtFAD2 polypeptide sequences, the first histidine motif was HECGHH, the exceptions being CtFAD2-5 and -6 which had HDCGHH and HDLGHH, respectively. The last amino acid of the first His box in CtFAD2-8 (HECGHQ) was a Q rather than a H. The inventors looked for this motif in 55 known plant FAD2 enzymes and the H to Q substitution is also present in a diverged FAD2 homologue from *Lesquerella lindheimeri* with predominantly fatty acid hydroxylase activity (Genbank Accession number EF432246; Dauk et al., 2007). The second histidine motif was highly conserved, as the amino acid sequence HRRHH, in several candidate safflower FAD2s, including CtFAD2-1, -2, -8, -9 and -10. It was noteworthy that the amino acid N was found in CtFAD2-11 at the +3 position of the motif, which was also seen in a number of functionally divergent FAD2-type enzymes including *Crepis alpina* CREP1, *Crepis palaestina* Cpal2 and sunflower vFAD2 (AY166773.1), *Calendula officinalis* FAC2 (AF343064.1), *Rudbeckia hirta* acetylenase (AY166776.1). The amino acid at this position in CtFAD2-3, -4, -5, -6 and -7 was either an S or a T.

In each of the CtFAD2-1, -2, -9 and -10 polypeptides, the amino acid immediately preceding the first histidine box was an alanine, the same as for other plant fatty acid Δ12-desaturase enzymes. The amino acid valine (V) rather than alanine was present at that position in CtFAD2-5, while the other six CtFAD2 polypeptides had a glycine in this position. It was proposed by Cahoon et al. (2003) that a glycine substitution for alanine at this position has been found in functionally divergent FAD2 enzymes, except fatty acid Δ12-hydroxylase. As described in the following Examples, subsequent heterologous expression experiments testing the function of the candidates demonstrated that each of the CtFAD2-1, -2 and -10 polypeptides were oleate Δ12-desaturases, while CtFAD2-9 showed desaturase specificity to palmitoleate (C16:1) rather than oleate.

It was noted that of the 11 candidate CtFAD2s, only the CtFAD2-11 polypeptide had a DVTH sequence in the −5 to −2 positions of the third Histidine box, which was consistent with the (D/N)VX(H/N) motif proposed to occur in all plant acetylenases (Blacklock et al., 2010). The five amino acids immediately after the third histidine box of the CtFAD2-1, -2 and -10 polypeptides were LFS™, as for other known plant FAD2 oleate desaturases. In contrast, CtFAD2-9, the palmitoleate specific fatty acid desaturase, had a LFSYI motif at this position with two amino acid substitutions at +4 and +5 position. In the CtFAD2-3, -4 and -5 polypeptides, the S at the +3 position was substituted by P, which was also present exclusively in other FAD2 fatty acid conjugases including those from *Calendula officinalis* (FAC2, accession AAK26632) and *Trichosanthes kirilowii* (accession AAO37751).

It has been shown that the Serine-185 of the soybean FAD2-1 enzyme is phosphorylated during seed development as a regulatory mechanism for its enzymatic activity (Tang et al., 2005). Among the 11 candidate CtFAD2 polypeptides, only CtFAD2-1 had a serine in the corresponding position (Serine-181) relative to soybean FAD2-1. It was concluded that the same posttranslational regulatory mechanism might operate during safflower seed development and oil accumulation through phosphorylation of the serine-185, to modulate microsomal Δ12 oleate desaturation in the developing seed.

Example 3. Isolation of Genomic Sequences for FAD2 Candidates

Isolation of 5'UTR Introns of the Candidate CtFAD2 Genes

The intron-exon structures of FAD2 genes are conserved in many flowering plants. All FAD2 genes studied so far contain only one intron which is located at the 5'UTR, with one exception being soybean FAD2-1 for which the intron is located in the coding region immediately following the first ATG, the translational initiation codon (Liu et al., 2001; Kim et al., 2006; Mroczka et al., 2010). Intron sequence divergence could be used as a measure of evolutionary distance between taxonomically closely related species (Liu et al., 2001).

In order to isolate the DNA sequences of possible introns situated within the 5'-UTRs of the candidate CtFAD2 genes, the typical intron splice sites (AG:GT) were predicted in the 5' UTR of each CtFAD2 cDNA sequence, and PCR primers were designed based on the flanking sequences of predicted splice sites. The primers are listed in Table 7. Genomic DNA isolated from safflower genotype SU was used as template in PCR reactions to amplify the genomic regions corresponding to the 5'UTRs. The amplifications were accomplished in 50 μL reactions with 100 ng of genomic DNA, 20 pmol of each primer and a Hotstar (Qiagen, Hilden, Germany) supplied by the manufacturer. PCR temperature cycling was performed as follows: 94° C. for 15 min for one cycle, 94° C. for 30 s, 55° C. for 1 min, 72° C. for 2 min for 35 cycles; 72° C. for 10 min using the Kyratec supercycler SC200 (Kyratec, Queensland, Australia). The PCR products were cloned into pGEM-T Easy and then sequenced.

The inventors were able to obtain the predicted 5' intron from 8 of the 11 candidate CtFAD2 genes, namely CtFAD2-1, -2, -3, -4, -5, -7, -10 and -11. The major features of these introns are given in Table 8. The intron was not amplified successfully from CtFAD2-6, -8 and -9, probably due to an insufficient length of the 5' UTR in which the introns were present. It appeared that an intron-less FAD2 has not been reported, although intron loss from nuclear genes has been commonly observed in higher plants (Loguercio et al., 1998; Small et al., 2000a;b).

TABLE 7

Oligonucleotide primers used for the amplification of 5'UTR regions ofc andidate FAD2 genes in safflower.

| Primer gene | Sense sequence | Antisense sequence |
|---|---|---|
| CtFAD2-1 | 5'-GAGATTTTCAGAGAGCAAGCGCTT -3'(SEQ ID NO: 100) | 5'-CTTTGGTCTCGGAGGCAGACATA -3'(SEQ ID NO: 101) |
| CtFAD2-2 | 5'-CAAAAGGAGTTTCAGAAAGCCTCC -3'(SEQ ID NO: 102) | 5'-ACTCGTTGGATGCCTTCGAGTTC- 3'(SEQ ID NO: 103) |
| CtFAD2-3 | 5' AATCAGCAGCAGCACAAGC -3'(SEQ ID NO: 104) | 5'-AAGGCGGTGACAATTATGATATC -3'(SEQ ID NO: 105) |
| CtFAD2-4 | 5'-CTCAGTAACCAGCCTCAAAACTTG -3'(SEQ ID NO: 106) | 5'-AAGGCGGAGACGATTATGATATC -3'(SEQ ID NO: 107) |
| CtFAD2-5 | 5'-ATCACAGGAAGCTCAAAGCATCT -3'(SEQ ID NO: 108) | 5'-ATCATCTCTTCGGTAGGTTATG -3'(SEQ ID NO: 109) |
| CtFAD2-7 | 5'-CAGATCCAACACTTCACCACCAG -3'(SEQ ID NO: 110) | 5'-CTAAAGAATTTCCATGGTGTTAC -3'(SEQ ID NO: 111) |
| CtFAD2-10 | 5'-ACTTCGCCCTCTGTTATCTGG -3'(SEQ ID NO: 112) | 5'-GAGAGACGGTGGAAGTAGGTG -3'(SEQ ID NO: 113) |
| CtFAD2-11 | 5'-CTCACAATAACTTCATCTCTCTC -3'(SEQ ID NO: 114) | 5'-AAAGACATAGGCAACAACGAGATC -3'(SEQ ID NO: 115) |

TABLE 8

The feature of candidate FAD2 gene introns.

| Feature | CtFAD2-1 | CtFAD2-2 | CtFAD2-3 | CtFAD2-4 | CtFAD2-5 | CtFAD2-7 | CtFAD2-10 | CtFAD2-11 |
|---|---|---|---|---|---|---|---|---|
| Position | -13 | -12 | -11 | -11 | -33 | -29 | -38 | -22 |
| Length | 1144 | 3090 | 114 | 124 | 122 | 253 | 2247 | 104 |
| AT content | 64.5% | 65.8% | 73.7% | 75.0% | 67.2% | 62.1% | 68.9% | 75% |
| CG content | 35.5% | 34.2% | 26.3% | 25.0% | 32.8% | 37.9% | 31.1% | 25% |
| 5'E/I boundary | AG:GTGCAT | AG:GTGAGA | AG:GTATGA | AG:GTAAGT | AG:GTGAAG | AG:GTATAC | TG:GTTCGT | AG:GTTTCT |
| 3'I/E boundary | TTGCAG:GT | TTGCAG:GT | ATGCAG:GT | GCGCAG:GT | TTTCAG:GT | TTGCAG:GT | ATATAG:GT | TTGCAG:GT |

The intron sequence in each of the eight genes was located within the 5'-UTR of each gene, at positions that ranged from 11 to 38 bp upstream of the putative translation start codon, the first ATG in each open reading frame. The intron length ranged from 104 bp (CtFAD2-11) to 3,090 bp (CtFAD2-2) (Table 8). For CtFAD2-1, the intron size was 1,144 bp, similar in size to introns identified in FAD2 genes from *Arabidopsis* (The Arabidopsis Information Resource, www.arabidopsis.org), cotton (Liu et al., 2001) and sesame (*Sesamum indicum*) (Kim et al., 2006). The dinucleotides at the putative splice sites, AG and GT, were conserved in all eight of the examined CtFAD2 genes, but otherwise the intron sequences were all divergent in sequence without any significant homology between them. The intron sequences were all A/T-rich with an A/T content of between 61% and 75%, which was consistent with many other intron sequences from dicotyledonous plants. In genes from other dicot plants, the *Arabidopsis* FAD2 gene had a 1,134-bp intron just 5 bp upstream from its ATG translation initiation codon. The size of the 5'-UTR intron of the *Gossypium* FAD2-1 gene was 1,133 bp, located 9 bp upstream from the translation initiation codon. In contrast, the cotton FAD2-4 and FAD2-3 genes had larger 5'-UTR introns of 2,780 bp and 2,967 bp, respectively, located 12 bp upstream from the translation start codon. Each candidate CtFAD2 gene could be distinguished by the differences in the position and size of the 5'-UTR intron in each gene. The differences could also be important in providing for differential expression of the genes. Such introns have been reported to have positive effects on the expression of reporter genes in sesame (Kim et al., 2006). A corresponding intron was shown to be an effective target for posttranscriptional gene silencing of FAD2 in soybean (Mroczka et al., 2010).

It has been known that introns may have dramatic effects on gene expression profiles. Analyzing the intron sequences by the PLACE program (www.dna.affrc.go.jp/PLACE/) identified several putative cis-regulatory elements. For instance, a few motifs, such as ABRE and SEF4, commonly present in the seed-specific promoters have been located in the seed-specific CtFAD2-1. An AG-motif which is normally found in the promoter of defence-related genes induced by various stresses such as wounding or elicitor treatment was located at CtFAD2-3 that is specifically expressed in the hypocotyls and cotyledons of safflower young seedlings.

Example 4. Southern Blot Hybridisation Analysis of the Candidate Safflower FAD2 Genes The complexity of the FAD2-like gene family in safflower was examined by Southern Blot hybridisation analysis. Low stringency hybridisation analysis showed that, in safflower, FAD2 was encoded by a complex multigene family (FIG. 2). By counting the hybridising fragments obtained by using various restriction enzymes to cleave the genomic DNA, it was estimated that there were more than 10 FAD2 or FAD2-like genes in safflower. The differences seen in the intensity of hybridization for the different fragments presumably correlated with the relative levels of sequence identity to the probe DNA that was used. Safflower is a diploid species and is thought to have a single wild progenitor species, *C. palaestinus* (Chapman and Burke, 2007). The inventors speculate that the unusually large FAD2 gene family in safflower is perhaps derived from some ancient gene duplications, leading to specialisation and differential activity of the different members of the gene family.

Example 5. Functional Analysis of Candidate Genes in Yeast and Plant Cells

Expression of Candidate CtFAD2 Genes in Yeast—Functional Analysis

As a convenient host cell, the yeast *S. cerevisiae* has been used for studying the functional expression of several plant FAD2 Δ12 oleate fatty acid desaturases (Covello and Reed 1996; Dyer et al., 2002; Hernández et al., 2005). *S. cerevisiae* has a relatively simple fatty acid profile and it contains ample oleic acid in its phospholipid which can be used as a substrate for FAD2 enzymes. It also lacks an endogenous FAD2 activity. Therefore, the 11 candidate CtFAD2 genes were tested in yeast strain YPH499 using pYES2 derived constructs, each open reading frame under the control of the GAL1 promoter, as described in Example 1.

As shown in FIG. 3, when the fatty acid composition of yeast cells containing the "empty vector" pYES2 was analysed, no linoleic acid (18:2) or hexadecadienoic acid (16:2) was detected, as expected since yeast lacks endogenous FAD2. In contrast, the gas chromatogram for fatty acids obtained from yeast cells expressing the CtFAD2-1, CtFAD2-2 and CtFAD2-10 open reading frames each showed a fatty acid peak with a retention time of 11.293 min, corresponding to linoleic acid (C18:2), and the gas chromatograms for CtFAD2-9 and CtFAD2-10 showed a fatty acid peak with retention time of 8.513 min, corresponding to C16:2. These data indicated that CtFAD2-1, CtFAD2-2 and CtFAD2-10 were able to convert oleic acid to linoleic acid and therefore were Δ12 oleate desaturases. However, the level of 18:2 produced was lower than for the *Arabidopsis* AtFAD2 construct which was used as positive control. CtFAD2-10 produced both linoleic acid (C18:2) and hexadecadienoic acid (C16:2) using oleic acid (C18:1) and palmitoleic acid (C16:1) as substrates, respectively, while CtFAD2-9 desaturated palmitoleic acid and was therefore a Δ12 palmitoleate desaturase. Two minor new peaks that appeared in the chromatograms of FAMEs from yeast cells expressing CtFAD2-11 were identified as linoleic acid ($18{:}2^{\Delta9(Z),12(Z)}$) and its trans isomer ($18{:}2^{\Delta9(Z),12(E)}$) by GC-MS of their pyrrolidide adducts, and DMOX (FIG. 3H). Table 9 summaries the fatty acid composition of yeast cells expressing CtFAD2 coding regions. No new peaks were detected in yeast cells expressing CtFAD2-3, -4, -5, -6, -7 and -8.

To examine whether any of the candidate CtFAD2 polypeptides had fatty acid hydroxylase activity, FAMEs prepared from the yeast cells expressing each of the CtFAD2 open reading frames were reacted with a silylating reagent that converts hydroxyl residues into TMS-ether derivatives from which the mass spectra could be examined. However, no hydroxyl derivatives of the common fatty acids such as oleic acid were detected in any of the yeast cell lines expressing the candidate CtFAD2 open reading frames. This indicated that none of the 11 CtFAD2 genes encoded polypeptides having fatty acid hydroxylase activity in yeast.

Additional experiments were carried out to detect Δ12-epoxygenase and Δ12-acetylenase activity, both of which use linoleic acid as the fatty acid substrate, by supplementing the growth media of the same yeast cell lines with free linoleic acid and analysing the fatty acid composition afterward. The supplementation was done after addition of galactose to the cultures to express the constructs. No novel fatty acid peaks were detected in the gas chromatograms, including those representing epoxy and acetylenic fatty acid derivatives. The heterologous expression of these novel fatty acids in yeast, with supplementation of exogenous free fatty acids, has encountered some difficulties in demonstrating activity (Lee et al., 1998; Cahoon et al., 2003). Therefore, functional analyses in plant cells were carried out as follows.

TABLE 9

Fatty acid composition of yeast cells expressing selected CtFAD2 genes.

| | C14:0 | C14:1 | C16:0 | C16:1 | C16:2 |
|---|---|---|---|---|---|
| Vector | 1.30 ± 0.15 | 0.31 ± 0.06 | 23.62 ± 1.62 | 36.04 ± 1.77 | |
| CtFAD2-1 | 1.17 ± 0.02 | 0.31 ± 0.01 | 22.96 ± 0.04 | 37.15 ± 0.16 | 0.28 ± 0.02 |
| CtFAD2-2 | 1.17 ± 0.06 | 0.29 ± 0.01 | 22.02 ± 0.46 | 36.60 ± 0.07 | |
| CtFAD2-9 | 1.13 ± 0.06 | 0.18 ± 0.01 | 21.30 ± 0.59 | 34.32 ± 0.54 | 1.61 ± 0.09 |
| CtFAD2-10 | 1.04 ± 0.01 | 0.27 ± 0.02 | 22.31 ± 0.03 | 34.79 ± 0.21 | 1.23 ± 0.03 |
| CtFAD2-11 | 0.63 ± 0.01 | 0.17 ± 0.00 | 18.41 ± 0.34 | 37.27 ± 0.16 | |
| | C18:0 | C18:1 | C18:1$^{\Delta 11}$ | C18:2 | C18:2$^{\Delta 9Z,\ 12E}$ |
| Vector | 7.69 ± 0.74 | 29.62 ± 0.99 | 1.42 ± 0.20 | | |
| CtFAD2-1 | 7.37 ± 0.12 | 26.36 ± 0.24 | 1.57 ± 0.02 | 2 82 ± 0.14 | |
| CtFAD2-2 | 7.38 ± 0.07 | 30.95 ± 0.51 | 1.48 ± 0.04 | 0.11 ± 0.01 | |
| CtFAD2-9 | 8.90 ± 0.13 | 31.29 ± 0.25 | 1.27 ± 0.08 | | |
| CtFAD2-10 | 8.08 ± 0.09 | 25.43 ± 0.07 | 1.34 ± 0.01 | 5.49 ± 0.09 | |
| CtFAD2-11 | 7.52 ± 0.07 | 33.25 ± 0.26 | 1.91 ± 0.01 | 0.32 ± 0.02 | 0.51 ± 0.03 |

(n = 3)

Transient Expression of Candidate CtFAD2 Genes in *N. benthamiana*

To express the genes in a constitutive fashion in plant cells, in particular in plant leaves, each of the CtFAD2 ORFs was inserted in the sense orientation into a modified pORE04 binary vector between the enhanced CaMV-35S promoter and the nos3' terminator containing a polyadenylation signal sequence (Coutu et al., 2007) (SEQ ID NO: 54). Previous research indicated that the expression of transgenes could be significantly enhanced by the co-expression of the viral silencing suppressor protein, P19, to reduce host transgene silencing in a *N. benthamiana* leaf-based transient assay (Voinnet et al., 2003; Wood et al., 2009; Petrie et al., 2010). These experiments were performed as described in Example 1.

As described above, the function of CtFAD2-11 was initially assessed by expression in *S. cerevisiae* and two novel fatty acids were identified by GC-MS as 18:2$^{\Delta 9(Z),12(Z)}$ and 18:2$^{\Delta 9(Z),12(E)}$, respectively. Consistent with the results obtained from yeast, expression of CtFAD2-11 in *N. benthamiana* leaves yielded a novel 18:2 trans isomer. The methyl ester of this isomer displayed a GC retention time that was identical to that of a methyl 18:2$^{\Delta 9(Z),12(E)}$ (FIG. 4B). The novel 18:2$^{\Delta 9(Z),12(E)}$ accounted for 0.35% of the fatty acids in leaves after transiently expressing CtFAD2-11 (Table 10). In addition, another new peak which was not observed in the yeast cultures was detected. The total ion chromatogram and mass spectrum of this new fatty acid were consistent with that of crepenynic acid (18:2$_{\Delta 9(Z),12(c)}$) (FIGS. 4B and C), demonstrating that the CtFAD2-11 polypeptide had Δ12-acetylenase activity. As shown in Table 10, crepenynic acid accounted for 0.51% of total fatty acids.

It was observed that the expression of CtFAD2-11 transiently in the *N. benthamiana* cells resulted in a reduction in the content of the 18:2$^{\Delta 9(Z),12(Z)}$ relative to the untransformed control (Table 10). This was likely due to the competition of CtFAD2-11 with the endogenous cis-Δ12 oleate desaturase in the *N. benthamiana* cells for the available pool of oleic acid, the substrate for both enzymes. Overall, the results from the yeast and *N. benthamiana* expression experiments indicated that CtFAD2-11 functioned primarily as an oleate Δ12-desaturase lacking stereospecificity, producing both linoleic acid and its trans-Δ12 isomers. In addition, it could also further desaturate the Δ12 double bond of linoleic acid to form the acetylenic bond of crepenynic acid.

The other ten candidate CtFAD2 polypeptides were also expressed transiently in *N. benthamiana* leaves in the same manner, but we did not observe any new fatty acids which were not present endogenously in *N. benthamiana* leaves, which already have high levels of FAD2.

TABLE 10

Fatty acid composition of *N. benthamiana* leaves transiently expressing CtFAD2-11.

| | C16:0 | C16:1 | C16:2 | C16:3 | C18:0 | C18:1 | C18:1$^{\Delta 11}$ |
|---|---|---|---|---|---|---|---|
| Control | 17.42 ± 0.48 | 0.25 ± 0.02 | 0.83 ± 0.12 | 7.24 ± 0.15 | 3.32 ± 0.33 | 1.02 ± 0.09 | 0.46 ± 0.03 |
| CtFAD2-11 | 23.70 ± 2.57 | 0.28 ± 0.05 | 0.62 ± 0.09 | 5.50 ± 0.81 | 5.30 ± 0.72 | 3.82 ± 0.30 | 1.15 ± 0.36 |
| | | C18:2$^{\Delta 9Z,\ 12E}$ | C18:2 | C18:3 | C20:0 | C20:1 | C18:2Ac |
| | Control | | 12.03 ± 0.65 | 56.79 ± 0.19 | 0.46 ± 0.10 | 0.18 ± 0.15 | |
| | CtFAD2-11 | 0.35 ± 0.07 | 11.63 ± 0.84 | 45.78 ± 4.01 | 0.95 ± 0.19 | 0.41 ± 0.04 | 0.51 ± 0.06 |

(n = 3)

DISCUSSION

The 11 candidate CtFAD2 genes described above that were identified in safflower represent the largest FAD2 gene family observed in any plant species that has been examined to date. Although only a single FAD2 gene was identified in *Arabidopsis* (Okuley et al., 1994), FAD2 appears to be encoded by multiple genes in most other plant genomes studied so far. Two distinct FAD2 genes have been described in soybean (Heppard et al., 1996), flax (Fofana et al., 2004; Khadake et al., 2009) and olive (Hernanze et al., 2005); three genes in sunflower (Martinez-Rivas et al., 2001) and *Camelina sativa* (Kang et al., 2011); and five genes in cotton (Liu et al., 1998). In the amphitetraploid species *Brassica napus,* 4-6 different FAD2 genes have been identified in each diploid sub-genome (Scheffler et al., 1997). All of the candidate CtFAD2 genes were expressed in safflower plants, since the sequences were isolated from cDNAs. This was examined further as described in Example 6.

Although comparable studies are lacking, it is clear that safflower is unusual with respect to FAD2 gene family evolution. Safflower is a self-pollinating diploid plant species which is most closely related to a wild diploid species *Carthamus* palaestinus and it is not known to have extensive genome duplication or re-arrangement (Chapman and Burke, 2007). The multiple FAD2 cDNAs that were identified could not be attributed to alternative splicing since the candidate FAD2 genes did not contain introns in the coding region sequence. Rather, gene duplication was more likely responsible for creating the FAD2 family complexity in safflower. The topology of the phylogenetic tree showed that gene duplications may have occurred at several hierarchical levels. For example, the CtFAD2-3, -4 and -5 polypeptides were more closely related to the others in that clade than they were to other safflower FAD2 sequences, indicating that more recent gene duplications may have been responsible for the emergence of this clade.

Example 6. Expression Level of FAD2 Candidate Genes in Safflower

Expression Profile of FAD2 Genes in Different Tissues

To determine tissue expression patterns of the various candidate CtFAD2 genes, RT-PCR analyses were carried out as described in Example 1. Total RNA was extracted from cotyledons, hypocotyls, root and leaf tissues derived from safflower seedlings of 10 DAG of high linoleic genotype SU, and from flower tissues and developing embryo from flowering plants, and used in the assays. The oligonucleotide primers used for the analyses are listed in Table 11.

TABLE 11

Oligonucleotide primers used for RT-qPCR in the expression profile study of safflower FAD2 genes.

| Primer gene | Sense sequence | Antisense sequence |
|---|---|---|
| CtFAD2-1 | 5'-GTGTATGTCTGCCTCCGAGA -3' (SEQ ID NO: 116) | 5'- GCAAGGTAGTAGAGGACGAAG -3' (SEQ ID NO: 117) |
| CtFAD2-2 | 5'-GCCTCCAAAGATTCATTCAGGTC -3' (SEQ ID NO: 118) | 5'- CAAGATGGATGCGATGGTAAGG -3' (SEQ ID NO: 119) |
| CtFAD2-3 | 5'-ACGTGGCGGTCTCAGGTT -3' (SEQ ID NO: 120) | 5'- AGGCGGTGACAATTATGATATC -3' (SEQ ID NO: 121) |
| CtFAD2-4 | 5'-AAGGCAGGCCGTGATGCCGAT -3' (SEQ ID NO: 122) | 5'- AGTATTTGATCAATCCGCTGG -3' (SEQ ID NO: 123) |
| CtFAD2-5 | 5'-CAATACGGTAGAGGCCACACAG -3' (SEQ ID NO: 124) | 5'- ATCATCTCTTCGGTAGGTTATG -3' (SEQ ID NO: 125) |
| CtFAD2-6 | 5'-GACATGTGCTCACGTGGTGCAT -3' (SEQ ID NO: 126) | 5'- GTTGCTAATATCCACACCCTA -3' (SEQ ID NO: 127) |
| CtFAD2-7 | 5'-CGAATCACACCCACGGGATC -3' (SEQ ID NO: 128) | 5'- CTAAAGAATTTCCATGGTGTTAC -3' (SEQ ID NO: 129) |
| CtFAD2-8 | 5'-GAGCAACGGAGAGAAGTAACC -3' (SEQ ID NO: 130) | 5'- GAGGGATGATAGAAAGAGGTCC -3' (SEQ ID NO: 131) |
| CtFAD2-9 | 5'-CATGTGTGGCTGGAGGATTCGA -3' (SEQ ID NO: 132) | 5'- GCACCGAGTTTAGCCTTTGTCT -3' (SEQ ID NO: 133) |
| CtFAD2-10 | 5'-CCAACAAACAAACCATCTCTCG -3' (SEQ ID NO: 134) | 5'- GAGAGACGGTGGAAGTAGGTG -3' (SEQ ID NO: 135) |
| CtFAD2-11 | 5'-CCATTGATCCACCCTTCACCTTA -3' (SEQ ID NO: 136) | 5'- AAAGACATAGGCAACAACGAGATC -3' (SEQ ID NO: 137) |
| KASII | 5'-CTGAACTGCAATTATCTAGG -3' (SEQ ID NO: 138) | 5'- GGTATTGGTATTGGATGGGCG -3' (SEQ ID NO: 139) |

The temporal and spatial expression pattern of the 11 CtFAD2 genes is shown in FIG. 5. The RT-qPCR assays showed that CtFAD2-1 was exclusively expressed in developing seeds. In contrast, CtFAD2-2 was expressed at low levels in seeds as well as other tissues examined. Further, no expression of CtFAD2-4, -5, -6, -7, -8, -9 was observed in developing embryos. Low, yet detectable, levels of CtFAD2-10 and -11 expression were observed in developing seeds, more so in the late developmental stage as the safflower seeds approach maturity. CtFAD2-4, -6, -7, -9 and -11 all showed high levels of expression in the young seedling tissues including in cotyledons and hypocotyls. CtFAD2-5 and -8 appeared to be root-specific and CtFAD2-10 was preferentially expressed in flower tissues, with relatively low levels detected in various other tissues examined, including developing seeds, and ten days old seedling tissues.

No amplification products were detected after 40 cycles of amplification in control reactions with total RNA template but without reverse transcriptase, indicating the absence of contaminating genomic DNA in the RNA preparations.

Example 7. Demonstration of the Genetic Mutation in the Safflower Line S317

The first identified high oleic trait in safflower, found in a safflower introduction from India, was controlled by a partially recessive allele designated ol at a single locus OL (Knowles and Hill, 1964). The oleic acid content of olol genotypes was usually 71-75% for greenhouse-grown plants (Knowles, 1989). Knowles (1968) incorporated the ol allele into a safflower breeding program and released the first high oleic (HO) safflower variety "UC-1" in 1966 in the US, which was followed by the release of improved varieties "Oleic Leed" and the Saffola series including Saffola 317 (S-317), S-517 and S-518. The high oleic (olol) genotypes were relatively stable at different temperatures (Bartholomew, 1971). In addition, Knowles (1972) also described a different allele $ol_1$ at the same locus, which produced in homozygous condition between 35 and 50% oleic acid. In contrast to olol genotype, the $ol_1ol_1$ genotype showed a strong response to temperature (Knowles, 1972).

Additional germplasm with higher oleic acid content (>85%) has been reported (Fernandez-Martinez et al., 1993; Bergman et al., 2006). Oleic content up to 89% in safflower was reported by Fernandez-Martinez et al. (1993) in the germplasm accession PI401472 originally sourced from Banglasesh. The Montola series developed by Bergman et al. (2006) contains more than 80% oleic acid, clearly beyond the uppermost level of oleic acid in "UC-1" variety containing the olol allele as described by Knowles and Hill (1964). Genetic analysis through the crosses and segregation analysis, the high oleic and very high oleic lines suggested that these two lines share the same alleles at the OL locus. The very high oleic content (85%) was generated by the combination of the ol alleles and modifying genes with a small positive effect on oleic acid (Hamdan et al., 2009).

In Vitro Biochemical Characterisation of the High Oleic Mutant Line S-317

Safflower microsomes were freshly prepared from developing seeds of the high oleic genotype S-317 at mid-maturity stage, about 15 days post anthesis (DPA), as described by Stymne and Appelqvist (1978). A standard 90 μL reaction mixture contained 40 μg microsomal protein, 2 nmol [$^{14}$C]oleoyl-CoA in 0.1 mmol potassium phosphate buffer pH7.2. Then, 10 μL of 50 mM NADH was added and the incubation continued for an additional 5, 10 or 20 min. The reactions were stopped by adding 90 μL of 0.15 M acetic acid and lipid extracted with 500 μL $CHCl_3$:MeOH (1:1). The lower CHCl3 phase was recovered and the polar lipids from it separated by thin layer chromatography (TLC) using the solvent system $CHCl_3$/MeOH/HAc/$H_2O$ (90:15:10:3 v/v/v/v). Spots corresponding to PC were scraped off the plate and the associated fatty acyl groups were transmethylated in 2 ml of 2% sulphuric acid in MeOH at 90° C. for 30 min. The resultant FAMEs were separated on $AgNO_3$ treated TLC plates with hexane:DEE:HAc (85:15:1 v/v/v). $^{14}$C labelled oleate and linoleate methylester standards were spotted on the plate as references. The plates were exposed and analysed by a Fujifilm FLA-5000 phosphorimager. The radioactivity of each sample was quantified with Fujifilm Multi Gauge software.

Upon the addition of NADH to the reactions with the wild-type microsomes, it was observed that the added [$^{14}$C] oleoyl-CoA disappeared rapidly, within 10 min, at the same time as the appearance of [$^{14}$C]linoleate, indicating the efficient conversion of oleate to linoleate in the wild type safflower microsomes. In contrast, for the high oleic genotype S-317, a significantly higher ratio of [$^{14}$C]oleate to [$^{14}$C]linoleate was found in the in vitro reactions throughout the time course (Table 12), indicating that the biosynthesis of linoleic acid via desaturation of oleate by the microsomes was drastically reduced in this genotype.

TABLE 12

Percentage of C18:2 product derived from C18:1 in safflower microsomes.

| Time | WT | | | HO |
|---|---|---|---|---|
| (min) | C18:1 | C18:2 | C18:1 | C18:2 |
| 0 | 99.2 ± 1.1 | 0.8 ± 1.1 | 100.0 ± 0.0 | 0.0 ± 0.0 |
| 5 | 79.6 ± 1.2 | 20.4 ± 1.2 | 99.4 ± 0.3 | 0.6 ± 0.3 |
| 10 | 69.6 ± 0.4 | 30.4 ± 0.4 | 95.4 ± 1.6 | 4.6 ± 1.6 |
| 20 | 60.6 ± 0.6 | 39.4 ± 0.6 | 95.1 ± 1.5 | 4.9 ± 1.5 |

n = 2

Molecular Characterisation of the High Oleic Allele of

To understand the molecular basis of the high oleic genotype (olol) in safflower, the two seed-expressed FAD2 cDNAs, namely CtFAD2-1 and CtFAD2-2, were amplified by PCR from three high oleic varieties: S-317, LeSaf 496 and CW99-OL and sequenced. The cDNAs covering the entire coding regions of the CtFAD2-1 genes from all three high oleic varieties were identical in nucleotide sequence to each other, and shared about 98% sequence identity with the CtFAD2-1 cDNA derived from the wild type variety SU, including one nucleotide deletion and 22 nucleotide substitutions in the HO genotype relative to the wild-type. The single base pair deletion was found at nucleotide 606 counting from the first ATG, in approximately the middle of the CtFAD2-1 coding region. This deletion caused a shift in the translational reading frame that created a stop codon soon after the deletion, so that the mutant gene in the three olol varieties encoded a predicted, truncated polypeptide without the third histidine box present in the wild-type protein (FIG. 6). It was noteworthy that there was a relatively high level of sequence variation in the DNA sequences near the deleted single nucleotide site of the ol allele, suggesting that additional mutations had accumulated in the mutant gene.

The DNA regions including the 5' UTR introns of CtFAD2-1 and CtFAD2-2 were also isolated from the olol mutant S-317 and compared to the wild-type introns. The CtFAD2-1 intron from S-317 was 1144 bp in length, 61 bp longer than the wild type SU intron which was 1083 bp in length. The comparison of the nucleotide sequences of the CtFAD2-1 introns showed an overall sequence identity of 76.8%, the introns differing in 27 indels and 95 single nucleotide substitutions (FIG. 7).

Interestingly, the nucleotide substitutions in the mutant gene were not distributed evenly throughout the 1142 bp long region corresponding to the coding region of the defective CtFAD2-1, in that 14 of the 22 (63.6%) substitutions were present near the nucleotide deletion, most within 123 bp just downstream of the single nucleotide deletion. In contrast, the CtFAD2-2 introns in the wild-type and mutant genotypes shared an overall 99.5% sequence identity, with only 12 nucleotide substitutions and one 2-nt indel. This indicates that either some selection pressure had occurred in the defective CtFAD2-1 gene in the HO mutant, or, perhaps more likely, that the CtFAD2-1 mutation was of ancient origin and might have originated from a progenitor species of safflower such as *C. palaestinus.*

An EMS mutant (S-901) derived from the commercial high oleic variety S-518 has been described in U.S. Pat. No. 5,912,416. Although genetic studies indicated that the so called $ol_2$ allele in this new genotype was distinct from the $ol_1$ and $ol_1$ alleles in the OL locus, its molecular nature was not determined by Weisker (U.S. Pat. No. 5,912,416). The S-901 genotype was characterised by an increase of the level of oleic acid to 89.5-91.5% of total fatty acids in mature seeds. There was a reduction of saturated fatty acids, i.e palmitic acid down to about 4% and stearic acid down to about 2.5%. However, S-901 did not display a normal plant phenotype and suffered some comprised growth and yield. Morphologically it was shorter and flower heads were smaller compared to its parent line S-518. It also flowered late and contained less oil in the seeds.

Designing Perfect PCR Markers for High Oleic Breeding

The single nucleotide deletion-sequence polymorphism in the mutant CtFAD2-1 allele, concluded to be the causative mutation responsible for the HO phenotype, was developed as the molecular basis of a highly efficient molecular marker for tracking the mutant ol allele. The inventors thus developed a molecular marker assay that allowed the identification and selection of the mutant ol allele for breeding purposes or varietal identification purposes, even when it was present in the heterozygous state. Molecular marker assisted selection thereby eliminates the need to produce an extra generation of plants that must be screened for the fatty acid phenotype. Simple genetics combined with perfect molecular marker assays will make it possible for safflower breeders to quickly incorporate the high oleic trait in their breeding program.

It appeared that there was insufficient sequence variation in the exons of CtFAD2-1 between the wild type SU and high oleic genotype S-317 to easily generate a differential marker based on PCR reactions. However, the inventors could take advantage of the relatively high sequence divergence in the 5' UTR intron of CtFAD2-1 between the OL and ol alleles. There were stretches of highly variable sequences between these two alleles which enabled the design of unique PCR primers. The following illustrative primers were designed to amplify a specific product of 315 bp long from the high-oleic genotypes carrying the olol mutant allele, but not in the wild type SU. HO-Sense: 5'-ATAAGGCTGTGTTCACGGGTTT-3' (SEQ ID NO: 140); and HO-Antisense: 5'-GCTCAGTTGGGGATA-CAAGGAT-3' (SEQ ID NO: 141) (FIG. 7). Another pair of illustrative primers specific for the wild-type gene in the variety SU which gave rise to a 603 bp PCR product as follows: HL-sense: 5'-AGTTATGGTTCGATGATCGACG-3' (SEQ ID NO: 142); and HL-antisense: 5'-TTGCTATA-CATATTGAAGGCACT-3' (SEQ ID NO: 143) (FIG. 7). A pair of primers derived from the safflower KASII gene, ctkasII-sense: 5'-CTGAACTGCAATTATCTAGG-3' (SEQ ID NO: 144) and ctkasII-antisense 5'-GGTATTGGTATTG-GATGGGCG-3' (SEQ ID NO: 145) were used as the positive control to ensure the equal loading and good PCR performance of the template DNA.

The PCR reaction conditions were 94° C. for 2 min, followed by 40 cycles of 94° C. for 30 sec, 58° C. for 30 sec and 72° C. for 30 sec. The reaction products were separated by electrophoresis on a 1% agarose gel and visualized under UV light following ethidium bromide staining of the gel. A fragment of about 300 bp was observed in the amplification reactions for all five high oleic genotypes examined, namely S-317, 5-517, CW99-OL, LeSaf496 and Ciano-OL, while such a fragment was absent for the wild-type genotype SU. Conversely, a fragment of about 600 bp was present in the amplifications for the wild-type safflower SU, but not in any of the high oleic varieties tested. As a positive control, a 198 bp band derived from KASII gene was amplified in the eractions for all of the tested lines. The amplicon's identities were verified by DNA sequencing.

The sequence divergence in the 5'UTR intron region of the CtFAD2-1 gene between the high oleic and wild type safflower alleles thereby facilitated the development of a PCR marker diagnostic for the presence or absence of the CtFAD2-1 mutation. It was completely linked to the ol allele whatever the genetic background, that is, it was a perfectly linked marker. However, that molecular marker was a dominant marker and consequently use of that marker alone would not allow the distinction between homozygous and heterozygous genotypes for the ol allele. To overcome this, another pair of PCR primers was designed which amplified only the wild type Ol allele. Consequently, the use of such wild-type specific primers in combination with high oleic specific PCR primers allowed the distinguishing between homozygous and heterozygous genotypes at the CtFAD2-1 locus.

CtFAD2-1 Expression is Drastically Reduced in High Oleic Genotypes

In above sections, it was shown that CtFAD2-1 was expressed only in the developing embryos of the developing seeds and not detectably in various other tissues examined, including in leaf, root, flower, cotyledon and hypocotyls derived from young safflower seedlings. CtFAD2-1 was highly expressed in developing seeds where the rate of fatty acid metabolism was high, and led to active oil accumulation having mostly C18:2 in a relatively short period of time. CtFAD2-1 had its highest expression level at about the mid point in seed development, with a more moderate expression level at both early and late stages of seed development.

Using the RT-qPCR assay method, the level of normalized gene expression of the CtFAD2-1 gene was measured in three high oleic varieties, namely S-317, Lesaff496 and CW99-OL, and compared to that in developing seeds of the wild-type genotype SU. As can be seen in FIG. 8, CtFAD2-1 expression was detected in all three stages of developing embryos in the wild-type safflower genotype SU, with the highest level of expression observed at the mid-maturity stage, consistent with the previous results and verifying the temporal transcription pattern for this key FAD2 gene. However, CtFAD2-1 transcripts were barely detectable in the three high oleic varieties S-317, Lesaff496 and CW99-OL (FIG. 8), indicating a high level of instability of the RNA transcripts from this gene in the mutant embryos.

In contrast, the levels of transcripts from CtFAD2-2 were similar for the wild-type and high oleic genotypes, showing that CtFAD2-2 expression was unaffected in the HO embryos as well as demonstrating that the RNA preparations were suitably pure for the assays. Therefore, it was concluded that CtFAD2-2 expression could also contribute to the Δ12-desaturation of fatty acids for storage lipids in developing safflower seeds, but at a much lower level than for CtFAD2-1 in the wild-type seeds, as well as being involved in Δ12-desaturation of fatty acids for membrane lipids in root, leaf and stem. There was no evidence that CtFAD2-2 expression was elevated in the high oleic mutant in response to, or as compensation for, the loss of CtFAD2-1 activity in the developing safflower seeds of the CtFAD2-1 mutant.

The Drastically Reduced CtFAD2-1 Transcripts in HO Lines are Caused by Non-Sense Mediated RNA Degradation (NMD)

The drastically reduced level of CtFAD2-1 transcripts in the HO embryos might have been caused by non-sense mediated mRNA degradation (NMD) of CtFAD2-1 mRNAs, since a premature stop codon was found in the middle of coding sequence soon after the single nucleotide deletion. The NMD system is considered to be a mechanism involved in the degradation of aberrant mRNAs that contain a premature termination codon (PTC) resulting from unexpected errors such as genomic mutations, transcriptional errors, and mis-splicing. It is a mechanism that is universally present in eukaryotes and, in particular it has been extensively studied in yeast and mammals. It is rather poorly studied in higher plants, but there are a few reports including the soybean Kunitz trypsin inhibitor gene (Kti3), phytohemagglutinin gene (PHA) from common bean (Jofuku et al., 1989; Voelker et al., 1990), pea ferredoxin gene (FED1) (Dickey et al., 1994) and rice waxy gene (Isshiki et al., 2001).

It was shown in these experiments that the ol mutation leading to the high oleic acid trait in safflower seedoil was correlated with low levels of CtFAD2-1 mRNA accumulation in the developing seeds. Previous research indicated that the ol allele was semi recessive, which was not consistent with a posttranscriptional gene silencing mechanism mediated by small RNAs. Gene silencing involves 21 to 24 nt siRNA produced from double strand RNA, resulting from transcription of antisense or hairpin RNA and can act genetically as a dominant or semi dominant locus (Brodersen and Voinnet, 2006). To confirm that the mechanism of the ol mutation was distinct from RNAi related gene silencing, we carried out a small RNA sequencing, as follows.

Two small RNA libraries, derived from the high oleic genotype S-317 and wild type SU, were generated using pooled RNA isolated from the mid-maturity developing embryos. Bulk sequencing of the small RNA libraries was performed with Solexa technology (Hafner et al., 2008). Sequencing of these two libraries was performed on the Illumina's Solexa Sequencer and the samples were run side by side. The sequencing of SU and S-317 small RNA libraries generated a total of 23,160,261 and 21,696,852 raw reads, respectively. Analysis of these reads resulted in identification of 22,860,098 and 21,427,392 sequences ranging in length from 18 to 30 nucleotides (nt), respectively. The presence and distribution of small RNA corresponding to CtFAD2-1 in the SU and S-317 libraries were determined. Only low, barely detectable levels of small RNAs corresponding to CtFAD2-1 were detected from both small RNA libraries and distributed almost evenly over the coding regions of CtFAD2-1 genes. There was no clear difference between the wild type and high oleic libraries.

From this data, it was concluded that small-RNA mediated post-transcriptional gene silencing was not the main mechanism by which the accumulation of the mutant CtFAD2-1 transcripts was prevented.

Transient Expression Studies in *N. benthamiana* Leaves

To investigate the NMD phenomenon further, the inventors performed experiments for the transient expression of CtFAD2-1 derived from both wild-type and high oleic genotypes in *N. benthamiana* leaves.

Each of the CtFAD2-1 ORFs was inserted in sense orientation into a modified pORE04 binary vector under the control of the CaMV-35S promoter. *Agrobacterium tumefaciens* strain AGL1 harbouring either the 35S:CtFAD2-1 or its mutant form 35S:CtFAD2-1Δ was infiltrated into the underside of the fully expanded leaves of *N. benthamiana* together with 35S:P19, as described in Example 5. Following a period of 5 days further growth at 24° C., the infiltrated regions were excised and total RNAs were obtained from the samples using an RNeasy Mini Kit (Qiagen). To measure the CtFAD2-1 RNA levels, Real Time qPCR assays were carried out in triplicate using Platinum SYBR Green qPCR SuperMix-UDG (Invitrogen) and run on ABI 7900HT Sequence Detection System as described in Example 1. PCR was carried out under the following conditions: an initial 48° C. for 30 min, then 95° C. for 10 min, followed by 40 cycles of 95° C. for 15 s and 60° C. for 60 s. The primers for the exogenous CtFAD2-1 gene were: sense: 5'-GTGTATGTCTGCCTCCGAGA-3' (SEQ ID NO: 146); antisense: 5'-GCAAGGTAGTAGAGGACGAAG-3' (SEQ ID NO: 147). A reference gene, safflower CtKASII, was used to normalize the expression levels; its specific primers were: sense: 5'-CTGAACTGCAATTATCTAGG-3' (SEQ ID NO: 144); and antisense: 5'-GGTATTGGTATTGGATGGGCG-3' (SEQ ID NO: 145). High levels of CtFAD2-1 expression were observed in the *N. benthamiana* leaves from the 35S-CtFAD2-1 gene derived from the wild-type SU variety. In comparison, much lower levels of expression were observed for the 35S-CtFAD2-1Δ gene derived from the high oleic genotype.

*A. thaliana* ecotype Col-0 plants were transformed with *A. tumefaciens* strain AGL1 carrying a binary vector harbouring a seed-specific promoter Fp1 driving either the CtFAD2-1 or the CtFAD2-14 coding region, according to the method of Clough and Bent (1998). Total RNA was isolated from siliques containing mid-maturity stage embryos of progeny of the resultant transformed plants using an RNeasy Mini Kit (Qiagen). Gene expression studies were done using the RNA preparations by the Real Time RT-qPCR assays, carried out in triplicate as described above. High levels of CtFAD2-1 expression were observed in the *Arabidopsis* siliques expressing the Fp1-CtFAD2-1 derived from SU, however, the expression of Fp1-CtFAD2-1Δ derived from the high oleic genotype was drastically reduced in comparison.

It was demonstrated that CtFAD2-1 specific small RNAs were not produced at significantly higher levels in developing high oleic safflower seeds compared to small RNAs from the wild-type gene, even though the mutant CtFAD2-1 transcript was drastically reduced in amount. It was therefore concluded that the reduction in CtFAD2-1 RNA in the high oleic genotype was due to NMD, distinct from a small RNA mediated posttranscriptional gene silencing mechanism. The NMD phenomenon was also observed when the mutant coding region was expressed exogenously in either the *N. benthamiana* leaves or the *Arabidopsis* siliques.

Example 8. Isolation of Safflower cDNAs which are Candidates for Encoding FATB Isolation of Safflower FATB cDNA Sequences Safflower seed oil contains approximately 7% palmitic acid. This fatty acid is synthesized in the plastids of the developing seed cells, from where it is exported to the cytosol of the cells for its incorporation into triacylglycerols. The key enzyme for palmitic acid export is palmitoyl-ACP thioesterase which hydrolyses the thioester bond between the palmitoyl moiety and the acyl carrier protein (ACP) to which the acyl group is covalently bound while it is synthesised in the plastid. The enzyme palmitoyl-ACP thioesterase belongs to a group of soluble plastid-targeted enzymes designated FATB. In seedoil plants, this enzyme displays specificity towards short chain saturated acyl-ACP as substrate. A gene encoding FATB enzyme was initially isolated from plant species accumulating medium chain-length saturated fatty acids, such as lauric acid (C12:0) from California bay tree (*Umbellularia californica*). Subsequent studies demonstrated that FATB orthologues were present in all plant tissues, predominantly in seeds, with substrate specificity ranging from C8:0-ACP to C18:0-ACP. In *Arabidopsis* and most temperate oilseed crops including safflower, palmitic acid is the major saturated fatty acid in seed oil.

To isolate safflower cDNAs that encoded candidates for FATB, the cDNA library of developing safflower seeds was screened using a heterologous probe consisting of a FATB cDNA fragment from cotton (*Gossypium hirsutum*) as described in Example 1. One full length cDNA, named CtFATB-T12, was isolated from safflower seed cDNA library. This cDNA contained an open reading frame of 1029 nucleotides in length, encoding a polypeptide of 343 amino acids. Its 5' and 3' UTRs were 236 nt and 336 nt in length, respectively. It was predicted that the CtFATB-T12 polypeptide had a predicted transit peptide of about 60 amino acids and a 210-amino acid residue core that contained two repeats of a helix and multi-stranded sheet fold common to the so-called hot dog fold proteins.

From the Compositae Genome Project (CGP) expressed sequence tag (EST) database for safflower (cgpdb.ucdavis.edu/cgpdb2), three different ESTs were identified with homology to CtFATB-T12, namely EL379517, EL389827, and EL396749. Each was partial length. The corresponding genes were designated CtFATB-A, CtFATB-B and CtFATB-C, respectively. The full length cDNA CtFATB-T12 isolated from the safflower seed cDNA library was identical in nucleotide sequence to the EST from CtFATB-C in their overlapping region. It appeared that CtFATB-A was more divergent in its nucleotide sequence in comparison to the other two CtFATB sequences.

Expression Profile of CtFATB Genes by Real-Time qPCR Analysis

The gene expression profile of the three CtFATB genes was studied with Real time qPCR as outlined in Example 1. Oligonucleotide primers corresponding to the unique region of each of the three genes were designed, including CtFATB-A, sense primer: 5'-AGAGATCATTGGAGACTAGAGTG-3' (SEQ ID NO: 148); antisense primer: 5'-CCCATCAAGCACAATTCTTCTTAG-3' (SEQ ID NO: 149); CtFATB-B, sense primer: 5'-CTACACAATCGGACTCTGGTGCT-3' (SEQ ID NO: 150); antisense primer: 5'-GCCATCCATGACACCTATTCTA-3' (SEQ ID NO: 151); CtFATB-C, sense primer: 5'-CCTCACTCTGGGACCAAGAAAT-3' (SEQ ID NO: 152); antisense primer: 5'-TTCTTGGGACATGTGACGTAGAA-3' (SEQ ID NO: 153). PCR reactions performed in triplicate as described in Example 1.

As shown in FIG. 9, CtFATB-A showed low expression levels in leaves, roots and in all three stages of developing embryos that were examined. CtFATB-B was active in leaves and roots, but showed lower expression in developing embryos than in leaves and roots. This suggested that this gene might play only a minor role, if any, in fatty acid biosynthesis in developing seeds. In contrast, CtFATB-C demonstrated high expression levels across all the tissues examined, particularly in the developing embryos. This indicated that CtFATB-C was the key gene encoding FATB for the production of palmitic acid in safflower seed oil. This was consistent with our recovery of only one FATB cDNA clone from the seed embryo library, namely CtFATB-T12 which was identical in sequence to CtFATB-C. Based on these data, an approximately 300 bp DNA fragment derived from CtFATB-T12 (CtFATB-C) was chosen as the gene sequence to be used in the preparation of hpRNA constructs for down-regulation of FATB in safflower seed, as described in the following Examples.

Example 9: Isolation and Expression of Safflower cDNA Encoding FAD6

Isolation of Safflower FAD6 cDNA Sequence

The distinct fatty acid compositions found in microsomal and chloroplastic membrane lipids and seed storage oils are the result of an intricate metabolic network that operates to control this composition by regulating fatty acid biosynthesis and flux through both the so-called prokaryotic and eukaryotic pathways. It is clear that microsomal FAD2 enzyme has a major role in converting oleate to linoleate in the ER following export of oleic acid from the plastid and conversion to CoA esters in the cytoplasm. Chloroplast omega-6 desaturase (FAD6) is an enzyme that desaturates 16:1 and 18:1 fatty acids to 16:2 and 18:2, respectively, on all 16:1- or 18:1-containing chloroplast membrane lipids including phosphatidyl glycerol, monogalactosyldiacylglycerol, digalactosyldiaclyglycerol, and sulfoguinovosyldiacylglycerol. An *Arabidopsis* fad6 mutant was reported to be deficient in desaturation of 16:1 and 18:1 to 16:2 and 18:2, respectively, on all chloroplast lipids (Browse et al., 1989). When the fad6 mutant was grown at low temperature (5° C.), the leaves become chlorotic and the growth rate was significantly reduced compared to the wild-type (Hugly and Somerville, 1992). A cDNA sequence encode FAD6 was first isolated from *Arabidopsis* by Falcone et al. (1994). Since then, cDNAs encoding FAD6 and FAD6 genes have been isolated from several plant species including *Brassica napus, Portulaca oleracea*, soybean, and *Ricinus communis*.

In order to isolate a cDNA clone encoding the chloroplast ω6 desaturase encoded by the FAD6 gene from safflower, the CPG database was searched for homologous sequences. Eight EST sequences, namely EL378905, EL380564, EL383438, EL385474, EL389341, EL392036, EL393518, EL411275 were identified and assembled into a single contig sequence of 808 nt. This sequence had an intact 5'end but was incomplete at 3'-end. The full length cDNA was subsequently obtained through 3' RACE PCR amplification using, as template, DNA extracted from a lambda cDNA library made from developing seeds of safflower (SU). PCR conditions were as described in Example 2. A single oligo primer, designated ctFAD6-s2 was used in the amplification reaction in combination with M13 Forward primer since the sequence for this primer was present in the vector of cDNA library. The sequence of the ctFAD6-s2 primer was: 5'-CATTGAAGTCGGTATTGATATCTG-3' (SEQ ID NO: 154). A cDNA of 1545 bp was obtained which had an open reading frame of 1305 bp that encoded a candidate FAD6 polypeptide of 435 amino acids. This polypeptide shared between 60-74% amino acid sequence identity with other cloned plant FAD6 polypeptides. A dendrogram showing the phylogenetic relationship between the safflower FAD6 sequence and representative FAD6 plastidial Δ12 desaturase identified in higher plants was generated by Vector NTI (FIG. 10).

Expression Profile of CtFAD6 by Real-Time qPCR Analysis

The expression profile of CtFAD6 was studied by Real time RT-qPCR which was carried out using Platinum SYBR Green qPCR SuperMix-UDG (Invitrogen) and run on an ABI 7900HT Sequence Detection System with defaults parameters as described in Example 1. The primers used were: ctFAD6-S2: 5'-CATTGAAGTCGGTATTGA-TATCTG-3' (SEQ ID NO: 155) and ctFAD6-a2: 5'-GTTC-CAACAATATCTTCCACCAGT-3' (SEQ ID NO: 156). Reactions were performed in triplicate in 10 μL total volumes containing 20 ng of total RNA template, 800 mM each primer, 0.25 μL of reverse transcriptase and 5 μL one-step RT-PCR master mix reagents. Conditions for RT and amplification were 48° C. for 30 min, then 95° C. for 10 min, followed by 40 cycles of 95° C. for 15 s and 60° C. for 60 s. Expression of a reference gene safflower CtkasII was used to normalize the FAD6 expression levels. The calculations were made as described in Example 1.

The analysis showed that CtFAD6 was expressed at relatively low levels in leaves, roots and three consecutive stages of developing embryos. The low expression levels observed in developing seeds was consistent with the notion that FAD6 might have a relatively minor role in the desaturation of oleate in seeds.

Example 10. Design and Preparation of Genetic Constructs to Silence Fatty Acid Biosynthesis Genes in Safflower Hairpin RNAs (hpRNA) are a type of RNA molecule that have been used extensively to reduce gene expression in plants. Hairpin RNAs are typically transcribed in plant cells from a DNA construct containing an inverted repeat of a sequence derived from a gene to be silenced. The hpRNA transcript thereby has complementary sense and antisense sequences which hybridise to form a double-stranded RNA (dsRNA) region joined by a loop sequence. Such dsRNA structures are processed by endogenous silencing machineries in the plant cells to form small RNA molecules of about 21 to 24 nucleotides corresponding in sequence to the gene to be reduced in activity. These small RNAs can form complexes with endogenous proteins that specifically silence the gene of interest. Such silencing can occur at the transcriptional level, mediated by DNA methylation of parts of the target gene, at the post-transcriptional level by degradation of the target mRNA, or by binding to the mRNAs to inhibit its translation and thereby reduce protein synthesis encoded by the gene. When the hpRNA includes a sequence that is in common between members of a gene family, the hpRNA can silence each of those genes that have the sequence.

Safflower has a large family of FAD2 genes, with at least 11 members identified as described herein (Examples 2 to 6). Safflower also has multiple genes encoding FATB polypeptides, with at least three members identified (Example 8), and at least one FAD6 gene (Example 9). Indeed, the experiments described above may not have identified all members of the gene families in safflower. To determine which members of the FAD2 and FATB gene families were involved in the biosynthesis of linoleic acid or of saturated fatty acids found in safflower seed oil, particularly palmitic acid, and whether FAD6 also was, several genetic constructs were made to express hpRNA molecules in safflower seed, to silence various combinations of FAD2, FATB and FAD6 genes. Each of these hpRNA constructs was designed to be expressed specifically in developing safflower seeds during the period of oil synthesis. This was done by using either foreign promoters or promoters isolated from safflower to express the constructs, which were introduced into safflower by plant transformation.

Construction of pCW600

A plant binary expression vector was designed for the expression of transgenes in seeds using the promoter of an *Arabidopsis* Olesoin1 gene (TAIR website gene annotation At4g25140) (SEQ ID NO: 52). The isolated promoter was 1192 bp in length starting from nucleotide 12899298 in Accession No. NC003075.7, except that within the 1198 bp sequence, 6 bp were omitted to avoid common restriction digestion sequences to aid later cloning steps. The AtOleosin promoter has previously been used for strong, seed-specific expression of transgenes in safflower and *Brassica* species (Nykiforuk et al., 1995; Vanrooijen and Moloney, 1995). This promoter was likely to be a bi-directional promoter, directing strong seed-specific expression of coding regions joined to both ends of the promoter fragment. The *Arabidopsis* oleosin promoter shares features with the *Brassica napus* oleosin promoter, characterised to have a bi-functional nature (Sadanandom et al., 1996). The promoter was chemically synthesised, cloned into pGEMT-Easy and the EcoRI fragment containing the promoter blunted via the Klenow fragment enzyme fill-in reaction, and ligated into the Klenow-blunted HindIII site of pCW265 (Belide et al., 2011), generating pCW600 (AtOleosinP::empty). This vector had a selectable marker gene that encoded a hygromycin phosphotransferase (HPT), thereby allowing selection for tolerance to hygomycin in tissue culture during the transformation process. The vector also included a 35S::GFP gene which allowed selection of transformed cells or tissues by fluorescence under UV light illumination. By inserting the AtOleosin promoter, the vector was designed for expression of a coding region of interest which could be inserted into a multiple cloning site situated downstream of the promoter and upstream of a nos polyadenylation signal (nos3'). This vector served as the backbone vector for the constructs pCW602 and pCW603 described below.

Construction of pXZP410

A flax linin promoter (U.S. Pat. No. 7,642,346) (SEQ ID NO: 53) was inserted as a NotI-XhoI fragment into the binary vector pT7-HELLSGATE12 (Wesley et al., 2001), generating the Gateway silencing binary vector pXZP410. The vector pXZP410 had a selectable marker gene which conferred resistance to kanamycin during tissue culture and allowing seed specific expression of hairpin RNA constructs under the control of the linin promoter. The vector had two introns, one in the sense orientation and the other in the antisense direction with respect to the promoter, and had AttL1 and AttL2 recombinational sites flanking the introns.

To make a silencing construct from pXZP410, two copies of a sequence from the target gene in the Gateway entry vector to be silenced were inserted into the vector, one inserted 5' and the other 3' of the two introns, in inverted orientation with respect to each other to form an inverted repeat. The recombinational sites readily allowed insertion of the two copies by using Gateway recombinase cloning systems (Invitrogen, Carlsbad, USA), as described previously (Wesley et al., 2001). This vector pXZP410 was used as a backbone vector for producing pCW631 and pCW632 as described below.

Construction of pCW571

A 300 bp sequence (SEQ ID NO: 50) identical to a region of the safflower gene CtFATB-3 corresponding to nucleotides 485-784 of the CtFATB-3 cDNA was chemically synthesised and inserted into pENTR/D topo (Invitrogen) according to the manufacturer's instructions, generating a Gateway entry clone designated pCW569. A 756 bp fragment (SEQ ID NO: 49) of the cDNA for CtFAD2-2, corresponding to nucleotides 427-1182, was synthesized and amplified by RT-PCR from RNA isolated from developing safflower seeds. The primers were D28-PstI-5 (5'-CCTGCAGGTACCAATGGCTCGACGACACTG-3') (SEQ ID NO: 157) and D28-AscI-3 (5'-CGGCGCGCCTTCACCTCCTCATCTTTATCC-3') (SEQ ID NO: 158) respectively. The primers included 5' PstI and 3' AscI restriction enzyme sites, thereby allowing the insertion of the amplified fragment into the corresponding sites of pCW569, generating pCW570. This vector contained the fused regions from the CtFATB and CtFAD2-2 genes as a fragment of 1080 bp flanked by recombinational sites, AttL1 and AttL2. Two copies of this FATB-FAD2-2 fragment were then inserted into pXZP410, the second copy inverted with respect to the first, using LR clonase according to the supplier's instructions (Invitrogen, Carlsbad, USA). The resultant plasmid pCW571 had the flax linin promoter to transcribe the inverted repeat region in a seed-specific manner, in order to produce a hpRNA for reducing expression of the CtFATB and CtFAD2-2 genes in seeds.

Construction of pCW603

The DNA fragment from pCW571 containing the inverted repeat of the CtFATB-CtFAD2-2 fragments with the two intervening introns was cut out with SpeI, blunted using the Klenow I fragment of DNA polymerase and ligated into the EcoRV site of pCW600, generating pCW603. This construct pCW603 was capable of expressing an hpRNA under the control of the AtOleosin promoter in seeds of safflower, to reduce expression of CtFATB and CtFAD2-2.

Construction of pCW581

A 590 bp fragment (SEQ ID NO: 51) of DNA made up of a 290 bp fragment of CtFAD6, corresponding to nucleotides 451 to 750 of the cDNA for CtFAD6, and a 300 bp fragment of CtFATB, as for pCW571, was chemically synthesised and inserted into pENTR/D topo, generating pCW579. A 780 bp fragment of CtFAD2-2, as described above for pCW570, was cloned into the AscI site of pCW579, generating pCW580. This construct was an entry clone vector containing the sequences from the CtFATB, CtFAD6 and CtFAD2-2 genes joined in that order as a DNA fragment of 1370 bp with flanking recombinational sites, AttL1 and AttL2. Two copies of this FATB-FAD6-FAD2-2 fragment were then inserted as an inverted repeat into pXZP410 using LR clonase, generating pCW581. This construct pCW581 was a binary vector having a flax linin promoter operably linked to the inverted repeat, which upon transcription in developing safflower seeds cells was capable of expressing an hpRNA to reduce expression of the CtFATB, CtFAD6 and CtFAD2-2 genes.

Construction of pCW602

The DNA fragment containing the inverted repeat of the joined CtFATB-CtFAD6-CtFAD2-2 regions, with the two intervening introns, was enzymatically cut out of pCW571 with NotI, blunted using Klenow I fragment and then ligated into the EcoRV site of pCW600, generating pCW602. pCW602 had the CtFATB-CtFAD6-CtFAD2-2 sequences under the control of the AtOleosin promoter, in contrast to pCW581 which had the same design and gene fragments except with the linin promoter.

Construction of pCW631 and pCW632

Although the linin promoter was useful for expressing hpRNA in seeds, both pCW571 and pCW581 had the selectable marker that conferred kanamycin tolerance. In preliminary safflower transformation experiments, we observed that the explants were not sufficiently susceptible to kanamycin. Therefore, the kanamycin resistance cassette of pCW571 and pCW581 was replaced with a hygromycin resistance cassette as the selectable marker gene. The hygromycin resistance gene made up of the enCUP promoter: hygromycin:nos3'polyadenylation region was cut out of pCW265 with SpeI-AvrII restriction digestion and used to replace the kanamycin resistance cassette in pCW571 and pCW581, thus generating pCW631 and 632, respectively.

In summary, the constructs used in this first set of safflower transformations contained the following main elements:

| Vector | Promoter | Gene fragments in the inverted repeat |
|---|---|---|
| pCW631 | linin | CtFAD2-2 and CtFATB |
| pCW632 | linin | CtFAD2-2, CtFAD6 and CtFATB |
| pCW602 | AtOleosin | CtFAD2-2, CtFAD6 and CtFATB |
| pCW603 | AtOleosin | CtFAD2-2 and CtFATB |

These constructs were introduced into *Agrobacterium* strain AGL1 and used to transform safflower as described in Example 1, with the results as follows.

Example 11. Transformation of Safflower with Gene Silencing Constructs

The genetic constructs were used to transform excised cotyledons and hypocotyls of safflower variety S317 using the *Agrobacterium*-mediated method with rescue of regenerated shoots using grafting (Belide et al., 2011). Over 30 independent transformed shoots growing on non-transformed root-stocks (hereinafter termed $T_0$ plants) were regenerated for the vector pCW603 and grown to maturity as described in Example 1. Integration of the T-DNAs in the $T_0$ safflower scions was checked by PCR using T-DNA vector-specific primers as described by Belide et al. (2011). Most plants found to be lacking the T-DNA used in the particular transformation, presumed to be "escapes" from the hygromycin selection during regeneration in tissue culture, were discarded. However, some were maintained as 'null' plants or negative controls for comparison with the transformed plants. These control plants were treated under the same conditions as the transformed material in tissue culture, grafting and glass house conditions.

Example 12. Analysis of the Fatty Acid Composition of Seedoil of Transgenic Safflower Fatty acid analyses were conducted on individual $T_1$ seeds obtained from the transformed safflower plants, as follows. 30 independent $T_0$ plants transformed with pCW603 in the S317 genetic background were grown in the greenhouse and self-fertilised to produce seed. As many as 10 mature seed from a single seedhead from each $T_0$ plant were analysed for the lipid composition using GC analysis as described in Example 1. Results of the fatty acid composition analysis from seeds of safflower S317 transformed with pCW603 are summarised in Table 13. As each transformed $T_0$ safflower plant was expected to be heterozygous for the T-DNA and therefore produce a segregating population of Ti seeds, it was expected that the analysis of 5-10 seeds from each plant would include some null (segregant) seeds. Such null segregant seeds were good negative controls in this experiment as they had grown and developed within the same seedhead as the transformed seeds from the same plant. As can be seen from the data in Table 13, levels of oleic acid above 87% (as a weight % of the total fatty acid content) were observed in 6 independent lines (Lines 9, 12, 14, 20, 34 and 36) of the 30 lines generated. Many of the transformed seeds had oleic acid contents in the range 87-91.7%, with linoleic acid levels of 2.15 to 5.9% and palmitic acid levels of 2.32-3.45%. The levels of other fatty acids in the seeds were not significantly different to the untransformed controls. The maximum oleic acid content observed in the Ti safflower seed transformed with pCW603 was 91.7%, compared to approximately 77% in the non-transformed S317 control seeds and the null segregant seeds. Notably, the seed lipids were also significantly reduced in the levels of 16:0, decreasing from 4.5% down to as low as 2.3%. The fatty acid profiles of the TAG fractions of the seedoils as purified on TLC plates were not significantly different to that of the total lipid extracted from the seeds.

Two metrics were calculated based on the total fatty acid composition of the safflower seeds, accounting for the most important fatty acids in the seedoil. These were the oleic acid desaturation proportion (ODP) and the palmitic+linoleic to oleic proportion (PLO). These were calculated for each seed and the data is shown in Table 13. Wild-type seeds (S317, untransformed) and the null segregants had an ODP ratio of about 0.1500 and a PLO value of about 0.2830. The seeds transformed with the T-DNA from pCW603 exhibited significant reductions in the ODP and PLO values. 13 seed generated from 6 independent events had a PLO value of less than 0.1 and an ODP less than 0.06. One transformed line had an ODP of 0.0229 and a PLO of 0.0514.

Mature individual single seeds of one elite line, S317 transformed with pCW603, line 9, and the untransformed parent S317 were subjected to LC-MS lipidomics analysis. These analyses clearly showed that the oil from the seeds transformed with the AtOleosinp:CtFATB-CtFAD2-2 RNAi hairpin construct had dramatically altered TAG and DAG compositions (FIGS. 11 and 12). There was a clear increase in the level of TAG (54:3) and a decrease of TAG (54:5), which were predominantly 18:1/18:1/18:1-TAG (triolein) and 18:1/18:2/18:2-TAG, respectively. Among the seeds analysed by LC-MS, the triolein (=54:3) content in TAG was as much as 64.6% (mol %) at the highest oleic acid level (>90%, Table 14) for seed from the RNAi silencing line, compared to the untransformed (S-317) parent which had triolein levels ranging between 47% to 53%. The second most abundant oleate-containing TAG was 18:0/18:1/18:1, followed by 18:1/18:1/18:2. The clearest difference between these safflower oils could also be seen in the DAG lipid class. The DAG(36:1) level was doubled in the seedoil from the transformed seed compared to the parent seed, while DAG(36:4) was reduced by up to 10%. DAG(36.1) is predominantly 18:0/18:1-DAG and DAG(36:4) is 18:2/18:2-DAG (di-linoleate). The DAGs in the seed lipids were only a minor component, as the levels of total TAGs were about 100 times higher than total DAGs (Table 15).

Growth and Morphology of the Transgenic Plants

The $T_0$ safflower transformants containing the T-DNA from pCW603 generated $T_1$ seed that segregated for the T-DNA yielding a set of homozygotes, hemizygotes and null segregants. The ratio of these sub-populations depended on the number and linkage of T-DNA insertion events in the $T_0$ plants, as was expected according to Mendelian genetics. Therefore Ti seeds from each $T_0$ plant were analysed individually. Analysis of the lipid profiles from individual seeds clearly showed that a single seed heads contained both null and transgenic events.

TABLE 13

Lipid fatty acid composition of individual safflower T1 seeds transformed with the T-DNA of pCW603 in the S-317 background. The level of each fatty acid (%) was expressed as a percentage of the total fatty acid content.

| Sample* | C16:0 | C18:0 | C18:1 | C18:1d11 | C18:2 | C18:3 | C20:0 | C20:1 | PLO** | ODP*** |
|---|---|---|---|---|---|---|---|---|---|---|
| S317 (1) | 4.60 | 1.47 | 75.69 | 0.69 | 16.49 | 0.00 | 0.31 | 0.26 | 0.27867 | 0.1789 |
| S317 (2) | 4.64 | 1.47 | 77.02 | 0.68 | 15.09 | 0.00 | 0.32 | 0.28 | 0.25620 | 0.1638 |
| S317 (3) | 4.56 | 1.38 | 76.20 | 0.68 | 16.14 | 0.00 | 0.32 | 0.26 | 0.27161 | 0.1748 |
| S317 (4) | 4.61 | 1.57 | 76.41 | 0.69 | 15.64 | 0.00 | 0.34 | 0.26 | 0.26506 | 0.1699 |
| S317 (5) | 4.55 | 1.51 | 77.90 | 0.69 | 14.28 | 0.00 | 0.33 | 0.25 | 0.24176 | 0.1549 |
| Null (1) | 4.77 | 2.10 | 78.07 | 0.85 | 13.82 | 0.00 | 0.38 | 0.00 | 0.23815 | 0.1504 |
| Null (2) | 4.93 | 1.96 | 76.02 | 0.89 | 15.55 | 0.00 | 0.38 | 0.28 | 0.26942 | 0.1698 |
| Null (3) | 5.59 | 2.22 | 75.15 | 0.92 | 15.68 | 0.00 | 0.45 | 0.00 | 0.28302 | 0.1726 |
| Null (4) | 4.61 | 1.65 | 78.52 | 0.78 | 13.58 | 0.00 | 0.35 | 0.28 | 0.23163 | 0.1474 |
| Null (5) | 5.57 | 2.93 | 78.10 | 0.93 | 11.96 | 0.00 | 0.51 | 0.00 | 0.22445 | 0.1328 |
| TS603.12 (5) | 2.56 | 2.05 | 91.73 | 0.84 | 2.15 | 0.00 | 0.37 | 0.29 | 0.05136 | 0.0229 |
| TS603.09 (4) | 2.32 | 1.87 | 91.45 | 0.74 | 3.09 | 0.00 | 0.20 | 0.34 | 0.05911 | 0.0326 |
| TS603.09 (5) | 2.66 | 2.43 | 91.41 | 0.78 | 2.45 | 0.00 | 0.27 | 0.00 | 0.05587 | 0.0261 |
| TS603.09 (1) | 2.42 | 2.08 | 91.17 | 0.74 | 3.02 | 0.00 | 0.23 | 0.33 | 0.05972 | 0.0321 |
| TS603.36 (1) | 2.65 | 2.40 | 91.01 | 0.67 | 2.25 | 0.00 | 0.45 | 0.32 | 0.05379 | 0.0241 |
| TS603.36 (2) | 2.73 | 1.77 | 90.53 | 0.69 | 3.36 | 0.00 | 0.36 | 0.32 | 0.06728 | 0.0358 |
| TS603.20 (4) | 2.94 | 1.31 | 89.63 | 0.88 | 4.58 | 0.00 | 0.31 | 0.34 | 0.08393 | 0.0486 |
| TS603.34 (4) | 3.21 | 2.55 | 89.62 | 0.89 | 2.92 | 0.00 | 0.48 | 0.32 | 0.06847 | 0.0316 |
| TS603.14 (2) | 2.99 | 1.74 | 89.31 | 0.88 | 4.39 | 0.00 | 0.35 | 0.34 | 0.08257 | 0.0468 |
| TS603.09 (3) | 2.90 | 1.75 | 89.00 | 0.83 | 5.52 | 0.00 | 0.00 | 0.00 | 0.09465 | 0.0584 |
| TS603.34 (5) | 3.36 | 2.23 | 88.92 | 0.85 | 3.89 | 0.00 | 0.43 | 0.32 | 0.08151 | 0.0419 |
| TS603.34 (2) | 3.24 | 1.76 | 88.74 | 1.02 | 4.51 | 0.00 | 0.37 | 0.37 | 0.08725 | 0.0483 |
| TS603.14 (1) | 3.21 | 1.51 | 88.65 | 0.88 | 5.05 | 0.00 | 0.34 | 0.37 | 0.09310 | 0.0539 |
| TS603.20 (3) | 3.29 | 1.39 | 88.44 | 0.98 | 5.90 | 0.00 | 0.00 | 0.00 | 0.10391 | 0.0625 |
| TS603.12 (2) | 3.00 | 1.63 | 88.42 | 0.75 | 5.60 | 0.00 | 0.31 | 0.30 | 0.09722 | 0.0595 |
| TS603.20 (2) | 3.45 | 1.66 | 88.36 | 0.99 | 5.54 | 0.00 | 0.00 | 0.00 | 0.10175 | 0.0590 |
| TS603.20 (1) | 3.30 | 1.46 | 88.16 | 0.89 | 5.53 | 0.00 | 0.33 | 0.31 | 0.10021 | 0.0590 |
| TS603.14 (5) | 3.45 | 1.66 | 87.43 | 0.87 | 5.88 | 0.00 | 0.36 | 0.35 | 0.10673 | 0.0630 |
| TS603.14 (4) | 3.37 | 1.84 | 87.36 | 0.88 | 5.81 | 0.00 | 0.39 | 0.35 | 0.10509 | 0.0624 |
| TS603.36 (4) | 3.24 | 2.21 | 87.33 | 0.67 | 5.60 | 0.00 | 0.42 | 0.30 | 0.10117 | 0.0602 |
| TS603.36 (3) | 3.42 | 2.33 | 86.82 | 0.71 | 5.68 | 0.00 | 0.45 | 0.32 | 0.10491 | 0.0614 |
| TS603.14 (3) | 3.58 | 1.61 | 86.50 | 0.86 | 6.74 | 0.00 | 0.36 | 0.35 | 0.11931 | 0.0723 |
| TS603.12 (4) | 3.68 | 1.39 | 85.46 | 0.92 | 7.97 | 0.00 | 0.29 | 0.30 | 0.13624 | 0.0853 |
| TS603.12 (3) | 3.55 | 2.06 | 85.01 | 0.74 | 8.02 | 0.00 | 0.35 | 0.27 | 0.13609 | 0.0862 |
| TS603.23 (5) | 4.93 | 1.75 | 82.63 | 1.04 | 8.75 | 0.00 | 0.41 | 0.31 | 0.16561 | 0.0958 |
| TS603.17 (5) | 4.68 | 1.57 | 82.06 | 0.70 | 10.37 | 0.00 | 0.33 | 0.31 | 0.18339 | 0.1122 |

TABLE 13-continued

Lipid fatty acid composition of individual safflower T1 seeds transformed with the T-DNA of pCW603 in the S-317 background. The level of each fatty acid (%) was expressed as a percentage of the total fatty acid content.

| Sample* | C16:0 | C18:0 | C18:1 | C18:1d11 | C18:2 | C18:3 | C20:0 | C20:1 | PLO** | ODP*** |
|---|---|---|---|---|---|---|---|---|---|---|
| TS603.17 (4) | 4.41 | 1.31 | 81.94 | 0.68 | 11.11 | 0.00 | 0.28 | 0.28 | 0.18940 | 0.1194 |
| TS603.24 (3) | 4.24 | 2.17 | 81.70 | 0.68 | 10.28 | 0.00 | 0.42 | 0.27 | 0.17772 | 0.1118 |
| TS603.24 (5) | 4.48 | 2.18 | 81.15 | 0.69 | 10.56 | 0.00 | 0.41 | 0.27 | 0.18541 | 0.1152 |
| TS603.24 (4) | 4.39 | 2.16 | 80.94 | 0.70 | 10.88 | 0.00 | 0.41 | 0.25 | 0.18869 | 0.1185 |
| TS603.23 (4) | 4.38 | 2.01 | 80.86 | 0.82 | 11.23 | 0.00 | 0.40 | 0.29 | 0.19312 | 0.1220 |
| TS603.24 (2) | 4.50 | 2.39 | 80.70 | 0.68 | 10.79 | 0.00 | 0.44 | 0.26 | 0.18946 | 0.1180 |
| TS603.17 (3) | 4.60 | 1.75 | 80.65 | 0.68 | 11.69 | 0.00 | 0.35 | 0.27 | 0.20203 | 0.1266 |
| TS603.24 (1) | 4.28 | 2.01 | 80.54 | 0.70 | 11.53 | 0.00 | 0.40 | 0.27 | 0.19632 | 0.1252 |
| TS603.17 (2) | 4.40 | 1.75 | 80.33 | 0.73 | 11.92 | 0.00 | 0.35 | 0.28 | 0.20316 | 0.1292 |
| TS603.06 (3) | 4.38 | 1.60 | 80.22 | 0.88 | 12.31 | 0.00 | 0.34 | 0.28 | 0.20803 | 0.1330 |
| TS603.06 (5) | 4.52 | 1.47 | 80.11 | 0.84 | 12.50 | 0.00 | 0.29 | 0.27 | 0.21245 | 0.1350 |
| TS603.15 (3) | 4.65 | 2.01 | 79.94 | 0.85 | 11.92 | 0.00 | 0.38 | 0.26 | 0.20720 | 0.1297 |
| TS603.34 (3) | 4.77 | 2.44 | 79.79 | 0.86 | 11.42 | 0.00 | 0.45 | 0.28 | 0.20281 | 0.1252 |
| TS603.36 (5) | 4.92 | 2.43 | 79.78 | 0.68 | 11.24 | 0.00 | 0.44 | 0.26 | 0.20258 | 0.1235 |
| TS603.06 (1) | 4.49 | 1.89 | 79.53 | 0.82 | 12.61 | 0.00 | 0.38 | 0.29 | 0.21495 | 0.1368 |
| TS603.23 (2) | 4.47 | 1.74 | 79.45 | 0.86 | 12.86 | 0.00 | 0.35 | 0.28 | 0.21810 | 0.1393 |
| TS603.28 (4) | 4.99 | 2.08 | 79.45 | 0.94 | 12.14 | 0.00 | 0.41 | 0.00 | 0.21554 | 0.1325 |
| TS603.28 (1) | 4.73 | 2.31 | 79.42 | 0.85 | 12.26 | 0.00 | 0.43 | 0.00 | 0.21390 | 0.1337 |
| TS603.28 (5) | 5.04 | 1.96 | 79.37 | 0.97 | 12.66 | 0.00 | 0.00 | 0.00 | 0.22301 | 0.1376 |
| TS603.28 (2) | 4.95 | 2.16 | 79.33 | 0.88 | 12.29 | 0.00 | 0.39 | 0.00 | 0.21728 | 0.1341 |
| TS603.15 (2) | 4.55 | 1.73 | 79.31 | 0.89 | 12.90 | 0.00 | 0.36 | 0.27 | 0.21995 | 0.1399 |
| TS603.06 (4) | 4.60 | 1.73 | 79.25 | 0.88 | 12.93 | 0.00 | 0.33 | 0.28 | 0.22121 | 0.1403 |
| TS603.15 (1) | 4.50 | 2.11 | 79.11 | 0.84 | 12.79 | 0.00 | 0.39 | 0.26 | 0.21860 | 0.1392 |
| TS603.12 (1) | 4.28 | 1.33 | 79.08 | 0.76 | 13.82 | 0.21 | 0.27 | 0.26 | 0.22880 | 0.1507 |
| TS603.06 (2) | 4.63 | 2.24 | 79.08 | 0.78 | 12.58 | 0.00 | 0.42 | 0.27 | 0.21765 | 0.1373 |
| TS603.09 (2) | 4.39 | 1.72 | 78.80 | 0.73 | 13.30 | 0.19 | 0.34 | 0.30 | 0.22453 | 0.1462 |
| TS603.23 (1) | 4.56 | 2.11 | 78.63 | 0.79 | 13.24 | 0.00 | 0.39 | 0.27 | 0.22648 | 0.1442 |
| TS603.17 (1) | 4.43 | 1.49 | 78.47 | 0.74 | 13.92 | 0.37 | 0.31 | 0.26 | 0.23386 | 0.1540 |
| TS603.15 (4) | 4.67 | 1.99 | 78.41 | 0.84 | 13.48 | 0.00 | 0.36 | 0.26 | 0.23138 | 0.1467 |
| TS603.28 (3) | 4.89 | 1.67 | 78.31 | 0.88 | 13.29 | 0.31 | 0.35 | 0.31 | 0.23208 | 0.1479 |
| TS603.34 (1) | 4.65 | 2.13 | 77.75 | 0.83 | 13.58 | 0.35 | 0.41 | 0.30 | 0.23441 | 0.1519 |
| TS603.23 (3) | 4.59 | 1.70 | 77.28 | 0.85 | 14.63 | 0.31 | 0.36 | 0.28 | 0.24866 | 0.1620 |
| TS603.15 (5) | 4.69 | 1.64 | 77.23 | 0.97 | 14.85 | 0.00 | 0.35 | 0.27 | 0.25302 | 0.1613 |

*samples labelled with this convention: TS603.12(5) denotes the plant transformed with vector pCW603, event 12, seed 5. Samples labelled as 'null' are determined via PCR analysis as non-transformed escapes in the plant transformation.
**PLO metric calculated as (16:0 + 18:2)/18:1
***ODP metric calculated as (18:2 + 18:3)/(18:1 + 18:2 + 18:3)

TABLE 14

Fatty acid composition in single seed total lipid (% of total fatty acids).

| Sample | C16:0 | C18:0 | C18:1 | C18:1d11 | C18:2 | C18:3 | C20:0 | C20:1 |
|---|---|---|---|---|---|---|---|---|
| S317 Seed 1 | 5.21 | 2.35 | 77.36 | 0.88 | 14.20 | 0.00 | 0.00 | 0.00 |
| S317 Seed 2 | 5.08 | 3.04 | 77.20 | 0.80 | 13.88 | 0.00 | 0.00 | 0.00 |
| S317 Seed 3 | 5.00 | 2.65 | 78.89 | 0.78 | 12.67 | 0.00 | 0.00 | 0.00 |
| TS603.9 Seed 1 | 3.76 | 3.07 | 87.93 | 0.91 | 4.34 | 0.00 | 0.00 | 0.00 |
| TS603.9 Seed 2 | 3.33 | 2.98 | 89.97 | 0.93 | 2.80 | 0.00 | 0.00 | 0.00 |
| TS603.9 Seed 4 | 3.61 | 4.28 | 88.20 | 0.87 | 3.05 | 0.00 | 0.00 | 0.00 |
| TS603.9 Seed 5 | 3.61 | 3.13 | 88.45 | 0.92 | 3.38 | 0.00 | 0.50 | 0.00 |
| TS603.9 Seed 6 | 4.45 | 3.04 | 85.50 | 0.90 | 5.62 | 0.00 | 0.51 | 0.00 |

TABLE 15

Relative TAG and DAG amount.

| Sample | TAG/DAG ratio |
|---|---|
| S317 Seed 1 | 60.4 |
| S317 Seed 2 | 84.7 |
| S317 Seed 3 | 71.2 |
| TS603.9 Seed 1 | 117.5 |
| TS603.9 Seed 2 | 124.2 |
| TS603.9 Seed 4 | 97.8 |
| TS603.9 Seed 5 | 96.5 |
| TS603.9 Seed 6 | 95.9 |

Seeds from the some of the transgenic lines were grown under controlled conditions (temperature, soil, optimal watering and fertilising, but under natural lighting) in the greenhouse to observe the plant morphology and growth rate. No phenotypic differences were observed between the transformed $T_1$ plants and their null segregant siblings. Transformed seeds germinated at the same rate as the untransformed seeds and yielded seedlings having the same early seedling growth rate (vigour). All of the sown seeds became established and grew into fully fertile plants. DNA was prepared from tips of true leaves from individual plants of the Ti generation and PCR analysis was conducted to determine the ratio of null and transgenic plants. As expected, null segregants were identified.

This phenotypic analysis indicated that safflower plants transformed with the T-DNA of pCW603 and expressing the transgenes did not suffer any detrimental effects compared to null segregants.

The safflower seeds of the T2 generation were tested for oil composition. Seed from several plants having high levels of oleic acid (Table 13) were grown into mature plants producing second generation seed (T2 seed). These seed were harvested when mature and analysed for the fatty acid composition of their oil. The data are given in Table 16. Although the T1 seed displayed up to about 92% oleic acid, the T2 seed reached 94.6% oleic acid. The observed increase in the T2 generation relative to the T1 generation may have been due to homozygosity of the transgene, or simply to the large number of lines analysed.

Southern blot hybridisation analysis is used to determine the number of T-DNA insertions in each transformed line, and lines with a single T-DNA insertion are selected. The oil content of T2 seeds is not significantly different to that in the control, untransformed seeds of the same genetic background and grown under the same conditions.

Analysis of Safflower Seeds Transformed with the T-DNA from pCW631

The T1 seed of safflower variety S-317 transformed with pCW631 were similarly analysed for their fatty acid composition. Table 17 shows the data and the ODP and PLO metrics for these seeds. The oleic acid content in lipid of these seeds was up to 94.19%. The palmitic acid content of seed TS631-01 T1 (21) having the highest level of oleic acid was 2.43%, the ODP was 0.0203 and the PLO was 0.0423. These analyses demonstrated that the hairpin RNA construct in pCW631 generally produced higher oleic acid levels that the construct in pCW603 when transformed into safflower of the S-317 genetic background. This observation indicated that the linin promoter used in pCW631 expressed the hairpin RNA more strongly or with a better timing of expression, or a combination of both, relative to the AtOleosin promoter used in pCW603.

The T2 seeds of safflower variety S-317 transformed with the T-DNA from pCW631 were analysed by GC. Levels of oleic acid up to 94.95% were observed with an ODP of 0.01 and PLO of 0.035.

Safflower seeds and plants transformed with the T-DNAs from the constructs pCW632 and pCW602 are analysed in the same manner as for the seed and plants transformed with pCW603 and pCW631. GC analysis of the T1 seed of safflower variety S-317 transformed with pCW632 showed oleic acid level of up to 94.88%, with ODP as 0.0102 and PLO as 0.0362. Their T2 seeds showed up to 93.14% oleic acid, with ODP as 0.0164 and PLO as 0.0452.

Extraction of Larger Volumes of Safflower Seed Oil

T4 seeds from the homozygous transgenic line designated TS603-22.6 were harvested and total seedoil extracted using the Soxhlet apparatus as described in Example 1. Aliquots of extracted oil were analysed by GC (Table 18). A total of 643 grams oil was recovered. Extractions 2, 3, 5, and 6 were pooled, while extractions 4, 7 and 8 were pooled in a separate lot. The mixtures were further analysed for fatty acid composition by GC. The data are shown in Table 18.

Example 13. Design and Preparation of Further Gene Silencing Constructs

Based on the results described in Examples 10-12, other gene silencing constructs were prepared as follows to increase the oleic acid content of safflower seed oil and decrease the ODP or PLO ratios. These gene silencing constructs included combining different promoters, from non-safflower sources as well as safflower sources, to achieve maximal reduction in the safflower FAD2-2, FATB-3 and FAD6 gene expression, and further silencing more than one FAD2 gene in addition to FAD2-2. These constructs are used to transform varieties of safflower which have inactivated versions of the endogenous CtFAD2-1 gene, such as S-317, Ciano-OL and Lesaff496.

Construction of pCW700

This plant binary expression vector has two foreign (non-safflower) promoters with different but overlapping expression patterns in safflower seed, rather than one promoter, to produce hairpin RNA to reduce expression of the endogenous CtFATB and CtFAD2-2. The two promoters are the AtOleosin promoter and the flax linin promoter and the two hpRNA expression cassettes are in the same T-DNA molecule. This vector is constructed by restriction digestion of the hpRNA gene expression cassette from pCW631, having the linin promoter and hpRNA encoding region for silencing of CtFAD2-2 and CtFATB, and inserted it into the T-DNA of pCW603, thus generating a construct encoding a hairpin RNA against these two safflower genes. This construct is used to transform safflower varieties such as Lesaff496, Ciano-OL and S-317.

TABLE 16

Fatty acid composition of lipid from individual safflower T2 seeds transformed with the T-DNA of pCW603 in the S-317 background. The level of each fatty acid (%) was expressed as a percentage of the total fatty acid content.

| Sample | C16:0 | C18:0 | C18:1 | C18:2 | C18:3 | C20:0 | C20:1 | ODP | PLO |
|---|---|---|---|---|---|---|---|---|---|
| TS603-22.3 T2 (4) | 2.4 | 0.9 | 94.6 | 1.7 | 0.0 | 0.2 | 0.0 | 0.0181 | 0.043956 |
| TS603-22.6(5) | 2.5 | 1.0 | 94.5 | 2.0 | 0.0 | 0.0 | 0.0 | 0.0214 | 0.048069 |
| TS603-22.6(2) | 2.1 | 0.9 | 94.4 | 2.5 | 0.0 | 0.0 | 0.0 | 0.0266 | 0.04934 |
| TS603-22.6(4) | 2.4 | 1.0 | 94.3 | 2.3 | 0.0 | 0.0 | 0.0 | 0.0239 | 0.049028 |
| TS603-22.4 T2 (2) | 2.2 | 1.5 | 94.3 | 1.8 | 0.0 | 0.0 | 0.1 | 0.0200 | 0.042739 |
| TS603-22.6 T2 (20) | 2.2 | 1.1 | 94.2 | 2.4 | 0.0 | 0.0 | 0.0 | 0.0256 | 0.048622 |
| TS603-22.05(4) T2 | 2.2 | 1.4 | 94.2 | 2.0 | 0.0 | 0.1 | 0.0 | 0.0212 | 0.044211 |
| TS603-22.8 T2 (1) | 2.1 | 1.1 | 93.9 | 2.5 | 0.2 | 0.1 | 0.0 | 0.0263 | 0.04839 |
| TS603-22.6 T2 (10) | 2.8 | 1.0 | 93.9 | 2.1 | 0.0 | 0.0 | 0.0 | 0.0223 | 0.052359 |
| TS603-22.6 T2 (6) | 2.9 | 1.1 | 93.9 | 2.0 | 0.0 | 0.0 | 0.0 | 0.0214 | 0.052318 |
| TS603-22.05(1) T2 | 2.2 | 1.3 | 93.8 | 2.2 | 0.1 | 0.2 | 0.0 | 0.0240 | 0.04783 |
| TS603-22.6 T2 (13) | 2.9 | 1.2 | 93.8 | 1.7 | 0.0 | 0.2 | 0.0 | 0.0185 | 0.049564 |
| TS603-22.6 T2 (16) | 2.9 | 0.9 | 93.8 | 2.3 | 0.0 | 0.0 | 0.0 | 0.0249 | 0.055517 |
| TS603-22.4 T2 (1) | 2.5 | 1.5 | 93.7 | 1.9 | 0.1 | 0.1 | 0.0 | 0.0204 | 0.046933 |
| TS603-22.6(1) | 2.7 | 1.2 | 93.7 | 2.3 | 0.0 | 0.0 | 0.0 | 0.0241 | 0.052497 |
| TS603-22.3 T2 (5) | 2.5 | 1.1 | 93.6 | 2.6 | 0.0 | 0.0 | 0.0 | 0.0278 | 0.05449 |

TABLE 16-continued

Fatty acid composition of lipid from individual safflower T2 seeds transformed with the T-DNA of pCW603 in the S-317 background. The level of each fatty acid (%) was expressed as a percentage of the total fatty acid content.

| Sample | C16:0 | C18:0 | C18:1 | C18:2 | C18:3 | C20:0 | C20:1 | ODP | PLO |
|---|---|---|---|---|---|---|---|---|---|
| TS603-08.2(4) | 2.2 | 0.8 | 93.6 | 3.3 | 0.0 | 0.0 | 0.0 | 0.0355 | 0.05861 |
| TS603-22.6 T2 (9) | 2.9 | 1.2 | 93.5 | 2.2 | 0.0 | 0.2 | 0.0 | 0.0235 | 0.054815 |
| TS603-22.6 T2 (19) | 2.9 | 1.1 | 93.5 | 2.3 | 0.0 | 0.0 | 0.0 | 0.0245 | 0.055483 |
| TS603-22.4 T2 (3) | 2.4 | 1.0 | 93.5 | 2.8 | 0.1 | 0.0 | 0.0 | 0.0299 | 0.056044 |
| TS603-22.1 T2 (2) | 2.7 | 0.9 | 93.5 | 2.9 | 0.0 | 0.0 | 0.0 | 0.0306 | 0.059281 |
| TS603-22.6 T2 (14) | 3.1 | 1.5 | 93.4 | 2.1 | 0.0 | 0.0 | 0.0 | 0.0222 | 0.054943 |
| TS603-08.2(3) | 2.7 | 0.9 | 93.4 | 2.9 | 0.0 | 0.0 | 0.0 | 0.0306 | 0.059851 |
| TS603-22.05(5) T2 | 2.3 | 1.6 | 93.4 | 2.5 | 0.2 | 0.0 | 0.0 | 0.0267 | 0.051234 |
| TS603-22.6 T2 (15) | 3.0 | 1.2 | 93.3 | 2.4 | 0.0 | 0.0 | 0.0 | 0.0261 | 0.057723 |
| TS603-22.5 T2 (11) | 2.2 | 1.2 | 93.3 | 2.3 | 0.0 | 0.3 | 0.4 | 0.0285 | 0.048123 |
| TS603-22.6 T2 (8) | 2.9 | 1.2 | 93.3 | 2.5 | 0.0 | 0.0 | 0.0 | 0.0265 | 0.057514 |
| TS603-22.5 T2 (12) | 2.2 | 1.3 | 93.3 | 2.3 | 0.0 | 0.3 | 0.4 | 0.0289 | 0.047835 |
| TS603-22.6 T2 (7) | 3.1 | 1.3 | 93.2 | 2.5 | 0.0 | 0.0 | 0.0 | 0.0265 | 0.059228 |
| TS603-22.4 T2 (8) | 2.1 | 1.8 | 93.2 | 2.0 | 0.0 | 0.3 | 0.3 | 0.0254 | 0.044186 |
| TS603-22.6 T2 (11) | 2.9 | 1.2 | 93.1 | 2.5 | 0.0 | 0.1 | 0.0 | 0.0271 | 0.057755 |
| TS603-22.3 T2 (1) | 2.5 | 1.2 | 93.1 | 3.1 | 0.0 | 0.0 | 0.0 | 0.0335 | 0.060295 |
| TS603-22.5 T2 (14) | 2.1 | 1.3 | 93.1 | 2.6 | 0.0 | 0.2 | 0.4 | 0.0318 | 0.050656 |
| TS603-22.5 T2 (16) | 2.3 | 1.5 | 93.0 | 2.3 | 0.0 | 0.3 | 0.3 | 0.0283 | 0.049621 |
| TS603-22.5 T2 (18) | 2.3 | 1.0 | 93.0 | 2.8 | 0.0 | 0.2 | 0.4 | 0.0341 | 0.05407 |
| TS603-22.5 T2 (15) | 2.0 | 0.9 | 92.9 | 3.0 | 0.0 | 0.3 | 0.5 | 0.0381 | 0.054149 |
| TS603-22.6 T2 (12) | 3.0 | 1.2 | 92.9 | 2.7 | 0.0 | 0.0 | 0.0 | 0.0294 | 0.061518 |
| TS603-22.05(3) T2 | 2.5 | 1.0 | 92.9 | 3.3 | 0.1 | 0.2 | 0.0 | 0.0350 | 0.061372 |
| TS603-22.6 T2 (18) | 2.9 | 0.8 | 92.9 | 3.2 | 0.0 | 0.0 | 0.0 | 0.0349 | 0.06593 |
| TS603-22.6(3) | 2.7 | 0.7 | 92.9 | 3.6 | 0.0 | 0.0 | 0.0 | 0.0383 | 0.067112 |
| TS603-22.8 T2 (4) | 2.6 | 1.2 | 92.9 | 3.3 | 0.0 | 0.0 | 0.0 | 0.0358 | 0.063416 |
| TS603-22.6 T2 (17) | 2.7 | 0.8 | 92.9 | 3.5 | 0.0 | 0.0 | 0.0 | 0.0375 | 0.067028 |
| TS603-22.1 T2 (1) | 2.7 | 1.1 | 92.8 | 3.1 | 0.2 | 0.0 | 0.0 | 0.0334 | 0.062312 |
| TS603-22.4 T2 (11) | 2.2 | 1.4 | 92.6 | 2.7 | 0.0 | 0.3 | 0.4 | 0.0340 | 0.053189 |
| TS603-22.4 T2 (12) | 2.1 | 1.4 | 92.6 | 2.9 | 0.0 | 0.3 | 0.4 | 0.0355 | 0.054077 |
| TS603-22.1 T2 (4) | 2.4 | 0.9 | 92.6 | 4.0 | 0.0 | 0.0 | 0.0 | 0.0434 | 0.069653 |
| TS603-44(2) T1 | 2.7 | 1.1 | 92.5 | 3.3 | 0.0 | 0.2 | 0.0 | 0.0358 | 0.065506 |
| TS603-22.8 T2 (5) | 2.9 | 1.1 | 92.4 | 3.5 | 0.0 | 0.0 | 0.0 | 0.0381 | 0.069194 |
| TS603-22.5 T2 (6) | 2.1 | 2.0 | 92.4 | 2.4 | 0.0 | 0.3 | 0.4 | 0.0305 | 0.049301 |
| TS603-22.4 T2 (5) | 2.8 | 1.7 | 92.4 | 2.9 | 0.0 | 0.0 | 0.0 | 0.0318 | 0.062593 |
| TS603-22.4 T2 (13) | 2.3 | 1.1 | 92.3 | 3.3 | 0.0 | 0.2 | 0.4 | 0.0406 | 0.060311 |
| TS603-22.3 T2 (3) | 2.7 | 1.4 | 92.3 | 3.4 | 0.1 | 0.1 | 0.0 | 0.0368 | 0.065979 |
| TS603-34.3 T2 (1) | 2.6 | 1.1 | 92.3 | 3.9 | 0.0 | 0.1 | 0.0 | 0.0421 | 0.070162 |
| TS603-34.3 T2 (13) | 2.4 | 1.7 | 92.2 | 2.7 | 0.0 | 0.3 | 0.3 | 0.0332 | 0.055508 |
| TS603-22.5 T2 (10) | 2.4 | 1.6 | 92.1 | 3.0 | 0.0 | 0.3 | 0.3 | 0.0366 | 0.058947 |
| TS603-19.02(3) T2 | 2.5 | 2.0 | 92.1 | 3.2 | 0.0 | 0.1 | 0.0 | 0.0345 | 0.061861 |
| TS603-08.2(1) | 2.6 | 1.0 | 92.1 | 4.1 | 0.0 | 0.0 | 0.0 | 0.0444 | 0.073162 |
| TS603-22.1 T2 (3) | 2.5 | 1.1 | 92.1 | 4.0 | 0.1 | 0.2 | 0.0 | 0.0435 | 0.070895 |
| TS603-22.5 T2 (8) | 2.2 | 1.6 | 92.1 | 3.1 | 0.0 | 0.3 | 0.4 | 0.0381 | 0.058128 |
| TS603-19.2 T2 (11) | 2.4 | 0.9 | 91.9 | 3.9 | 0.0 | 0.2 | 0.4 | 0.0463 | 0.067902 |
| TS603-44(1) T1 | 3.0 | 0.9 | 91.9 | 4.0 | 0.0 | 0.1 | 0.0 | 0.0439 | 0.076059 |
| TS603-19.02(1) T2 | 2.4 | 1.8 | 91.7 | 3.4 | 0.2 | 0.2 | 0.1 | 0.0384 | 0.063629 |
| TS603-22.3 T2 (2) | 3.0 | 1.1 | 91.7 | 4.0 | 0.0 | 0.0 | 0.0 | 0.0434 | 0.076459 |
| TS603-22.5 T2 (7) | 2.3 | 1.7 | 91.7 | 3.2 | 0.0 | 0.3 | 0.4 | 0.0392 | 0.060643 |
| TS603-22.4 T2 (9) | 2.3 | 1.3 | 91.7 | 3.6 | 0.0 | 0.3 | 0.5 | 0.0442 | 0.064255 |
| TS603-22.5 T2 (9) | 2.4 | 1.6 | 91.6 | 3.4 | 0.0 | 0.3 | 0.4 | 0.0414 | 0.063679 |
| TS603-22.4 T2 (7) | 2.4 | 1.3 | 91.5 | 3.9 | 0.0 | 0.3 | 0.4 | 0.0462 | 0.068489 |
| TS603-22.4 T2 (10) | 2.4 | 1.4 | 91.5 | 3.7 | 0.0 | 0.3 | 0.5 | 0.0453 | 0.066056 |
| TS603-34.3 T2 (2) | 2.7 | 1.6 | 91.4 | 3.9 | 0.0 | 0.1 | 0.1 | 0.0442 | 0.072984 |
| TS603-22.4 T2 (4) | 2.7 | 1.3 | 91.4 | 4.2 | 0.1 | 0.1 | 0.0 | 0.0461 | 0.076004 |
| TS603-19.02(5) T2 | 2.4 | 1.9 | 91.4 | 4.1 | 0.1 | 0.2 | 0.0 | 0.0445 | 0.070234 |
| TS603-10.02(2) T2 | 2.7 | 1.5 | 91.2 | 4.4 | 0.1 | 0.1 | 0.0 | 0.0480 | 0.077276 |
| TS603-22.5 T2 (13) | 2.4 | 1.5 | 91.2 | 4.1 | 0.0 | 0.2 | 0.4 | 0.0489 | 0.071172 |
| TS603-19.02(4) | 2.6 | 1.8 | 91.1 | 4.3 | 0.2 | 0.1 | 0.0 | 0.0471 | 0.075467 |
| TS603-22.4 T2 (6) | 2.4 | 1.6 | 91.0 | 4.1 | 0.0 | 0.3 | 0.4 | 0.0488 | 0.07045 |
| TS603-34.4 T2 (2) | 2.7 | 1.7 | 90.8 | 4.4 | 0.1 | 0.1 | 0.0 | 0.0487 | 0.078563 |
| TS603-27.5 T2 (1) | 2.7 | 1.3 | 90.7 | 4.3 | 0.0 | 0.3 | 0.3 | 0.0511 | 0.076932 |
| TS603-19.02(2) T2 | 2.7 | 1.7 | 90.6 | 4.8 | 0.0 | 0.2 | 0.0 | 0.0532 | 0.083056 |
| TS603-22.5 T2 (17) | 2.7 | 1.7 | 90.5 | 4.0 | 0.0 | 0.4 | 0.4 | 0.0480 | 0.074387 |
| TS603-08.2(5) | 3.0 | 1.1 | 90.5 | 5.3 | 0.0 | 0.0 | 0.0 | 0.0583 | 0.091395 |
| TS603-19.2 T2 (17) | 2.6 | 1.8 | 90.5 | 4.2 | 0.0 | 0.3 | 0.3 | 0.0504 | 0.074894 |
| TS603-19.2 T2 (10) | 2.5 | 2.2 | 90.4 | 3.9 | 0.0 | 0.4 | 0.3 | 0.0464 | 0.070963 |
| TS603-34.3 T2 (3) | 2.8 | 1.5 | 90.2 | 5.2 | 0.1 | 0.1 | 0.0 | 0.0575 | 0.088097 |
| TS603-19.2 T2 (19) | 2.5 | 2.3 | 90.2 | 4.0 | 0.0 | 0.3 | 0.3 | 0.0481 | 0.073009 |
| TS603-09.8 T2 (1) | 2.8 | 1.3 | 90.0 | 5.0 | 0.0 | 0.3 | 0.3 | 0.0589 | 0.086178 |
| S317 (1) | 5.57 | 2.93 | 78.10 | 11.96 | 0.00 | 0.51 | 0.00 | 0.1531 | 0.224455 |
| S317 (2) | 4.77 | 2.10 | 78.07 | 13.82 | 0.00 | 0.38 | 0.00 | 0.1770 | 0.23815 |
| S317 (3) | 4.55 | 1.51 | 77.90 | 14.28 | 0.00 | 0.33 | 0.25 | 0.1865 | 0.241763 |
| S317 (4) | 4.61 | 1.65 | 78.52 | 13.58 | 0.00 | 0.35 | 0.28 | 0.1764 | 0.231634 |

TABLE 17

Lipid fatty acid composition analysis of individual safflower T2 seeds transformed with the T-DNA of pCW631 in the S-317 background. The level of each fatty acid (%) was expressed as a percentage of the total fatty acid content.

| FAME ID# | Sample | C16:0 | C16:1 | C18:0 | C18:1 | C18:2 | C20:0 | C20:1 | C22:0 | ODP | PLO |
|---|---|---|---|---|---|---|---|---|---|---|---|
| 916 | TS631-01 T1 (21) | 2.43 | 0.13 | 1.06 | 94.19 | 1.56 | 0.24 | 0.39 | 0.27 | 0.0203 | 0.0423 |
| 912 | TS631-01 T1 (17) | 2.37 | 0.10 | 1.17 | 93.73 | 1.87 | 0.23 | 0.34 | 0.19 | 0.0230 | 0.0452 |
| 913 | TS631-01 T1 (18) | 2.57 | 0.11 | 0.97 | 93.27 | 2.56 | 0.22 | 0.38 | 0.19 | 0.0305 | 0.0550 |
| 897 | TS631-01 T1 (16) | 2.50 | 0.10 | 1.04 | 93.24 | 2.35 | 0.21 | 0.37 | 0.18 | 0.0247 | 0.0521 |
| 910 | TS631-03 T1 (1) | 2.42 | 0.11 | 1.60 | 93.00 | 2.01 | 0.30 | 0.34 | 0.23 | 0.0250 | 0.0476 |
| 921 | TS631-04 T1 (1) | 2.49 | 0.11 | 1.31 | 92.93 | 2.34 | 0.27 | 0.34 | 0.20 | 0.0275 | 0.0521 |
| 895 | TS631-01 T1 (14) | 2.54 | 0.11 | 1.07 | 92.82 | 2.56 | 0.25 | 0.37 | 0.20 | 0.0316 | 0.0549 |
| 917 | TS631-01 T1 (22) | 2.66 | 0.17 | 1.16 | 92.75 | 2.68 | 0.28 | 0.42 | 0.30 | 0.0334 | 0.0576 |
| 918 | TS631-03 T1 (2) | 2.36 | 0.11 | 2.02 | 92.64 | 1.92 | 0.36 | 0.32 | 0.25 | 0.0242 | 0.0463 |
| 914 | TS631-01 T1 (19) | 2.68 | 0.12 | 1.23 | 92.30 | 2.84 | 0.28 | 0.34 | 0.21 | 0.0345 | 0.0598 |
| 898 | TS631-02 T1 (1) | 2.99 | 0.12 | 1.21 | 90.79 | 4.06 | 0.26 | 0.32 | 0.26 | 0.0483 | 0.0777 |
| 915 | TS631-01 T1 (20) | 3.74 | 0.00 | 1.07 | 90.67 | 4.14 | 0.00 | 0.00 | 0.38 | 0.0456 | 0.0869 |
| 919 | TS631-03 T1 (3) | 4.23 | 0.10 | 1.50 | 81.70 | 11.92 | 0.30 | 0.29 | 0.27 | 0.1494 | 0.1976 |
| 899 | TS631-02 T1 (2) | 4.54 | 0.08 | 1.61 | 80.87 | 12.07 | 0.31 | 0.26 | 0.25 | 0.1525 | 0.2054 |
| 900 | TS631-02 T1 (3) | 4.47 | 0.08 | 2.07 | 80.64 | 11.90 | 0.37 | 0.24 | 0.23 | 0.1506 | 0.2030 |
| 901 | TS631-02 T1 (4) | 4.60 | 0.09 | 1.83 | 80.24 | 12.51 | 0.29 | 0.22 | 0.22 | 0.1586 | 0.2132 |
| 906 | TS631-02 T1 (9) | 4.44 | 0.09 | 1.74 | 80.20 | 12.76 | 0.31 | 0.23 | 0.24 | 0.1619 | 0.2144 |
| 903 | TS631-02 T1 (6) | 4.47 | 0.10 | 1.60 | 79.99 | 13.06 | 0.30 | 0.25 | 0.24 | 0.1664 | 0.2191 |
| 907 | TS631-02 T1 (10) | 4.39 | 0.09 | 1.82 | 79.90 | 12.98 | 0.33 | 0.24 | 0.24 | 0.1655 | 0.2174 |
| 909 | TS631-02 T1 (12) | 4.31 | 0.09 | 1.52 | 79.87 | 13.48 | 0.27 | 0.26 | 0.19 | 0.1720 | 0.2227 |
| 905 | TS631-02 T1 (8) | 4.46 | 0.09 | 1.57 | 79.58 | 13.47 | 0.30 | 0.30 | 0.23 | 0.1730 | 0.2254 |
| 902 | TS631-02 T1 (5) | 4.72 | 0.08 | 1.45 | 79.05 | 13.87 | 0.32 | 0.27 | 0.24 | 0.1789 | 0.2351 |

TABLE 18

Soxhlet Extraction of oil and fatty acid profile of oil.

| Extraction | Dry seed | Meal | Recovered | Oil | Fatty acid composition (Wt %) | | | | | | | | |
|---|---|---|---|---|---|---|---|---|---|---|---|---|---|
| No | weight (g) | weight (g) | oil (g) | content (%) | 16:0 | 16:1 | 18:0 | 18:1 | 18:2 | 18:3 | 20:0 | 20:1 | 22:0 |
| Ext-1 | 223.00 | 219.89 | 68.14 | 30.99 | 2.7 | 0.1 | 1.3 | 92.7 | 2.6 | 0.0 | 0.3 | 0.3 | 0.1 |
| Ext-2 | 233.24 | 232.71 | 64.68 | 27.79 | 2.8 | 0.1 | 1.4 | 91.9 | 3.0 | 0.0 | 0.3 | 0.3 | 0.1 |
| Ext-3 | 240.07 | 238.72 | 72.37 | 30.32 | 3.1 | 0.1 | 1.5 | 91.9 | 2.8 | 0.0 | 0.3 | 0.3 | 0.1 |
| Ext-4 | 231.59 | 229.96 | 66.69 | 29.00 | 3.0 | 0.1 | 1.5 | 91.4 | 3.6 | 0.0 | 0.3 | 0.3 | 0.1 |
| Ext-5 | 220.22 | 219.54 | 62.64 | 28.53 | 2.9 | 0.1 | 1.3 | 92.1 | 3.0 | 0.0 | 0.3 | 0.3 | 0.1 |
| Ext-6 | 288.97 | 288.20 | 77.75 | 26.98 | 2.7 | 0.1 | 1.5 | 92.3 | 2.8 | 0.0 | 0.3 | 0.3 | 0.1 |
| Ext-7 | 241.10 | 239.73 | 71.96 | 30.02 | 2.9 | 0.1 | 1.4 | 91.9 | 3.2 | 0.0 | 0.3 | 0.2 | 0.1 |
| Ext-8 | 243.68 | 242.90 | 67.04 | 27.60 | 2.9 | 0.1 | 1.6 | 91.4 | 3.4 | 0.0 | 0.3 | 0.3 | 0.1 |
| Ext-9 | 321.26 | 320.76 | 92.15 | 28.73 | 3.3 | 0.1 | 1.6 | 89.6 | 4.8 | 0.0 | 0.3 | 0.3 | 0.1 |
| Mixtures | | | | | | | | | | | | | |
| Ext-2/3/5/6 | | | | | 2.9 | 0.1 | 1.4 | 92.0 | 2.9 | 0.0 | 0.3 | 0.3 | 0.2 |
| Ext-4/7/8 | | | | | 2.9 | 0.1 | 1.5 | 91.3 | 3.4 | 0.0 | 0.3 | 0.3 | 0.2 |

Construction of pCW701-pCW710

Safflower-derived promoters, expected to have optimal activity in safflower seeds, are isolated using DNA sequencing technologies that provide accurate sequence information for the regions of DNA upstream and downstream of an expressed gene. Previous results, as described in Examples 2 to 6, have shown that the CtFAD2-1 gene is highly expressed during seed development in safflower. Therefore, the promoter region of this gene is an excellent candidate for driving efficient transgene expression in safflower seeds. As shown in Example 6, CtFAD2-2 was active in genetic backgrounds where CtFAD2-1 was inactivated by mutation. Therefore the promoter of CtFAD2-2 is used in safflower to drive expression of hairpin RNAs targeting CtFAD2-2 activity, amongst other genes. Other promoter elements useful for expression of transgenes in safflower seeds include endogenous (i.e. safflower) promoter elements in the upstream parts of genes for Oleosin (CtOleosin) and seed-storage proteins such as 2S and 11S proteins (Ct2S and Ct11S). The promoter elements of CtFAD2-1, CtOleosin, Ct2S and Ct11S are isolated using standard PCR-based techniques based on safflower genome sequences, and incorporated into plant binary expression vectors. These promoter elements are used to express hpRNA silencing molecules in the constructs pCW701-pCW710 or in conjunction with other non-safflower promoters expressing the same or different hpRNA genes such as in pCW602, pCW603, pCW631 or pCW632. Combinations of hpRNA genes with different promoters are also produced by crossing transformed plants with the individual genes, typically where the hpRNA genes are unlinked.

To isolate the CtFAD2-1 promoter, a genomic DNA fragment of about 3000 bp upstream of the CtFAD2-1 translation start ATG codon is isolated using PCR-based techniques and used to replace the AtOleosin promoter from pCW603 and pCW602, thus generating the constructs pCW701 and pCW702, respectively.

To isolate the CtFAD2-2 promoter, a genomic DNA fragment of about 3000 bp upstream of the CtFAD2-2 translation start ATG codon is isolated using PCR-based techniques and used to replace the AtOleosin promoter from pCW603 and pCW602, thus generating the constructs pCW703 and pCW704, respectively.

To isolate the CtOleosin-1 promoter, a genomic DNA fragment of about 1500 base pairs upstream of the CtOleosin translation start ATG codon is isolated using PCR-based techniques and used to replace the AtOleosin promoter from pCW603 and pCW602, thus generating the constructs pCW705 and pCW706, respectively.

To isolate the Ct2S promoter, a genomic DNA fragment of about 1500 base pairs upstream of the Ct2S translation start ATG codon is isolated and used to replace the AtOleosin promoter from pCW603 and pCW602, thus generating the vectors pCW707 and pCW708, respectively.

To isolate the Ct11S promoter, a genomic DNA fragment of about 1500 base pairs upstream of the Ct11S start ATG is isolated from genomic DNA of safflower using PCR-based techniques and used to replace the AtOleosin promoter from pCW603 and pCW602, thus generating the vectors pCW709 and pCW710, respectively.

Each of these vectors is transformed into safflower varieties as described in Example 1.

Example 14. Field Performance of Safflower Varieties

A series of non-transformed varieties and accessions of safflower were grown in the summer of 2011-2012 at a field station located at Narrabri, New South Wales. Seeds were sown within 5 m×3 m field plots into heavy clay soil commonly found in the Narrabri region. Plants were exposed to natural light and rainfall except that they were irrigated once after 4 weeks of growth. Mature seed were harvested and samples of about 50 seeds were analysed for lipid content and fatty acid composition in seedoil. The oleic acid contents in seedoil of the various varieties and accessions are shown in Table 19 and FIG. 13.

The data from the field trial indicated that there was a range of oleic acid contents of the safflower seed, surprising in the extent of the observed range. Most notably, various accessions described as ‘high oleic’ and previously reported to provide seedoil with at least 70% oleic acid, such Ciano-OL, only produced about 42-46% oleic acid. Linoleic acid levels were much higher than expected based on previous reports. In contrast, other accessions that were reported to give high oleic contents did indeed produce high oleic acid levels (60%-76%) in seedoils under field conditions, such as accessions PI-5601698 and PI-560169. The reason for the considerably lower oleic acid levels than expected in some accessions was believed to be related to the presence of CtFAD2-1 alleles other than the ol allele, such as for example, the ol1 allele which is temperature sensitive, and to growing conditions that were less than ideal in the 2011-12 season. Further fatty acid analysis on the seed obtained from field grown safflower will be carried out to confirm the variation observed in the oleic acid content of some accessions.

This experiment also showed that the level of oleic acid in seedoil obtained from plants grown in the field was typically about 5-10% lower than from plants grown in the

TABLE 19

Lipid fatty acid composition of safflower varieties grown in the field.

| ID | C16:0 | C16:1 | C18:0 | C18:1 | C18:2 | C18:3 | C20:0 | C20:1 |
|---|---|---|---|---|---|---|---|---|
| PI 613463 | 5.3 | <0.1 | 5.5 | 9.1 | 78.8 | 0.1 | 0.6 | 0.2 |
| PI 537677 | 6.3 | 0.2 | 2.3 | 10.3 | 79.9 | 0.1 | 0.3 | 0.2 |
| PI 537645 | 7.8 | 0.2 | 2.2 | 10.5 | 78.0 | 0.1 | 0.4 | 0.2 |
| PI 572433 | 6.4 | 0.1 | 2.5 | 10.7 | 78.7 | 0.2 | 0.4 | 0.2 |
| PI 572472 | 6.3 | 0.2 | 2.4 | 11.1 | 78.7 | 0.2 | 0.4 | 0.2 |
| RC 1002 L | 6.8 | 0.2 | 2.7 | 11.5 | 77.3 | 0.2 | 0.4 | 0.2 |
| PI 537701 | 6.7 | 0.2 | 2.3 | 11.6 | 77.8 | 0.2 | 0.4 | 0.2 |
| CC1485-3-1-1-1-1 | 7.8 | 0.2 | 2.2 | 11.6 | 76.9 | 0.2 | 0.4 | 0.2 |
| PI 560163 | 7.0 | 0.2 | 1.9 | 11.7 | 77.8 | 0.1 | 0.4 | 0.2 |
| PI 451958 | 7.1 | 0.2 | 2.7 | 11.8 | 77.1 | <0.1 | 0.4 | 0.2 |
| PI 306609 | 6.6 | 0.2 | 2.5 | 12.0 | 77.3 | 0.2 | 0.4 | 0.2 |
| PI 451950 | 6.6 | 0.1 | 2.2 | 12.4 | 77.5 | 0.1 | 0.4 | 0.2 |
| PI 537705 | 6.6 | 0.2 | 2.6 | 13.1 | 76.3 | 0.2 | 0.4 | 0.2 |
| PI 413718 | 7.1 | 0.2 | 2.9 | 13.4 | 74.9 | 0.2 | 0.6 | 0.2 |
| PI 560161 | 7.1 | 0.2 | 2.1 | 14.4 | 75.0 | 0.1 | 0.4 | 0.2 |
| PI 560180 | 6.5 | 0.2 | 2.0 | 18.3 | 71.5 | 0.3 | 0.4 | 0.2 |
| PI 401477 | 5.8 | 0.2 | 2.3 | 36.8 | 53.2 | 0.2 | 0.5 | 0.2 |
| PI 537712 | 6.5 | 0.2 | 2.5 | 40.5 | 48.5 | 0.2 | 0.5 | 0.2 |
| PI 537695 | 6.0 | 0.2 | 2.3 | 41.9 | 47.9 | 0.2 | 0.5 | 0.3 |
| CIANO-OL | 6.9 | 0.3 | 1.9 | 42.9 | 46.5 | 0.2 | 0.5 | 0.3 |
| PI 538779 | 6.6 | 0.2 | 2.1 | 43.2 | 46.2 | 0.2 | 0.4 | 0.3 |
| Sinonaria | 6.0 | 0.2 | 2.1 | 43.5 | 46.6 | 0.2 | 0.4 | 0.2 |
| PI 401479 | 5.9 | 0.2 | 2.1 | 48.2 | 41.7 | 0.3 | 0.5 | 0.4 |
| PI 560166 | 5.7 | 0.2 | 2.3 | 55.0 | 35.0 | 0.1 | 0.5 | 0.3 |
| PI 401474 | 5.5 | 0.3 | 1.9 | 59.3 | 30.6 | 0.4 | 0.6 | 0.6 |
| PI 560177 | 5.1 | 0.2 | 1.9 | 60.7 | 30.3 | 0.2 | 0.4 | 0.3 |
| PI 603207 | 5.6 | 0.2 | 2.0 | 65.2 | 25.0 | 0.2 | 0.5 | 0.3 |
| PI 560167 | 5.8 | 0.2 | 1.6 | 65.9 | 24.8 | 0.2 | 0.4 | 0.3 |
| PI 560174 | 5.9 | 0.3 | 1.8 | 67.6 | 22.6 | 0.3 | 0.5 | 0.3 |
| PI 603208 | 5.4 | 0.2 | 2.3 | 68.3 | 21.7 | 0.2 | 0.6 | 0.3 |
| PI 538025 | 5.3 | 0.2 | 2.3 | 68.5 | 21.6 | 0.3 | 0.4 | 0.3 |
| PI 560168 | 5.9 | 0.2 | 1.8 | 68.5 | 21.8 | 0.3 | 0.5 | 0.3 |
| PI 560169 | 5.6 | 0.2 | 1.9 | 71.8 | 18.6 | 0.2 | 0.5 | 0.3 |
| PI 577808 | 5.3 | 0.2 | 2.0 | 75.0 | 15.5 | 0.3 | 0.5 | 0.3 |
| PI 612967 | 5.4 | 0.2 | 1.8 | 76.3 | 14.5 | 0.2 | 0.4 | 0.3 |

greenhouse, even for the best performed accessions in the field. The reason for this was thought to be that field growing conditions were less ideal than in the greenhouse.

In a further experiment, plants of safflower cultivar S317 were grown in either the field or the greenhouse to compare the fatty acid composition of seedoil. Even though the field conditions were more favourable during the growing season compared to the 2011-12 season, the weight of 20 seeds from plants grown in the field was 0.977 g compared to 1.202 g from plants grown in the greenhouse. Eighteen to 20 seeds of each group were analysed for fatty acid composition by GC analysis. The oleic acid level in field grown seeds ranged from 74.83 to 80.65 with a mean (+/1 s.d.) of 78.52+/−1.53, compared to a range in greenhouse grown seeds of 75.15-78.44 with a mean of 76.33+/−1.00. Other fatty acids were present at level in Table 20.

TABLE 20

Fatty acid composition of S317 seedoil grown in either the field or the greenhouse.

| Sample | 16:0 | 16:1 Δ9z | 18:0 | 18:1 Δ9z | 18:1 Δ11z | 18:2 Δ9z Δ12z | 18:3 Δ9z Δ12z Δ15z | 20:0 | 20:1 Δ11z | 22:0 |
|---|---|---|---|---|---|---|---|---|---|---|
| Field-grown | | | | | | | | | | |
| Average | 4.90 | 0.00 | 2.40 | 78.52 | 0.75 | 12.5 | 0.00 | 0.47 | 0.20 | 0.21 |
| Standard deviation | 0.24 | 0.00 | 0.31 | 1.53 | 0.28 | 1.66 | 0.00 | 0.05 | 0.13 | 0.13 |
| Greenhouse-grown | | | | | | | | | | |
| Average | 4.80 | 0.04 | 2.72 | 76.33 | 0.72 | 14.2 | 0.00 | 0.46 | 0.23 | 0.25 |
| Standard deviation | 0.1 | 0.04 | 0.3 | 1.00 | 0.17 | 1.06 | 0.00 | 0.12 | 0.06 | 0.06 |

Example 15. Crossing of Transgenes into Other Safflower Varieties

Safflower varieties are manually crossed using well-established methods, for example as described in Mündel and Bergman (2009). The best of the transformed lines containing the constructs described above are selected, particularly transformed lines containing only a single T-DNA insertion, and crossed with plants of other varieties of safflower, non-transformed or already transformed with a different construct, which have optimal agronomic performance. Using repeated rounds of back-crossing with the recurrent parent, for example for 4 or 5 backcrosses, and then selfing, plants are produced which are homozygous for the desired construct(s) in the genetic background for optimal agronomic performance. Marker assisted selection may be used in the breeding process, such as for example the use of a perfect marker for the ol allele as described in Example 7.

Example 16. Modification of Seedoil Composition by Artificial MicroRNA-Mediated Gene Silencing MicroRNAs (miRNAs) are a class of 20-24-nucleotide (nt) regulatory small RNAs (sRNA) endogenous to both plants and animals which regulate endogenous gene activity. Transgenic expression of modified miRNA precursor RNAs (artificial miRNA precursors) represents a recently developed RNA-based and sequence specific strategy to silence endogenous genes. It has been demonstrated that the substitution of several nucleotides within the miRNA precursor sequence to make an artificial miRNA precursor does not affect the biogenesis of the miRNA as long as the positions of matches and mismatches within the precursor stem loop remain unaffected.

The CSIRO software package MatchPoint (www.pi.csiro.au/RNAi) (Horn and Waterhouse, 2010) was used to identify specific 21-mer sequences in the *Arabidopsis* FAD2, FATB and FAE1 genes which were unique in the *Arabidopsis* genome and therefore less likely to cause silencing of non-target genes (off-gene targeting) when expressed as artificial miRNAs. A unique 21-mer sequence was selected for each of the 3 genes, the 21-mer in each case being fully complementary (antisense) to a region of the transcript of the corresponding gene. An artificial miRNA precursor molecule was designed for each, based on the *A. thaliana* ara-miR159b precursor sequence. In each case, the miR159b precursor sequence was modified in its stem to accommodate the antisense 21-mer sequence. Three constructs each encoding one of the precursor RNAs were made, each under the control of the seed-specific FP1 promoter, and cloned into a binary expression vector to generate the constructs designated pJP1106, pJP1109 and pJP1110.

These constructs were separately transformed into *A. tumefaciens* strain AGL1 by electroporation and the transformed strains used to introduce the genetic construct into *A. thaliana* (ecotype Columbia) by the floral dipping method (Example 1). Seeds (Ti seeds) from the treated plants were plated out on MS media supplemented with 3.5 mg/L PPT to select transformed seedlings, which were transferred to soil to establish confirmed Ti transgenic plants. Most of these Ti plants were expected to be heterozygous for the introduced genetic construct. T2 seed from the transgenic plants were collected at maturity and analysed for their fatty acid composition. These T2 plants included lines that were homozygous for the genetic construct as well as ones which were heterozygous. Homozygous T2 plants were self-fertilised to produce T3 seed, and T3 progeny plants obtained from these seed in turn used to obtain T4 progeny plants. This therefore allowed the analysis of the stability of the gene silencing over three generations of progeny plants.

The fatty acid profiles of seedoil obtained from the T2, T3 and T4 seed lots were analysed by GC as described in Example 1. Alterations to the activity of the Δ12-desaturase caused by the action of the FAD2-based transgene were seen as an increase in the amount of oleic acid in the seed oil profiles. A related method of assessing the cumulative effects of Δ12-desaturase activity during seed fatty acid synthesis was through calculating the oleic desaturation proportion (ODP) parameter for each seedoil, obtained by using the following formula: ODP=%18:2+%18:3/%18:1+%18:2+%18:3. Wild-type *Arabidopsis* seedoil typically has an ODP value of around 0.70 to 0.79, meaning that 70% to 79% of 18:1 formed during fatty acid synthesis in the seed was subsequently converted to the polyunsaturated C18 fatty acids, first of all by the action of Δ12-desaturase to produce 18:2 and then by further desaturation to 18:3. The ODP parameter was therefore useful in determining the extent of FAD2 gene-silencing on the level of endogenous Δ12-desaturase activity.

Levels of $C18:1^{\Delta 9}$ (oleic acid) in $T_2$ seed transformed with the pJP1106 construct (FAD2 target) ranged from 32.9% to 62.7% in 30 transgenic events compared to an average wild-type C18:1 level of 14.0%±0.2. A highly silenced line (plant ID-30) which had a single transgene insertion, determined by segregation ratios (3:1) of the plant selectable marker (PPT), was forwarded to the next generation (T3). Similarly high levels of the $18:1^{\Delta 9}$ were observed in T3 seed ranging from 46.0% to 63.8% with an average of 57.3+5.0%. In the following generation, T4 seed also showed similarly high levels of $18:1^{\Delta 9}$ ranging from 61% to 65.8% with an average of 63.3+1.06%. The total PUFA content (18:2+18:3) in T2 transgenic seedoil ranged from 6.1% to 38%, but in the seedoil from the homozygous line ID-30, the total PUFA content was further reduced and ranged from 4.3 to 5.7%. The control *Arabidopsis* ecotype Columbia seedoil had an ODP value ranging from 0.75-0.79, meaning that over 75% of oleic acid produced in the developing seed was subsequently converted to 18:2 or 18:3. In contrast, the seedoil from the fad2-1 mutant of *Arabidopsis* had an ODP value of 0.17, indicating about a 75% reduction in Δ12-desaturation due to the fad2-1 mutation. The ODP value ranged from 0.08 to 0.48 in the T2 transgenic seedoil, 0.07-0.32 in the T3 seedoil and 0.06-0.08 in the T4 seedoil, in contrast to the value of 0.75 in the control *Arabidopsis* seedoil. The drastic reduction in ODP values in the transgenic lines clearly indicated the efficient silencing of the endogenous FAD2 gene using the artificial microRNA approach. This experiment also showed the stability of the gene silencing over three generations. Similar extents of gene silencing were seen with the other two constructs to down-regulate their corresponding genes.

The degree of FAD2 gene silencing and the amount of $18:1^{\Delta 9}$ (63.3±1.06%) observed in this study using artificial microRNA was higher than in the well characterised FAD2-2 mutant (59.4%), the FAD2 silenced line using the hairpin RNA approach (56.9±3.6%) and the hairpin-antisense approach (61.7±2.0%). The mean 18:2+18:3% content in FAD2 silenced seedoil using amiRNA was 4.8±0.37%, which was lower than in the previously reported FAD2-2 mutant (7.5±1.1%) and the FAD2 silenced line using the hairpin-antisense approach (7.2±1.4%). These data therefore showed the advantages of the artificial microRNA in the extent of silencing, as well as the stability of silencing over the generations of progeny.

Example 17. Assaying Sterol Content and Composition in Oils

The phytosterols from 12 vegetable oil samples purchased from commercial sources in Australia were characterised by GC and GC-MS analysis as O-trimethylsilyl ether (OTMSi-ether) derivatives as described in Example 1. Sterols were identified by retention data, interpretation of mass spectra and comparison with literature and laboratory standard mass spectral data. The sterols were quantified by use of a 5β(H)-Cholan-24-ol internal standard. The basic phytosterol structure and the chemical structures of some of the identified sterols are shown in FIG. 14 and Table 21.

TABLE 21

IUPAC/systematic names of identified sterols.

| Sterol No. | Common name(s) | IUPAC/Systematic name |
|---|---|---|
| 1 | cholesterol | cholest-5-en-3β-ol |
| 2 | brassicasterol | 24-methylcholesta-5,22E-dien-3β-ol |
| 3 | chalinasterol/24-methylene cholesterol | 24-methylcholesta-5,24(28)E-dien-3β-ol |
| 4 | campesterol/24-methylcholesterol | 24-methylcholest-5-en-3β-ol |
| 5 | campestanol/24-methylcholestanol | 24-methylcholestan-3β-ol |
| 7 | Δ5-stigmasterol | 24-ethylcholesta-5,22E-dien-3β-o l |
| 9 | ergost-7-en-3β-ol | 24-methylcholest-7-en-3β-ol |
| 11 | eburicol | 4,4,14-trimthylergosta-8,24(28)-dien-3β-ol |
| 12 | β-sitosterol/24-ethylcholesterol | 24-ethylcholest-5-en-3β-ol |
| 13 | Δ5-avenasterol/isofucosterol | 24-ethylcholesta-5,24(28)Z-dien-3β-ol |
| 19 | Δ7-stigmasterol/stigmast-7-en-3b-ol | 24-ethylcholest-7-en-3β-ol |
| 20 | Δ7-avenasterol | 24-ethylcholesta 7,24(28)-dien-3β-ol |

The vegetable oils analysed were from: sesame (*Sesamum indicum*), olive (*Olea europaea*), sunflower (*Helianthus annus*), castor (*Ricinus communis*), canola (*Brassica napus*), safflower (*Carthamus tinctorius*), peanut (*Arachis hypogaea*), flax (*Linum usitatissimum*) and soybean (*Glycine max*). In decreasing relative abundance, across all of the oil samples, the major phytosterols were: β-sitosterol (range 28-55% of total sterol content), Δ5-avenasterol (isofucosterol) (3-24%), campesterol (2-33%), □5-stigmasterol (0.7-18%), Δ7-stigmasterol (1-18%) and Δ7-avenasterol (0.1-5%). Several other minor sterols were identified, these were: cholesterol, brassicasterol, chalinasterol, campestanol and eburicol. Four C29:2 and two C30:2 sterols were also detected, but further research is required to complete identification of these minor components. In addition, several other unidentified sterols were present in some of the oils but due to their very low abundance, the mass spectra were not intense enough to enable identification of their structures.

The sterol contents expressed as mg/g of oil in decreasing amount were: canola oil (6.8 mg/g), sesame oil (5.8 mg/g), flax oil (4.8-5.2 mg/g), sunflower oil (3.7-4.1 mg/g), peanut oil (3.2 mg/g), safflower oil (3.0 mg/g), soybean oil (3.0 mg/g), olive oil (2.4 mg/g), castor oil (1.9 mg/g). The % sterol compositions and total sterol content are presented in Table 22.

Among all the seed oil samples, the major phytosterol was generally β-sitosterol (range 30-57% of total sterol content). There was a wide range amongst the oils in the proportions of the other major sterols: campesterol (2-17%), Δ5-stigmasterol (0.7-18%), Δ5-avenasterol (4-23%), Δ7-stigmasterol (1-18%). Oils from different species had a different sterol profile with some having quite distinctive profiles. Canola oil had the highest proportion of campesterol (33.6%), while the other species samples generally had lower levels, e.g. up to 17% in peanut oil. Safflower oil had a relatively high proportion of Δ7-stigmasterol (18%), while this sterol was usually low in the other species oils, up to 9% in sunflower oil. Because they were distinctive for each species, sterol profiles can therefore be used to help in the identification of specific vegetable or plant oils and to check their genuineness or adulteration with other oils.

Two samples each of sunflower and safflower were compared, in each case one was produced by cold pressing of seeds and unrefined, while the other was not cold-pressed and refined. Although some differences were observed, the two sources of oils had similar sterol compositions and total sterol contents, suggesting that processing and refining had little effect on these two parameters. The sterol content among the samples varied three-fold and ranged from 1.9 mg/g to 6.8 mg/g. Canola oil had the highest and castor oil the lowest sterol content.

showed the similarity of the phytosterol profiles from the control and modified safflower seed samples.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/638,447 filed 25 Apr. 2012, and AU 2012903992 filed 11 Sep. 2012, both of which are incorporated herein by reference.

TABLE 22

Sterol content and composition of assayed plant oils.

| Sterol number* | Sterol common name | Sesame | Olive | Sunflower | Sunflower cold-pressed | Castor | Canola | Safflower | Safflower cold-pressed | Peanut | Flax (linseed) | Flax (linseed) | Soybean |
|---|---|---|---|---|---|---|---|---|---|---|---|---|---|
| 1 | cholesterol | 0.2 | 0.8 | 0.2 | 0.0 | 0.1 | 0.3 | 0.2 | 0.1 | 0.2 | 0.4 | 0.4 | 0.2 |
| 2 | brassicasterol | 0.1 | 0.0 | 0.0 | 0.0 | 0.3 | 0.1 | 0.0 | 0.0 | 0.0 | 0.2 | 0.2 | 0.0 |
| 3 | chalinasterol/24-methylene cholesterol | 1.5 | 0.1 | 0.3 | 0.1 | 1.1 | 2.4 | 0.2 | 0.1 | 0.9 | 1.5 | 1.4 | 0.8 |
| 4 | campesterol/24-methylcholesterol | 16.2 | 2.4 | 7.4 | 7.9 | 8.4 | 33.6 | 12.1 | 8.5 | 17.4 | 15.7 | 14.4 | 16.9 |
| 5 | campestanol/24-methylcholestanol | 0.7 | 0.3 | 0.3 | 0.1 | 0.9 | 0.2 | 0.8 | 0.8 | 0.3 | 0.2 | 0.2 | 0.7 |
| 6 | C29:2* | 0.0 | 0.0 | 0.1 | 0.2 | 0.0 | 0.1 | 0.5 | 0.5 | 0.0 | 1.2 | 1.3 | 0.1 |
| 7 | Δ5-stigmasterol | 6.4 | 1.2 | 7.4 | 7.2 | 18.6 | 0.7 | 7.0 | 4.6 | 6.9 | 5.1 | 5.8 | 17.6 |
| 8 | unknown | 0.5 | 1.3 | 0.7 | 0.6 | 0.8 | 0.7 | 0.7 | 1.3 | 0.4 | 0.7 | 0.6 | 1.3 |
| 9 | ergost-7-en-3β-ol | 0.1 | 0.1 | 1.9 | 1.8 | 0.2 | 0.4 | 2.7 | 4.0 | 1.4 | 1.4 | 1.4 | 1.0 |
| 10 | unknown | 0.0 | 1.3 | 0.9 | 0.8 | 1.2 | 0.9 | 1.8 | 0.7 | 1.2 | 0.7 | 0.5 | 0.7 |
| 11 | eburicol | 1.6 | 1.8 | 4.1 | 4.4 | 1.5 | 1.0 | 1.9 | 2.9 | 1.2 | 3.5 | 3.3 | 0.9 |
| 12 | β-sitosterol/24-ethylcholesterol | 55.3 | 45.6 | 43.9 | 43.6 | 37.7 | 50.8 | 40.2 | 35.1 | 57.2 | 29.9 | 28.4 | 40.2 |
| 13 | Δ5-avenasterol/isofucosterol | 8.6 | 16.9 | 7.2 | 4.1 | 19.3 | 4.4 | 7.3 | 6.3 | 5.3 | 23.0 | 24.2 | 3.3 |
| 14 | triterpenoid alcohol | 0.0 | 2.4 | 0.9 | 1.1 | 0.0 | 0.0 | 1.6 | 1.9 | 0.0 | 0.0 | 0.0 | 0.9 |
| 15 | triterpenoid alcohol | 0.0 | 0.0 | 0.7 | 0.6 | 0.0 | 0.0 | 2.8 | 1.8 | 0.0 | 0.0 | 0.3 | 0.0 |
| 16 | C29:2* | 0.0 | 0.5 | 0.7 | 0.7 | 1.5 | 1.2 | 2.8 | 1.9 | 2.0 | 1.0 | 0.7 | 0.5 |
| 17 | C29:2* | 1.0 | 0.9 | 2.3 | 2.4 | 0.6 | 0.4 | 1.3 | 1.9 | 0.9 | 1.0 | 1.0 | 1.0 |
| 18 | C30:2* | 0.0 | 0.0 | 0.0 | 0.0 | 1.9 | 0.0 | 0.0 | 0.0 | 0.0 | 0.0 | 0.0 | 0.0 |
| 19 | Δ7-stigmasterol/stigmast-7-en-3β-ol | 2.2 | 7.1 | 9.3 | 10.9 | 2.3 | 0.9 | 10.5 | 18.3 | 1.1 | 7.9 | 8.7 | 5.6 |
| 20 | Δ7-avenasterol | 1.3 | 0.1 | 4.0 | 3.6 | 0.6 | 0.2 | 2.0 | 4.7 | 0.7 | 0.4 | 0.4 | 0.6 |
| 21 | unknown | 0.7 | 7.1 | 0.9 | 0.8 | 0.0 | 0.4 | 0.3 | 0.4 | 0.0 | 3.0 | 3.6 | 0.0 |
| 22 | unknown | 0.3 | 0.0 | 0.3 | 0.9 | 0.0 | 0.0 | 1.2 | 1.3 | 0.2 | 0.1 | 0.0 | 0.3 |
| 23 | unknown | 0.2 | 0.2 | 0.3 | 0.3 | 0.2 | 0.1 | 0.3 | 0.2 | 0.2 | 0.1 | 0.2 | 0.5 |
| 24 | unknown | 0.0 | 3.1 | 0.9 | 1.3 | 0.6 | 0.4 | 0.2 | 0.4 | 0.7 | 1.7 | 1.9 | 0.8 |
| 25 | unknown | 0.9 | 0.4 | 0.3 | 0.5 | 0.3 | 0.1 | 0.5 | 0.7 | 0.3 | 0.1 | 0.1 | 0.6 |
| 26 | C30:2 | 2.2 | 6.0 | 4.6 | 5.7 | 1.4 | 0.6 | 1.0 | 1.2 | 1.2 | 1.2 | 1.1 | 5.2 |
| 27 | unknown | 0.0 | 0.4 | 0.4 | 0.3 | 0.3 | 0.2 | 0.1 | 0.2 | 0.3 | 0.1 | 0.0 | 0.3 |
| | Sum | 100.0 | 100.0 | 100.0 | 100.0 | 100.0 | 100.0 | 100.0 | 100.0 | 100.0 | 100.0 | 100.0 | 100.0 |
| | Total sterol (mg/g oil) | 5.8 | 2.4 | 4.1 | 3.7 | 1.9 | 6.8 | 3.2 | 3.0 | 3.2 | 4.8 | 5.2 | 3.0 |

C29:2* and and C30:2* denotes a C29 sterol with two double bonds and a C30 sterol with two double bonds, respectively A separate analysis was performed of safflower oils from green house derived control seed (S series), genetically modified high oleic acid seed (T series) and two commercial safflower oils. Several features were observed (Table 23). First, there is a high degree of similarity in sterol pattern between the control and modified seeds and secondly the commercial safflower oils are in a separate grouping and are therefore shown to have significantly different phytosterol profile. Further examination of the phytosterol profiles also All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

TABLE 23

Sterol composition (% of total sterols) and content (mg/g) of safflower seed oil samples.

| Sterol No* | common name(s) | IUPAC/systematic name | P2589 S317 (1) | P2590 S317 (2) | P2591 TS603.9.2 T1 | P2592 TS603.9.4 T1 | P2593 TS603.9.5 T1 |
|---|---|---|---|---|---|---|---|
| 1 | cholesterol | cholest-5-en-3β-ol | 0.5 | 0.6 | 0.5 | 3.0 | 1.1 |
| 2 | brassicasterol | 24-methylcholesta-5,22E-dien-3β-ol | 0.0 | 0.0 | 0.1 | 0.0 | 0.1 |
| 3 | chalinasterol/24-methylene cholesterol | 24-methylcholesta-5,24(28)E-dien-3β-ol | 0.8 | 0.8 | 1.1 | 1.1 | 1.2 |
| 4 | campesterol/24-methylcholesterol | 24-methylcholest-5-en-3β-ol | 10.5 | 11.6 | 11.0 | 11.8 | 11.8 |
| 5 | campestanol/24-methylcholestanol | 24-methylcholestan-3β-ol | 0.0 | 0.1 | 0.2 | 0.0 | 0.3 |
| 6 | C29:2** | | 0.9 | 0.8 | 0.2 | 7.2 | 0.4 |
| 7 | Δ5-stigmasterol | 24-ethylcholesta-5,22E-dien-3β-o l | 0.7 | 0.9 | 0.8 | 0.8 | 0.6 |
| 8 | unk*** | | 1.8 | 2.1 | 2.3 | 2.1 | 2.0 |
| 9 | ergost-7-en-3β-ol | 24-methylcholest-7-en-3β-ol | 2.8 | 3.3 | 2.6 | 2.3 | 2.6 |
| 10 | unk*** | | 1.5 | 1.6 | 1.3 | 1.8 | 1.4 |
| 11 | eburicol | 4,4,14-trimthylergosta-8,24(28)-dien-3β-ol | 1.7 | 2.2 | 5.0 | 2.8 | 2.6 |
| 12 | β-sitosterol/24-ethylcholesterol | 24-ethylcholest-5-en-3β-ol | 35.9 | 37.0 | 35.7 | 36.2 | 37.5 |
| 13 | Δ5-avenasterol/isofucosterol | 24-ethylcholesta-5,24(28)Z-dien-3β-ol | 10.4 | 8.2 | 10.0 | 7.9 | 9.3 |
| 14 | triterpenoid alcohol | | 1.6 | 1.9 | 1.4 | 1.2 | 1.4 |
| 15 | triterpenoid alcohol | | 1.8 | 2.2 | 1.3 | 0.9 | 1.6 |
| 16 | C29:2** | | 4.4 | 0.6 | 3.1 | 2.8 | 2.1 |
| 17 | C29:2** | | 2.2 | 2.2 | 2.1 | 2.1 | 1.7 |
| 18 | C30:2** | | 1.9 | 0.8 | 1.8 | 1.9 | 2.1 |
| 19 | Δ7-stigmasterol/stigmast-7-en-3β-ol | 24-ethylcholest-7-en-3β-ol | 11.4 | 13.6 | 10.3 | 8.9 | 10.7 |
| 20 | Δ7-avenasterol**** | 24-ethylcholesta 7,24(28)Z-dien-3β-ol | 6.1 | 5.7 | 5.3 | 3.4 | 4.9 |
| 21 | unk*** | | 0.2 | 0.4 | 0.2 | 0.5 | 0.4 |
| 22 | unk*** | | 0.9 | 1.0 | 1.1 | 1.1 | 0.9 |
| 23 | unk*** | | 0.0 | 0.0 | 0.0 | 0.0 | 0.0 |
| 24 | unk*** | | 0.2 | 0.6 | 0.9 | 1.5 | 0.9 |
| 25 | unk*** | | 0.9 | 0.6 | 0.3 | 1.0 | 0.5 |
| 26 | C30:2 | | 0.9 | 1.0 | 0.5 | 2.9 | 1.4 |
| 27 | unk*** | | 0.0 | 0.1 | 0.8 | 2.2 | 0.4 |
| | Sum | | 100.0 | 100.0 | 100.0 | 100.0 | 100.0 |
| | Total sterol (mg/g oil) | | 1.9 | 2.2 | 2.0 | 2.0 | 1.8 |

*Sterol numbers refer to GC traces.

**C29:2 and and C30:2 denotes C29 sterol with two double bonds and C30 sterol with two double bonds, respectively.

***unk denotes unknown.

****tentative identification.

S317 samples are unmodified parental controls and TS samples are high oleic acid modified safflower oil samples

REFERENCES

Abdullah et al. (1986) Biotech. 4:1087.

Almeida and Allshire (2005) TRENDS Cell Biol 15: 251-258. Alonso et al. (2010) Green Chem. 12:1493-1513.

Ascherio and Willett (1997) Am. J. Clin. Nutr. 66:1006S-1010S.

Bartholomew (1971) Temperature effects on the fatty acid composition of developing seeds in safflower, *Carthamus tinctorius* L.

Baumlein et al. (1991) Mol. Gen. Genet. 225:459-467. Baumlein et al. (1992) Plant J. 2:233-239.

Beclin et al. (2002) Current Biology 12:684-688.

Belide et al. (2011) Plant Methods 7:12.

Bergman et al. (2006) Crop Sci. 46:1818-1819.

Blacklock et al. (2010) J Biol Chem 285: 28442-28449. Bligh and Dyer (1959) Canadian Journal of Biochemistry and Physiology 37:911-7.

Bonanome and Grundy (1988). N. Engl. Med. 318: 1244-1248.

Brodersen and Voinnet (2006) Trends Genet. 22:268-280.

Broothaerts et al. (2005) Nature 433:629-633.

Broun et al. (1998) Plant J. 13:201-210. Broun et al. (1999) Annu. Rev. Nutr. 19: 197-216.

Browse et al. (1989) Plant Physiol. 90:522-529.

Cahoon et al. (2003) Plant J. 34:671-683.

Chapman and Burke (2007) Evolution 61:1773-1780.

Cheng et al. (1996) Plant Cell Rep. 15:653-657.

Chung et al. (2006) BMC Genomics 7:120.

Clough and Bent (1998) Plant J. 16:735-743.

Comai et al. (2004) Plant J 37: 778-786.

Coutu et al. (2007) Transgenic Research 16:771-781.

Covello and Reed (1996) Plant Physiol. 111:223-226.

Dauk et al. (2007) Plant Science 173:43-49.

Dickey et al. (1994) Plant Cell 6:1171-1176.

Dougherty et al. (1995). Am. J. Clin. Nutr. 61:1120-1128.

Durrett et al. (2008) Plant J. 54:593-607.

Dyer et al. (2002) Plant Physiology 130:2027-2038.

Ellerstrom et al. (1996) Plant Mol. Biol. 32:1019-1027.

Endalew et al. (2011) Biomass and Bioenergy 35:3787-3809.

Falcone et al. (1994) Plant Physiol. 106:1453-1459.

Fenandez San Juan (1995). Alimentaria 33: 93-98.

Fernández-Martinez et al. (1993) Euphytica 69: 115-122.

Fofana et al. (2004) Plant Science 166:1487-1496.

Fujimura et al. (1985) Plant Tissue Culture Lett. 2:74.

Gamez et al. (2003) Food Res International 36: 721-727.

Glevin et al. (2003) Microbiol. Mol. Biol. Rev. 67:16-37.

Gong and Jiang (2011) Biotechnol. Lett. 33:1269-1284.

Grant et al. (1995) Plant Cell Rep. 15:254-258.

Greenwell et al. (2011) J. R. Soc. Interface 7:703-726.

Gunstone (2001) Inform 11: 1287-1289.

Hafner et al. (2008) Methods 44:3-12.

Hamdan et al. (2009) Euphytica 168: 61-69.

Henikoff et al. (2004) Plant Physiol 135: 630-636.

Heppard et al. (1996) Plant Physiology 110:311-319.

Hernández et al. (2005) Phytochemistry 66:1417-1426.

Hill and Knowles (1968) Crop Sci. 8:275-277.

Hinchee et al. (1988) Biotechnology 6:915-922.

Hu et al. (1997). N. Engl. J. Med. 337: 1491-1499.

Hugly and Somerville (1992) Plant Physiol. 99:197-202.
Isshiki et al. (2001) Plant Physiol. 125:1388-1395.
Jofuku et al. (1989) Plant Cell 1:427-435.
Kang et al. (2011) Plant Physiology and Biochemistry 49:223-229.
Karmakar et al. (2010) Bioresource Technology 101:7201-7210.
Khadake et al. (2009) Mol Biotechnol. 42: 168-174.
Kim et al. (2006) Molecular Genetics and Genomics 276: 351-368.
Knothe (2005) Fuel Process. Technol. 86:1059-1070.
Knothe and Steidley (2005) Fuel 84:1059-1065
Knowles (1968) Economic Botany 22: 195-200.
Knowles (1969) Economic Botany 23:324-329.
Knowles (1972) Journal of the American Oil Chemists' Society 49:27-29.
Knowles (1989) Oil crops of the world: their breeding and utilization/ed G. Robbelen, R. Keith Downey, A. Ashri. McGraw-Hill, New York.
Knowles and Hill (1964) Crop Science 4:406-409.
Lacroix et al. (2008) Proc. Natl. Acad. Sci. U.S.A. 105: 15429-15434.
Langridge et al. (2001) Aust J Agric Res 52: 1043-1077.
Lee et al. (1998) Science 280:915-918.
Lemieux (2000) Current Genomics 1: 301-311.
Liu (1998) The isolation and characterisation of fatty acid desaturase genes in cotton.
PhD. Thesis University of Sydney.
Liu et al. (1999) Functional Plant Biology 26:101-106.
Liu et al. (2001) American Journal of Botany 88:92-102.
Liu et al. (2002a). J. Am. Coll. Nutr. 21: 205S-211S.
Liu et al. (2002b). Plant Physiol. 129: 1732-1743.
Liu et al. (2010) Fuel 89:2735-2740.
Loguercio (1998) Current genetics 34:241-249.
Maher and Bressler (2007) Bioresource Technology 98:2351-2368.
Marangoni et al. (1995) Trends in Food Sci. Technol. 6: 329-335.
Martínez-Rivas et al. (2001) Molecular Breeding 8:159-168.
McCartney et al. (2004) Plant J 37: 156-173.
Mensink and Katan (1990). N. Engl. J. Med. 323: 439-445.
Millar and Waterhouse (2005) Funct Integr Genomics 5:129-135.
Mroczka et al. (2010) Plant Physiology 153:882-891.
Mundel and Bergman (2009) Safflower. Oil Crops: Handbook of Plant Breeding 4. Ed.
J. Vollman and I. Rajcan. Springer Science. Pp 423-447.
Needleman and Wunsch (1970) J. Mol. Biol. 48:443-453.
Niedz et al. (1995) Plant Cell Reports 14:403.
Noakes and Clifton (1998) Am. J. Clin. Nutr. 98: 242-247.
Nykiforuk et al. (2011) Plant Biotechnology Journal 9:250-263.
Oil World Annual (2004) International Seed Testing Association (ISTA) Mielke GmbH, Hamburg, Germany
Okuley et al. (1994) Plant Cell 6:147-158.
Ow et al. (1986) Science 234:856-859.
Pasquinelli et al. (2005) Curr Opin Genet Develop 15: 200-205.
Paterson et al. (1993) Plant Molecular Biology Reporter 11: 122-127.
Perez-Vich et al. (1998) JAOCS 75:547-555
Perrin et al. (2000) Mol Breed 6:345-352.
Peterson et al. (1997) Plant Molecular Biology Reporter 15:148-153.
Petrie et al. (2010) Plant Methods 6: 8-14.
Phillips et al. (2002) Journal of Food Composition and Analysis 12:123-142.
Potenza et al. (2004) In Vitro Cell Dev. Biol. Plant 40:1-22.
Prasher et al. (1985) Biochem. Biophys. Res. Commun. 127:31-36.
Roche and Gibney (2000) Am. J. Clin. Nutr. 71: 232S-237S.
Ryan et al. (1984) J. Am. Oil Chem. Soc. 61:1610-1619.
Sadanandom et al. (1996) Plant Journal 10:235-242.
Scarth and Tang (2006) Crop Science 46:1225-1236.
Scheffler et al. (1997) TAG Theoretical and Applied Genetics 94:583-591.
Schmittgen (2008) Nature Protocols 3: 1101-1108.
Sebedio et al. (1994) Fett. Wiss. Technol. 96: 235-239.
Semwal et al. (2011) Bioresource Technology 102:2151-2161.
Shanklin and Cahoon (1998) Annual Review of Plant Physiology and Plant Molecular Biology 49:611-641.
Slade and Knauf (2005) Transgenic Res 14: 109-115.
Small (2000a) Genetics 155: 1913-1926.
Small (2000b) Molecular phylogenetics and evolution 16:73-84.
Smith et al. (2000) Nature 407: 319-320.
Speranza et al. (2012) Process Biochemistry (In Press)
Stalker et al. (1988) Science 242: 419-423.
Stymne and Appelqvist (1978) European Journal of Biochemistry 90:223-229.
Tang et al. (2005) The Plant Journal 44:433-446.
Taylor (1997) The Plant Cell 9:1245-1249.
Thelen and Ohlrogge (2002) Metabolic Engineering 4: 12-21
Thillet et al. (1988) J. Biol. Chem 263:12500-12508.
Tholstrup et al. (1994) Am. J. Clin. Nutr. 59: 371-377.
Toriyama et al. (1986) Theor. Appl. Genet. 205:34.
Tzfira and Citovsky (2006) Curr. Opin. Biotech. 17:147-154.
Vanrooijen and Moloney (1995) Bio-Technology 13:72-77.
Voinnet et al. (2003) Plant Journal 33:949-956.
Voinnet et al. (2003) Plant Journal 33: 949-956.
Voelker et al. (1990) Plant Cell 2:255-261.
Waterhouse et al. (1998) Proc. Natl. Acad. Sci. USA 95: 13959-13964.
Wesley et al. (2001) Plant Journal 27: 581-590.
Wood (2009) Plant Biotechnology Journal 7: 914-924.
Wood et al. (2009) Plant Biotechnology Journal 7:914-924.
Zhou et al. (2006) Plant Science 170:665-673.
Zhou et al. (2011) Journal of Biological Chemistry 286: 2877-2885.
Zock and Katan (1992) J. Lipid Res. 33:399-410.
Zock et al. (1994) Arterioscler Thromb. 14: 567-575.

The invention claimed is:

1. A safflower seed comprising (a) a first exogenous polynucleotide which encodes a first silencing RNA which is a double-stranded RNA (dsRNA) molecule or a microRNA comprising a sequence which is complementary to a region of a mRNA of a CtFAD2-2 gene and which is capable of reducing expression of the CtFAD2-2 gene in a developing safflower seed relative to a corresponding safflower seed lacking the exogenous polynucleotide, and wherein the first exogenous polynucleotide is operably linked to a promoter which directs expression of the polynucleotide in the developing safflower seed, and (b) a second exogenous polynucleotide which encodes a second silencing RNA which is a double-stranded RNA (dsRNA) molecule or a microRNA comprising a sequence which is complementary to a region of a mRNA of a CtFATB-3 gene and which is capable of reducing expression of the CtFATB-3 gene in a developing oilseed or safflower seed relative to a corresponding oilseed or safflower seed lacking the second exogenous polynucleotide, and wherein the second exogenous polynucleotide is operably linked to a promoter which directs expression of the polynucleotide in the developing oilseed or safflower seed, wherein:

(i) the first silencing RNA reduces the expression of both CtFAD2-1 and CtFAD2-2 genes; or (ii) the safflower seed comprises a homozygous mutation in a CtFAD2-1 gene, wherein the mutation reduces the activity of the CtFAD2-1 gene in developing safflower seed relative to a corresponding safflower seed lacking the mutation, and wherein 90% to 95% by weight of the total fatty acids of the oil content of the safflower seed is oleic acid.

2. A safflower plant which produces the safflower seed of claim 1.

3. The safflower seed according to claim 1 which comprises a third exogenous polynucleotide which encodes a third silencing RNA which is a double-stranded RNA (dsRNA) molecule or a microRNA comprising a sequence which is complementary to a region of a mRNA of a plastidial ω6 fatty acid desaturase (FAD6) gene and which is capable of reducing expression of the FAD6 gene in a developing safflower seed relative to a corresponding safflower seed lacking the third exogenous polynucleotide, and wherein the third exogenous polynucleotide is operably linked to a promoter which directs expression of the polynucleotide in the developing safflower seed.

4. The safflower seed according to claim 1, wherein the first exogenous polynucleotide and the second exogenous polynucleotide are covalently joined on a single DNA molecule, optionally with a linking DNA sequence between the first and second exogenous polynucleotides.

5. The safflower seed of claim 4, wherein the first exogenous polynucleotide and the second exogenous polynucleotide are under the control of a single promoter such that, when the first exogenous polynucleotide and the second exogenous polynucleotide are transcribed in the developing safflower seed, the first silencing RNA and the second silencing RNA are covalently linked as parts of a single RNA transcript.

6. The safflower seed according to claim 1, which comprises a single transfer DNA integrated into the genome of the safflower seed, and wherein the single transfer DNA comprises the first exogenous polynucleotide and the second exogenous polynucleotide.

7. The safflower seed of claim 6 which is homozygous for the transfer DNA.

8. The safflower seed according to claim 1, wherein all of the promoters are seed specific and preferentially expressed in the embryo of a developing safflower seed.

9. The safflower seed of claim 1, which comprises a homozygous mutation in a CtFAD2-1 gene wherein the mutation is selected from a deletion, an insertion, an inversion, a frameshift, a premature translation stop codon, or one or more non-conservative amino acid substitutions.

10. The safflower seed of claim 9, wherein the mutation is a null mutation in the CtFAD2-1 gene.

11. The safflower seed according to claim 1 comprising an ol allele of the CtFAD2-1 gene or an oil allele of the CtFAD2-1 gene, or both alleles.

12. The safflower seed according to claim 1 wherein the first silencing RNA reduces the expression of both CtFAD2-1 and CtFAD2-2 genes.

13. A safflower plant which produces the safflower seed of claim 3.

14. The safflower plant of claim 2 which is transgenic and homozygous for an insertion into its genome which comprises the first exogenous polynucleotide and the second exogenous polynucleotide.

15. The safflower seed of claim 1, wherein (a) the first silencing RNA comprises at least 19 consecutive nucleotides complementary to a region of SEQ ID NO:2; and (b) the second silencing RNA comprises at least 19 consecutive nucleotides complementary to a region of SEQ ID NO:41.

* * * * *

SEQUENCE LISTING

```
<160> NUMBER OF SEQ ID NOS: 171

<210> SEQ ID NO 1
<211> LENGTH: 1214
<212> TYPE: DNA
<213> ORGANISM: Carthamus tinctorius
```

<400> SEQUENCE: 1

```
ctctgtagcc atatcaattc aggttgaaag caagatggga ggaggagggt gtatgtctgc      60
ctccgagacc aaagctgaag aaaagaagaa cccactcgac cgagtccctt gtgcaaaacc     120
tcctttcacc atcagtgaca tcaagcaagc cattccttcc cactgtttca accgttccct     180
tatccgttcc ttctcttaca ttgtctatga ccttgctata gccttcgtct tctactacct     240
tgccaccacc tacatccacc gtctcccaac ccctttctcc tatctggcat ggctggctta     300
ctggatagtc caaggctgcg tgctcaccgg agcttgggtc gtagcccacg aatgcggcca     360
ccatgccttt agcgattatc aatgggttga cgacaccgtg ggcttcatag tccactcctt     420
tttactcgtc ccctacttct cgtggaaata cagtcatcgg cgccaccact cgaacactgc     480
atcgctcgag cgcgatgaag tctttgtccc aaagcccaga tcaaaactcc cttggtactc     540
gaaatacttg aacaacccgc ctggccgcat catcagcctg ttcgccactc tcactctcgg     600
ctggcccttg tacttgtctt tcaacgtctc tggaagaccc tatgaccgct tcgcctgcca     660
ctacgctcct aacagcccga tatacaacca ccgtgaacgc ctccagattt ggctctctga     720
tgtgggaatc gtggccatgg cattcgtcct ttaccgtgtt gcactggtga aaggcgtgag     780
ctgggtggtc tgtgtgtatg ggataccgtt gttgatcgtg aacgggttcc tggtgttgat     840
cacgttcctt cagcatacgc acccttcgtt gcctcactac gacgggtcgg aatgggactg     900
gctgagaggg gcgttggcga cggtggaccg agactacggt gtgctgaaca aggtgttcca     960
taacatcacg gacacgcacg tggtgcacca tctgttctcg acaatgccgc attatcatgc    1020
gatggaggca acgagggcgg tgaaggggtt gctgggggag tattatcagt ttgacgagac    1080
cccgttttac gcagcgatgt ggagagaggc aaaggagtgt ctgtttgtgg aggcagatga    1140
agggaaagga ggtgtgtttt ggtacaagaa taagtaaagt tgtgatgtgg tgtgcttagg    1200
aggtttatgg aatc                                                      1214
```

<210> SEQ ID NO 2
<211> LENGTH: 1456
<212> TYPE: DNA
<213> ORGANISM: Carthamus tinctorius

<400> SEQUENCE: 2

```
gcacgaggcc caaacggccc atttcgctat tcaaaaggag tttcagaaag cctccaaaga      60
ttcattcagg tcattgaaca atgggtgcag gcgggcgaat gtcgaacccc tccgagggcg     120
aaaagaaaac cgaactcgaa ggcatccaac gagtcccata ccaaaaacct ccgttcacag     180
tcggggatgt caaaaaagcc atcccacctc attgtttcaa tcgatcggtc atccgctctt     240
tctcgtacgt cgtttacgac cttaccatcg catccatctt gtactacatc gccacaactt     300
tcatcccgct cctcccgcac ccgctcgcct acgtggcctg gcccatttac tgggccgttc     360
agggctgtgt catgaccggg gtctgggtca tagcccacga atgcggccat cacgccttta     420
gcgactacca atggctcgac gacactgtcg gccttatcct acattctgtt cttcttgttc     480
cttacttctc gtggaaatac agccaccgcc gccaccactc caacaccggc tcgattgagc     540
acgacgaggt cttcgtcccg aaactcaaat ccggggtccg gtccaccgca aaatacctaa     600
acaacccccc cggccggatc ttgacccttc ttgtcaccct caccctcggc tggccgttgt     660
acctcatgtt caacgtctcc ggccgctact acgaccgctt tgcctgccat tttgacccaa     720
acagccccat ctactcgaac cgtgaacgtg cccagatctt catctccgac gccgggatct     780
```

```
tcgccgtcct ctacgggctc taccggctcg cggcggtcaa agggctcgtg tgggtcctga    840

ccgtctatgc cggaccgttg ctcgtggtca acgggtttct tgtcctgatc acgttcctcc    900

agcacaccca cccgtcgttg ccgcactacg actcaaccga gtgggactgg ctccgtgggg    960

ccctggccac catcgaccgt gactacggga ttttaaacaa ggtgttccac aacatcaccg   1020

acacccacgt gacccaccat ctgttttcga cgatgccgca ttatcacgcg atggaggcca   1080

cgaaggcgat aattccgatc ctcggggatt attatcagtt cgatgggacg tcagttttta   1140

aggcgatgta tagggagacg aaggagtgca tttatgtgga taaagatgag gaggtgaagg   1200

atggggttta ctggtaccgg aataagattt gaagatgatg gatgaaatga aaaaatggta   1260

ttaatagagt ggcgaaatgg tgtctttaat tagtgttgtt ttagagtatg gttttatgag   1320

ttatgatatg ccatttaaat ggacatggaa ttgttagtga tttgaataac ttttgtactc   1380

tgaatatggt gtttgtaggc tatgtagcca ctctgttttt agctttttaa atgcatctat   1440

ctatgttgga acctta                                                   1456
```

```
<210> SEQ ID NO 3
<211> LENGTH: 1285
<212> TYPE: DNA
<213> ORGANISM: Carthamus tinctorius

<400> SEQUENCE: 3

aatcagcagc agcacaagct caaaacttgt gcaaaaggtt gaaaccatgg gggctggtgg     60

acgaatgaac gtggcggtct caggttccga aaaaccccac gccttcaagc gcgttccggt    120

ctccaagcct ccattcgagc ttagcgatct caagaaagca gtcccaccac actgtttcaa    180

acgatctctt gtacgctcct ttgcagccct tttccgtgat atcataattg tcaccgcctt    240

atactacctg gccgcaacca tcattccggt gctccctaaa ccccttacat acgtagcgtg    300

gccgctttat tggttcttcc aaggagccta tcttatgggt ttgtgggtca ttggccacga    360

gtgcggccat catggcttca gcgagtacca atggctcgat gacaccgttg gtttcatcgt    420

ccactccttc attctcactc cgtactttgg gttcaaatac agccaccgaa cccaccacgc    480

caacaccaac tccatcgaat acgatgaggt ttggatccct aaacgcaagt ctgataaatt    540

gtactcggaa gttctcaaca acccactcgg atcctttatt gtatttgtgt tcaagatcgt    600

tcttggattt cccttgtact tcgtattcaa tctttacgga aggaagtacg agaagggaat    660

cacaagccac ttttacccgt atagtcccat ctttaacgat agcgagcgct tccagatctt    720

tctcaccgat cttggagtct ttggcacttt gtacggtgtc taccgtcttg cgttgataaa    780

gggcacggaa tgggtgatca acttctacgg aatgccgatc cttttcatga gtgggttttt    840

catcttgttg acatatcttc accacaccca cccttccatc cctcactacg attccacgga    900

atgggactgg cttagaggtg ctttggccac ggtggaccga aactttgggt tcttgaacca    960

tgctttccat gacgtaactc gaactcacgc cgtacaccat ctgttcccaa ccatcccaca   1020

ttaccatact ttcgaggcaa ggcaggccgt gatgccgatc ttgggcgatt actacaaata   1080

cgacgatacc ccgattctac aggccatatg gagagaaaca aaagattgca tctttatcga   1140

acctgaagag gttaatggag agaaaaaggg tatctactgg ttttacaaat agatggaggt   1200

tgcttaatta tatatgtatg ttgtgttgaa ttttcctcct atataataag ggctatatat   1260

tgagtagcat ttggtggtat gtttg                                         1285
```

```
<210> SEQ ID NO 4
<211> LENGTH: 1346
```

<212> TYPE: DNA
<213> ORGANISM: Carthamus tinctorius

<400> SEQUENCE: 4

```
ctcagtaacc agcctcaaaa cttgatctaa agggttgaaa tcatgggggc tggaggacga     60
atggatgttg cggcaagctc cgagaaaccg cacgccttta aacgtgttcc ggtctcgaag    120
cctccattcg agcttagcga tctcaagaaa gcagttccac cacactgttt caagcgatct    180
cttgtgcgct cctttgcagc ccttttccgt gatatcataa tcgtctccgc cttatactat    240
ctggccgcaa ccgtcattcc ggtgctccct aaacccctta cgtacgtagc atggccgctt    300
tattggttct tccaaggagc ttatcttatg ggtttgtggg tcattggcca cgaatgcggc    360
catcatggct tcagcgagta ccaatggctc gatgacaccg ttggtttcat cgtccactcc    420
ttgattctca ctccgtactt tgggttcaaa tacagccacc gaacccacca cgccaacacc    480
aactccatcg aatacgatga ggtttggatc cctaaacgca agtctgataa attgtactcg    540
gaaatcctca acaacccact cggatccttt gttgtatttg tgttcaagat cgttcttgga    600
tttcccttgt acttcgtgtt caatctttat ggaaggaagt acgagaaggg aatcacgagc    660
cacttttacc catacagtcc catcttcaac gatagcgagc gtttccagat ctttctcacc    720
gatctcggag tctttggcac tttgtatggt gtctaccgtc ttgcgttgat aaagggcacg    780
gaatgggtga tcaacttcta cggaatgccg atccttttca tgagtgggtt tttcatcttg    840
ttgacatatc ttcaccacac ccacccttcc atccctcact acgattccac cgaatgggac    900
tggcttagag gtgctttggc cacggtggac cgaaactttg ggttcttgaa ccatgccttc    960
catgacgtaa ctcgaactca cgcggtacac catctgttcc caaccatccc acattaccat   1020
actttcgagg caaggcaggc cgtgatgccg atcttgggtg attactacaa atacgatgat   1080
accccgattc tagaggccgt ttggagagag acgaaagact gcatctttat cgaacctgaa   1140
gaggttaacg gggagaaaaa gggtatttac tggttctata agtagagaaa tcataattat   1200
atatgtacca tactgaaaga attggattaa gtacatccag cggattgatc aaatacttgt   1260
gttttgtact ggttttactt tgtataatta ataaatgttg ttatctgaaa aaaaaaaaaa   1320
aaaaaagtac tagtcgacgc gtggcc                                        1346
```

<210> SEQ ID NO 5
<211> LENGTH: 1215
<212> TYPE: DNA
<213> ORGANISM: Carthamus tinctorius

<400> SEQUENCE: 5

```
atcacaggaa gctcaaagca tctgttaaca ggttctttga tttccttgga aattagttaa     60
ggatgggagc aggagggcga atgaatgacg acgctacgag ggaaagagat gtcttcaaac    120
atgttcccgt cgagaagcct tcattcggga ttgctgatct caagaaggcc ataccaccac    180
actgtttcaa gcggtcccta accacctctt tctactacct tttccgtgat ttgggtctca    240
tctacgcttt ctactatatt gcaacaaaat acattaccca tctcccccaa ccctactcgt    300
ttgtggcatg gccactttat tggatcgccc aaggtgccat ttgcatgggt ttatggaata    360
tcgtccatga ttgtggtcat cactgcttta gcgattatca atggcttgat gacaccattg    420
gcttcatctg ccactccttt ctgctcactc catacttctc tttcaaatac agtcaccgta    480
ctcatcatgc taacaccagt tcactcgaaa gggatgaagt atgggtccca aaacgcaagc    540
acgatacttg gttttatgag gttctcagca acccagtggg aagctttatc atgcttgtgt    600
```

```
ttaggttatt ttttggcttt cccttgtact ttatgttcaa tcttcatggt aggatataca    660

agggtttccc tagccacttc aacccgttag gccccatctt caacgaccga gagcgtgcta    720

atatctggct ctctgatgcc ggagttctta ccgttgtcta tgcgctctac cgtattgggg    780

caaaagaagg tctccagtcg gtacttttcg tctatattta tcccttgatg gctatgagtg    840

ccttttttcat catgttcaca tatctacacc acactcatcc ttccatcgct cactacgatt    900

cgtcggaatg ggattggttg agaggtgctt tgtcaaccgt ggatagggat tatgggatct    960

tgaacaacat cttccatgac gtaacaagtg ctcatgtggt gcaccatcta ttctcgagca   1020

ttccgcatta caatacggta gaggccacac agtacatcaa gccaatcttg ggcgactact   1080

acaactacga ttatactccc attctcaagg caatctggag agacacaaaa gaatgtctct   1140

ttattgaaga agatccagag aaaaaaggtg tatactggtt ccacaagtag gtgtcacgat   1200

tgttacataa cctac                                                     1215
```

<210> SEQ ID NO 6
<211> LENGTH: 1148
<212> TYPE: DNA
<213> ORGANISM: Carthamus tinctorius

<400> SEQUENCE: 6

```
gatttgaaga cgttaagatg ggagctggtg gtcggatgaa cgatgctacc actgacaaag     60

atgttctgaa gcgtgtcccc accgcaaaaa ctcctttcga gattagtgat ctcaagaaag    120

caataccgcc acattgcttc aagcgatctc ttaccacctc tttctactac cttttccgtg    180

atatttgcat atgctatacc tggtaccacc tcggatcaaa ttacctcccc ctcctcccta    240

aaccccttgc ctacatagca tggccacttt attggttctg ccaaggtagt agtttcatgg    300

gtatatggag cataggtcac gatttgggcc atcatgcctt tagcgagtac cagtggcttg    360

atgatgcact tggtttcgta atccactccg ctttcctcac tccatacttt tctttcaaat    420

acagtcaccg tagccaccat gctcacacca actcaatgga atacgatgag gtatggatcc    480

ctaaaagaaa ggccgatacc atgtattctg aagtcctcaa caacccactc ggaaacttgt    540

tcatgactgt cgttaggttg cttttcagct ttcccatgta ctttaccttc aacattcatg    600

gaaggccgta taacgggttt gtaagccact tctacccaca aagtcctatg ttcaatgaca    660

gtgagcgcaa actagtgtgg ctctctgatg ccggaatggt tgcagctttc tatgggcttt    720

acaagattgc ggcaagcacg agtgcaacat ggttgttttg catctacgga gctcctttgt    780

tggttatgaa tgctcatttc atctttttca ctttcctaca ccatagccat gtttcccttg    840

cccactacga ttcaagagag tgggattgga tcagaggtgc tctatccacg gtggatagaa    900

actacggaat cctaaacact gttttccatg atgtgacctg tgctcacgtg gtgcatcatc    960

tgatctcaac cattccgcat taccatacag tagaggccac caatgcagtc aagcccatct   1020

taggtgacta ctacaaatac gatgatacac ccatcctaaa ggctttctgg agagaaacaa   1080

agaactgcat ttacgtcgag ccagatgaag gtgcagagga tagtggcgtt tactggttcc   1140

gtaggtag                                                            1148
```

<210> SEQ ID NO 7
<211> LENGTH: 1210
<212> TYPE: DNA
<213> ORGANISM: Carthamus tinctorius

<400> SEQUENCE: 7

```
gattcagatc caacacttca ccaccaggtg taatataggg tttcattcga aaccatggga     60
```

```
gccggtggcc gaatgaagac cgaggagaaa gacatcatga aacatgtccc ggttgcgaaa    120

cccccattcg ggatctccga tctcaagaaa gccataccac cgcactgttt caaacgatct    180

cttatatggt cgtttggctc cttctttcga gatcttatcg taatctacag cttctactat    240

ctcgcatcga ctttcattcc tttgctccct cccgccctct cgtacgtagc gtggccgcta    300

tactggttcg cccagggcag cattctaatg ggggttttgga tccttggtca tgaatgtggt   360

catcatgcct ttagcgagta ccaatgggtg gacgatgccg ttggcttctt catccattcg    420

gtttgcctca ccccgtactt ttccttcaag tacagccacc gtagccacca cgcccacacg    480

aactccatcg agtacgacga ggtctacatc ccgaaacgca aggccgacac cttctactcc    540

gagttcctaa acaacggacc cggaaacgtc ttcaccctcc tcctacggac gacgctcggc    600

ttacccttgt acctgatctt caacacctac ggccgcgact acaacggatt cgcaaaccat    660

ttcctaccgc aatcgggcat tttcaacgac agcgagcgcg cccaggtcgt gctctcggac    720

gtcgggatct tcgcggtcct ctacgcgctc taccggctcg tcctcatcca aggcctgaaa    780

tcgacgatct tcctccaggg gattccgttg ttcgtgatga gcggcttctt catcttcttg    840

acttacctaa accacaccca tccggcgatc gctcactacg actccaccga atggactgg     900

ctaagaggcg ccctatcgac catcgatagg gatttcggaa tcttgaaccg ggtttttccac   960

aacgcgaatc acacccacgg gatccaccat ctgttcccca cgatcccgca ttaccacgcg   1020

atcgaggccc gggaggccgt gaagcccatc ttaggcgact actacatgta cgacgatacc   1080

ccgatactaa aggccatgtg gagagacaca aaggagtgca tctacgtcga accggacgac   1140

gagaagaaag gtgtttactg gtatttcaag tagtttatat tatgtaacac catggaaatt   1200

ctttagatct                                                          1210
```

<210> SEQ ID NO 8
<211> LENGTH: 1269
<212> TYPE: DNA
<213> ORGANISM: Carthamus tinctorius

<400> SEQUENCE: 8

```
actagtgatt ctgctctcta cgacactaaa ttcactagga aggtcataag tttgaaagat     60

gggttccggt ggccgagcaa cggagagaag taaccccgag agtgaagtcg tcgtgaagcg    120

ggccccatcc tcgaagcccc cattcaccct tggcgacata aagaaagcca taccaccaca    180

ctgcttcgag cgatccctca tccgatcttc ctcctacctt ttcttggacc tctttctatc    240

atccctcttt tactacgtgg cggccgtcta catcccccgc cttccgatct ctctttcgta    300

cgtggcatgg cccgtttatt ggatcctcca agggagcgtc cagatgggtt tgtgggtcat    360

tggccacgag tgcggccacc aagccttcag tgactacccg tggtttaatg acaccattgg    420

ttaccttcta cacaccggta tgcttgcccc ttatttctct tggaaataca gccaccgtcg    480

ccaccattcc aacacgggct cactcgagct cgacgaatct ttcgtcccca aaaagaagtc    540

cagcctaaac tccgtagcca ggctgctcaa caccccaccc ggccgtctct ttaggcttac    600

gatcttatgc accgtaggct ggctcttgta catttgcttc aatgtttccg gccgcaagta    660

tgagaagttc gccaaccact ttgacccaaa gagtcctatc tacaacgacc gcgagcgctt    720

tcaaatcctc ctgaccgaca tcgggcttct agtaacaagc tacgggctct acaaactggc    780

cttagcccaa ggattcgctt ggctcataac catctacttt gctcctttgg ttattgttta    840

cgggttcctg gtggtgatca cttggttgca ccacacccac cggtcgctgc cacactacga    900
```

```
ctccaccgag tggaactggt tgaggggagc tttgtcgacg atggatcgag attacggcgt    960

tttcaacacc gttctacatc acatcaccga cacgcacgtt gcgcaccatt tgttcttcac   1020

cattcctcat tataatgcca tggaggccac gaaagcaatc aaacctttct taggagaata   1080

ctatcagttc gacgacaccc cgataatcaa agcgatgtgg agagaagcta ccgagtgctt   1140

ctttgttgaa gctgatgaag gggaaggcaa gagcaaaggt gtctattggt tcaacaataa   1200

gatgtaaaat aagttgtaaa agatcttctt cattcagtat tgttccttga tactcattag   1260

atagaaatc                                                           1269
```

```
<210> SEQ ID NO 9
<211> LENGTH: 1296
<212> TYPE: DNA
<213> ORGANISM: Carthamus tinctorius

<400> SEQUENCE: 9

ctgaattcac acccacagat agctagctag ctacccatta aaagcttaat cagctcatcc     60

cctcaattcc aaaacctcaa attgaaccca tttctttaag aatcatgggt gccggtggcc    120

gatcgaatcc tcgcgatcta gacgttaaga aattcgatac cgtagaaggt atcaagagag    180

ccccaacttc aaaacctcca ttcacattag cagatatcaa gaaagccata ccaccccatt    240

gcttccaaag atccctaatt cgatcctttt cgtatctcgt atacgacctc accgcggtct    300

cgattttcta ctatcttgcc acgacttaca tcccgcagct cccctaccct cttgcctacg    360

ttgcctggcc ggtttactgg tttgttcaag gctgtgtgtt catggggctt tggcttattg    420

ctcatgaatg cggtcaccat gccttcagtg atcatgtgtg gctggaggat tcgatcgggt    480

ttgttttaca ttcatgcctt ttgacccctt acttttcatg gaagataagc caccgtcgac    540

atcatgcgaa cacgggttcg cttgagcacg atgaggttta tgtcccgaag acaaaggcta    600

aactcggtgc ctccgcgttt tacctggaca acccaatcgg tcgaacccta accctgatgg    660

ttaagctcac tcttggatgg tacatctact tggcgatcaa tgctgcggga agaccttacg    720

aaaaattcgc aagccattac gaccccagaa gtgagatgtt ttccgataac gagagggtct    780

tgatactcat gtccgatatc ggacttttga gcttctcctt cttgctttac aaagtggcca    840

tggttcaagg gtttgcttgg gtcttctgcg tctacggagg tgcgttgatg gtgatgaacg    900

cttttctcgt gacgattacg taccttcacc atacccaccc ttctttgccc cactacgacg    960

actccgaatg gaactggatg aaaggcgcat tcgcgaccgt cgatagggat tacggagtag   1020

ttctaaacaa ggtgttccac aacatcaccg acacgcatgt tttacaccat ttgttctcgt   1080

acattcctca ttatcatgcc atggaagcca cgaaggctat ccggccggtt ctcggggagt   1140

tttaccagat cgataggact ccgtttttcg tggcgttgtg gagggaatcc aagagctgct   1200

tgttcattga gcccgatgaa agcgatgaga agaacaaagg tatctactgg tacaggagta   1260

agtactgaag gaatagttaa agctaagaag ggatgt                             1296
```

```
<210> SEQ ID NO 10
<211> LENGTH: 1316
<212> TYPE: DNA
<213> ORGANISM: Carthamus tinctorius

<400> SEQUENCE: 10

acttcgccct ctgttatctg gttgaattat ccgatcaagc ggcattggac aacaatatgg     60

gcggaggagg gtgcataccc gcaagcaaaa ccgaagccca acaaacaaac catctctcga    120

gagttcctta cgaaaaaccg gccttcactg ttggtgacat caagcgagtc atccctcccc    180
```

actgttttca acgttccctt atccgttcct tctcttatgt cgcatatgac cttgccatag 240
ccttcctgtc gtaccacctc gccaccacct acttccaccg tctctcgccg cccctctcct 300
acctcgcatg gtccgcttac tggatcgttc aagggtgtgt gctcaccggg gtctgggtca 360
tagcccacga gtgcggtcac catgcgttta gcgaccacca atgggtcgat gacacagtcg 420
gcctcatcct ccactcggcc ttactcgtcc cctacttctc ctggaaatgc agccaccgcc 480
gccaccacct caacaccgcg tcactggaac gcgatgaagt gttcgtcccc aaacccaaat 540
cgaaaatccc gtggtactct aaatacctga acaacccacc gggccgtttg ataatcgtgt 600
tcaccacgct cgttctcggc tggccgttgt acctggcctt taacgtttcc ggacggccct 660
acgaccgttt tgcctgccac tacgctccta acagcccgat cttcacaaac cgtgaacgcc 720
tccaaatctg gatttccgat gccgggatta tcgcagtttc gtatctgctt taccgtatgg 780
ctttagccaa aagcgtcgct tgggtcgttt gcatctatgg tgtcccgttg ctgatcgtga 840
acgggttttt ggtcatgatc acataccttc aacacaccca cccttcattg ccccactatg 900
acgattccga gtgggactgg ctccgggggg ctttagcgac cgtggaccgt gactacggtc 960
tcctgaacaa ggtcttccat aacataaccg acacgcacgt ggtgcaccat ctgttctcga 1020
ccatgccgca ttatcatgcc atggaggcaa cgaaggcggt cgagccggtg cttgggggt 1080 actatcggtt tgacgacacc ccgttttacg tggccatgtg gagggaggcg aaggagtgtc 1140
tctatgtgga gaccgatgag aagaaaggtg gcgtgttttg gtacaagaat aagtactgat 1200
gcgagcgcga tggatggatg tcgagttcgc ttttagtgaa agagtagcta ttttatcgtg 1260
tgtttcgtgt ttaagtaagt gaacttttcg gtatcgtgta ggatgtatgt gtatgg 1316

<210> SEQ ID NO 11
<211> LENGTH: 1213
<212> TYPE: DNA
<213> ORGANISM: Carthamus tinctorius

<400> SEQUENCE: 11
actcacaata acttcatctc tctctaaggt tgatcatata tcaacaacat gggagcaggt 60
ggtcggatgt cggattcatc tgaaagcaca gatatcctga aacgtgtccc cattgatcca 120
cccttcacct taagtgatct aaagaaagca atcccggctc attgcttcga gagatctctc 180
atccgttcat cttactatgt tgttcatgat ctcgttgttg cctatgtctt ttactacctt 240
gccgacacat atattcctca gcttcctact ccactggcgt acctagcctg gcccatttac 300
tggttttgtc aagctagcat ctgcactggc ttatgggtca tcggtcatga atgtggtcac 360
catgccttta gtgagcatca gtggattggt gacattgttg gaatggtcct ccattctgct 420
ctttttacgc cttatttcgc ctggaaatac agccatcgaa atcaccatgc aaacacgaac 480
tcactcgata acgatgaagt ttacattcct aaacgtaagt ccaagatcgc gatttattca 540
aaacttctca acaacccacc tggtcgagtt tttaccttgg tttttaggtt gaccctagga 600
tttcctttgt acctcctcac aaatatttct ggcaagaaat acggaaggtt tgccaaccac 660
tttgatccaa tgagtccaat tttcactgag cgtgaacgaa ttcaggtttt ggtatcggat 720
cttggtattc ttgccgttat ttacgcaatc aagcttgctg tagcagcaaa aggagccgct 780
tgggtaattt ccatgtacgg aattccagtc ataggcgtac atgttttctt tgttttgatc 840
acttatctac atcacaccca tctctctttg cctcattacg attcaaccga atggaactgg 900
atccgaggag ccttatcgac aatcgacagg gactttggat tcctgaacag ggttttccat 960

```
gacgttacac acactcacgt attgcatcat ttgatctcat acattccaca ttatcatgcc   1020

aaggaggcaa gggatgcgat caagcctatt ttgggcgagt actataagat cgataggacc   1080

ccaattttca aagctatgtg gagggaggcc aaagaatgca tctacattga acctgatgag   1140

gacagcgagc acaagggtac atactggtac cataaaatgt gatcgatggc cgaagacatt   1200

gtatggctag tag                                                      1213
```

```
<210> SEQ ID NO 12
<211> LENGTH: 1143
<212> TYPE: DNA
<213> ORGANISM: Carthamus tinctorius

<400> SEQUENCE: 12

atgggaggag gagggtgtat gtctgcctcc gagaccaaag ctgaagaaaa gaagaaccca     60

ctcgaccgag tcccttgtgc aaaacctcct ttcaccatca gtgacatcaa gcaagccatt    120

ccttcccact gtttcaaccg ttcccttatc cgttccttct cttacattgt ctatgacctt    180

gctatagcct tcgtcttcta ctaccttgcc accacctaca tccaccgtct cccaacccct    240

ttctcctatc tggcatggct ggcttactgg atagtccaag gctgcgtgct caccggagct    300

tgggtcgtag cccacgaatg cggccaccat gcctttagcg attatcaatg ggttgacgac    360

accgtgggct tcatagtcca ctccttttta ctcgtcccct acttctcgtg gaaatacagt    420

catcggcgcc accactcgaa cactgcatcg ctcgagcgcg atgaagtctt tgtcccaaag    480

cccagatcaa aactcccttg gtactcgaaa tacttgaaca acccgcctgg ccgcatcatc    540

agcctgttcg ccactctcac tctcggctgg cccttgtact tgtctttcaa cgtctctgga    600

agaccctatg accgcttcgc ctgccactac gctcctaaca gcccgatata caaccaccgt    660

gaacgcctcc agatttggct ctctgatgtg ggaatcgtgg ccatggcatt cgtcctttac    720

cgtgttgcac tggtgaaagg cgtgagctgg gtggtctgtg tgtatgggat accgttgttg    780

atcgtgaacg ggttcctggt gttgatcacg ttccttcagc atacgcaccc ttcgttgcct    840

cactacgacg ggtcggaatg ggactggctg agaggggcgt tggcgacggt ggaccgagac    900

tacggtgtgc tgaacaaggt gttccataac atcacggaca cgcacgtggt gcaccatctg    960

ttctcgacaa tgccgcatta tcatgcgatg gaggcaacga gggcggtgaa ggggttgctg   1020

ggggagtatt atcagtttga cgagaccccg ttttacgcag cgatgtggag agaggcaaag   1080

gagtgtctgt ttgtggaggc agatgaaggg aaaggaggtg tgttttggta caagaataag   1140

taa                                                                 1143
```

```
<210> SEQ ID NO 13
<211> LENGTH: 1152
<212> TYPE: DNA
<213> ORGANISM: Carthamus tinctorius

<400> SEQUENCE: 13

atgggtgcag gcgggcgaat gtcgaacccc tccgagggcg aaaagaaaac cgaactcgaa     60

ggcatccaac gagtcccata ccaaaaacct ccgttcacag tcggggatgt caaaaaagcc    120

atcccacctc attgtttcaa tcgatcggtc atccgctctt tctcgtacgt cgtttacgac    180

cttaccatcg catccatctt gtactacatc gccacaactt tcatcccgct cctcccgcac    240

ccgctcgcct acgtggcctg gcccatttac tgggccgttc agggctgtgt catgaccggg    300

gtctgggtca tagcccacga atgcggccat cacgccttta gcgactacca atggctcgac    360

gacactgtcg gccttatcct acattctgtt cttcttgttc cttacttctc gtggaaatac    420
```

```
agccaccgcc gccaccactc caacaccggc tcgattgagc acgacgaggt cttcgtcccg    480
aaactcaaat ccggggtccg gtccaccgca aaatacctaa acaacccccc cggccggatc    540
ttgacccttc ttgtcaccct caccctcggc tggccgttgt acctcatgtt caacgtctcc    600
ggccgctact acgaccgctt tgcctgccat tttgacccaa acagccccat ctactcgaac    660
cgtgaacgtg cccagatctt catctccgac gccgggatct tcgccgtcct ctacgggctc    720
taccggctcg cggcggtcaa agggctcgtg tgggtcctga ccgtctatgc cggaccgttg    780
ctcgtggtca acgggtttct tgtcctgatc acgttcctcc agcacaccca cccgtcgttg    840
ccgcactacg actcaaccga gtgggactgg ctccgtgggg ccctggccac catcgaccgt    900
gactacggga ttttaaacaa ggtgttccac aacatcaccg acacccacgt gacccaccat    960
ctgttttcga cgatgccgca ttatcacgcg atggaggcca cgaaggcgat aattccgatc   1020
ctcggggatt attatcagtt cgatgggacg tcagttttta aggcgatgta tagggagacg   1080
aaggagtgca tttatgtgga taaagatgag gaggtgaagg atggggttta ctggtaccgg   1140
aataagattt ga                                                       1152
```

<210> SEQ ID NO 14
<211> LENGTH: 1128
<212> TYPE: DNA
<213> ORGANISM: Carthamus tinctorius

<400> SEQUENCE: 14

```
atgaacgtgg cggtctcagg ttccgaaaaa ccccacgcct tcaagcgcgt tccggtctcc     60
aagcctccat tcgagcttag cgatctcaag aaagcagtcc caccacactg tttcaaacga    120
tctcttgtac gctcctttgc agcccttttc cgtgatatca taattgtcac cgccttatac    180
tacctggccg caaccatcat tccggtgctc cctaaacccc ttacatacgt agcgtggccg    240
ctttattggt tcttccaagg agcctatctt atgggtttgt gggtcattgg ccacgagtgc    300
ggccatcatg gcttcagcga gtaccaatgg ctcgatgaca ccgttggttt catcgtccac    360
tccttcattc tcactccgta ctttgggttc aaatacagcc accgaaccca ccacgccaac    420
accaactcca tcgaatacga tgaggtttgg atccctaaac gcaagtctga taaattgtac    480
tcggaagttc tcaacaaccc actcggatcc tttattgtat ttgtgttcaa gatcgttctt    540
ggatttccct tgtacttcgt attcaatctt tacggaagga agtacgagaa gggaatcaca    600
agccactttt acccgtatag tcccatcttt aacgatagcg agcgcttcca gatctttctc    660
accgatcttg gagtctttgg cactttgtac ggtgtctacc gtcttgcgtt gataaagggc    720
acggaatggg tgatcaactt ctacggaatg ccgatccttt tcatgagtgg gtttttcatc    780
ttgttgacat atcttcacca cacccaccct tccatccctc actacgattc cacggaatgg    840
gactggctta gaggtgcttt ggccacggtg gaccgaaact ttgggttctt gaaccatgct    900
ttccatgacg taactcgaac tcacgccgta caccatctgt tcccaaccat cccacattac    960
catactttcg aggcaaggca ggccgtgatg ccgatcttgg gcgattacta caaatacgac   1020
gataccccga ttctacaggc catatggaga gaaacaaaag attgcatctt tatcgaacct   1080
gaagaggtta atggagagaa aaagggtatc tactggtttt acaaatag                1128
```

<210> SEQ ID NO 15
<211> LENGTH: 1125
<212> TYPE: DNA
<213> ORGANISM: Carthamus tinctorius

<400> SEQUENCE: 15

```
atggatgttg cggcaagctc cgagaaaccg cacgccttta aacgtgttcc ggtctcgaag      60
cctccattcg agcttagcga tctcaagaaa gcagttccac cacactgttt caagcgatct     120
cttgtgcgct cctttgcagc ccttttccgt gatatcataa tcgtctccgc cttatactat     180
ctggccgcaa ccgtcattcc ggtgctccct aaaccccttta cgtacgtagc atggccgctt    240
tattggttct tccaaggagc ttatcttatg ggtttgtggg tcattggcca cgaatgcggc     300
catcatggct tcagcgagta ccaatggctc gatgacaccg ttggtttcat cgtccactcc     360
ttgattctca ctccgtactt tgggttcaaa tacagccacc gaacccacca cgccaacacc     420
aactccatcg aatacgatga ggtttggatc cctaaacgca agtctgataa attgtactcg     480
gaaatcctca acaacccact cggatccttt gttgtatttg tgttcaagat cgttcttgga     540
tttcccttgt acttcgtgtt caatctttat ggaaggaagt acgagaaggg aatcacgagc     600
cacttttacc catacagtcc catcttcaac gatagcgagc gtttccagat ctttctcacc     660
gatctcggag tctttggcac tttgtatggt gtctaccgtc ttgcgttgat aaagggcacg     720
gaatgggtga tcaacttcta cggaatgccg atccttttca tgagtgggtt tttcatcttg     780
ttgacatatc ttcaccacac ccacccttcc atccctcact acgattccac cgaatgggac     840
tggcttagag gtgctttggc cacggtggac cgaaactttg ggttcttgaa ccatgccttc     900
catgacgtaa ctcgaactca cgcggtacac catctgttcc caaccatccc acattaccat     960
actttcgagg caaggcaggc cgtgatgccg atcttgggtg attactacaa atacgatgat    1020
accccgattc tagaggccgt ttggagagag acgaaagact gcatctttat cgaacctgaa    1080
gaggttaacg ggagaaaaaa gggtatttac tggttctata agtag                    1125
```

<210> SEQ ID NO 16
<211> LENGTH: 1128
<212> TYPE: DNA
<213> ORGANISM: Carthamus tinctorius

<400> SEQUENCE: 16

```
atgggagcag gagggcgaat gaatgacgac gctacgaggg aaagagatgt cttcaaacat      60
gttcccgtcg agaagccttc attcgggatt gctgatctca agaaggccat accaccacac     120
tgtttcaagc ggtccctaac cacctctttc tactaccttt tccgtgattt gggtctcatc     180
tacgctttct actatattgc aacaaaatac attacccatc tcccccaacc ctactcgttt     240
gtggcatggc cactttattg gatcgcccaa ggtgccattt gcatgggttt atggaatatc     300
gtccatgatt gtggtcatca ctgctttagc gattatcaat ggcttgatga caccattggc     360
ttcatctgcc actcctttct gctcactcca tacttctctt tcaaatacag tcaccgtact     420
catcatgcta acaccagttc actcgaaagg gatgaagtat gggtcccaaa acgcaagcac     480
gatacttggt tttatgaggt tctcagcaac ccagtgggaa gctttatcat gcttgtgttt     540
aggttatttt ttggctttcc cttgtacttt atgttcaatc ttcatggtag gatatacaag     600
ggtttcccta gccacttcaa cccgttaggc cccatcttca acgaccgaga gcgtgctaat     660
atctggctct ctgatgccgg agttcttacc gttgtctatg cgctctaccg tattggggca     720
aaagaaggtc tccagtcggt acttttcgtc tatatttatc ccttgatggc tatgagtgcc     780
tttttcatca tgttcacata tctacaccac actcatcctt ccatcgctca ctacgattcg     840
tcggaatggg attggttgag aggtgctttg tcaaccgtgg atagggatta tgggatcttg     900
aacaacatct tccatgacgt aacaagtgct catgtggtgc accatctatt ctcgagcatt     960
```

ccgcattaca atacggtaga ggccacacag tacatcaagc caatcttggg cgactactac 1020
aactacgatt atactcccat tctcaaggca atctggagag acacaaaaga atgtctcttt 1080
attgaagaag atccagagaa aaaaggtgta tactggttcc acaagtag 1128

<210> SEQ ID NO 17
<211> LENGTH: 1131
<212> TYPE: DNA
<213> ORGANISM: Carthamus tinctorius

<400> SEQUENCE: 17
atgggagctg gtggtcggat gaacgatgct accactgaca aagatgttct gaagcgtgtc 60
cccaccgcaa aaactccttt cgagattagt gatctcaaga aagcaatacc gccacattgc 120
ttcaagcgat ctcttaccac ctctttctac taccttttcc gtgatatttg catatgctat 180
acctggtacc acctcggatc aaattacctc cccctcctcc ctaaacccct tgcctacata 240
gcatggccac tttattggtt ctgccaaggt agtagtttca tgggtatatg gagcataggt 300
cacgatttgg gccatcatgc ctttagcgag taccagtggc ttgatgatgc acttggtttc 360
gtaatccact ccgctttcct cactccatac ttttctttca aatacagtca ccgtagccac 420
catgctcaca ccaactcaat ggaatacgat gaggtatgga tccctaaaag aaaggccgat 480
accatgtatt ctgaagtcct caacaaccca ctcggaaact tgttcatgac tgtcgttagg 540
ttgcttttca gctttcccat gtactttacc ttcaacattc atggaaggcc gtataacggg 600
tttgtaagcc acttctaccc acaaagtcct atgttcaatg acagtgagcg caaactagtg 660
tggctctctg atgccggaat ggttgcagct ttctatgggc tttacaagat tgcggcaagc 720
acgagtgcaa catggttgtt ttgcatctac ggagctcctt tgttggttat gaatgctcat 780
ttcatctttt tcactttcct acaccatagc catgtttccc ttgcccacta cgattcaaga 840
gagtgggatt ggatcagagg tgctctatcc acggtggata gaaactacgg aatcctaaac 900
actgttttcc atgatgtgac ctgtgctcac gtggtgcatc atctgatctc aaccattccg 960
cattaccata cagtagaggc caccaatgca gtcaagccca tcttaggtga ctactacaaa 1020
tacgatgata cacccatcct aaaggctttc tggagagaaa caaagaactg catttacgtc 1080
gagccagatg aaggtgcaga ggatagtggc gtttactggt tccgtaggta g 1131

<210> SEQ ID NO 18
<211> LENGTH: 1119
<212> TYPE: DNA
<213> ORGANISM: Carthamus tinctorius

<400> SEQUENCE: 18
atgggagccg gtggccgaat gaagaccgag gagaaagaca tcatgaaaca tgtcccggtt 60
gcgaaacccc cattcgggat ctccgatctc aagaaagcca taccaccgca ctgtttcaaa 120
cgatctctta tatggtcgtt tggctccttc tttcgagatc ttatcgtaat ctacagcttc 180
tactatctcg catcgacttt cattcctttg ctccctcccg ccctctcgta cgtagcgtgg 240
ccgctatact ggttcgccca gggcagcatt ctaatggggt tttggatcct tggtcatgaa 300
tgtggtcatc atgcctttag cgagtaccaa tgggtggacg atgccgttgg cttcttcatc 360
cattcggttt gcctcacccc gtacttttcc ttcaagtaca gccaccgtag ccaccacgcc 420
cacacgaact ccatcgagta cgacgaggtc tacatcccga aacgcaaggc cgacaccttc 480
tactccgagt tcctaaacaa cggacccgga aacgtcttca ccctcctcct acggacgacg 540

```
ctcggcttac ccttgtacct gatcttcaac acctacggcc gcgactacaa cggattcgca    600

aaccatttcc taccgcaatc gggcattttc aacgacagcg agcgcgccca ggtcgtgctc    660

tcggacgtcg ggatcttcgc ggtcctctac gcgctctacc ggctcgtcct catccaaggc    720

ctgaaatcga cgatcttcct ccaggggatt ccgttgttcg tgatgagcgg cttcttcatc    780

ttcttgactt acctaaacca cacccatccg gcgatcgctc actacgactc caccgaatgg    840

gactggctaa gaggcgccct atcgaccatc gatagggatt tcggaatctt gaaccgggtt    900

ttccacaacg cgaatcacac ccacgggatc caccatctgt tccccacgat cccgcattac    960

cacgcgatcg aggcccggga ggccgtgaag cccatcttag gcgactacta catgtacgac   1020

gatacccccga tactaaaggc catgtggaga gacacaaagg agtgcatcta cgtcgaaccg  1080

gacgacgaga agaaaggtgt ttactggtat ttcaagtag                          1119
```

```
<210> SEQ ID NO 19
<211> LENGTH: 1149
<212> TYPE: DNA
<213> ORGANISM: Carthamus tinctorius

<400> SEQUENCE: 19

atgggttccg gtggccgagc aacggagaga agtaaccccg agagtgaagt cgtcgtgaag     60

cgggccccat cctcgaagcc cccattcacc cttggcgaca taaagaaagc cataccacca    120

cactgcttcg agcgatccct catccgatct tcctcctacc ttttcttgga cctctttcta    180

tcatccctct tttactacgt ggcggccgtc tacatccccc gccttccgat ctctctttcg    240

tacgtggcat ggcccgttta ttggatcctc caagggagcg tccagatggg tttgtgggtc    300

attggccacg agtgcggcca ccaagccttc agtgactacc cgtggtttaa tgacaccatt    360

ggttaccttc tacacaccgg tatgcttgcc ccttatttct cttggaaata cagccaccgt    420

cgccaccatt ccaacacggg ctcactcgag ctcgacgaat ctttcgtccc caaaaagaag    480

tccagcctaa actccgtagc caggctgctc aacaccccac ccggccgtct ctttaggctt    540

acgatcttat gcaccgtagg ctggctcttg tacatttgct tcaatgtttc cggccgcaag    600

tatgagaagt tcgccaacca ctttgaccca aagagtccta tctacaacga ccgcgagcgc    660

tttcaaatcc tcctgaccga catcgggctt ctagtaacaa gctacgggct ctacaaactg    720

gccttagccc aaggattcgc ttggctcata accatctact ttgctccttt ggttattgtt    780

tacgggttcc tggtggtgat cacttggttg caccacaccc accggtcgct gccacactac    840

gactccaccg agtggaactg gttgagggga gctttgtcga cgatggatcg agattacggc    900

gttttcaaca ccgttctaca tcacatcacc gacacgcacg ttgcgcacca tttgttcttc    960

accattcctc attataatgc catggaggcc acgaaagcaa tcaaaccttt cttaggagaa   1020

tactatcagt tcgacgacac cccgataatc aaagcgatgt ggagagaagc taccgagtgc   1080

ttctttgttg aagctgatga aggggaaggc aagagcaaag gtgtctattg gttcaacaat   1140

aagatgtaa                                                           1149
```

```
<210> SEQ ID NO 20
<211> LENGTH: 1164
<212> TYPE: DNA
<213> ORGANISM: Carthamus tinctorius

<400> SEQUENCE: 20

atgggtgccg gtggccgatc gaatcctcgc gatctagacg ttaagaaatt cgataccgta     60

gaaggtatca agagagcccc aacttcaaaa cctccattca cattagcaga tatcaagaaa    120
```

```
gccataccac cccattgctt ccaaagatcc ctaattcgat ccttttcgta tctcgtatac    180

gacctcaccg cggtctcgat tttctactat cttgccacga cttacatccc gcagctcccc    240

taccctcttg cctacgttgc ctggccggtt tactggtttg ttcaaggctg tgtgttcatg    300

gggctttggc ttattgctca tgaatgcggt caccatgcct tcagtgatca tgtgtggctg    360

gaggattcga tcgggtttgt tttacattca tgccttttga ccccttactt ttcatggaag    420

ataagccacc gtcgacatca tgcgaacacg ggttcgcttg agcacgatga ggtttatgtc    480

ccgaagacaa aggctaaact cggtgcctcc gcgttttacc tggacaaccc aatcggtcga    540

accctaaccc tgatggttaa gctcactctt ggatggtaca tctacttggc gatcaatgct    600

gcgggaagac cttacgaaaa attcgcaagc cattacgacc ccagaagtga gatgttttcc    660

gataacgaga gggtcttgat actcatgtcc gatatcggac ttttgagctt ctccttcttg    720

ctttacaaag tggccatggt tcaagggttt gcttgggtct tctgcgtcta cggaggtgcg    780

ttgatggtga tgaacgcttt tctcgtgacg attacgtacc ttcaccatac ccacccttct    840

ttgccccact acgacgactc cgaatggaac tggatgaaag gcgcattcgc gaccgtcgat    900

agggattacg gagtagttct aaacaaggtg ttccacaaca tcaccgacac gcatgtttta    960

caccatttgt tctcgtacat tcctcattat catgccatgg aagccacgaa ggctatccgg   1020

ccggttctcg ggagtttta ccagatcgat aggactccgt tttcgtggc gttgtggagg   1080

gaatccaaga gctgcttgtt cattgagccc gatgaaagcg atgagaagaa caaaggtatc   1140

tactggtaca ggagtaagta ctga                                          1164
```

```
<210> SEQ ID NO 21
<211> LENGTH: 1143
<212> TYPE: DNA
<213> ORGANISM: Carthamus tinctorius

<400> SEQUENCE: 21

atgggcggag gagggtgcat acccgcaagc aaaaccgaag cccaacaaac aaaccatctc     60

tcgagagttc cttacgaaaa accggccttc actgttggtg acatcaagcg agtcatccct    120

ccccactgtt ttcaacgttc ccttatccgt tccttctctt atgtcgcata tgaccttgcc    180

atagccttcc tgtcgtacca cctcgccacc acctacttcc accgtctctc gccgcccctc    240

tcctacctcg catggtccgc ttactggatc gttcaagggt gtgtgctcac cggggtctgg    300

gtcatagccc acgagtgcgg tcaccatgcg tttagcgacc accaatgggt cgatgacaca    360

gtcggcctca tcctccactc ggccttactc gtcccctact tctcctggaa atgcagccac    420

cgccgccacc acctcaacac cgcgtcactg gaacgcgatg aagtgttcgt ccccaaaccc    480

aaatcgaaaa tcccgtggta ctctaaatac ctgaacaacc caccgggccg tttgataatc    540

gtgttcacca cgctcgttct cggctggccg ttgtacctgg cctttaacgt ttccggacgg    600

ccctacgacc gttttgcctg ccactacgct cctaacagcc cgatcttcac aaaccgtgaa    660

cgcctccaaa tctggatttc cgatgccggg attatcgcag tttcgtatct gctttaccgt    720

atggctttag ccaaaagcgt cgcttgggtc gtttgcatct atggtgtccc gttgctgatc    780

gtgaacgggt ttttggtcat gatcacatac cttcaacaca cccacccttc attgccccac    840

tatgacgatt ccgagtggga ctggctccgg ggggctttag cgaccgtgga ccgtgactac    900

ggtctcctga acaaggtctt ccataacata accgacacgc acgtggtgca ccatctgttc    960

tcgaccatgc cgcattatca tgccatggag gcaacgaagg cggtcgagcc ggtgcttggg   1020
```

```
gggtactatc ggtttgacga caccccgttt tacgtggcca tgtggaggga ggcgaaggag   1080

tgtctctatg tggagaccga tgagaagaaa ggtggcgtgt tttggtacaa gaataagtac   1140

tga                                                                 1143


<210> SEQ ID NO 22
<211> LENGTH: 1134
<212> TYPE: DNA
<213> ORGANISM: Carthamus tinctorius

<400> SEQUENCE: 22

atgggagcag gtggtcggat gtcggattca tctgaaagca cagatatcct gaaacgtgtc     60

cccattgatc caccccttcac cttaagtgat ctaaagaaag caatcccggc tcattgcttc   120

gagagatctc tcatccgttc atcttactat gttgttcatg atctcgttgt tgcctatgtc    180

ttttactacc ttgccgacac atatattcct cagcttccta ctccactggc gtacctagcc    240

tggcccattt actggttttg tcaagctagc atctgcactg gcttatgggt catcggtcat    300

gaatgtggtc accatgcctt tagtgagcat cagtggattg gtgacattgt tggaatggtc    360

ctccattctg ctctttttac gccttatttc gcctggaaat acagccatcg aaatcaccat    420

gcaaacacga actcactcga taacgatgaa gtttacattc ctaaacgtaa gtccaagatc    480

gcgatttatt caaaacttct caacaaccca cctggtcgag tttttacctt ggtttttagg    540

ttgaccctag gatttccttt gtacctcctc acaaatattt ctggcaagaa atacggaagg    600

tttgccaacc actttgatcc aatgagtcca attttcactg agcgtgaacg aattcaggtt    660

ttggtatcgg atcttggtat tcttgccgtt atttacgcaa tcaagcttgc tgtagcagca    720

aaaggagccg cttgggtaat ttccatgtac ggaattccag tcataggcgt acatgttttc    780

tttgttttga tcacttatct acatcacacc catctctctt tgcctcatta cgattcaacc    840

gaatggaact ggatccgagg agccttatcg acaatcgaca gggactttgg attcctgaac    900

agggttttcc atgacgttac acacactcac gtattgcatc atttgatctc atacattcca    960

cattatcatg ccaaggaggc aagggatgcg atcaagccta ttttgggcga gtactataag   1020

atcgatagga ccccaatttt caaagctatg tggagggagg ccaaagaatg catctacatt   1080

gaacctgatg aggacagcga gcacaagggt acatactggt accataaaat gtga         1134


<210> SEQ ID NO 23
<211> LENGTH: 1083
<212> TYPE: DNA
<213> ORGANISM: Carthamus tinctorius

<400> SEQUENCE: 23

gtgcattctc tcattctcaa aacctttctg ctattcatct gatcaatgta ttcagttatg     60

gttcgatgat cgacgattat tgtttgttat tttaatttta atttttaggt tgatttagct    120

gcattgttgg tcgatgaata gatctgtgga ttacggtctt ctgcagtttc agtttgattt    180

atttcagtcc gtttttctcc tgtaaatttg tgtatctatc tgtgttgcat gtaattttgt    240

ttcctttaga ttatagaaat gaaaatccat aattttaggg ctgcttgtct tgtttggatt    300

tgtgttatta ggttttgatc acagtaactt ccgtacgttt aatatgttaa atgctaaaca    360

aaatgattta ttttttatat ttatggcttc tcggtggtcg gatttgtgtt tttaattcct    420

gaagtttctg tatacaatga tttcgaattt tggcgattag gcatctcttt actttggaag    480

gaatttcaga ttttcttaat ctcatagaga agtgctgatt gggaatttgc ttaaagatat    540

aagcactttt cagttcattg attgtttgat ggacatcaga tggttttttt gctgatgcca    600
```

```
tgatgtctat tgtgttgaat gtatcttcaa taagtgcctt caatatgtat agcaaaactg    660
agctaaggct gtgtttggca aactacctga taagctatat gttgactgat aagctagttt    720
gtgaataaat tatgtttggc aaaaactagc atatgagtat gtaaaatgac taaaaagggt    780
atcttggggt ataatagtta atattgataa ggatagaatt ggagaaggct acaaaaagcc    840
cttgaaatgc tactccaact agtgtttcaa taagctggct tatggtctat ccaaacatgt    900
actagattat catctagctt atttttgcca aacacagcct aaatgtttga tggtcgatgg    960
ctggcacttg acaatttgac atcattataa ctgaaacaat aatattcacc tttacataac   1020
attcaccttt agccaaaaac tagatgttca cctacgaact gatccatatg gaacattttg   1080
cag                                                                 1083
```

<210> SEQ ID NO 24
<211> LENGTH: 3092
<212> TYPE: DNA
<213> ORGANISM: Carthamus tinctorius

<400> SEQUENCE: 24

```
gtgagatcga tcatcttctt tcataaacat ctgattagta ataatcggta tccaagctgt     60
atgtgtgtga atttgtggaa ttttgaattt gaatgtcgtg atttgaatct gttaggattt    120
agggttgaaa gagtcggttt acttgataga tctgaatttt tttaagagtt tagtagcttc    180
ggatgttgat ttaggtggaa tgcggcttaa gtttttgcgg atctgagcac cggttcttct    240
aaatctaaag gttactgatt ataatcgatc ttctttcgat ttctatgaat ttactccttt    300
tttttttcct tggaaaaagg tgctactact ttatttgagc tgagatctgc gctgcttttg    360
attccgattc cctttttgga tcaaatagtt gaaaactgca atgtttatgg tcaaattttt    420
gcttctaatt tttccaggag catgcctaat tatgcttctt attggattgg aattcagaaa    480
taaaattaag tttgaatatt atacaggtat tagattcaaa gaagtggaat aaaaagcaga    540
ggcttaatag atgctagctt gtagatgaag gacctgtttt aagtagtcat taaaacttgc    600
atgtcccaaa ataagcaaac atttacacta tttgatattt tgatttaaaa agggaatcca    660
atgttactga atgaagcaaa ccacaatcaa tatcaacaca gatccagctc aaatggaaaa    720
actaaatttt tttctccaag aagaaaccta aacaaaaaga gtaaagttaa caaaaaatgga    780
agaaggcttg tatagttcct gtttgttttg ataataatca gtaacctcta attcttacac    840
cataaataat caagatttaa aaaactggtg ctcagatcta caaaactgaa gccatatact    900
accttaaatc agattgattg ttagttactt aagagttata cttatttctg tgttttgtcc    960
tcagtctgtt tcatatggtg gacctgtcac atgggcctaa accaaacttt tgtaacttgg   1020
tgaattgatt ttattaagcc aagttgtacc atccttttca gaaagccctc tcattaatgg   1080
catattccca aaagcaaatc cttttggggt catatgaaat gatcttttct gagcttatca   1140
aaaaagacgc tgaactgtta gccataaatt agtagctttt tgaaaagcta tattaggtag   1200
cgttgcaata accccggat gttatttctt ttcttccagt tatgccgttt attattttcc   1260
gagtaatcta aagcaagtta ctttaggtca tatttattgc aaacttaccg cccgcccgcc   1320
cattaccaac ggagctttat tataggtcat attacgttgt cgttttatca actggcttgt   1380
caaacatatc tttggttcta agtggctcca cttgttccta tgattctcca ttttactata   1440
ctagatattt atgatgctga attggtcaac ataaggttga gtagttgcat aacttttgga   1500
tgctttgaaa gattgcagtc aaaattggag tattggcatg aatagtccct ttttttcttt   1560
```

```
tttgtgcaaa gcagtatgtt ttgcattatt gaagtttttt attccaagaa aacgtggctc   1620
tttttctttt tttggtaaat ttggacctat ttttgaatga ttagcctaat tttttcaaat   1680
ccatgtgcat tgaaggcact ataaacatga cttcttatgg gttatcatca taagtgttac   1740
ataattggaa aaggtaattg ctttataact acccttataa atttttttgtc acaaagtagc   1800
taaaaaacca caagatactt ttcttgctga ttcgcaagct gcgaaacggg cttgcggttc   1860
cacatctctt ggcgttggct tgttctttta tgcgtagacg caagagacta aaataccccc   1920
aacttgcggt tttttattgg tttttgtgat ggacccactt tttccactgg attggtagat   1980
tttctgagaa ctcgcttata aaagtgcctt gtagcgttta cttgcgtttt gatagccgtt   2040
tttttgtttt ttgtttttct agtgaggcgg ccatttgaga tgataacctt ttttctttat   2100
ttcttttctt tggggcaaga ggtcactttc ccactggctt cactatggtt ttattattat   2160
ttttctaatc gtggatgtct aggtcagatt taacacttga tagcccctaa ttctcgtatt   2220
cttcttgttc ctatatttaa attttctttg caaatcaacc atggttctta tgagtttgtg   2280
acaccccacc cccctcattc ggcatggtgt caatatgtgt ggattctttt tctgtatttt   2340
ttttttgtaa aacaaacaaa atatatttat gatgatttag gtggtatact gtacttgcac   2400
aaacagtttc gagtttctta gctgcactgt aggagttaca acttacaatt cctttatggt   2460
atctttaatg gacaacatca agtcttacac caaatccata aaaattagtg tagaatttgg   2520
agaaaacaat actccaatgg ataacactga attttgcacc aaaatgtaag gacgcttttg   2580
gaattggttg tgaaaaagat ttttggaaaa ctacaaaaat cagttttcta atttacatag   2640
aagttacaaa acaaaatttt ttggaactaa acacgttttc taaattttca tttttcttgg   2700
aaaactgtga aattttccgc tagtataaat gaacagtgct acaccaaatt tggcgtatga   2760
tttgatttct ccctcggaga tttggtgtaa gatttggtct cgtgattgga gatggtctta   2820
gggattaagt tctttgtgac gtgtgaacac ttggtccata aaccagccac ctaacaagcc   2880
gttgtgtatc tgattgatta taaaccgttt ttccacaaaa aggaaatcaa tccctttttcg   2940
gtaagcagat tttgtgataa tactgatcac atggtcctgt ctaatttagt cgatcctttt   3000
caatgctagc tggtcctttt gcattctttc aatagctaaa catcaattca gcctctttaa   3060
atgtcataaa gagtaattca tatcttttgc ag                                 3092
```

<210> SEQ ID NO 25
<211> LENGTH: 2247
<212> TYPE: DNA
<213> ORGANISM: Carthamus tinctorius

<400> SEQUENCE: 25

```
gttcgttttt tcttcttagt gaatctcctt caatcaaatg catattttgg atgttgatat     60
gatgatctta tcatgaatca tgtttaattc agtgattaat tccgaaatta gtaatatagg    120
taataggttt gatgattata atccattccg agattgattt gattgattga tggattgatt    180
gagctgcatt gttaattgat atgaagatct ctggattctg atcttctaat cgttcaattt    240
cgacctgttt tactcgattc gtctacaaat ttgcgtatgt gttttgtttc tggctgtgaa    300
tcaatgcact tgcgtatgaa attgttgtat tctgtttaga tttccgtttc ttaataattt    360
atttgatttg aggatgatat attgaataat tgatattagt gcttcatttt gatctgctaa    420
accttgtgaa ttgtgataat ttatgtattc attctccttt tatttacaat gaaattgtta    480
aaaaggtctt ttgctgttaa tcaaatatat gagagatcag gagaaagcaa atttgataaa    540
aaactcatgt atcagaatct atgaagccag tattatcaat gatttgctat gaatttggaa    600
```

```
aaagacaatt ccaaggaaag aaatgttttt ttttttttcc ttttagtttc aggatgacta    660

caaaaaatgt taactaagaa tagaaaagtt tacatgtttt ttgttgccat agaaagttat    720

gaagatagct tgttttgttt ttcttctttg gtaagtgata ataaatgctt ctatgatcaa    780

tcacatatga aatttcccta aatttctttg aagtaaagtc atgaaatgta tgtcctaagt    840

caactggaac agggaacgaa cggatcgatg cttcggcata tcgagttgta ctctgcgcat    900

gtttgattct ttagacgaat aagacaaacc tttgagtttg aaaataatgt agtttgtgct    960

cataatacag ctgaaagaga tggttgttga atttagtagc cccataaaca ttttgaattt   1020

tagagctttg aatgctaccc tctagtgaat ttgtattcta gccatcatat ttataatttt   1080

gctgtaaatg aaccatcata cttgttaaaa tgcaagtgtt actaaaaatg taaaagatac   1140

cataatgtgc agatttaatt agaagtctga ttgagtaaca cagaatttaa tggttcttat   1200

atccatgtaa tcgtatgtta ccgttatgct gtgttagcta tactgtgtaa atatgtatag   1260

tttaggagct gtttctgtta ctggttgtct agttcatagt ctagtctagg tatatatttc   1320

gatttcgatt cagagatgaa tagagtttcc tctgaagaaa ccaaactgaa agggtagcct   1380

aaactcacaa ccaatttctt gatcagattg atagcagact aggaagcatc atgattcatg   1440

catcaagtac atgaaatcca taatcagaaa caaagatgta aagagtagga tttagtgcct   1500

atttagaatt catatatatg attcatggac tgatgaagca gtaaaagtct aaaaaaggga   1560

tgctaaaatc aacctgaatt tttgtatgag aacttatgag aagatccatc accttgttca   1620

gagatctgaa tctgagctat agttcaatat ttatatccac atttataatg gaacaaacat   1680

agctattgat gtgttatgga agaacaatct ataccatctt ccaagtttta ctaaaatctc   1740

aacaaatcag tcgaattcaa ttgccaataa cttttgaacc ttcatgtaaa gatcaagttg   1800

ttcatcattt tgccttattg taaagaattt attacttaac tcgagccaga cttttgtggc   1860

attgatcatc gtttattggc ttatcttgat tataaactcg atgcttgttg gagattatat   1920

gtctttccgt taacaatcct gtcttttcct tttgttgtct cttacaccgt cttctcaaat   1980

gctaaatgga tattccaaag catcagaaac aaatcccata tggttcaatg tctcttctga   2040

aattgctcca ttcttattgc ttagtttgat atagttaaaa aaacctcaat cttgctatgt   2100

tttagtatca tatatttgct gtcatttgca aatttacata aaacttagta tttgttattc   2160

agagaatatc tctctatgcc attagttgat cctagattac agtcttaatt tacagattgc   2220

ataaaatata taactgccat cttacag                                       2247
```

<210> SEQ ID NO 26
<211> LENGTH: 1195
<212> TYPE: DNA
<213> ORGANISM: Carthamus tinctorius

<400> SEQUENCE: 26

```
attgattcag gttgaaagca agatgggagg aggagggtgt atgtctgcct ccgagaccaa     60

agctgaagaa aagaagaacc cactcgaccg agtcccttgt gcaaaacctc ctttcaccat    120

cagtgacatc aagcaagcca ttccttccca ctgtttcaac cgttccctta tccgttcctt    180

ctcttacatt gtctatgacc ttgctatagc cttcgtcctc tactaccttg ccaccaccta    240

catccaccgt ctcccaaccc ctttctccta tctagcgtgg ctggcttact ggatcgtcca    300

aggctgcgtg ctcaccggag cttgggtcgt agcccacgaa tgcggccacc atgcctttag    360

cgattatcaa tgggttgacg acaccgtggg cttcatagtc cactcctttt tactcgtccc    420
```

```
ctacttctcg tggaaataca gtcatcggcg ccaccactcg aacactgcat cgctcgagcg    480

cgatgaggtc tttgtcccaa agcccagatc aaaactccct tggtactcga aatacttgaa    540

caacccgcct ggccgcatca tcagcctgtt cgccactctc actctcggct ggcccttgta    600

cttgtctttc aacgtctctg gaagacctac aaccgtttcg cctgccacta tgctcccaac    660

agcccgattt acaaccatcg cgaacgcctc cagatttggc tctctgacgt ggggatcgtg    720

gccatgtcgt tcatccttta ccgtgttgcg ctggtgaaag gcgtgagctg ggtggtctgt    780

gtgtatggga taccgttgtt gatcgtgaac gggttcctgg tgttgatcac gttccttcag    840

catacgcacc cttcgttgcc tcactacgac gggtcggaat gggactggct gagaggagcg    900

ttggcgacgg tggaccgaga ctacggtgtg ctgaacaagg tgttccataa catcacggac    960

acgcacgtgg tgcaccatct gttctcgaca atgccgcatt atcatgcgat ggaggcaacg   1020

agggcggtga gggggttgct gggggagtat tatcagtttg acgagacccc gttttacgca   1080

gcgatgtgga gaggggcaaa ggagtgtctg tttgtggagg cagatgaagg gaaaggaggt   1140

gtgttttggt acaagaataa gtaaagttgt gatgtggtgt gcttagaatc actag        1195
```

<210> SEQ ID NO 27
<211> LENGTH: 380
<212> TYPE: PRT
<213> ORGANISM: Carthamus tinctorius

<400> SEQUENCE: 27

```
Met Gly Gly Gly Gly Cys Met Ser Ala Ser Glu Thr Lys Ala Glu Glu
1               5                   10                  15

Lys Lys Asn Pro Leu Asp Arg Val Pro Cys Ala Lys Pro Pro Phe Thr
            20                  25                  30

Ile Ser Asp Ile Lys Gln Ala Ile Pro Ser His Cys Phe Asn Arg Ser
        35                  40                  45

Leu Ile Arg Ser Phe Ser Tyr Ile Val Tyr Asp Leu Ala Ile Ala Phe
    50                  55                  60

Val Phe Tyr Tyr Leu Ala Thr Thr Tyr Ile His Arg Leu Pro Thr Pro
65                  70                  75                  80

Phe Ser Tyr Leu Ala Trp Leu Ala Tyr Trp Ile Val Gln Gly Cys Val
                85                  90                  95

Leu Thr Gly Ala Trp Val Val Ala His Glu Cys Gly His His Ala Phe
            100                 105                 110

Ser Asp Tyr Gln Trp Val Asp Asp Thr Val Gly Phe Ile Val His Ser
        115                 120                 125

Phe Leu Leu Val Pro Tyr Phe Ser Trp Lys Tyr Ser His Arg Arg His
    130                 135                 140

His Ser Asn Thr Ala Ser Leu Glu Arg Asp Glu Val Phe Val Pro Lys
145                 150                 155                 160

Pro Arg Ser Lys Leu Pro Trp Tyr Ser Lys Tyr Leu Asn Asn Pro Pro
                165                 170                 175

Gly Arg Ile Ile Ser Leu Phe Ala Thr Leu Thr Leu Gly Trp Pro Leu
            180                 185                 190

Tyr Leu Ser Phe Asn Val Ser Gly Arg Pro Tyr Asp Arg Phe Ala Cys
        195                 200                 205

His Tyr Ala Pro Asn Ser Pro Ile Tyr Asn His Arg Glu Arg Leu Gln
    210                 215                 220

Ile Trp Leu Ser Asp Val Gly Ile Val Ala Met Ala Phe Val Leu Tyr
225                 230                 235                 240
```

```
Arg Val Ala Leu Val Lys Gly Val Ser Trp Val Val Cys Val Tyr Gly
            245                 250                 255

Ile Pro Leu Leu Ile Val Asn Gly Phe Leu Val Leu Ile Thr Phe Leu
            260                 265                 270

Gln His Thr His Pro Ser Leu Pro His Tyr Asp Gly Ser Glu Trp Asp
        275                 280                 285

Trp Leu Arg Gly Ala Leu Ala Thr Val Asp Arg Asp Tyr Gly Val Leu
    290                 295                 300

Asn Lys Val Phe His Asn Ile Thr Asp Thr His Val Val His His Leu
305                 310                 315                 320

Phe Ser Thr Met Pro His Tyr His Ala Met Glu Ala Thr Arg Ala Val
                325                 330                 335

Lys Gly Leu Leu Gly Glu Tyr Tyr Gln Phe Asp Glu Thr Pro Phe Tyr
            340                 345                 350

Ala Ala Met Trp Arg Glu Ala Lys Glu Cys Leu Phe Val Glu Ala Asp
        355                 360                 365

Glu Gly Lys Gly Gly Val Phe Trp Tyr Lys Asn Lys
    370                 375                 380


<210> SEQ ID NO 28
<211> LENGTH: 383
<212> TYPE: PRT
<213> ORGANISM: Carthamus tinctorius

<400> SEQUENCE: 28

Met Gly Ala Gly Gly Arg Met Ser Asn Pro Ser Glu Gly Glu Lys Lys
1               5                   10                  15

Thr Glu Leu Glu Gly Ile Gln Arg Val Pro Tyr Gln Lys Pro Pro Phe
            20                  25                  30

Thr Val Gly Asp Val Lys Lys Ala Ile Pro Pro His Cys Phe Asn Arg
        35                  40                  45

Ser Val Ile Arg Ser Phe Ser Tyr Val Val Tyr Asp Leu Thr Ile Ala
    50                  55                  60

Ser Ile Leu Tyr Tyr Ile Ala Thr Thr Phe Ile Pro Leu Leu Pro His
65                  70                  75                  80

Pro Leu Ala Tyr Val Ala Trp Pro Ile Tyr Trp Ala Val Gln Gly Cys
                85                  90                  95

Val Met Thr Gly Val Trp Val Ile Ala His Glu Cys Gly His His Ala
            100                 105                 110

Phe Ser Asp Tyr Gln Trp Leu Asp Asp Thr Val Gly Leu Ile Leu His
        115                 120                 125

Ser Val Leu Leu Val Pro Tyr Phe Ser Trp Lys Tyr Ser His Arg Arg
    130                 135                 140

His His Ser Asn Thr Gly Ser Ile Glu His Asp Glu Val Phe Val Pro
145                 150                 155                 160

Lys Leu Lys Ser Gly Val Arg Ser Thr Ala Lys Tyr Leu Asn Asn Pro
                165                 170                 175

Pro Gly Arg Ile Leu Thr Leu Leu Val Thr Leu Thr Leu Gly Trp Pro
            180                 185                 190

Leu Tyr Leu Met Phe Asn Val Ser Gly Arg Tyr Tyr Asp Arg Phe Ala
        195                 200                 205

Cys His Phe Asp Pro Asn Ser Pro Ile Tyr Ser Asn Arg Glu Arg Ala
    210                 215                 220

Gln Ile Phe Ile Ser Asp Ala Gly Ile Phe Ala Val Leu Tyr Gly Leu
225                 230                 235                 240
```

```
Tyr Arg Leu Ala Ala Val Lys Gly Leu Val Trp Val Leu Thr Val Tyr
                245                 250                 255

Ala Gly Pro Leu Leu Val Val Asn Gly Phe Leu Val Leu Ile Thr Phe
            260                 265                 270

Leu Gln His Thr His Pro Ser Leu Pro His Tyr Asp Ser Thr Glu Trp
        275                 280                 285

Asp Trp Leu Arg Gly Ala Leu Ala Thr Ile Asp Arg Asp Tyr Gly Ile
    290                 295                 300

Leu Asn Lys Val Phe His Asn Ile Thr Asp Thr His Val Thr His His
305                 310                 315                 320

Leu Phe Ser Thr Met Pro His Tyr His Ala Met Glu Ala Thr Lys Ala
                325                 330                 335

Ile Ile Pro Ile Leu Gly Asp Tyr Tyr Gln Phe Asp Gly Thr Ser Val
            340                 345                 350

Phe Lys Ala Met Tyr Arg Glu Thr Lys Glu Cys Ile Tyr Val Asp Lys
        355                 360                 365

Asp Glu Glu Val Lys Asp Gly Val Tyr Trp Tyr Arg Asn Lys Ile
    370                 375                 380


<210> SEQ ID NO 29
<211> LENGTH: 381
<212> TYPE: PRT
<213> ORGANISM: Carthamus tinctorius

<400> SEQUENCE: 29

Met Gly Ala Gly Gly Arg Met Asn Ala Glu Val Ser Gly Ser Glu Lys
1               5                   10                  15

Pro His Ala Phe Lys Arg Val Pro Val Ser Lys Pro Pro Phe Glu Leu
            20                  25                  30

Ser Asp Leu Lys Lys Ala Val Pro Pro His Cys Phe Lys Arg Ser Leu
        35                  40                  45

Val Arg Ser Phe Ala Ala Leu Phe Arg Asp Ile Ile Ile Val Thr Ala
    50                  55                  60

Leu Tyr Tyr Leu Ala Ala Thr Ile Ile Pro Val Leu Pro Lys Pro Leu
65                  70                  75                  80

Thr Tyr Val Ala Trp Pro Leu Tyr Trp Phe Phe Gln Gly Ala Tyr Leu
                85                  90                  95

Met Gly Leu Trp Val Ile Gly His Glu Cys Gly His His Gly Phe Ser
            100                 105                 110

Glu Tyr Gln Trp Leu Asp Asp Thr Val Gly Phe Ile Val His Ser Leu
        115                 120                 125

Ile Leu Thr Pro Tyr Phe Gly Phe Lys Tyr Ser His Arg Thr His His
    130                 135                 140

Ala Asn Thr Asn Ser Ile Glu Tyr Asp Glu Val Trp Ile Pro Lys Arg
145                 150                 155                 160

Lys Ser Asp Lys Leu Tyr Ser Glu Ile Leu Asn Asn Pro Leu Gly Ser
                165                 170                 175

Phe Val Val Phe Val Phe Lys Ile Val Leu Gly Phe Pro Leu Tyr Phe
            180                 185                 190

Val Phe Asn Leu Tyr Gly Arg Lys Tyr Glu Lys Gly Ile Thr Ser His
        195                 200                 205

Phe Tyr Pro Tyr Ser Pro Ile Phe Asn Asp Ser Glu Arg Phe Gln Ile
    210                 215                 220

Phe Leu Thr Asp Leu Gly Val Phe Gly Thr Leu Tyr Gly Val Tyr Arg
```

```
225                 230                 235                 240

Leu Ala Leu Ile Lys Gly Thr Glu Trp Val Ile Asn Phe Tyr Gly Met
                245                 250                 255

Pro Ile Leu Phe Met Ser Gly Phe Phe Ile Leu Leu Thr Tyr Leu His
            260                 265                 270

His Thr His Pro Ser Ile Pro His Tyr Asp Ser Thr Glu Trp Asp Trp
        275                 280                 285

Leu Arg Gly Ala Leu Ala Thr Val Asp Arg Asn Phe Gly Phe Leu Asn
    290                 295                 300

His Ala Phe His Asp Val Thr Arg Thr His Ala Val His His Leu Phe
305                 310                 315                 320

Pro Thr Ile Pro His Tyr His Thr Phe Glu Ala Arg Gln Ala Val Met
                325                 330                 335

Pro Ile Leu Gly Asp Tyr Tyr Lys Tyr Asp Asp Thr Pro Ile Leu Glu
            340                 345                 350

Ala Val Trp Arg Glu Thr Lys Asp Cys Ile Phe Ile Glu Pro Glu Glu
        355                 360                 365

Val Asn Gly Glu Lys Lys Gly Ile Tyr Trp Phe Tyr Lys
    370                 375                 380


<210> SEQ ID NO 30
<211> LENGTH: 380
<212> TYPE: PRT
<213> ORGANISM: Carthamus tinctorius

<400> SEQUENCE: 30

Met Gly Ala Gly Gly Arg Met Asp Val Ala Ala Ser Ser Glu Lys Pro
1               5                   10                  15

His Ala Phe Lys Arg Val Pro Val Ser Lys Pro Pro Phe Glu Leu Ser
            20                  25                  30

Asp Leu Lys Lys Ala Val Pro Pro His Cys Phe Lys Arg Ser Leu Val
        35                  40                  45

Arg Ser Phe Ala Ala Leu Phe Arg Asp Ile Ile Ile Val Ser Ala Leu
    50                  55                  60

Tyr Tyr Leu Ala Ala Thr Val Ile Pro Val Leu Pro Lys Pro Leu Thr
65                  70                  75                  80

Tyr Val Ala Trp Pro Leu Tyr Trp Phe Phe Gln Gly Ala Tyr Leu Met
                85                  90                  95

Gly Leu Trp Val Ile Gly His Glu Cys Gly His His Gly Phe Ser Glu
            100                 105                 110

Tyr Gln Trp Leu Asp Asp Thr Val Gly Phe Ile Val His Ser Leu Ile
        115                 120                 125

Leu Thr Pro Tyr Phe Gly Phe Lys Tyr Ser His Arg Thr His His Ala
    130                 135                 140

Asn Thr Asn Ser Ile Glu Tyr Asp Glu Val Trp Ile Pro Lys Arg Lys
145                 150                 155                 160

Ser Asp Lys Leu Tyr Ser Glu Ile Leu Asn Asn Pro Leu Gly Ser Phe
                165                 170                 175

Val Val Phe Val Phe Lys Ile Val Leu Gly Phe Pro Leu Tyr Phe Val
            180                 185                 190

Phe Asn Leu Tyr Gly Arg Lys Tyr Glu Lys Gly Ile Thr Ser His Phe
        195                 200                 205

Tyr Pro Tyr Ser Pro Ile Phe Asn Asp Ser Glu Arg Phe Gln Ile Phe
    210                 215                 220
```

```
Leu Thr Asp Leu Gly Val Phe Gly Thr Leu Tyr Gly Val Tyr Arg Leu
225                 230                 235                 240

Ala Leu Ile Lys Gly Thr Glu Trp Val Ile Asn Phe Tyr Gly Met Pro
                245                 250                 255

Ile Leu Phe Met Ser Gly Phe Phe Ile Leu Leu Thr Tyr Leu His His
            260                 265                 270

Thr His Pro Ser Ile Pro His Tyr Asp Ser Thr Glu Trp Asp Trp Leu
        275                 280                 285

Arg Gly Ala Leu Ala Thr Val Asp Arg Asn Phe Gly Phe Leu Asn His
    290                 295                 300

Ala Phe His Asp Val Thr Arg Thr His Ala Val His His Leu Phe Pro
305                 310                 315                 320

Thr Ile Pro His Tyr His Thr Phe Glu Ala Arg Gln Ala Val Met Pro
                325                 330                 335

Ile Leu Gly Asp Tyr Tyr Lys Tyr Asp Asp Thr Pro Ile Leu Glu Ala
            340                 345                 350

Val Trp Arg Glu Thr Lys Asp Cys Ile Phe Ile Glu Pro Glu Glu Val
        355                 360                 365

Asn Gly Glu Lys Lys Gly Ile Tyr Trp Phe Tyr Lys
    370                 375                 380


<210> SEQ ID NO 31
<211> LENGTH: 375
<212> TYPE: PRT
<213> ORGANISM: Carthamus tinctorius

<400> SEQUENCE: 31

Met Gly Ala Gly Gly Arg Met Asn Asp Asp Ala Thr Arg Glu Arg Asp
1               5                   10                  15

Val Phe Lys His Val Pro Val Glu Lys Pro Ser Phe Gly Ile Ala Asp
            20                  25                  30

Leu Lys Lys Ala Ile Pro Pro His Cys Phe Lys Arg Ser Leu Thr Thr
        35                  40                  45

Ser Phe Tyr Tyr Arg Phe Arg Asp Leu Gly Leu Ile Tyr Ala Phe Tyr
    50                  55                  60

Tyr Ile Ala Thr Lys Tyr Ile Thr His Leu Pro Gln Pro Tyr Ser Phe
65                  70                  75                  80

Val Ala Trp Pro Leu Tyr Trp Ile Ala Gln Gly Ala Ile Cys Met Gly
                85                  90                  95

Leu Trp Asn Ile Val His Asp Cys Gly His His Cys Phe Ser Asp Tyr
            100                 105                 110

Gln Trp Leu Asp Asp Thr Ile Gly Phe Ile Cys His Ser Phe Leu Leu
        115                 120                 125

Thr Pro Tyr Phe Ser Phe Lys Tyr Ser His Arg Thr His His Ala Asn
    130                 135                 140

Thr Ser Ser Leu Glu Arg Asp Glu Val Trp Val Pro Lys Arg Lys His
145                 150                 155                 160

Asp Thr Trp Phe Tyr Glu Val Leu Ser Asn Pro Val Gly Ser Phe Ile
                165                 170                 175

Met Leu Val Phe Arg Leu Phe Phe Gly Phe Pro Leu Tyr Phe Met Phe
            180                 185                 190

Asn Leu His Gly Arg Ile Tyr Lys Gly Phe Pro Ser His Phe Asn Pro
        195                 200                 205

Leu Gly Pro Ile Phe Asn Asp Arg Glu Arg Ala Asn Ile Trp Leu Ser
    210                 215                 220
```

```
Asp Ala Gly Val Leu Thr Val Val Tyr Ala Leu Tyr Arg Ile Gly Ala
225                 230                 235                 240

Lys Glu Gly Leu Gln Trp Val Leu Phe Val Tyr Ile Tyr Pro Leu Met
                245                 250                 255

Ala Met Ser Ala Phe Phe Ile Met Phe Thr Tyr Leu His His Thr His
            260                 265                 270

Pro Ser Ile Ala His Tyr Asp Ser Ser Glu Trp Asp Trp Leu Arg Gly
        275                 280                 285

Ala Leu Ser Thr Val Asp Arg Asp Tyr Gly Ile Leu Asn Asn Ile Phe
    290                 295                 300

His Asp Val Thr Ser Ala His Val Val His His Leu Phe Ser Ser Ile
305                 310                 315                 320

Pro His Tyr Asn Thr Val Glu Ala Thr Gln Tyr Ile Lys Pro Ile Leu
                325                 330                 335

Gly Glu Tyr Tyr Asn Tyr Asp Tyr Thr Pro Ile Leu Lys Ala Ile Trp
            340                 345                 350

Arg Asp Thr Lys Glu Cys Leu Phe Ile Glu Glu Asp Pro Glu Lys Lys
        355                 360                 365

Gly Val Tyr Trp Phe His Lys
    370                 375
```

<210> SEQ ID NO 32
<211> LENGTH: 376
<212> TYPE: PRT
<213> ORGANISM: Carthamus tinctorius

<400> SEQUENCE: 32

```
Met Gly Ala Gly Gly Arg Met Asn Asp Ala Thr Thr Asp Lys Asp Val
1               5                   10                  15

Leu Lys Arg Val Pro Thr Ala Lys Thr Pro Phe Glu Ile Ser Asp Leu
            20                  25                  30

Lys Lys Ala Ile Pro Pro His Cys Phe Lys Arg Ser Leu Thr Thr Ser
        35                  40                  45

Phe Tyr Tyr Leu Phe Arg Asp Ile Cys Ile Cys Tyr Thr Trp Tyr His
    50                  55                  60

Leu Gly Ser Asn Tyr Leu Pro Leu Leu Pro Lys Pro Leu Ala Tyr Ile
65                  70                  75                  80

Ala Trp Pro Ile Tyr Trp Phe Cys Gln Gly Ser Ser Phe Met Gly Ile
                85                  90                  95

Trp Ser Ile Gly His Asp Leu Gly His His Ala Phe Ser Glu Tyr Gln
            100                 105                 110

Trp Leu Asp Asp Ala Leu Gly Phe Val Ile His Ser Ala Phe Leu Thr
        115                 120                 125

Pro Tyr Phe Ser Phe Lys Tyr Ser His Arg Ser His His Ala His Thr
    130                 135                 140

Asn Ser Met Glu Tyr Asp Glu Val Trp Ile Pro Lys Arg Lys Ala Asp
145                 150                 155                 160

Thr Met Tyr Ser Glu Val Leu Asn Asn Pro Leu Gly Asn Leu Phe Met
                165                 170                 175

Thr Val Val Arg Leu Leu Phe Ser Phe Pro Met Tyr Phe Thr Phe Asn
            180                 185                 190

Ile His Gly Arg Pro Tyr Asn Gly Phe Val Ser His Phe Tyr Pro Gln
        195                 200                 205

Ser Pro Met Phe Asn Asp Ser Glu Arg Lys Leu Val Trp Leu Ser Asp
```

```
    210                 215                 220

Ala Gly Met Val Ala Ala Phe Tyr Gly Leu Tyr Lys Ile Ala Gln Ser
225                 230                 235                 240

Thr Ser Ala Thr Trp Leu Phe Cys Ile Tyr Gly Ala Pro Leu Leu Val
                245                 250                 255

Met Asn Ala His Phe Ile Phe Phe Thr Phe Leu His His Ser His Val
            260                 265                 270

Ser Leu Ala His Tyr Asp Ser Arg Glu Trp Asp Trp Ile Arg Gly Ala
        275                 280                 285

Leu Ser Thr Val Asp Arg Asn Tyr Gly Ile Leu Asn Thr Val Phe His
    290                 295                 300

Asp Val Thr Cys Ala His Val Val His His Leu Ile Ser Thr Ile Pro
305                 310                 315                 320

His Tyr His Thr Val Glu Ala Thr Asn Ala Val Lys Pro Ile Leu Gly
                325                 330                 335

Asp Tyr Tyr Lys Tyr Asp Asp Thr Pro Ile Leu Lys Ala Phe Trp Arg
            340                 345                 350

Glu Thr Lys Asn Cys Ile Tyr Val Glu Pro Asp Glu Gly Ala Glu Asp
        355                 360                 365

Ser Gly Val Tyr Trp Phe Arg Arg
    370                 375


<210> SEQ ID NO 33
<211> LENGTH: 372
<212> TYPE: PRT
<213> ORGANISM: Carthamus tinctorius

<400> SEQUENCE: 33

Met Gly Ala Gly Gly Arg Met Lys Thr Glu Glu Lys Asp Ile Met Lys
1               5                   10                  15

His Val Pro Val Ala Lys Pro Pro Phe Gly Ile Ser Asp Leu Lys Lys
            20                  25                  30

Ala Thr Pro Pro His Cys Phe Lys Arg Ser Leu Ile Trp Ser Phe Gly
        35                  40                  45

Ser Phe Phe Arg Asp Leu Ile Val Ile Tyr Ser Phe Tyr Tyr Leu Ala
    50                  55                  60

Ser Thr Phe Ile Pro Leu Leu Pro Pro Ala Leu Ser Tyr Val Ala Trp
65                  70                  75                  80

Pro Leu Tyr Trp Phe Ala Gln Gly Ser Ile Leu Met Gly Phe Trp Ile
                85                  90                  95

Leu Gly His Glu Cys Gly His His Ala Phe Ser Glu Tyr Gln Trp Val
            100                 105                 110

Asp Asp Ala Val Gly Phe Phe Ile His Ser Val Cys Leu Thr Pro Tyr
        115                 120                 125

Phe Ser Phe Lys Tyr Ser His Arg Ser His His Ala His Thr Asn Ser
    130                 135                 140

Ile Glu Tyr Asp Glu Val Tyr Ile Pro Lys Arg Lys Ala Asp Thr Phe
145                 150                 155                 160

Tyr Ser Glu Phe Leu Asn Asn Gly Pro Gly Asn Val Phe Thr Leu Leu
                165                 170                 175

Leu Arg Thr Thr Leu Gly Leu Pro Leu Tyr Leu Ile Phe Asn Thr Tyr
            180                 185                 190

Gly Arg Asp Tyr Asn Gly Phe Ala Asn His Phe Leu Pro Gln Ser Gly
        195                 200                 205
```

```
Ile Phe Asn Asp Ser Glu Arg Ala Gln Val Val Leu Ser Asp Val Gly
    210                 215                 220

Ile Phe Ala Val Leu Tyr Ala Leu Tyr Arg Leu Val Leu Ile Gln Gly
225                 230                 235                 240

Leu Lys Ser Thr Ile Phe Leu Gln Gly Ile Pro Leu Phe Val Met Ser
                245                 250                 255

Gly Phe Phe Ile Phe Leu Thr Tyr Leu Asn His Thr His Pro Ala Ile
            260                 265                 270

Ala His Tyr Asp Ser Thr Glu Trp Asp Trp Leu Arg Gly Ala Leu Ser
        275                 280                 285

Thr Ile Asp Arg Asp Phe Gly Ile Leu Asn Arg Val Phe His Asn Ala
    290                 295                 300

Asn His Thr His Gly Ile His His Leu Phe Pro Thr Ile Pro His Tyr
305                 310                 315                 320

His Ala Ile Glu Ala Arg Glu Ala Val Lys Pro Ile Leu Gly Asp Tyr
                325                 330                 335

Tyr Met Tyr Asp Asp Thr Pro Ile Leu Lys Ala Met Trp Arg Asp Thr
            340                 345                 350

Lys Glu Cys Ile Tyr Val Glu Pro Asp Asp Glu Lys Lys Gly Val Tyr
        355                 360                 365

Trp Tyr Phe Lys
    370


<210> SEQ ID NO 34
<211> LENGTH: 382
<212> TYPE: PRT
<213> ORGANISM: Carthamus tinctorius

<400> SEQUENCE: 34

Met Gly Ser Gly Gly Arg Ala Thr Glu Arg Ser Asn Pro Glu Ser Glu
1               5                   10                  15

Val Val Val Lys Arg Ala Pro Ser Ser Lys Pro Pro Phe Thr Leu Gly
            20                  25                  30

Asp Ile Lys Lys Ala Ile Pro Pro His Cys Phe Glu Arg Ser Leu Ile
        35                  40                  45

Arg Ser Ser Ser Tyr Leu Phe Leu Asp Leu Phe Leu Ser Ser Leu Phe
    50                  55                  60

Tyr Tyr Val Ala Ala Val Tyr Ile Pro Arg Leu Pro Ile Ser Leu Ser
65                  70                  75                  80

Tyr Val Ala Trp Pro Val Tyr Trp Ile Leu Gln Gly Ser Val Gln Met
                85                  90                  95

Gly Leu Trp Val Ile Gly His Glu Cys Gly His Gln Ala Phe Ser Asp
            100                 105                 110

Tyr Pro Trp Phe Asn Asp Thr Ile Gly Tyr Leu Leu His Thr Gly Met
        115                 120                 125

Leu Ala Pro Tyr Phe Ser Trp Lys Tyr Ser His Arg Arg His His Ser
    130                 135                 140

Asn Thr Gly Ser Leu Glu Leu Asp Glu Ser Phe Val Pro Lys Lys Lys
145                 150                 155                 160

Ser Ser Leu Asn Ser Val Ala Arg Leu Leu Asn Thr Pro Pro Gly Arg
                165                 170                 175

Leu Phe Arg Leu Thr Ile Leu Cys Thr Val Gly Trp Leu Leu Tyr Ile
            180                 185                 190

Cys Phe Asn Val Ser Gly Arg Lys Tyr Glu Lys Phe Ala Asn His Phe
        195                 200                 205
```

```
Asp Pro Lys Ser Pro Ile Tyr Asn Asp Arg Glu Arg Phe Gln Ile Leu
    210                 215                 220

Leu Thr Asp Ile Gly Leu Leu Val Thr Ser Tyr Gly Leu Tyr Lys Leu
225                 230                 235                 240

Ala Leu Ala Gln Gly Phe Ala Trp Leu Ile Thr Ile Tyr Phe Ala Pro
                245                 250                 255

Leu Val Ile Val Tyr Gly Phe Leu Val Val Ile Thr Trp Leu His His
            260                 265                 270

Thr His Arg Ser Leu Pro His Tyr Asp Ser Thr Glu Trp Asn Trp Leu
        275                 280                 285

Arg Gly Ala Leu Ser Thr Met Asp Arg Asp Tyr Gly Val Phe Asn Thr
    290                 295                 300

Val Leu His His Ile Thr Asp Thr His Val Ala His His Leu Phe Phe
305                 310                 315                 320

Thr Ile Pro His Tyr Asn Ala Met Glu Ala Thr Lys Ala Ile Lys Pro
                325                 330                 335

Phe Leu Gly Glu Tyr Tyr Gln Phe Asp Asp Thr Pro Ile Ile Lys Ala
            340                 345                 350

Met Trp Arg Glu Ala Thr Glu Cys Phe Phe Val Glu Ala Asp Glu Gly
        355                 360                 365

Glu Gly Lys Ser Lys Gly Val Tyr Trp Phe Asn Asn Lys Met
    370                 375                 380
```

<210> SEQ ID NO 35
<211> LENGTH: 387
<212> TYPE: PRT
<213> ORGANISM: Carthamus tinctorius

<400> SEQUENCE: 35

```
Met Gly Ala Gly Gly Arg Ser Asn Pro Arg Asp Leu Asp Val Lys Lys
1               5                   10                  15

Phe Asp Thr Val Glu Gly Ile Lys Arg Ala Pro Thr Ser Lys Pro Pro
            20                  25                  30

Phe Thr Leu Gly Asp Ile Lys Lys Ala Ile Pro Pro His Cys Phe Lys
        35                  40                  45

Arg Ser Leu Ile Arg Ser Phe Ser Tyr Leu Val Tyr Asp Leu Thr Ala
    50                  55                  60

Val Ser Ile Phe Tyr Tyr Leu Ala Thr Thr Tyr Ile Pro Gln Leu Pro
65                  70                  75                  80

Tyr Pro Leu Ala Tyr Val Ala Trp Pro Val Tyr Trp Phe Val Gln Gly
                85                  90                  95

Cys Val Phe Met Gly Leu Trp Leu Ile Ala His Glu Cys Gly His His
            100                 105                 110

Ala Phe Ser Asp His Val Trp Leu Glu Asp Ser Ile Gly Phe Val Leu
        115                 120                 125

His Ser Cys Leu Leu Thr Pro Tyr Phe Ser Trp Lys Ile Ser His Arg
    130                 135                 140

Arg His His Ala Asn Thr Gly Ser Leu Glu His Asp Glu Val Tyr Val
145                 150                 155                 160

Pro Lys Thr Lys Ala Lys Leu Gly Ala Ser Ala Phe Tyr Leu Asp Asn
                165                 170                 175

Pro Ile Gly Arg Thr Leu Thr Leu Met Val Lys Leu Thr Leu Gly Trp
            180                 185                 190

Tyr Ile Tyr Leu Ala Ile Asn Ala Ala Gly Arg Pro Tyr Glu Lys Phe
```

```
        195                 200                 205

Ala Ser His Tyr Asp Pro Arg Ser Glu Met Phe Ser Asp Asn Glu Arg
    210                 215                 220

Val Leu Ile Leu Met Ser Asp Ile Gly Leu Leu Ser Phe Ser Phe Leu
225                 230                 235                 240

Leu Tyr Lys Val Ala Met Val Gln Gly Phe Ala Trp Val Phe Cys Val
                245                 250                 255

Tyr Gly Gly Ala Leu Met Val Met Asn Ala Phe Leu Val Thr Ile Thr
            260                 265                 270

Tyr Leu His His Thr His Pro Ser Leu Pro His Tyr Asp Asp Ser Glu
        275                 280                 285

Trp Asn Trp Met Lys Gly Ala Phe Ala Thr Val Asp Arg Asp Tyr Gly
    290                 295                 300

Val Val Leu Asn Lys Val Phe His Asn Ile Thr Asp Thr His Val Leu
305                 310                 315                 320

His His Leu Phe Ser Tyr Ile Pro His Tyr His Ala Met Glu Ala Thr
                325                 330                 335

Lys Ala Ile Arg Pro Val Leu Gly Glu Phe Tyr Gln Ile Asp Arg Thr
            340                 345                 350

Pro Phe Phe Val Ala Leu Trp Arg Glu Ser Lys Ser Cys Leu Phe Ile
        355                 360                 365

Glu Pro Asp Glu Ser Asp Glu Lys Asn Lys Gly Ile Tyr Trp Tyr Arg
    370                 375                 380

Ser Lys Tyr
385


<210> SEQ ID NO 36
<211> LENGTH: 380
<212> TYPE: PRT
<213> ORGANISM: Carthamus tinctorius

<400> SEQUENCE: 36

Met Gly Gly Gly Gly Cys Ile Pro Ala Ser Lys Thr Glu Ala Gln Gln
1               5                   10                  15

Thr Asn His Leu Ser Arg Val Pro Tyr Glu Lys Pro Ala Phe Thr Val
            20                  25                  30

Gly Asp Ile Lys Arg Val Ile Pro Pro His Cys Phe Gln Arg Ser Leu
        35                  40                  45

Ile Arg Ser Phe Ser Tyr Val Ala Tyr Asp Leu Ala Ile Ala Phe Leu
    50                  55                  60

Ser Tyr His Leu Ala Thr Thr Tyr Phe His Arg Leu Ser Pro Pro Leu
65                  70                  75                  80

Ser Tyr Leu Ala Trp Ser Ala Tyr Trp Ile Val Gln Gly Cys Val Leu
                85                  90                  95

Thr Gly Val Trp Val Ile Ala His Glu Cys Gly His His Ala Phe Ser
            100                 105                 110

Asp His Gln Trp Val Asp Asp Thr Val Gly Leu Ile Leu His Ser Ala
        115                 120                 125

Leu Leu Val Pro Tyr Phe Ser Trp Lys Cys Ser His Arg Arg His His
    130                 135                 140

Leu Asn Thr Ala Ser Leu Glu Arg Asp Glu Val Phe Val Pro Lys Pro
145                 150                 155                 160

Lys Ser Lys Ile Pro Trp Tyr Ser Lys Tyr Leu Asn Asn Pro Pro Gly
                165                 170                 175
```

```
Arg Leu Ile Ile Val Phe Thr Thr Leu Val Leu Gly Trp Pro Leu Tyr
            180                 185                 190

Leu Ala Phe Asn Val Ser Gly Arg Pro Tyr Asp Arg Phe Ala Cys His
        195                 200                 205

Tyr Ala Pro Asn Ser Pro Ile Phe Thr Asn Arg Glu Arg Leu Gln Ile
    210                 215                 220

Trp Ile Ser Asp Ala Gly Ile Ile Ala Val Ser Tyr Leu Leu Tyr Arg
225                 230                 235                 240

Met Ala Leu Ala Lys Ser Val Ala Trp Val Val Cys Ile Tyr Gly Val
                245                 250                 255

Pro Leu Leu Ile Val Asn Gly Phe Leu Val Met Ile Thr Tyr Leu Gln
            260                 265                 270

His Thr His Pro Ser Leu Pro His Tyr Asp Asp Ser Glu Trp Asp Trp
        275                 280                 285

Leu Arg Gly Ala Leu Ala Thr Val Asp Arg Asp Tyr Gly Leu Leu Asn
    290                 295                 300

Lys Val Phe His Asn Ile Thr Asp Thr His Val Val His His Leu Phe
305                 310                 315                 320

Ser Thr Met Pro His Tyr His Ala Met Glu Ala Thr Lys Ala Val Glu
                325                 330                 335

Pro Val Leu Gly Gly Tyr Tyr Arg Phe Asp Asp Thr Pro Phe Tyr Val
            340                 345                 350

Ala Met Trp Arg Glu Ala Lys Glu Cys Leu Tyr Val Glu Thr Asp Glu
        355                 360                 365

Lys Lys Gly Gly Val Phe Trp Tyr Lys Asn Lys Tyr
    370                 375                 380


<210> SEQ ID NO 37
<211> LENGTH: 379
<212> TYPE: PRT
<213> ORGANISM: Carthamus tinctorius

<400> SEQUENCE: 37

Met Gly Ala Gly Gly Arg Met Ser Asp Ser Ser Glu Ser Ser Thr Asp
1               5                   10                  15

Ile Leu Lys Arg Val Pro Ile Asp Pro Pro Phe Thr Leu Ser Asp Leu
            20                  25                  30

Lys Lys Ala Ile Pro Ala Arg Cys Phe Glu Arg Ser Leu Ile Arg Ser
        35                  40                  45

Ser Tyr Tyr Val Val His Asp Leu Val Val Ala Tyr Val Phe Tyr Tyr
    50                  55                  60

Leu Ala Asp Thr Tyr Ile Pro Gln Leu Pro Thr Pro Leu Ala Tyr Leu
65                  70                  75                  80

Ala Trp Pro Ile Tyr Trp Phe Cys Gln Ala Ser Ile Cys Thr Gly Leu
                85                  90                  95

Trp Val Ile Gly His Glu Cys Gly His His Ala Phe Ser Glu Gln Gln
            100                 105                 110

Trp Ile Gly Asp Ile Val Gly Ile Val Leu His Ser Ala Leu Phe Thr
        115                 120                 125

Pro Tyr Phe Ala Trp Lys Tyr Ser His Arg Asn His His Ala Asn Thr
    130                 135                 140

Asn Ser Leu Asp Asn Asp Glu Val Tyr Ile Pro Lys Arg Lys Ser Lys
145                 150                 155                 160

Val Ala Ile Tyr Ser Lys Leu Leu Asn Asn Pro Pro Gly Arg Val Phe
                165                 170                 175
```

```
Thr Leu Val Phe Arg Leu Thr Leu Gly Phe Pro Leu Tyr Leu Leu Thr
            180                 185                 190

Asn Ile Ser Gly Lys Lys Tyr Gly Arg Phe Ala Asn His Phe Asp Pro
        195                 200                 205

Met Ser Pro Ile Phe Thr Glu Arg Glu Arg Ile Gln Val Leu Val Ser
    210                 215                 220

Asp Leu Gly Ile Leu Ala Val Leu Tyr Ala Ile Lys Leu Ala Val Ala
225                 230                 235                 240

Ala Lys Gly Ala Ala Trp Val Ile Ala Met Tyr Gly Ile Pro Val Val
                245                 250                 255

Gly Val His Val Phe Phe Val Leu Ile Thr Tyr Leu His His Thr His
            260                 265                 270

Leu Ser Leu Pro His Tyr Asp Ser Thr Glu Trp Asp Trp Ile Arg Gly
        275                 280                 285

Ala Leu Ser Thr Ile Asp Arg Asp Phe Gly Phe Leu Asn Arg Val Phe
    290                 295                 300

His Asp Val Thr His Thr His Val Leu His His Leu Ile Ser Tyr Ile
305                 310                 315                 320

Pro His Tyr His Ala Lys Glu Ala Arg Asp Ala Ile Lys Pro Ile Leu
                325                 330                 335

Gly Glu Tyr Tyr Lys Ile Asp Arg Thr Pro Ile Phe Lys Ala Met Trp
            340                 345                 350

Arg Glu Ala Lys Glu Ser Ile Tyr Ile Glu Pro Asp Glu Asn Ser Glu
        355                 360                 365

His Lys Gly Thr Tyr Trp Tyr His Lys Glu Leu
    370                 375

<210> SEQ ID NO 38
<211> LENGTH: 244
<212> TYPE: PRT
<213> ORGANISM: Carthamus tinctorius

<400> SEQUENCE: 38

Met Gly Gly Gly Gly Cys Met Ser Ala Ser Glu Thr Lys Ala Glu Glu
1               5                   10                  15

Lys Lys Asn Pro Leu Asp Arg Val Pro Cys Ala Lys Pro Pro Phe Thr
            20                  25                  30

Ile Ser Asp Ile Lys Gln Ala Ile Pro Ser His Cys Phe Asn Arg Ser
        35                  40                  45

Leu Ile Arg Ser Phe Ser Tyr Ile Val Tyr Asp Leu Ala Ile Ala Phe
    50                  55                  60

Val Leu Tyr Tyr Leu Ala Thr Thr Tyr Ile His Arg Leu Pro Thr Pro
65                  70                  75                  80

Phe Ser Tyr Leu Ala Trp Leu Ala Tyr Trp Ile Val Gln Gly Cys Val
                85                  90                  95

Leu Thr Gly Ala Trp Val Val Ala His Glu Cys Gly His His Ala Phe
            100                 105                 110

Ser Asp Tyr Gln Trp Val Asp Asp Thr Val Gly Phe Ile Val His Ser
        115                 120                 125

Phe Leu Leu Val Pro Tyr Phe Ser Trp Lys Tyr Ser His Arg Arg His
    130                 135                 140

His Ser Asn Thr Ala Ser Leu Glu Arg Asp Glu Val Phe Val Pro Lys
145                 150                 155                 160

Pro Arg Ser Lys Leu Pro Trp Tyr Ser Lys Tyr Leu Asn Asn Pro Pro
```

```
                165                 170                 175

Gly Arg Ile Ile Ser Leu Phe Ala Thr Leu Thr Leu Gly Trp Pro Leu
            180                 185                 190

Tyr Leu Ser Phe Asn Val Ser Gly Arg Pro Thr Thr Val Ser Pro Ala
        195                 200                 205

Thr Met Leu Pro Thr Ala Arg Phe Thr Thr Ile Ala Asn Ala Ser Arg
    210                 215                 220

Phe Gly Ser Leu Thr Trp Gly Ser Trp Pro Cys Arg Ser Ser Phe Thr
225                 230                 235                 240

Val Leu Arg Trp
```

```
<210> SEQ ID NO 39
<211> LENGTH: 501
<212> TYPE: DNA
<213> ORGANISM: Carthamus tinctorius

<400> SEQUENCE: 39

tcaatggggc cggttacatc tcaacgcatc aagtccgcga ccactaactc tgtcactgtc     60

gcacgggtgt cagacggtct tgtggggcga gcaatctcaa ctcactctgt tgcttctaga    120

cggttatacg ttgaagctgg acatgatcct gcagagatca ttggagacta gagtgcggcc    180

catgatcaag accgacgata agtctacgtg acatgtcttt tcaatatttt ccaccccgtt    240

gacggattgc agcatgatcc ttgctgaaat cacaagtggc tacttgcctg cagactaaca    300

atggatgatg ctggattgga aaacaaagcg gcctgacatg ctcgctgatc tagaatcctt    360

ttggtctaag aagaattgtg cttgatgggc ttgtattccg ccaaaccttc tctattatat    420

cccatgaaat atgggctgat cgaactggat cgttagagac agctaatgat tcatttgcaa    480

gaaactgccc ttaatcaagt a                                              501


<210> SEQ ID NO 40
<211> LENGTH: 672
<212> TYPE: DNA
<213> ORGANISM: Carthamus tinctorius

<400> SEQUENCE: 40

gcgctattac gtcagacgtc taggccggta agactgcccc taggtgggac tatatcttgt     60

aaaacgacgc ccagtcctgc gcgctgaagc tccggcaaca aaggtaaact ggctggagat    120

taaagtgcac tgagccgagg agtccgctat tccgagcctg tttagaagtg actacttaac    180

agaactacat tcggtagtta agagtttctt gaccatggtg gatactgctg ctactgcttc    240

gctgtttccg gtttcttcta cacaatcgga ctctggtgct aagaactccg gtaagcatgg    300

aggtgggctg ggaagtgtgg atgtgcgcgg gattaagaca aaatcttctg ggagtttgca    360

agttaagaca catgcgcagg cccccgcaaa ggtgaatggt tctagaatag gtgtcatgga    420

tggcctcaag atggatgata attcgtcgtc ggctgccccg aggactttta tcaaccaatt    480

gcctgattgg agcatgcttc ttgctgccat cacgactatt ttcttggctg ctgagaagca    540

atggatgatg ctagagtgga agactaagcg gccggacatg ctttcggaaa tggatccttt    600

tggtttaggg agaattgtgg aggatagttt catatttcgt caaaactttt ctattaggtc    660

gtatgaaata gg                                                        672


<210> SEQ ID NO 41
<211> LENGTH: 1671
<212> TYPE: DNA
<213> ORGANISM: Carthamus tinctorius
```

<400> SEQUENCE: 41
gcacgaggct ggccctcctc cttctctctc tctcttcttt cagcttccct gcctgctaaa 60
attccactaa acaaatacaa aaggaatcca aattcaacat tcttccccaa tcgcacgcct 120
tagggatata tgctgttctt tggtcatctt tgaacaatta tttataattt ggtgagcacg 180
tctgaaacca ataggtttga ctgataaaca tacgggttaa tctgaatact ttaatcatgg 240
ttgctacggc tgctactgca tcactgtttc cggtttcttc tccacaacct cactctggga 300
ccaagaaatc tggtaagctt ggaggtgtgc cagatggcgt tgatgtgcgt ggaatcaaga 360
caaaatctgt tacttctggc ggtttgcaag ttaaggctgc acaggctcct gcagaggtaa 420
atgggactag agtgcggccc atgatcaaga cagacgataa ttctacgtca catgtcccaa 480
gaacctttat caaccagttg ccggattgga gcatgcttct tgctgcaatc accacaatct 540
tcttggctgc agagaaacaa tggatgatgc tggattggaa aaccaagcgg cctgacatgc 600
ttgctgatct ggatcctttt ggtttaggga gaattgtgca ggatgggctt gtattccgtc 660
aaaacttctc tattagatcc tatgaaatag gggctgatcg aactgcgtcg atagagacgc 720
taatgaatca tttgcaggaa actgccctta atcatgtaaa gactgcggga ctcttgggtg 780
atggctttgg ctcaacacct gaaatgtgca agaagaatct attctgggtg gtgacaaaga 840
tgcaggtgat ggtagaccgt tatccaactt ggggtgatgt tgttcaagta gatacatggg 900
tagctcgatc tgggaaaaac ggcatgcgcc gtgattggct gcttcgtgat tgcaaaacag 960
gcgaggtcgt aacaagagct tcaagtaatt gggttatgat gaataaagag acaaggaggt 1020
tatcaaaaat tccagatgaa gtccgagctg aaatagaaca gtactttgta gatgcacctc 1080
cggtcgtgga tgatgacagc agaaaattgc ctaaacttga agacaccact gctgactatg 1140
ttcgcaatgg tttaactcca aggtggagtg atctggatgt caaccaacat gttaacaatg 1200
tgaagtatat tggttggatc cttgagagtg ctccacaaca agttgtggag aagtatgagc 1260
ttgctggctt gactctggaa taccgtcgag aatgtaggaa ggatagcgtg ctgagtcgct 1320
gacatcggta ttgggtggca atggtgatgg aatagctgat tccgattcca gtgatgttga 1380
ttgccagcat gtgctgctat ttgagagtgg tggtgaaggt gaggttgtga aaggaaggac 1440
tgcatggcga ccaaaaaaag ataaggatgg aattagaagc agcattgctg acttctttgc 1500
tggaaatgga aatggaaatg gaagtgccta ataccatgtt tcatgttttg cccttttgcc 1560
tcatttcaat gtgtataaaa gaatcatcat cactcatcct atttatgctg gctcttggaa 1620
ataacttgca atgtcctgcc cccacatata tacatatttt tctattttgt a 1671

<210> SEQ ID NO 42
<211> LENGTH: 458
<212> TYPE: DNA
<213> ORGANISM: Carthamus tinctorius

<400> SEQUENCE: 42
atggtggata ctgctgctac tgcttcgctg tttccggttt cttctacaca atcggactct 60
ggtgctaaga actccggtaa gcatggaggt gggctgggaa gtgtggatgt gcgcgggatt 120
aagacaaaat cttctgggag tttgcaagtt aagacacatg cgcaggcccc cgcaaaggtg 180
aatggttcta gaataggtgt catggatggc ctcaagatgg atgataattc gtcgtcggct 240
gccccgagga cttttatcaa ccaattgcct gattggagca tgcttcttgc tgccatcacg 300
actattttct tggctgctga gaagcaatgg atgatgctag agtggaagac taagcggccg 360

```
gacatgcttt cggaaatgga tccttttggt ttagggagaa ttgtggagga tagtttcata    420

tttcgtcaaa acttttctat taggtcgtat gaaatagg                            458


<210> SEQ ID NO 43
<211> LENGTH: 1086
<212> TYPE: DNA
<213> ORGANISM: Carthamus tinctorius

<400> SEQUENCE: 43

atggttgcta cggctgctac tgcatcactg tttccggttt cttctccaca acctcactct     60

gggaccaaga aatctggtaa gcttggaggt gtgccagatg gcgttgatgt gcgtggaatc    120

aagacaaaat ctgttacttc tggcggtttg caagttaagg ctgcacaggc tcctgcagag    180

gtaaatggga ctagagtgcg gcccatgatc aagacagacg ataattctac gtcacatgtc    240

ccaagaacct ttatcaacca gttgccggat tggagcatgc ttcttgctgc aatcaccaca    300

atcttcttgg ctgcagagaa acaatggatg atgctggatt ggaaaaccaa gcggcctgac    360

atgcttgctg atctggatcc ttttggttta gggagaattg tgcaggatgg gcttgtattc    420

cgtcaaaact tctctattag atcctatgaa ataggggctg atcgaactgc gtcgatagag    480

acgctaatga atcatttgca ggaaactgcc cttaatcatg taaagactgc gggactcttg    540

ggtgatggct ttggctcaac acctgaaatg tgcaagaaga atctattctg ggtggtgaca    600

aagatgcagg tgatggtaga ccgttatcca acttggggtg atgttgttca agtagataca    660

tgggtagctc gatctgggaa aaacggcatg cgccgtgatt ggctgcttcg tgattgcaaa    720

acaggcgagg tcgtaacaag agcttcaagt aattgggtta tgatgaataa agagacaagg    780

aggttatcaa aaattccaga tgaagtccga gctgaaatag aacagtactt tgtagatgca    840

cctccggtcg tggatgatga cagcagaaaa ttgcctaaac ttgaagacac cactgctgac    900

tatgttcgca atggtttaac tccaaggtgg agtgatctgg atgtcaacca acatgttaac    960

aatgtgaagt atattggttg gatccttgag agtgctccac aacaagttgt ggagaagtat   1020

gagcttgctg gcttgactct ggaataccgt cgagaatgta ggaaggatag cgtgctgagt   1080

cgctga                                                              1086


<210> SEQ ID NO 44
<211> LENGTH: 152
<212> TYPE: PRT
<213> ORGANISM: Carthamus tinctorius

<400> SEQUENCE: 44

Met Val Asp Thr Ala Ala Thr Ala Ser Leu Phe Pro Val Ser Ser Thr
1               5                   10                  15

Gln Ser Asp Ser Gly Ala Lys Asn Ser Gly Lys His Gly Gly Gly Leu
            20                  25                  30

Gly Ser Val Asp Val Arg Gly Ile Lys Thr Lys Ser Ser Gly Ser Leu
        35                  40                  45

Gln Val Lys Thr His Ala Gln Ala Pro Ala Lys Val Asn Gly Ser Arg
    50                  55                  60

Ile Gly Val Met Asp Gly Leu Lys Met Asp Asp Asn Ser Ser Ser Ala
65                  70                  75                  80

Ala Pro Arg Thr Phe Ile Asn Gln Leu Pro Asp Trp Ser Met Leu Leu
                85                  90                  95

Ala Ala Ile Thr Thr Ile Phe Leu Ala Ala Glu Lys Gln Trp Met Met
            100                 105                 110
```

```
Leu Glu Trp Lys Thr Lys Arg Pro Asp Met Leu Ser Glu Met Asp Pro
        115                 120                 125

Phe Gly Leu Gly Arg Ile Val Glu Asp Ser Phe Ile Phe Arg Gln Asn
    130                 135                 140

Phe Ser Ile Arg Ser Tyr Glu Ile
145                 150


<210> SEQ ID NO 45
<211> LENGTH: 361
<212> TYPE: PRT
<213> ORGANISM: Carthamus tinctorius

<400> SEQUENCE: 45

Met Val Ala Thr Ala Ala Thr Ala Ser Leu Phe Pro Val Ser Ser Pro
1               5                   10                  15

Gln Pro His Ser Gly Thr Lys Lys Ser Gly Lys Leu Gly Gly Val Pro
            20                  25                  30

Asp Gly Val Asp Val Arg Gly Ile Lys Thr Lys Ser Val Thr Ser Gly
        35                  40                  45

Gly Leu Gln Val Lys Ala Ala Gln Ala Pro Ala Glu Val Asn Gly Thr
    50                  55                  60

Arg Val Arg Pro Met Ile Lys Thr Asp Asp Asn Ser Thr Ser His Val
65                  70                  75                  80

Pro Arg Thr Phe Ile Asn Gln Leu Pro Asp Trp Ser Met Leu Leu Ala
                85                  90                  95

Ala Ile Thr Thr Ile Phe Leu Ala Ala Glu Lys Gln Trp Met Met Leu
            100                 105                 110

Asp Trp Lys Thr Lys Arg Pro Asp Met Leu Ala Asp Leu Asp Pro Phe
        115                 120                 125

Gly Leu Gly Arg Ile Val Gln Asp Gly Leu Val Phe Arg Gln Asn Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Glu Thr Ala Leu Asn His Val Lys Thr
                165                 170                 175

Ala Gly Leu Leu Gly Asp Gly Phe Gly Ser Thr Pro Glu Met Cys Lys
            180                 185                 190

Lys Asn Leu Phe Trp Val Val Thr Lys Met Gln Val Met Val Asp Arg
        195                 200                 205

Tyr Pro Thr Trp Gly Asp Val Val Gln Val Asp Thr Trp Val Ala Arg
    210                 215                 220

Ser Gly Lys Asn Gly Met Arg Arg Asp Trp Leu Leu Arg Asp Cys Lys
225                 230                 235                 240

Thr Gly Glu Val Val Thr Arg Ala Ser Ser Asn Trp Val Met Met Asn
                245                 250                 255

Lys Glu Thr Arg Arg Leu Ser Lys Ile Pro Asp Glu Val Arg Ala Glu
            260                 265                 270

Ile Glu Gln Tyr Phe Val Asp Ala Pro Pro Val Val Asp Asp Asp Ser
        275                 280                 285

Arg Lys Leu Pro Lys Leu Glu Asp Thr Thr Ala Asp Tyr Val Arg Asn
    290                 295                 300

Gly Leu Thr Pro Arg Trp Ser Asp Leu Asp Val Asn Gln His Val Asn
305                 310                 315                 320

Asn Val Lys Tyr Ile Gly Trp Ile Leu Glu Ser Ala Pro Gln Gln Val
                325                 330                 335
```

```
Val Glu Lys Tyr Glu Leu Ala Gly Leu Thr Leu Glu Tyr Arg Arg Glu
            340                 345                 350

Cys Arg Lys Asp Ser Val Leu Ser Arg
        355                 360


<210> SEQ ID NO 46
<211> LENGTH: 1545
<212> TYPE: DNA
<213> ORGANISM: Carthamus tinctorius

<400> SEQUENCE: 46

cggggatcca acaacaaaca gattctatcc ttggattgac agaattggag gaaggggttt      60

acttattatc gtaaacccta ctgaatctct ctacaggggt ttgctgaatt tgctcctttt     120

cttctccttc caatggcttg cagactcgca gattctagtt tccttttgaa gggtccccaa     180

caaaagccat tgcatgggta tagatttggg tcactctatc cagcaggcac atctttttttg    240

aagtgggata ttctacctaa atgtagaacc aaacatcaaa catatgtagt tcctttgaga     300

aggactaaaa tagtacaagc agtgactagt tctgttacag caccattacc atcagacagt     360

gcagaagaga ggaaagaatt atgtgaaagt tacggtttcc ggcaaattgg agaaccactc     420

ccggacaata tcaccttgaa gaacattatc gatactcttc ccaaaactgt gtttgagatt     480

gataacgtga aagcattgaa gtcggtattg atatctgcaa cttcatatgc tttggggctt     540

ttcatgattg ccaaatctcc atggtatctt cttccattgg cttgggcatg gacaggaact     600

gcagttacag ggttctttgt aataggtcat gattgtgcac acaaatcttt ctcaaagaac     660

aaactggtgg aagatattgt tggaactttg gccttcctgc cattgatata cccttatgag     720

ccatggcgtt tcaagcatga tcgacatcat gcaaaaacaa acatgttgga tgaagataca     780

gcttggcacc ctgtaatgga aacacatttc aaggagaacc caattttcca gaaggcaatc     840

atattcggat atggtcctat tcgccccatc atgtctatat cgcactggtt aatctggcat     900

ttcaatttga ataaattcag accgaatgaa attggaagag taaagatcag tcttgcttgt     960

gtttttgcat tcatggcaat tggatggccg ttaattgtct acaaggccgg gatagttgga    1020

tggataaagt tttggttaat gccatggttg ggctatcatt tttggatgag cactttcaca    1080

atggttcacc acacagcacc tcacgtacct ttcaaatttt cggacgagtg gaatgcagct    1140

aaggcacaac ttagtggcac cgtgcactgt gattatcctc gctggataga gatcctttgt    1200

catgatatca acgttcatat cccccaccat gtctcctcaa agattccaag ttacaacttg    1260

cgtgcagctc ataaatctct tcaagagaat tggggaaaat atatgaatga ggcctcatgg    1320

aactggcgct taatgaagac gatcttgacg atttgccatg tctacgacaa agagcgtaat    1380

tacatctcgt ttgaagagat tgctcccgag atatcccagc ccaatcgcat tacttagaag    1440

ggtaatgccc gactatgctt aactcaatca tttgtttttt tatttacata tttcattaat    1500

tgttaatgct atatattttc ctttatatac aaaaaaagtt acacc                    1545


<210> SEQ ID NO 47
<211> LENGTH: 1305
<212> TYPE: DNA
<213> ORGANISM: Carthamus tinctorius

<400> SEQUENCE: 47

atggcttgca gactcgcaga ttctagtttc cttttgaagg gtccccaaca aaagccattg      60

catgggtata gatttgggtc actctatcca gcaggcacat ctttttttgaa gtgggatatt    120
```

```
ctacctaaat gtagaaccaa acatcaaaca tatgtagttc ctttgagaag gactaaaata    180

gtacaagcag tgactagttc tgttacagca ccattaccat cagacagtgc agaagagagg    240

aaagaattat gtgaaagtta cggtttccgg caaattggag aaccactccc ggacaatatc    300

accttgaaga acattatcga tactcttccc aaaactgtgt ttgagattga taacgtgaaa    360

gcattgaagt cggtattgat atctgcaact tcatatgctt tggggctttt catgattgcc    420

aaatctccat ggtatcttct tccattggct tgggcatgga caggaactgc agttacaggg    480

ttctttgtaa taggtcatga ttgtgcacac aaatctttct caaagaacaa actggtggaa    540

gatattgttg gaactttggc cttcctgcca ttgatatacc cttatgagcc atggcgtttc    600

aagcatgatc gacatcatgc aaaaacaaac atgttggatg aagatacagc ttggcaccct    660

gtaatggaaa cacatttcaa ggagaaccca attttccaga aggcaatcat attcggatat    720

ggtcctattc gccccatcat gtctatatcg cactggttaa tctggcattt caatttgaat    780

aaattcagac cgaatgaaat tggaagagta aagatcagtc ttgcttgtgt tttgcattc    840

atggcaattg gatggccgtt aattgtctac aaggccggga tagttggatg gataaagttt    900

tggttaatgc catggttggg ctatcatttt tggatgagca ctttcacaat ggttcaccac    960

acagcacctc acgtaccttt caaattttcg gacgagtgga atgcagctaa ggcacaactt   1020

agtggcaccg tgcactgtga ttatcctcgc tggatagaga tcctttgtca tgatatcaac   1080

gttcatatcc cccaccatgt ctcctcaaag attccaagtt acaacttgcg tgcagctcat   1140

aaatctcttc aagagaattg gggaaaatat atgaatgagg cctcatggaa ctggcgctta   1200

atgaagacga tcttgacgat ttgccatgtc tacgacaaag agcgtaatta catctcgttt   1260

gaagagattg ctcccgagat atcccagccc aatcgcatta cttag                  1305
```

<210> SEQ ID NO 48
<211> LENGTH: 434
<212> TYPE: PRT
<213> ORGANISM: Carthamus tinctorius

<400> SEQUENCE: 48

```
Met Ala Cys Arg Leu Ala Asp Ser Ser Phe Leu Leu Lys Gly Pro Gln
1               5                   10                  15

Gln Lys Pro Leu His Gly Tyr Arg Phe Gly Ser Leu Tyr Pro Ala Gly
            20                  25                  30

Thr Ser Phe Leu Lys Trp Asp Ile Leu Pro Lys Cys Arg Thr Lys His
        35                  40                  45

Gln Thr Tyr Val Val Pro Leu Arg Arg Thr Lys Ile Val Gln Ala Val
    50                  55                  60

Thr Ser Ser Val Thr Ala Pro Leu Pro Ser Asp Ser Ala Glu Glu Arg
65                  70                  75                  80

Lys Glu Leu Cys Glu Ser Tyr Gly Phe Arg Gln Ile Gly Glu Pro Leu
                85                  90                  95

Pro Asp Asn Ile Thr Leu Lys Asn Ile Ile Asp Thr Leu Pro Lys Thr
            100                 105                 110

Val Phe Glu Ile Asp Asn Val Lys Ala Leu Lys Ser Val Leu Ile Ser
        115                 120                 125

Ala Thr Ser Tyr Ala Leu Gly Leu Phe Met Ile Ala Lys Ser Pro Trp
    130                 135                 140

Tyr Leu Leu Pro Leu Ala Trp Ala Trp Thr Gly Thr Ala Val Thr Gly
145                 150                 155                 160

Phe Phe Val Ile Gly His Asp Cys Ala His Lys Ser Phe Ser Lys Asn
```

```
                165                 170                 175

Lys Leu Val Glu Asp Ile Val Gly Thr Leu Ala Phe Leu Pro Leu Ile
            180                 185                 190

Tyr Pro Tyr Glu Pro Trp Arg Phe Lys His Asp Arg His His Ala Lys
        195                 200                 205

Thr Asn Met Leu Asp Glu Asp Thr Ala Trp His Pro Val Met Glu Thr
    210                 215                 220

His Phe Lys Glu Asn Pro Ile Phe Gln Lys Ala Ile Ile Phe Gly Tyr
225                 230                 235                 240

Gly Pro Ile Arg Pro Ile Met Ser Ile Ser His Trp Leu Ile Trp His
                245                 250                 255

Phe Asn Leu Asn Lys Phe Arg Pro Asn Glu Ile Gly Arg Val Lys Ile
            260                 265                 270

Ser Leu Ala Cys Val Phe Ala Phe Met Ala Ile Gly Trp Pro Leu Ile
        275                 280                 285

Val Tyr Lys Ala Gly Ile Val Gly Trp Ile Lys Phe Trp Leu Met Pro
    290                 295                 300

Trp Leu Gly Tyr His Phe Trp Met Ser Thr Phe Thr Met Val His His
305                 310                 315                 320

Thr Ala Pro His Val Pro Phe Lys Phe Ser Asp Glu Trp Asn Ala Ala
                325                 330                 335

Lys Ala Gln Leu Ser Gly Thr Val His Cys Asp Tyr Pro Arg Trp Ile
            340                 345                 350

Glu Ile Leu Cys His Asp Ile Asn Val His Ile Pro His His Val Ser
        355                 360                 365

Ser Lys Ile Pro Ser Tyr Asn Leu Arg Ala Ala His Lys Ser Leu Gln
    370                 375                 380

Glu Asn Trp Gly Lys Tyr Met Asn Glu Ala Ser Trp Asn Trp Arg Leu
385                 390                 395                 400

Met Lys Thr Ile Leu Thr Ile Cys His Val Tyr Asp Lys Glu Arg Asn
                405                 410                 415

Tyr Ile Ser Phe Glu Glu Ile Ala Pro Glu Ile Ser Gln Pro Asn Arg
            420                 425                 430

Ile Thr


<210> SEQ ID NO 49
<211> LENGTH: 756
<212> TYPE: DNA
<213> ORGANISM: Artificial Sequence
<220> FEATURE:
<223> OTHER INFORMATION: RNAi vector construction

<400> SEQUENCE: 49

taccaatggc tcgacgacac tgtcggcctt atcctacatt ctgttcttct tgttccttac     60

ttctcgtgga aatacagcca ccgccgccac cactccaaca ccggctcgat tgagcacgac    120

gaggtcttcg tcccgaaact caaatccggg gtccggtcca ccgcaaaata cctaaacaac    180

ccccccggcc ggatcttgac ccttcttgtc accctcaccc tcggctggcc gttgtacctc    240

atgttcaacg tctccggccg ctactacgac cgctttgcct gccattttga cccaaacagc    300

cccatctact cgaaccgtga acgtgcccag atcttcatct ccgacgccgg gatcttcgcc    360

gtcctctacg ggctctaccg gctcgcggcg gtcaaagggc tcgtgtgggt cctgaccgtc    420

tatgccggac cgttgctcgt ggtcaacggg tttcttgtcc tgatcacgtt cctccagcac    480

acccacccgt cgttgccgca ctacgactca accgagtggg actggctccg tggggccctg    540
```

```
gccaccatcg accgtgacta cgggatttta aacaaggtgt tccacaacat caccgacacc    600

cacgtgaccc accatctgtt ttcgacgatg ccgcattatc acgcgatgga ggccacgaag    660

gcgataattc cgatcctcgg ggattattat cagttcgatg ggacgtcagt ttttaaggcg    720

atgtataggg agacgaagga gtgcatttat gtggat                              756
```

<210> SEQ ID NO 50
<211> LENGTH: 300
<212> TYPE: DNA
<213> ORGANISM: Artificial Sequence
<220> FEATURE:
<223> OTHER INFORMATION: RNAi vector construction

<400> SEQUENCE: 50

```
ctttatcaac cagttgccgg attggagcat gcttcttgct gcaatcacca caatcttctt     60

ggctgcagag aaacaatgga tgatgctgga ttggaaaacc aagcggcctg acatgcttgc    120

tgatctggat ccttttggtt tagggagaat tgtgcaggat gggcttgtat tccgtcaaaa    180

cttctctatt agatcctatg aaataggggc tgatcgaact gcgtcgatag agacgctaat    240

gaatcatttg caggaaactg cccttaatca tgtaaagact gcgggactct tgggtgatgg    300
```

<210> SEQ ID NO 51
<211> LENGTH: 290
<212> TYPE: DNA
<213> ORGANISM: Artificial Sequence
<220> FEATURE:
<223> OTHER INFORMATION: RNAi vector construction

<400> SEQUENCE: 51

```
ccaaaactgt gtttgagatt gataacgtga aagcattgaa gtcggtattg atatctgcaa     60

cttcatatgc tttggggctt ttcatgattg ccaaatctcc atggtatctt cttccattgg    120

cttgggcatg gacaggaact gcagttacag ggttctttgt aataggtcat gattgtgcac    180

acaaatcttt ctcaaagaac aaactggtgg aagatattgt tggaactttg gccttcctgc    240

cattgatata cccttatgag ccatggcgtt tcaagcatga tcgacatcat              290
```

<210> SEQ ID NO 52
<211> LENGTH: 1200
<212> TYPE: DNA
<213> ORGANISM: Arabidopsis thaliana

<400> SEQUENCE: 52

```
tatgtagaac taaagactaa gggacagaga gttcgtctaa acaggtgaat ctagtcgttg     60

ttatctaata aacaattcag ccccaaatgc agaacacaca tagagctctc tattgattca    120

aattacgatc tgatactgat aacgtctaga tttttagggt taaagcaatc aatcacctga    180

cgattcaagg tggttggatc atgacgattc cagaaaacat caagcaagct ctcaaagcta    240

cactctttgg gatcatactg aactctaaca acctcgttat gtcccgtagt gccagtacag    300

acatcctcgt aactcggatt gtgcacgatg ccatggctat acccaacctc ggtcttggtc    360

acaccaggaa ctctctggta agctagctcc actccccaga aacaaccgcc gccaaattgc    420

gcgaattgct gacctgaaga cggaacatca tcgtcgggtc cttgggcgat tgcggcggaa    480

gatgggtcag cttgggcttg aggacgagac ccgaatccga gtctgttgaa aaggttgttc    540

attggggatt tgtatacgga gattggtcgt cgagaggttt gagggaaagg acaaatgggt    600

ttggctctgg agaaagagag tgcggcttta gagagagaat tgagaggttt agagagagat    660
```

gcggcggcga tgagcggagg agagacgacg aggacctgca ttatcaaagc agtgacgtgg 720
tgaaatttgg aacttttaag aggcagatag atttattatt tgtatccatt ttcttcattg 780
ttctagaatg tcgcggaaca aattttaaaa ctaaatccta aatttttcta attttgttgc 840
caatagtgga tatgtgggcc gtatagaagg aatctattga aggcccaaac ccatactgac 900
gagcccaaag gttcgttttg cgttttatgt ttcggttcga tgccaacgcc acattctgag 960
ctaggcaaaa aacaaacgtg tctttgaata gactcctctc gttaacacat gcagcggctg 1020
catggtgacg ccattaacac gtggcctaca attgcatgat gtctccattg acacgtgact 1080
tctcgtctcc tttcttaata tatctaacaa acactcctac ctcttccaaa atatatacac 1140
atctttttga tcaatctctc attcaaaatc tcattctctc tagtaaacaa gaacaaaaaa 1200

<210> SEQ ID NO 53
<211> LENGTH: 2033
<212> TYPE: DNA
<213> ORGANISM: Linum usitatissimum

<400> SEQUENCE: 53
ctcaagcata cggacaaggg taaataacat agtcaccaga acataataaa caaaaagtgc 60
agaagcaaga ctaaaaaaat tagctatgga cattcaggtt catattggaa acatcattat 120
cctagtcttg tgaccatcct tcctcctgct ctagttgaga ggccttggga ctaacgagag 180
gtcagttggg atagcagatc cttatcctgg actagccttt ctggtgtttc agagtcttcg 240
tgccgccgtc tacatctatc tccattaggt ctgaagatga ctcttcacac caacgacgtt 300
taaggtctct atcctactcc tagcttgcaa tacctggctt gcaatacctg gagcatcgtg 360
cacgatgatt ggatactgtg gaggaggagt gtttgctgat ttagagctcc cggttgggtg 420
atttgacttc gatttcagtt taggcttgtt gaaatttttc aggttccatt gtgaagcctt 480
tagagcttga gcttccttcc atgttaatgc cttgatcgaa tactcctaga gaaaagggaa 540
gtcgatctct gagtattgaa atcgaagtgc acattttttt tcaacgtgtc caatcaatcc 600
acaaacaaag cagaagacag gtaatctttc atacttatac tgacaagtaa tagtcttacc 660
gtcatgcata ataacgtctc gttccttcaa gaggggtttt ccgacatcca taacgacccg 720
aagcctcatg aaagcattag ggaagaactt ttggttcttc ttgtcatggc ctttataggt 780
gtcagccgag ctcgccaatt cccgtccgac tggctccgca aaatattcga acggcaagtt 840
atggacttgc aaccataact ccacggtatt gagcaggacc tattgtgaag actcatctca 900
tggagcttca gaatgtggtt gtcagcaaac caatgaccga aatccatcac atgacggacg 960
tccagtgggt gagcgaaacg aaacaggaag cgcctatctt tcagagtcgt gagctccaca 1020
ccggattccg gcaactacgt gttgggcagg cttcgccgta ttagagatat gttgaggcag 1080
acccatctgt gccactcgta caattacgag agttgttttt tttgtgattt tcctagtttc 1140
tcgttgatgg tgagctcata ttctacatcg tatggtctct caacgtcgtt tcctgtcatc 1200
tgatatcccg tcatttgcat ccacgtgcgc cgcctcccgt gccaagtccc taggtgtcat 1260
gcacgccaaa ttggtggtgg tgcgggctgc cctgtgcttc ttaccgatgg gtggaggttg 1320
agtttggggg tctccgcggc gatggtagtg ggttgacggt ttggtgtggg ttgacggcat 1380
tgatcaattt acttcttgct tcaaattctt tggcagaaaa caattcatta gattagaact 1440
ggaaaccaga gtgatgagac ggattaagtc agattccaac agagttacat ctcttaagaa 1500
ataatgtaac ccctttagac tttatatatt tgcaattaaa aaaataattt aacttttaga 1560
ctttatatat agttttaata actaagttta accactctat tatttatatc gaaactattt 1620

```
gtatgtctcc cctctaaata aacttggtat tgtgtttaca gaacctataa tcaaataatc   1680

aatactcaac tgaagtttgt gcagttaatt gaagggatta acggccaaaa tgcactagta   1740

ttatcaaccg aatagattca cactagatgg ccatttccat caatatcatc gccgttcttc   1800

ttctgtccac atatcccctc tgaaacttga gagacacctg cacttcattg tccttattac   1860

gtgttacaaa atgaaaccca tgcatccatg caaactgaag aatggcgcaa gaacccttcc   1920

cctccatttc ttatgtggcg accatccatt tcaccatctc ccgctataaa acacccccat   1980

cacttcacct agaacatcat cactacttgc ttatccatcc aaaagatacc cac          2033


<210> SEQ ID NO 54
<211> LENGTH: 253
<212> TYPE: DNA
<213> ORGANISM: Artificial Sequence
<220> FEATURE:
<223> OTHER INFORMATION: Nos polyadenylation signal

<400> SEQUENCE: 54

gatcgttcaa acatttggca ataaagtttc ttaagattga atcctgttgc cggtcttgcg     60

atgattatca tataatttct gttgaattac gttaagcatg taataattaa catgtaatgc    120

atgacgttat ttatgagatg ggtttttatg attagagtcc cgcaattata catttaatac    180

gcgatagaaa acaaaatata gcgcgcaaac taggataaat tatcgcgcgc ggtgtcatct    240

atgttactag atc                                                       253


<210> SEQ ID NO 55
<211> LENGTH: 708
<212> TYPE: DNA
<213> ORGANISM: Artificial Sequence
<220> FEATURE:
<223> OTHER INFORMATION: Ocs polyadenylation signal

<400> SEQUENCE: 55

ctgctttaat gagatatgcg agacgcctat gatcgcatga tatttgcttt caattctgtt     60

gtgcacgttg taaaaaacct gagcatgtgt agctcagatc cttaccgccg gtttcggttc    120

attctaatga atatatcacc cgttactatc gtatttttat gaataatatt ctccgttcaa    180

tttactgatt gtaccctact acttatatgt acaatattaa aatgaaaaca atatattgtg    240

ctgaataggt ttatagcgac atctatgata gagcgccaca ataacaaaca attgcgtttt    300

attattacaa atccaatttt aaaaaaagcg gcagaaccgg tcaaacctaa aagactgatt    360

acataaatct tattcaaatt tcaaaaggcc ccaggggcta gtatctacga cacaccgagc    420

ggcgaactaa taacgttcac tgaagggaac tccggttccc cgccggcgcg catgggtgag    480

attccttgaa gttgagtatt ggccgtccgc tctaccgaaa gttacgggca ccattcaacc    540

cggtccagca cggcggccgg gtaaccgact tgctgccccg agaattatgc agcatttttt    600

tggtgtatgt gggccccaaa tgaagtgcag gtcaaacctt gacagtgacg acaaatcgtt    660

gggcgggtcc agggcgaatt ttgcgacaac atgtcgaggc tcagcagg                 708


<210> SEQ ID NO 56
<211> LENGTH: 50
<212> TYPE: DNA
<213> ORGANISM: Carthamus tinctorius

<400> SEQUENCE: 56

tgtctttcaa cgtctccgga agaccctatg accgtttcgc ctgccactac                50
```

<210> SEQ ID NO 57
<211> LENGTH: 49
<212> TYPE: DNA
<213> ORGANISM: Carthamus tinctorius

<400> SEQUENCE: 57
tgtctttcaa cgtctctgga agacctacaa ccgtttcgcc tgccactat 49

<210> SEQ ID NO 58
<211> LENGTH: 25
<212> TYPE: DNA
<213> ORGANISM: Artificial Sequence
<220> FEATURE:
<223> OTHER INFORMATION: oligonucleotide

<400> SEQUENCE: 58
cttcagcgag taccaatggc tcgac 25

<210> SEQ ID NO 59
<211> LENGTH: 22
<212> TYPE: DNA
<213> ORGANISM: Artificial Sequence
<220> FEATURE:
<223> OTHER INFORMATION: oligionucleotide

<400> SEQUENCE: 59
ggtttcatcg tccactcctt ga 22

<210> SEQ ID NO 60
<211> LENGTH: 25
<212> TYPE: DNA
<213> ORGANISM: Artificial Sequence
<220> FEATURE:
<223> OTHER INFORMATION: oligionucleotide

<400> SEQUENCE: 60
cttcagcgag taccaatggc tcgac 25

<210> SEQ ID NO 61
<211> LENGTH: 22
<212> TYPE: DNA
<213> ORGANISM: Artificial Sequence
<220> FEATURE:
<223> OTHER INFORMATION: oligionucleotide

<400> SEQUENCE: 61
ggtttcatcg tccactcctt ga 22

<210> SEQ ID NO 62
<211> LENGTH: 25
<212> TYPE: DNA
<213> ORGANISM: Artificial Sequence
<220> FEATURE:
<223> OTHER INFORMATION: oligionucleotide

<400> SEQUENCE: 62
atgacaccat tggcttcatc tgcca 25

<210> SEQ ID NO 63
<211> LENGTH: 22
<212> TYPE: DNA
<213> ORGANISM: Artificial Sequence
<220> FEATURE:
<223> OTHER INFORMATION: oligionucleotide

<400> SEQUENCE: 63
ctttctgctc actccatact tc 22

<210> SEQ ID NO 64
<211> LENGTH: 25
<212> TYPE: DNA
<213> ORGANISM: Artificial Sequence
<220> FEATURE:
<223> OTHER INFORMATION: oligionucleotide

<400> SEQUENCE: 64
agcgaatatc agtggcttga cgatg 25

<210> SEQ ID NO 65
<211> LENGTH: 23
<212> TYPE: DNA
<213> ORGANISM: Artificial Sequence
<220> FEATURE:
<223> OTHER INFORMATION: oligionucleotide

<400> SEQUENCE: 65
actccgcttt cctcactccg tac 23

<210> SEQ ID NO 66
<211> LENGTH: 26
<212> TYPE: DNA
<213> ORGANISM: Artificial Sequence
<220> FEATURE:
<223> OTHER INFORMATION: oligionucleotide

<400> SEQUENCE: 66
catgaatgtg gtcatcatgc ctttag 26

<210> SEQ ID NO 67
<211> LENGTH: 22
<212> TYPE: DNA
<213> ORGANISM: Artificial Sequence
<220> FEATURE:
<223> OTHER INFORMATION: oligionucleotide

<400> SEQUENCE: 67
cttcttcatc cattcggttt gc 22

<210> SEQ ID NO 68
<211> LENGTH: 26
<212> TYPE: DNA
<213> ORGANISM: Artificial Sequence
<220> FEATURE:
<223> OTHER INFORMATION: oligionucleotide

<400> SEQUENCE: 68
cgtggttgaa tgacaccatt ggttac 26

<210> SEQ ID NO 69
<211> LENGTH: 23
<212> TYPE: DNA
<213> ORGANISM: Artificial Sequence
<220> FEATURE:
<223> OTHER INFORMATION: oligionucleotide

<400> SEQUENCE: 69
accttctaca caccggtatg cct 23

<210> SEQ ID NO 70
<211> LENGTH: 27
<212> TYPE: DNA

<213> ORGANISM: Artificial Sequence
<220> FEATURE:
<223> OTHER INFORMATION: oligionucleotide

<400> SEQUENCE: 70
catggaagat aagccaccgt cgacatc 27

<210> SEQ ID NO 71
<211> LENGTH: 23
<212> TYPE: DNA
<213> ORGANISM: Artificial Sequence
<220> FEATURE:
<223> OTHER INFORMATION: oligionucleotide

<400> SEQUENCE: 71
aacacgggtt cgcttgagca cga 23

<210> SEQ ID NO 72
<211> LENGTH: 22
<212> TYPE: DNA
<213> ORGANISM: Artificial Sequence
<220> FEATURE:
<223> OTHER INFORMATION: oligionucleotide

<400> SEQUENCE: 72
tgcatacccg caagcaaaac cg 22

<210> SEQ ID NO 73
<211> LENGTH: 22
<212> TYPE: DNA
<213> ORGANISM: Artificial Sequence
<220> FEATURE:
<223> OTHER INFORMATION: oligionucleotide

<400> SEQUENCE: 73
ccatctctcg agagttcctt ac 22

<210> SEQ ID NO 74
<211> LENGTH: 25
<212> TYPE: DNA
<213> ORGANISM: Artificial Sequence
<220> FEATURE:
<223> OTHER INFORMATION: oligionucleotide

<400> SEQUENCE: 74
atgtggtcac catgccttta gtgag 25

<210> SEQ ID NO 75
<211> LENGTH: 23
<212> TYPE: DNA
<213> ORGANISM: Artificial Sequence
<220> FEATURE:
<223> OTHER INFORMATION: oligonucleotide

<400> SEQUENCE: 75
tggaatggtc ctccattccg ctc 23

<210> SEQ ID NO 76
<211> LENGTH: 23
<212> TYPE: DNA
<213> ORGANISM: Artificial Sequence
<220> FEATURE:
<223> OTHER INFORMATION: oligonucleotide

<400> SEQUENCE: 76
acctaacgac agtcatgaac aag 23

<210> SEQ ID NO 77
<211> LENGTH: 23
<212> TYPE: DNA
<213> ORGANISM: Artificial Sequence
<220> FEATURE:
<223> OTHER INFORMATION: oligonucleotide

<400> SEQUENCE: 77
gtgaggaaag cggagtggac aac 23

<210> SEQ ID NO 78
<211> LENGTH: 21
<212> TYPE: DNA
<213> ORGANISM: Artificial Sequence
<220> FEATURE:
<223> OTHER INFORMATION: oligonucleotide

<400> SEQUENCE: 78
tgaaagcaag atgggaggag g 21

<210> SEQ ID NO 79
<211> LENGTH: 22
<212> TYPE: DNA
<213> ORGANISM: Artificial Sequence
<220> FEATURE:
<223> OTHER INFORMATION: oligonucleotide

<400> SEQUENCE: 79
tcacaacttt acttattctt gt 22

<210> SEQ ID NO 80
<211> LENGTH: 20
<212> TYPE: DNA
<213> ORGANISM: Artificial Sequence
<220> FEATURE:
<223> OTHER INFORMATION: oligonucleotide

<400> SEQUENCE: 80
attgaacaat gggtgcaggc 20

<210> SEQ ID NO 81
<211> LENGTH: 21
<212> TYPE: DNA
<213> ORGANISM: Artificial Sequence
<220> FEATURE:
<223> OTHER INFORMATION: oligonucleotide

<400> SEQUENCE: 81
catcatcttc aaatcttatt c 21

<210> SEQ ID NO 82
<211> LENGTH: 19
<212> TYPE: DNA
<213> ORGANISM: Artificial Sequence
<220> FEATURE:
<223> OTHER INFORMATION: oligonucleotide

<400> SEQUENCE: 82
aatcagcagc agcacaagc 19

<210> SEQ ID NO 83
<211> LENGTH: 23
<212> TYPE: DNA
<213> ORGANISM: Artificial Sequence
<220> FEATURE:

<223> OTHER INFORMATION: oligonucleotide

<400> SEQUENCE: 83
caaacatacc accaaatgct act 23

<210> SEQ ID NO 84
<211> LENGTH: 24
<212> TYPE: DNA
<213> ORGANISM: Artificial Sequence
<220> FEATURE:
<223> OTHER INFORMATION: oligonucleotide

<400> SEQUENCE: 84
ctcagtaacc agcctcaaaa cttg 24

<210> SEQ ID NO 85
<211> LENGTH: 22
<212> TYPE: DNA
<213> ORGANISM: Artificial Sequence
<220> FEATURE:
<223> OTHER INFORMATION: oligonucleotide

<400> SEQUENCE: 85
gcggattgat caaatacttg tg 22

<210> SEQ ID NO 86
<211> LENGTH: 23
<212> TYPE: DNA
<213> ORGANISM: Artificial Sequence
<220> FEATURE:
<223> OTHER INFORMATION: oligonucleotide

<400> SEQUENCE: 86
atcacaggaa gctcaaagca tct 23

<210> SEQ ID NO 87
<211> LENGTH: 21
<212> TYPE: DNA
<213> ORGANISM: Artificial Sequence
<220> FEATURE:
<223> OTHER INFORMATION: oligonucleotide

<400> SEQUENCE: 87
gtaggttatg taacaatcgt g 21

<210> SEQ ID NO 88
<211> LENGTH: 23
<212> TYPE: DNA
<213> ORGANISM: Artificial Sequence
<220> FEATURE:
<223> OTHER INFORMATION: oligonucleotide

<400> SEQUENCE: 88
tgaagacgtt aagatgggag ctg 23

<210> SEQ ID NO 89
<211> LENGTH: 21
<212> TYPE: DNA
<213> ORGANISM: Artificial Sequence
<220> FEATURE:
<223> OTHER INFORMATION: oligonucleotide

<400> SEQUENCE: 89
gtaggttatg taacaatcgt g 21

<210> SEQ ID NO 90
<211> LENGTH: 23
<212> TYPE: DNA
<213> ORGANISM: Artificial Sequence
<220> FEATURE:
<223> OTHER INFORMATION: oligonucleotide

<400> SEQUENCE: 90
cagatccaac acttcaccac cag 23

<210> SEQ ID NO 91
<211> LENGTH: 23
<212> TYPE: DNA
<213> ORGANISM: Artificial Sequence
<220> FEATURE:
<223> OTHER INFORMATION: oligonucleotide

<400> SEQUENCE: 91
agatctaaag aatttccatg gtg 23

<210> SEQ ID NO 92
<211> LENGTH: 25
<212> TYPE: DNA
<213> ORGANISM: Artificial Sequence
<220> FEATURE:
<223> OTHER INFORMATION: oligonucleotide

<400> SEQUENCE: 92
ctgctctcta cgacactaaa ttcac 25

<210> SEQ ID NO 93
<211> LENGTH: 24
<212> TYPE: DNA
<213> ORGANISM: Artificial Sequence
<220> FEATURE:
<223> OTHER INFORMATION: oligonucleotide

<400> SEQUENCE: 93
tctatctaat gagtatcaag gaac 24

<210> SEQ ID NO 94
<211> LENGTH: 26
<212> TYPE: DNA
<213> ORGANISM: Artificial Sequence
<220> FEATURE:
<223> OTHER INFORMATION: oligonucleotide

<400> SEQUENCE: 94
ctgaattcac acccacagat agctag 26

<210> SEQ ID NO 95
<211> LENGTH: 23
<212> TYPE: DNA
<213> ORGANISM: Artificial Sequence
<220> FEATURE:
<223> OTHER INFORMATION: oligonucleotide

<400> SEQUENCE: 95
acatcccttc ttagctttaa cta 23

<210> SEQ ID NO 96
<211> LENGTH: 21
<212> TYPE: DNA
<213> ORGANISM: Artificial Sequence
<220> FEATURE:
<223> OTHER INFORMATION: oligonucleotide

<400> SEQUENCE: 96
acttcgccct ctgttatctg g 21

<210> SEQ ID NO 97
<211> LENGTH: 24
<212> TYPE: DNA
<213> ORGANISM: Artificial Sequence
<220> FEATURE:
<223> OTHER INFORMATION: oligonucleotide

<400> SEQUENCE: 97
ccatacacat acatcctaca cgat 24

<210> SEQ ID NO 98
<211> LENGTH: 24
<212> TYPE: DNA
<213> ORGANISM: Artificial Sequence
<220> FEATURE:
<223> OTHER INFORMATION: oligonucleotide

<400> SEQUENCE: 98
actcacaata acttcatctc tctc 24

<210> SEQ ID NO 99
<211> LENGTH: 23
<212> TYPE: DNA
<213> ORGANISM: Artificial Sequence
<220> FEATURE:
<223> OTHER INFORMATION: oligonucleotide

<400> SEQUENCE: 99
ctactagcca tacaatgtct tcg 23

<210> SEQ ID NO 100
<211> LENGTH: 24
<212> TYPE: DNA
<213> ORGANISM: Artificial Sequence
<220> FEATURE:
<223> OTHER INFORMATION: oligonucleotide

<400> SEQUENCE: 100
gagattttca gagagcaagc gctt 24

<210> SEQ ID NO 101
<211> LENGTH: 23
<212> TYPE: DNA
<213> ORGANISM: Artificial Sequence
<220> FEATURE:
<223> OTHER INFORMATION: oligonucleotide

<400> SEQUENCE: 101
ctttggtctc ggaggcagac ata 23

<210> SEQ ID NO 102
<211> LENGTH: 24
<212> TYPE: DNA
<213> ORGANISM: Artificial Sequence
<220> FEATURE:
<223> OTHER INFORMATION: oligonucleotide

<400> SEQUENCE: 102
caaaaggagt ttcagaaagc ctcc 24

<210> SEQ ID NO 103
<211> LENGTH: 23

<212> TYPE: DNA
<213> ORGANISM: Artificial Sequence
<220> FEATURE:
<223> OTHER INFORMATION: oligonucleotide

<400> SEQUENCE: 103
actcgttgga tgccttcgag ttc 23

<210> SEQ ID NO 104
<211> LENGTH: 19
<212> TYPE: DNA
<213> ORGANISM: Artificial Sequence
<220> FEATURE:
<223> OTHER INFORMATION: oligonucleotide

<400> SEQUENCE: 104
aatcagcagc agcacaagc 19

<210> SEQ ID NO 105
<211> LENGTH: 23
<212> TYPE: DNA
<213> ORGANISM: Artificial Sequence
<220> FEATURE:
<223> OTHER INFORMATION: oligonucleotide

<400> SEQUENCE: 105
aaggcggtga caattatgat atc 23

<210> SEQ ID NO 106
<211> LENGTH: 24
<212> TYPE: DNA
<213> ORGANISM: Artificial Sequence
<220> FEATURE:
<223> OTHER INFORMATION: oligonucleotide

<400> SEQUENCE: 106
ctcagtaacc agcctcaaaa cttg 24

<210> SEQ ID NO 107
<211> LENGTH: 23
<212> TYPE: DNA
<213> ORGANISM: Artificial Sequence
<220> FEATURE:
<223> OTHER INFORMATION: oligonucleotide

<400> SEQUENCE: 107
aaggcggaga cgattatgat atc 23

<210> SEQ ID NO 108
<211> LENGTH: 23
<212> TYPE: DNA
<213> ORGANISM: Artificial Sequence
<220> FEATURE:
<223> OTHER INFORMATION: oligonucleotide

<400> SEQUENCE: 108
atcacaggaa gctcaaagca tct 23

<210> SEQ ID NO 109
<211> LENGTH: 22
<212> TYPE: DNA
<213> ORGANISM: Artificial Sequence
<220> FEATURE:
<223> OTHER INFORMATION: oligonucleotide

<400> SEQUENCE: 109
atcatctctt cggtaggtta tg 22

<210> SEQ ID NO 110
<211> LENGTH: 23
<212> TYPE: DNA
<213> ORGANISM: Artificial Sequence
<220> FEATURE:
<223> OTHER INFORMATION: oligonucleotide

<400> SEQUENCE: 110
cagatccaac acttcaccac cag 23

<210> SEQ ID NO 111
<211> LENGTH: 23
<212> TYPE: DNA
<213> ORGANISM: Artificial Sequence
<220> FEATURE:
<223> OTHER INFORMATION: oligonucleotide

<400> SEQUENCE: 111
ctaaagaatt tccatggtgt tac 23

<210> SEQ ID NO 112
<211> LENGTH: 21
<212> TYPE: DNA
<213> ORGANISM: Artificial Sequence
<220> FEATURE:
<223> OTHER INFORMATION: oligonucleotide

<400> SEQUENCE: 112
acttcgccct ctgttatctg g 21

<210> SEQ ID NO 113
<211> LENGTH: 21
<212> TYPE: DNA
<213> ORGANISM: Artificial Sequence
<220> FEATURE:
<223> OTHER INFORMATION: oligonucleotide

<400> SEQUENCE: 113
gagagacggt ggaagtaggt g 21

<210> SEQ ID NO 114
<211> LENGTH: 23
<212> TYPE: DNA
<213> ORGANISM: Artificial Sequence
<220> FEATURE:
<223> OTHER INFORMATION: oligonucleotide

<400> SEQUENCE: 114
ctcacaataa cttcatctct ctc 23

<210> SEQ ID NO 115
<211> LENGTH: 24
<212> TYPE: DNA
<213> ORGANISM: Artificial Sequence
<220> FEATURE:
<223> OTHER INFORMATION: oligonucleotide

<400> SEQUENCE: 115
aaagacatag gcaacaacga gatc 24

<210> SEQ ID NO 116
<211> LENGTH: 20
<212> TYPE: DNA
<213> ORGANISM: Artificial Sequence
<220> FEATURE:
<223> OTHER INFORMATION: oligonucleotide

<400> SEQUENCE: 116
gtgtatgtct gcctccgaga 20

<210> SEQ ID NO 117
<211> LENGTH: 21
<212> TYPE: DNA
<213> ORGANISM: Artificial Sequence
<220> FEATURE:
<223> OTHER INFORMATION: oligonucleotide

<400> SEQUENCE: 117
gcaaggtagt agaggacgaa g 21

<210> SEQ ID NO 118
<211> LENGTH: 23
<212> TYPE: DNA
<213> ORGANISM: Artificial Sequence
<220> FEATURE:
<223> OTHER INFORMATION: oligonucleotide

<400> SEQUENCE: 118
gcctccaaag attcattcag gtc 23

<210> SEQ ID NO 119
<211> LENGTH: 22
<212> TYPE: DNA
<213> ORGANISM: Artificial Sequence
<220> FEATURE:
<223> OTHER INFORMATION: oligonucleotide

<400> SEQUENCE: 119
caagatggat gcgatggtaa gg 22

<210> SEQ ID NO 120
<211> LENGTH: 18
<212> TYPE: DNA
<213> ORGANISM: Artificial Sequence
<220> FEATURE:
<223> OTHER INFORMATION: oligonucleotide

<400> SEQUENCE: 120
acgtggcggt ctcaggtt 18

<210> SEQ ID NO 121
<211> LENGTH: 22
<212> TYPE: DNA
<213> ORGANISM: Artificial Sequence
<220> FEATURE:
<223> OTHER INFORMATION: oligonucleotide

<400> SEQUENCE: 121
aggcggtgac aattatgata tc 22

<210> SEQ ID NO 122
<211> LENGTH: 21
<212> TYPE: DNA
<213> ORGANISM: Artificial Sequence
<220> FEATURE:
<223> OTHER INFORMATION: oligonucleotide

<400> SEQUENCE: 122
aaggcaggcc gtgatgccga t 21

<210> SEQ ID NO 123
<211> LENGTH: 21
<212> TYPE: DNA
<213> ORGANISM: Artificial Sequence
<220> FEATURE:
<223> OTHER INFORMATION: oligonucleotide

<400> SEQUENCE: 123
agtatttgat caatccgctg g 21

<210> SEQ ID NO 124
<211> LENGTH: 22
<212> TYPE: DNA
<213> ORGANISM: Artificial Sequence
<220> FEATURE:
<223> OTHER INFORMATION: oligonucleotide

<400> SEQUENCE: 124
caatacggta gaggccacac ag 22

<210> SEQ ID NO 125
<211> LENGTH: 22
<212> TYPE: DNA
<213> ORGANISM: Artificial Sequence
<220> FEATURE:
<223> OTHER INFORMATION: oligonucleotide

<400> SEQUENCE: 125
atcatctctt cggtaggtta tg 22

<210> SEQ ID NO 126
<211> LENGTH: 22
<212> TYPE: DNA
<213> ORGANISM: Artificial Sequence
<220> FEATURE:
<223> OTHER INFORMATION: oligonucleotide

<400> SEQUENCE: 126
gacatgtgct cacgtggtgc at 22

<210> SEQ ID NO 127
<211> LENGTH: 21
<212> TYPE: DNA
<213> ORGANISM: Artificial Sequence
<220> FEATURE:
<223> OTHER INFORMATION: oligonucleotide

<400> SEQUENCE: 127
gttgctaata tccacaccct a 21

<210> SEQ ID NO 128
<211> LENGTH: 20
<212> TYPE: DNA
<213> ORGANISM: Artificial Sequence
<220> FEATURE:
<223> OTHER INFORMATION: oligonucleotide

<400> SEQUENCE: 128
cgaatcacac ccacgggatc 20

<210> SEQ ID NO 129
<211> LENGTH: 23
<212> TYPE: DNA
<213> ORGANISM: Artificial Sequence
<220> FEATURE:
<223> OTHER INFORMATION: oligonucleotide

<400> SEQUENCE: 129
ctaaagaatt tccatggtgt tac 23

<210> SEQ ID NO 130
<211> LENGTH: 21
<212> TYPE: DNA
<213> ORGANISM: Artificial Sequence
<220> FEATURE:
<223> OTHER INFORMATION: oligonucleotide

<400> SEQUENCE: 130
gagcaacgga gagaagtaac c 21

<210> SEQ ID NO 131
<211> LENGTH: 22
<212> TYPE: DNA
<213> ORGANISM: Artificial Sequence
<220> FEATURE:
<223> OTHER INFORMATION: oligonucleotide

<400> SEQUENCE: 131
gagggatgat agaaagaggt cc 22

<210> SEQ ID NO 132
<211> LENGTH: 22
<212> TYPE: DNA
<213> ORGANISM: Artificial Sequence
<220> FEATURE:
<223> OTHER INFORMATION: oligonucleotide

<400> SEQUENCE: 132
catgtgtggc tggaggattc ga 22

<210> SEQ ID NO 133
<211> LENGTH: 22
<212> TYPE: DNA
<213> ORGANISM: Artificial Sequence
<220> FEATURE:
<223> OTHER INFORMATION: oligonucleotide

<400> SEQUENCE: 133
gcaccgagtt tagcctttgt ct 22

<210> SEQ ID NO 134
<211> LENGTH: 22
<212> TYPE: DNA
<213> ORGANISM: Artificial Sequence
<220> FEATURE:
<223> OTHER INFORMATION: oligonucleotide

<400> SEQUENCE: 134
ccaacaaaca aaccatctct cg 22

<210> SEQ ID NO 135
<211> LENGTH: 21
<212> TYPE: DNA
<213> ORGANISM: Artificial Sequence
<220> FEATURE:
<223> OTHER INFORMATION: oligonucleotide

<400> SEQUENCE: 135
gagagacggt ggaagtaggt g 21

<210> SEQ ID NO 136

<211> LENGTH: 23
<212> TYPE: DNA
<213> ORGANISM: Artificial Sequence
<220> FEATURE:
<223> OTHER INFORMATION: oligonucleotide

<400> SEQUENCE: 136
ccattgatcc acccttcacc tta 23

<210> SEQ ID NO 137
<211> LENGTH: 24
<212> TYPE: DNA
<213> ORGANISM: Artificial Sequence
<220> FEATURE:
<223> OTHER INFORMATION: oligonucleotide

<400> SEQUENCE: 137
aaagacatag gcaacaacga gatc 24

<210> SEQ ID NO 138
<211> LENGTH: 20
<212> TYPE: DNA
<213> ORGANISM: Artificial Sequence
<220> FEATURE:
<223> OTHER INFORMATION: oligonucleotide

<400> SEQUENCE: 138
ctgaactgca attatctagg 20

<210> SEQ ID NO 139
<211> LENGTH: 21
<212> TYPE: DNA
<213> ORGANISM: Artificial Sequence
<220> FEATURE:
<223> OTHER INFORMATION: oligonucleotide

<400> SEQUENCE: 139
ggtattggta ttggatgggc g 21

<210> SEQ ID NO 140
<211> LENGTH: 22
<212> TYPE: DNA
<213> ORGANISM: Artificial Sequence
<220> FEATURE:
<223> OTHER INFORMATION: oligonucleotide

<400> SEQUENCE: 140
ataaggctgt gttcacgggt tt 22

<210> SEQ ID NO 141
<211> LENGTH: 22
<212> TYPE: DNA
<213> ORGANISM: Artificial Sequence
<220> FEATURE:
<223> OTHER INFORMATION: oligonucleotide

<400> SEQUENCE: 141
gctcagttgg ggatacaagg at 22

<210> SEQ ID NO 142
<211> LENGTH: 22
<212> TYPE: DNA
<213> ORGANISM: Artificial Sequence
<220> FEATURE:
<223> OTHER INFORMATION: oligonucleotide

<400> SEQUENCE: 142
agttatggtt cgatgatcga cg 22

<210> SEQ ID NO 143
<211> LENGTH: 23
<212> TYPE: DNA
<213> ORGANISM: Artificial Sequence
<220> FEATURE:
<223> OTHER INFORMATION: oligonucleotide

<400> SEQUENCE: 143
ttgctataca tattgaaggc act 23

<210> SEQ ID NO 144
<211> LENGTH: 20
<212> TYPE: DNA
<213> ORGANISM: Artificial Sequence
<220> FEATURE:
<223> OTHER INFORMATION: oligonucleotide

<400> SEQUENCE: 144
ctgaactgca attatctagg 20

<210> SEQ ID NO 145
<211> LENGTH: 21
<212> TYPE: DNA
<213> ORGANISM: Artificial Sequence
<220> FEATURE:
<223> OTHER INFORMATION: oligonucleotide

<400> SEQUENCE: 145
ggtattggta ttggatgggc g 21

<210> SEQ ID NO 146
<211> LENGTH: 20
<212> TYPE: DNA
<213> ORGANISM: Artificial Sequence
<220> FEATURE:
<223> OTHER INFORMATION: oligonucleotide

<400> SEQUENCE: 146
gtgtatgtct gcctccgaga 20

<210> SEQ ID NO 147
<211> LENGTH: 21
<212> TYPE: DNA
<213> ORGANISM: Artificial Sequence
<220> FEATURE:
<223> OTHER INFORMATION: oligonucleotide

<400> SEQUENCE: 147
gcaaggtagt agaggacgaa g 21

<210> SEQ ID NO 148
<211> LENGTH: 23
<212> TYPE: DNA
<213> ORGANISM: Artificial Sequence
<220> FEATURE:
<223> OTHER INFORMATION: oligonucleotide

<400> SEQUENCE: 148
agagatcatt ggagactaga gtg 23

<210> SEQ ID NO 149
<211> LENGTH: 24
<212> TYPE: DNA

<213> ORGANISM: Artificial Sequence
<220> FEATURE:
<223> OTHER INFORMATION: oligonucleotide

<400> SEQUENCE: 149
cccatcaagc acaattcttc ttag 24

<210> SEQ ID NO 150
<211> LENGTH: 23
<212> TYPE: DNA
<213> ORGANISM: Artificial Sequence
<220> FEATURE:
<223> OTHER INFORMATION: oligonucleotide

<400> SEQUENCE: 150
ctacacaatc ggactctggt gct 23

<210> SEQ ID NO 151
<211> LENGTH: 22
<212> TYPE: DNA
<213> ORGANISM: Artificial Sequence
<220> FEATURE:
<223> OTHER INFORMATION: oligonucleotide

<400> SEQUENCE: 151
gccatccatg acacctattc ta 22

<210> SEQ ID NO 152
<211> LENGTH: 22
<212> TYPE: DNA
<213> ORGANISM: Artificial Sequence
<220> FEATURE:
<223> OTHER INFORMATION: oligonucleotide

<400> SEQUENCE: 152
cctcactctg ggaccaagaa at 22

<210> SEQ ID NO 153
<211> LENGTH: 23
<212> TYPE: DNA
<213> ORGANISM: Artificial Sequence
<220> FEATURE:
<223> OTHER INFORMATION: oligonucleotide

<400> SEQUENCE: 153
ttcttgggac atgtgacgta gaa 23

<210> SEQ ID NO 154
<211> LENGTH: 24
<212> TYPE: DNA
<213> ORGANISM: Artificial Sequence
<220> FEATURE:
<223> OTHER INFORMATION: oligonucleotide

<400> SEQUENCE: 154
cattgaagtc ggtattgata tctg 24

<210> SEQ ID NO 155
<211> LENGTH: 24
<212> TYPE: DNA
<213> ORGANISM: Artificial Sequence
<220> FEATURE:
<223> OTHER INFORMATION: oligonucleotide

<400> SEQUENCE: 155
cattgaagtc ggtattgata tctg 24

<210> SEQ ID NO 156
<211> LENGTH: 24
<212> TYPE: DNA
<213> ORGANISM: Artificial Sequence
<220> FEATURE:
<223> OTHER INFORMATION: oligonucleotide

<400> SEQUENCE: 156
gttccaacaa tatcttccac cagt 24

<210> SEQ ID NO 157
<211> LENGTH: 30
<212> TYPE: DNA
<213> ORGANISM: Artificial Sequence
<220> FEATURE:
<223> OTHER INFORMATION: oligonucleotide

<400> SEQUENCE: 157
cctgcaggta ccaatggctc gacgacactg 30

<210> SEQ ID NO 158
<211> LENGTH: 30
<212> TYPE: DNA
<213> ORGANISM: Artificial Sequence
<220> FEATURE:
<223> OTHER INFORMATION: oligonucleotide

<400> SEQUENCE: 158
cggcgcgcct tcacctcctc atctttatcc 30

<210> SEQ ID NO 159
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 159

His Glu Cys Gly His
1 5

<210> SEQ ID NO 160
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 160

His Asp Cys Gly His
1 5

<210> SEQ ID NO 161
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 161

His Asp Leu Gly His
1 5

<210> SEQ ID NO 162
<211> LENGTH: 5

<212> TYPE: PRT
<213> ORGANISM: Artificial Sequence
<220> FEATURE:
<223> OTHER INFORMATION: Motifs of CtFAD2 enzyme

<400> SEQUENCE: 162

His Arg Arg His His
1               5

<210> SEQ ID NO 163
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 163

His Arg Thr His His
1               5

<210> SEQ ID NO 164
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 164

His Arg Ser His His
1               5

<210> SEQ ID NO 165
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 165

His Arg Asn His His
1               5

<210> SEQ ID NO 166
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 166

His Val Val His His
1               5

<210> SEQ ID NO 167
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 167

His Val Thr His His
1               5

<210> SEQ ID NO 168
<211> LENGTH: 5
<212> TYPE: PRT

<213> ORGANISM: Artificial Sequence
<220> FEATURE:
<223> OTHER INFORMATION: Motifs of CtFAD2 enzyme

<400> SEQUENCE: 168

His Ala Val His His
1 5

<210> SEQ ID NO 169
<211> LENGTH: 5
<212> TYPE: PRT
<213> ORGANISM: Artificial Sequence
<220> FEATURE:
<223> OTHER INFORMATION: Motifs of CtFAD2 enzyme

<400> SEQUENCE: 169

His Val Leu His His
1 5

<210> SEQ ID NO 170
<211> LENGTH: 1083
<212> TYPE: DNA
<213> ORGANISM: Artificial Sequence
<220> FEATURE:
<223> OTHER INFORMATION: CtFAD2-1-SU introns wild type

<400> SEQUENCE: 170
gtgcattctc tcattctcaa aacctttctg ctattcatct gatcaatgta ttcagttatg 60
gttcgatgat cgacgattat tgtttgttat tttaatttta atttttaggt tgatttagct 120
gcattgttgg tcgatgaata gatctgtgga ttacggtctt ctgcagtttc agtttgattt 180
atttcagtcc gtttttctcc tgtaaatttg tgtatctatc tgtgttgcat gtaattttgt 240
ttcctttaga ttatagaaat gaaaatccat aattttaggg ctgcttgtct tgtttggatt 300
tgtgttatta ggttttgatc acagtaactt ccgtacgttt aatatgttaa atgctaaaca 360
aaatgattta ttttttatat ttatggcttc tcggtggtcg gatttgtgtt tttaattcct 420
gaagtttctg tatacaatga tttcgaattt tggcgattag gcatctcttt actttggaag 480
gaatttcaga ttttcttaat ctcatagaga agtgctgatt gggaatttgc ttaaagatat 540
aagcactttt cagttcattg attgtttgat ggacatcaga tggtttttt gctgatgcca 600 tgatgtctat tgtgttgaat gtatcttcaa taagtgcctt caatatgtat agcaaaactg 660
agctaaggct gtgtttggca aactacctga taagctatat gttgactgat aagctagttt 720
gtgaataaat tatgtttggc aaaaactagc atatgagtat gtaaaatgac taaaaagggt 780
atcttggggt ataatagtta atattgataa ggatagaatt ggagaaggct acaaaaagcc 840
cttgaaatgc tactccaact agtgtttcaa taagctggct tatggtctat ccaaacatgt 900
actagattat catctagctt atttttgcca aacacagcct aaatgtttga tggtcgatgg 960
ctggcacttg acaatttgac atcattataa ctgaaacaat aatattcacc tttacataac 1020
attcaccttt agccaaaaac tagatgttca cctacgaact gatccatatg gaacattttg 1080
cag 1083

<210> SEQ ID NO 171
<211> LENGTH: 1144
<212> TYPE: DNA
<213> ORGANISM: Artificial Sequence
<220> FEATURE:
<223> OTHER INFORMATION: CtFAD2-1-ol CtFAD2 intron

<400> SEQUENCE: 171

-continued

```
gtgcattctc tcaaccttcc tgcttttcgt ctgatcaatg ttaatgtatt cagttatcgt     60
ttcgatgatt tcctattaaa tgtcgacgat tatcgtttgt tattttttat tttaggtaga    120
tttagctgca ttgttggttg atgaatagat ctgtagatta cggtcctctg cgctttcagt    180
ttttgattca tttcactccg ttttcttctg taaatttgtg tatctatctg tgctgcatgt    240
aattttgttt cctttagatt atagaaatga aaatccataa ttttagggct gcttctcttg    300
tttggatttg tgttattagg ttttaattac agtaacttcc gtacgtttaa tatgtcaaat    360
gctaaacaaa atgatttgtt ttttatattt atggcttctc ggtggtcgga tttgtgtttt    420
taattcctga agtttctgta tacaatgatt tcgaatttg gcgattaggc atctctttac     480
tttggaagga tttctagatt ttctttgccg gattccttaa tcttatatag aaatgatgat    540
atcattgaca aatggcaatt gcttaaagat acaagcattt ttcagttcat tgaatgtttg    600
atggacatca aaatggattt tttgctgatg tctactgtgt tgaatgtacc ttcaataagg    660
ctgtgttcac gggtttggca tgctagctga tagctgataa gctagcttat gaataaatta    720
tgtttggtaa aaactagctt atgagtatgt aaaatgacaa aaaaggtacc tcggagtgta    780
ataattaata ttaataaggg tataattgga agagcctact aaaagctcct agaacgctac    840
tccaactaac gtttcaataa gcttaactta tggtccatcc aaacatgtac tagcttataa    900
gcgagcttat ttttgccaaa cacagccaaa gtactttcat ggttgatatc cttgtatccc    960
caactgagct aaatggtccg atggtcgacg agttgacatc attataatta tatatttttg   1020
aatccttaag gctaacgttt ccttagtttt tatttatgtt gtgatggtgg cattacataa   1080
tattcacctt tagctaaaaa ctagatgttc acctacgaac tgatccatat ggaacatttt   1140
gcag                                                                1144
```